United States Patent [19]

Sugiura et al.

[11] Patent Number: 5,216,183

[45] Date of Patent: Jun. 1, 1993

[54] CYCLOPENTANONE/CYCLOPENTENONE DERIVATIVE

[75] Inventors: Satoshi Sugiura; Toru Minoshima; Atsuo Hazato; Yoshinori Kato, all of Hino, Japan

[73] Assignee: Teijin Limited, Osaka, Japan

[21] Appl. No.: 836,562

[22] Filed: Feb. 18, 1992

Related U.S. Application Data

[63] Continuation-in-part of Ser. No. 759,785, Sep. 3, 1991, Pat. No. 5,116,869, which is a continuation of Ser. No. 340,207, Apr. 19, 1989, abandoned, and a continuation-in-part of Ser. No. 690,889, Jun. 19, 1991.

[30] Foreign Application Priority Data

Apr. 19, 1988 [JP] Japan ................................. 63-94687
Jan. 24, 1989 [JP] Japan ................................. 1-13036
Oct. 19, 1989 [JP] Japan ................................. 1-272296

[51] Int. Cl.[5] .................. C07D 303/14; C07D 303/16; C07D 303/18
[52] U.S. Cl. .................................. 549/546; 549/215; 549/422; 568/43
[58] Field of Search ......................... 549/546, 215, 422

[56] References Cited

FOREIGN PATENT DOCUMENTS

| | | |
|---|---|---|
| 0106576 | 4/1984 | European Pat. Off. . |
| 0131441 | 1/1985 | European Pat. Off. . |
| 0180399 | 5/1986 | European Pat. Off. . |
| 338796 | 10/1989 | European Pat. Off. ............ 549/546 |
| 58-109468 | 6/1983 | Japan . |
| 58-216155 | 12/1983 | Japan . |
| 59-59646 | 4/1984 | Japan . |
| 59-184158 | 10/1984 | Japan . |
| 60-4129 | 1/1985 | Japan . |
| 62-96438 | 5/1987 | Japan . |
| 2-275849 | 11/1990 | Japan . |
| 8503706 | 8/1985 | PCT Int'l Appl. . |
| 18704159 | 7/1987 | PCT Int'l Appl. . |
| A5632992 | 11/1982 | Switzerland . |

OTHER PUBLICATIONS

J. Amer. Chem. Soc., 95, 6831 (1973).
Biochem Biophys. Res. Commun., 87, 795 (1979).
Prostaglandins and Cancer: First International Conference 365–368 (1982).
Proc. Natl. Acad. Sci. 81, 1317–1321 (1984).
Tetrahedron Lett. 23, 5171 (1982).
Tetrahedron Lett. 23, 5331 (1982).
Cancer and Chemotherapy, 10, 1930 (1983) Japanese J. and English Summary) p. 3, Lines 14–5.
J. Am. Chem. Soc., 106, 3384 (1984).
Tetrahedron Letters, 25, 33, 3621–3624 (1984).
J. of American Chemical Society, 107, 2976 (1985).
Proceedings of the Japanese Cancer Association, Collected Abstracts of the 43rd Meeting Of Japanese Society Of Cancer, p. 258 (1984).
Biochemical Society of Japan (Collected Abstracts), p. 767, 1988 (and English Summary) p. 7, Lines 21–22.
T. W. Greene, "Protective Groups in Organic Synthesis" John Wiley & Sons (1981).
*Chemical and Pharmaceutical Bulletin:* vol. 33, No. 7, (1985); Katsuhide Motoba et al.; "Reduction of Vinylogous Thioesters With Lithium Aluminum Hydride. II", pp. 3001–3005 Particularly, Refer to Compounb Vb on p. 3002.

*Primary Examiner*—Joseph E. Evans
*Attorney, Agent, or Firm*—Sughrue, Mion, Zinn, Macpeak & Seas

[57] ABSTRACT

A 2,3-epoxycyclopentanone represented by the formula (IV):

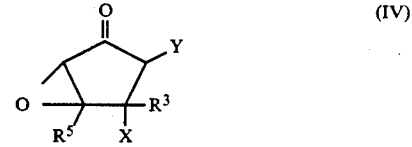

wherein the variables are as defined in the specification, which is used in the preparation of a 2-substituted-2-cyclopentanone compound suitable for use as an anticancer agent and a bone formation accelerator.

3 Claims, No Drawings

CYCLOPENTANONE/CYCLOPENTENONE DERIVATIVE

CROSS REFERENCE TO RELATED APPLICATION

The present application is a continuation-in-part of Ser. No. 07/759,785, filed Sep. 3, 1991, now U.S. Pat. No. 5,116,869, which is a continuation application of Ser. No. 07/340,207, filed Apr. 19, 1989, now abandoned, and the present application is also a continuation-in-part of Ser. No. 07/690,889, filed Jun. 19, 1991, which was based upon PCT/JP90/01343 filed Oct. 18, 1990.

BACKGROUND OF THE INVENTION

1. Filed of the Invention

The present invention relates to a cyclopentanone or cyclopentanone derivative intermediate compound for a 2-substituted-2-cyclopentenone compound having superior pharmacological activities, such as an anticancer activity and bone formation activity.

2. Description of the Related Art

A prostaglandin is a compound having specific biological activities, such as a platelet agglutination inhibitory activity and a vasodepressor activity, and is a useful naturally occurring substance which is now used in the medical field as a therapeutic agent for diseases of the peripheral cardiovascular system. Among the prostaglandins, prostaglandin A compounds are known as a prostaglandin having a double bond in its cyclopentane ring. For example, European Unexamined Patent Publication No. 0106576 (publication date: Apr. 25, 1984) discloses 4,5-substituted-2-cyclopentenone compounds embracing the prostaglandin A compounds, which include 5-alkylidene-4-substituted-2-cyclopentene compounds represented by the following formula:

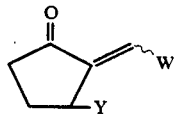

wherein
W stands for a substituted or unsubstituted hydrocarbon group having 1 to 12 carbon atoms; and
Y stands for a substituted or unsubstituted hydrocarbon group having 1 to 12 carbon atoms,
and 5-(1-hydroxy-hydrocarbon)-4-substituted-2-cyclopentenone compounds represented by the following formula:

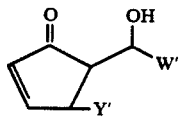

wherein W' and Y' are the same as W and Y, respectively.

Further, the above publication also states that the above-described compounds are useful for treating a malignant tumor.

European Unexamined Patent Publication No. 0131441 (publication date: Jan. 16, 1985) discloses 5-alkylidene-2-halo-4-substituted-2-cyclopentenone compounds represented by the following formula:

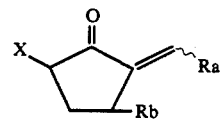

wherein Ra stands for a substituted or unsubstituted hydrocarbon having 1 to 12 carbon atoms or a substituted or unsubstituted phenyl group; Rb stands for a substituted or unsubstituted hydrocarbon having 1 to 12 carbon atoms; and X stands for a halogen atom, and further discloses that the above-described compounds are similarly useful for treating a malignant tumor.

Further, it is also known that prostaglandin D compounds and prostaglandin J compounds, although different from the prostaglandin A compounds, are useful as an antitumor agent [see Japanese Unexamined Patent Publication (Kokai) No. 58-216155 and Proc. Natl. Acad. Sci., U.S.A., 81, 1317–1321 (1984)].

Japanese Unexamined Patent Publication (Kokai) No. 62-96438 discloses 4-hydroxy-2-cyclopentenone compounds represented by the general formula:

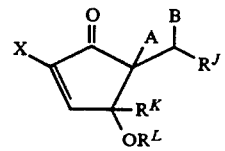

wherein X stands for a hydrogen atom or a halogen atom; A and B stand for a hydrogen atom and a hydroxyl group, respectively, or are combined with each other to form a single bond; $R^J$ stands for a substituted or unsubstituted alkyl, alkenyl or alkynyl group having 1 to 10 carbon atoms; $R^K$ stands for a substituted or unsubstituted alkyl, alkenyl or alkynyl group having 1 to 10 carbon atoms; and $R^L$ stands for a hydrogen atom or a protecting group for a hydroxyl group, provided that $R^K$ is not 2-octenyl, 8-acetoxy-2-octenyl or 2,5-octadienyl, and states that the above-described compounds are useful for the treatment of a malignant tumor.

It is commonly recognized that the metabolism of the bone of healthy persons is established by a good balance of the repetition of the absorption of bone by osteoclasts and the formation of bone by osteoblasts, and it is considered that the breaking of the balance between the absorption of bone and the formation of bone leads to diseases such as osteoporosis and osteomalalacia. Active vitamin preparations, calcitonin preparations, diphosphonic acid preparations, estrogen preparations, calcium preparations, etc. are used as a therapeutic agent for these diseases of bone. Nevertheless, although it has been reported that many of these preparations have a bone absorption inhibitory activity, there is no report clearly showing that they exhibit a bone formation accelerative activity. Further, since the effect of these preparations is not clear, the development of a preparation capable of more surely attaining the effect and having an activity through which the formation of bone by the osteoblasts is accelerated has been desired in the art.

Koshihara et al. reported in Biochemical Society of Japan (Preprints, 1988, p.767) that prostaglandin $D_2$ has an activity through which the calcification by human osteoblasts is accelerated, and suggested that this activity is derived from the action of $^{12}\Delta$-prostaglandin $J_2$, which is a decomposition product of the prostaglandin $D_2$.

SUMMARY OF THE INVENTION

An object of the present invention is to provide a novel 2,3-epoxycyclopentanone compound or a 2-substituted-2-cyclopentenone compound useful as a starting compound for producing the 2-substituted-2-cyclopentenone compound, that is, a 2-cyclopentenone compound having in its 2-position a group bonded to the skeleton through a sulfur atom, which is useful as an antitumor agent or a bone formation accelerator.

Other objects and advantages of the present invention will be apparent from the following description.

In accordance with the present invention, there is provided 2,3-epoxyclopentanones represented by the formula (IV):

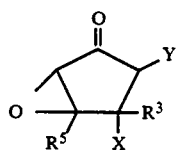

(IV)

wherein
- $R^3$ represents a substituted or unsubstituted (i) apliphatic hydrocarbon group having 1 to 10 carbon atoms, (ii) alicyclic hydrocarbon group having 4 to 10 carbon atoms, or (iii) aromatic hydrocarbon group having 6 lo 10 carbon atoms;
- $R^5$ represents a hydrogen atom, or a substituted or unsubstituted (i) aliphatic hydrocarbon group having 1 to 10 carbon atom or (ii) alicyclic hydrocarbon group having 4 to 10 carbon atoms;
- X represents a hydrogen atom or a group —$OR^4$ where $R^4$ is a hydrogen atom, an alkyl group having 1 to 4 carbon atoms, an acyl group having 2 to 7 carbon atoms, tri($C_1$-$C_7$) hydrocarbon silyl group, or a group capable of forming an acetal bond together with the oxygen atoms attached to the $R^4$; and
- Y represents a hydrogen atom or a group —CH(OH)—$R^2$ where $R^2$ is a substituted or unsubstituted (i) aliphatic hydrocarbon group having 1 to 10 carbon atoms, (ii) alicylic hydrocarbon group having 4 lo 10 carbon atoms, (iii) aromatic hydrocarbon group having 6 to 10 carbon atoms or (iv) heterocyclic group having 1 to 9 carbon atoms; with the proviso that, when X is a hydrogen atom Y is a group —CH(OH)—$R^2$ and that, when X is a group —$OR^4$, Y is a hydrogen atom.

In accordance with the present invention, there is also provided 2-substituted-2-cyclopentenones represented by the formula (I-C):

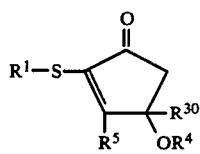

(I-C)

wherein
- $R^1$ represents a substituted or unsubstituted (i) aliphatic hydrocarbon group having 1 to 10 carbon atoms, (ii) alicyclic hydrocarbon group having 4 to 10 carbon atoms, (iii) aromatic hydrocarbon group having 6 to 10 carbon atoms, or (iv) heterocyclic group having 1 to 9 carbon atoms;
- $R^{30}$ represents a hydrogen atom or a substituted or unsubstituted (i) aliphatic hydrocarbon group having 1 to 10 carbon atoms, (ii) alicyclic hydrocarbon group having 4 to 10 carbon atoms or (iii) aromatic hydrocarbon group having 6 to 10 carton atoms;
- $R^4$ represents a hydrogen atom, an alkyl group having 1 to 4 carbon atoms, an acyl group having 2 to 7 carbom atoms, an alkoxycarbonyl group having 2 to 5 carbon atoms, a tri($C_1$-$C_7$) hydrocarbon silyl group or a group capable of forming an acetal bond together with the oxygen atom attached to the $R^4$; and
- $R^5$ represents a hydrogen atom or a substituted or unsubstituted (i) aliphatic hydrocarbon group having 1 to 10 carbon atoms or (ii) alicyclic hydrocarbon group having 4 to 10 carbon atoms; with the proviso that both $R^5$ and $R^{30}$ are not a hydrogen atom at the same time.

DESCRIPTION OF THE PREFERRED EMBODIMENT

2-Substituted-2-cyclopentenone compounds prepared from the cyclopentanone/cyclopentenone derivatives have the following formula (I):

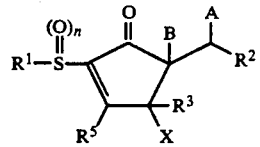

(I)

wherein
- $R^1$ stands for a substituted or unsubstituted (i) aliphatic hydrocarbon group having 1 to 10 carbon atoms, (ii) alicyclic hydrocarbon group having 4 to 10 carbon atoms, (iii) aromatic hydrocarbon group having 6 to 10 carbon atoms or (iv) heterocyclic group having 1 to 9 carbon atoms;
- $R^2$ stands for a substituted or unsubstituted (i) aliphatic hydrocarbon group having 1 to 10 carbon atoms, (ii) alicyclic hydrocarbon group having 4 to 10 carbon atoms, (iii) aromatic hydrocarbon group having 6 to 10 carbon atoms or (iv) heterocyclic group having 1 to 9 carbon atoms;
- $R^3$ stands for a hydrogen atom or a substituted or unsubstituted (i) aliphatic hydrocarbon group having 1 to 10 carbon atoms, (ii) alicyclic hydrocarbon group having 4 to 10 carbon atoms or (iii) aromatic hydrocarbon group having 6 to 10 carbon atoms;
- X stands for a hydrogen atom, or —$OR^4$ (wherein $R^4$ stands for a hydrogen atom, an alkyl group having 1 to 4 carbon atoms, an acyl group having 2 to 7 carbon atoms, an alkoxycarbonyl group having 2 to 5 carbon atoms, a tri($C_1$-$C_7$) hydrocarbon silyl group or a group capable of forming an acetal bond together with the oxygen atom attached to the $R^4$), provided that X is absent when $R^3$ is bonded to the carbon atom bonding thereto through a double bond;

$R^5$ stands for a hydrogen atom, or a substituted or unsubstituted (i) aliphatic hydrocarbon group having 1 to 10 carbon atoms or (ii) an alicyclic hydrocarbon group having 4 to 10 carbon atoms;

B stands for a hydrogen atom when A stands for a hydrogen atom, a hydroxyl group, an acyloxy group having 2 to 7 carbon atoms, an alkoxycarbonyloxy group having 2 to 5 carbon atoms, a sulfonyloxy group having 1 to 7 carbon atoms or

or A and B are combined with each other to form a bond line;

m and n, which may be the same or different from each other, stand for 0, 1 or 2.

In the above-described formula (I), regarding A and B stands for a hydrogen atom when A stands for a hydrogen atom, a hydroxyl group, an acyloxy group having 2 to 7 carbon atoms, an alkoxycarbonyloxy group having 2 to 5 carbon atoms, a sulfonyloxy group having 1 to 7 carbon atoms or

or A and B are combined with each other to form a bond line.

That is, when A stands for a hydrogen atom, a hydroxyl group, an acyloxy group having 2 to 7 carbon atoms, an alkoxycarbonyloxy group having 2 to 5 carbon atoms, or a sulfonyloxy group having 1 to 7 carbon atoms and B stands for a hydrogen atom, the above-described formula (I) represents 2-substituted-2-cyclopentenone compounds represented by the following formula (I-B'):

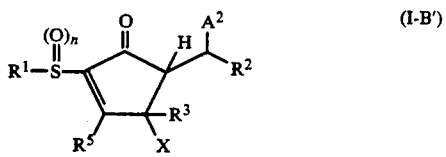

wherein
$R^1$, $R^2$, $R^3$, $R^5$, X and n are as defined above, and
$A^2$ stands for a hydrogen atom, a hydroxyl group, an acyloxy group having 2 to 7 carbon atoms, an alkoxycarbonyloxy group having 2 to 5 carbon atoms or a sulfonyloxy group having 1 to 7 carbon atoms;

When A stands for

and B stands for a hydrogen atom, the above-described formula (I) represents 2-substituted-2-cyclopentenone compounds represented by the following formula (I-B'')

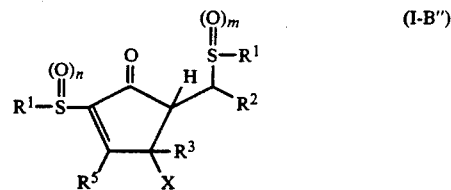

wherein $R^1$, $R^2$, $R^3$, $R^5$, X, m and n are as defined above; and when A and B are combined with each other to form a bond line, the above-described formula (I) represents 2-substituted-2-cyclopentenone compounds represented by the following formula (I-A):

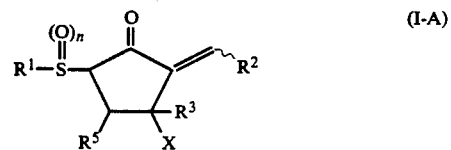

wherein $R^1$, $R^2$, $R^3$, $R^5$, X and n are as defined above and represents that the substituent attached to the double bond is in an E-configuration or a Z-configuration or a mixture thereof in any proportion, and further there are provided anticancer agents and bone formation accelerators comprising the above compounds as an active ingredient.

In the above-described formula (I), when A stands for an acyloxy group having 2 to 7 carbon atoms, examples of the acyloxy group having 2 to 7 carbon atoms include acetoxy, propionyloxy, isopropionyloxy, butyryloxy, isobutyryloxy, s-butyryloxy, valeryloxy, isovaleryloxy, hexanoyloxy, heptanoyloxy and benzoyloxy.

In the above-described formula (I), when A stands for an alkoxycarbonyloxy group having 2 to 5 carbon atoms, examples of the alkoxycarbonyloxy group having 2 to 5 carbon atoms include methoxycarbonyloxy, ethoxycarbonyloxy, propoxycarbonyloxy, isopropoxycarbonyloxy, butoxycarbonyloxy, isobutoxycarbonyloxy, s-butoxycarbonyloxy and t-butoxycarbonyloxy.

In the above-described formula (I), when A stands for a sulfonyloxy group having 1 to 7 carbon atoms, examples of the sulfonyloxy group having 1 to 7 carbon atoms include an alkylsulfonyloxy group having 1 to 4 carbon atoms which may be substituted with a halogen atom, a substituted or unsubstituted phenylsulfonyloxy group and a substituted or unsubstituted phenyl ($C_1$-$C_2$) alkylsulfonyloxy group.

Examples of the alkylsulfonyloxy group having 1 to 4 carbon atoms which may be substituted with a halogen atom include methanesulfonyloxy, ethanesulfonyloxy, butanesulfonyloxy, t-butanesulfonyloxy, chloromethanesulfonyloxy, dichloromethanesulfonyloxy, trifluoromethanesulfonyloxy and nonafluorobutanesulfonyloxy groups. Examples of the substituted or unsubstituted phenylsulfonyloxy group include benzenesulfonyloxy, p-bromobenzenesulfonyloxy and toluenesulfonyloxy groups. Examples of the substituted or unsubstituted phenyl ($C_1$-$C_2$) alkylsulfonyloxy group include benzylsulfonyloxy, α-phenetylsulfonyloxy and β-phenetylsulfonyloxy groups.

In the above-described formula (I), $R^1$ stands for a substituted or unsubstituted aliphatic hydrocarbon group having 1 to 10 carbon atoms, an alicyclic hydrocarbon group having 4 to 10 carbon atoms, an aromatic hydrocarbon group having 6 to 10 carbon atoms or a heterocyclic group having 1 to 9 carbon atoms.

Examples of the unsubstituted aliphatic hydrocarbon group having 1 to 10 carbon atoms in the $R^1$ include alkyl groups such as methyl, ethyl, propyl, isopropyl, butyl, isobutyl, s-butyl, t-butyl, pentyl, isopentyl, neopentyl, t-pentyl, hexyl, heptyl, octyl, 3,7-dimethyloctyl, nonyl and decyl groups; alkenyl groups such as 2-propenyl, 2-butenyl, 3-butenyl, 2-pentenyl, 4-pentenyl, 2-hexenyl, 3-hexenyl and 5-hexenyl; and alkynyl groups such as 2-propynyl, 2-butynyl, 2-pentynyl, 2-hexynyl and 3-hexynyl.

Examples of the unsubstituted alicyclic hydrocarbon groups having 4 to 10 carbon atoms in the $R^1$ include cyclobutyl, cyclopentyl, cyclohexyl, 3-cyclohexenyl, 4-cyclohexenyl, cycloheptyl, cyclooctyl and bicyclo[4.4.0]decan-2-yl groups.

Examples of the unsubstituted aromatic hydrocarbon group having 6 to 10 carbon groups in the $R^1$ include phenyl, 1-naphthyl and 2-naphthyl groups.

Examples of the unsubstituted heterocyclic group having 1 to 9 carbon atoms in the $R^1$ include monocyclic or bicyclic groups having an oxygen, nitrogen or sulfur atom, such as furyl, thienyl, pyrrolyl, oxazolyl, isooxazolyl, thiazolyl, isothiazolyl, imidazolyl, pyrazolyl, triazolyl, tetrazolyl, pyranyl, pyridyl, pyrazinyl, pyrimidinyl, benzofuranyl, indolyl, benzimidazolyl, benzothiazolyl, benzoxazolyl, quinolyl, isoquinolyl, quinazolyl, purinyl, pteridinyl, morpholinyl and piperidinyl groups.

$R^1$ may be a group comprising, attached to each other, any combination of the above-described aliphatic hydrocarbon group having 1 to 10 carbon atoms, alicyclic hydrocarbon group having 4 to 10 carbon atoms, aromatic hydrocarbon group having 6 to 10 carbon atoms and heterocyclic group having 1 to 9 carbon atoms. Among them, preferred examples of the $R^1$ include a substituted or unsubstituted ($r^1$—a) aliphatic hydrocarbon group having 1 to 10 carbon atoms which may be substituted with one or a plurality of alkoxy groups having 1 to 4 carbon atoms;

($r^1$—b) alicyclic hydrocarbon group having 4 to 10 carbon atoms which may be substituted with one or a plurality of alkyl groups having 1 to 4 carbon atoms or alkoxy groups having 1 to 4 carbon atoms;

($r^1$—c) aromatic hydrocarbon group having 6 to 10 carbon atoms which may be substituted with one or a plurality of alkyl groups having 1 to 4 carbon atoms or alkoxy groups having 1 to 4 carbon atoms;

($r^1$—d) heterocyclic group having 1 to 9 carbon atoms which may be substituted with one or a plurality of alkyl groups having 1 to 4 carbon atoms or alkoxy groups having 1 to 4 carbon atoms;

($r^1$—e) aliphatic hydrocarbon group having 1 to 10 carbon atoms substituted with an alicyclic hydrocarbon group having 4 to 10 carbon atoms and which may be substituted with one or a plurality of alkyl groups having 1 to 4 carbon atoms or alkoxy groups having 1 to 4 carbon atoms;

($r^1$—f) aliphatic hydrocarbon group having 1 to 10 carbon atoms substituted with an aromatic hydrocarbon group having 6 to 10 carbon atoms and which may be substituted with one or a plurality of alkyl groups having 1 to 4 carbon atoms or alkoxy groups having 1 to 4 carbon atoms; and ($r^1$—g) aliphatic hydrocarbon group having 1 to 10 carbon atoms substituted with a heterocyclic group having 1 to 9 carbon atoms and which may be substituted with one or a plurality of alkyl groups having 1 to 4 carbon atoms or alkoxy groups having 1 to 4 carbon atoms.

Preferred examples of the unsubstituted group ($r^1$—a) include methyl, ethyl, propyl, isopropyl, butyl, isobutyl, s-butyl, t-butyl, pentyl, hexyl, octyl, decyl, 2-propenyl and 4-pentenyl groups. Preferred examples of the unsubstituted group ($r^1$—b) include cyclopentyl, cyclohexyl, cyclooctyl, 3-methylcyclopentyl, 4-methylcyclohexyl, 4-butylcyclohexyl, 3,4-dimethylcyclohexyl and 4-methoxycyclohexyl groups. Preferred examples of the unsubstituted group ($r^1$—c) include phenyl, 1-naphthyl, 2-naphthyl, 2-methylphenyl, 3-methylphenyl, 4-methylphenyl, 2,4-dimethylphenyl, 3,5-dimethylphenyl, 4-ethylphenyl, 4-butylphenyl, 3-t-butylphenyl, 2-methoxyphenyl, 3-methoxyphenyl, 4-methoxyphenyl, 4-ethoxyphenyl, 6-methoxy-2-naphthyl, 7-methoxy-2-naphthyl and 6,7-dimethoxy-2-naphthyl groups. Preferred examples of the unsubstituted group ($r^1$—d) include 2-oxazolyl, 2-thiazolyl, 2-imidazolyl, 2-pyridyl, 4-pyridyl, 2-pyrimidinyl, 2-benzimidazolyl, 2-benzoxazolyl, 2-benzothiazolyl, 6-purinyl, 1-methylimidazol-2-yl, 4-methyl-1,2,4-triazol-3-yl, 1-methyl-5-tetrazolyl, 5-methyl-2-benzimidazolyl, 6-ethoxy-2-benzothiazolyl, 4-methyl-2-pyrimidinyl, 4,6-dimethyl-2-pyrimidinyl and 6-propyl-2-pyrimidinyl groups.

Preferred examples of the unsubstituted group ($r^1$—e) include cyclopentylmethyl, cyclohexylmethyl, 2-cyclohexylethyl, 2-cyclohexylpropyl, 3-cyclohexylpropyl, 4-cyclohexylbutyl, 1-cyclohexyl-1-methylethyl, (4-t-butylcyclohexyl)methyl and (4-methoxycyclohexyl)methyl groups. Preferred examples of the unsubstituted group ($r^1$—f) include benzyl, 2-phenylethyl, 3-phenylpropyl, 4-phenylbutyl, (1-naphthyl)methyl, (2-naphthyl)methyl, 2-(2-naphthyl)ethyl, (4-methylphenyl)methyl, (3-methylphenyl)methyl, (4-ethylphenyl)methyl, (4-butylphenyl)methyl, (4-methoxyphenyl)methyl, 2-(3,4-dimethoxyphenyl)ethyl and (6-methoxynaphthyl)methyl groups. Preferred examples of the unsubstituted group ($r^1$—g) include furfuryl and 3-(4-morpholinyl)propyl groups.

The above-described groups ($r^1$—a) to ($r^1$—g) may be substituted with a plurality of different groups, and examples of the substituent include (i) a halogen atom; (ii) an oxo group; (iii) a cyano group; (iv) a nitro group; (v) —COOR$^{61}$ (wherein R$^{61}$ stands for a hydrogen atom; one equivalent of cation; a residue of a saccharide; or an aliphatic hydrocarbon group having 1 to 10 carbon atoms which may be substituted with a halogen atom, an oxo group, a hydroxyl group, a tri($C_1$–$C_7$) hydrocarbon silyloxy group, an acyloxy group having 2 to 7 carbon atoms, an alkoxycarbonyloxy group having 2 to 5 carbon atoms, an alkoxy group having 1 to 4 carbon atoms, an alicyclic hydrocarbon group having 4 to 10 carbon atoms or an aromatic hydrocarbon group having 6 to 10 carbon atoms); (vi) —OR$^{71}$ (wherein R$^{71}$ stands for a hydrogen atom; an alkyl group having 1 to 4 carbon atoms; an acyl group having 2 to 7 carbon atoms; an alkoxycarbonyl group having 2 to 5 carbon atoms; a tri($C_1$–$C_7$) hydrocarbon silyl group; a group capable of forming an acetal bond together with the oxygen atom attached to the R$^{71}$; an aliphatic hydrocarbon group having 1 to 10 carbon atoms or an alicyclic hydrocarbon group having 4 to 10 carbon atoms which may be substituted with a halogen atom, an oxo group, a hydroxyl group, a carboxyl group, a tri($C_1$–$C_7$) hydrocarbon silyloxy group, an acyloxy group having 2 to 7 carbon atoms, an alkoxycarbonyloxy group having 2 to 5 carbon atoms, an alkoxy group having 1 to 4 carbon atoms, an alkoxycarbonyl group having 2 to 5 carbon atoms or an aromatic hydrocarbon group having 6 to 10 carbon atoms; or an aromatic hydrocarbon group having 6 to 10 carbon atoms which may be substituted with a halogen atom, a hydroxyl group, a nitro group, a tri($C_1$–$C_7$) hydrocarbon silyloxy group, an alkoxy group having 1 to 4 carbon atoms, an acyloxy group having 2 to 7 carbon atoms, an alkoxycarbonyloxy group having 2 to 5 carbon atoms, an acyl group having 2 to 7 carbon atoms, a carboxyl group, an alkoxycarbonyl group having 2 to 5 carbon atoms or an alkyl group having 1 to 4 carbon atoms); (vii) (wherein $R^{81}$ and $R^{810}$ which may be the same or different from each other stand for a hydrogen atom; an aliphatic hydrocarbon group having 1 to 10 carbon atoms or an alicyclic hydrocarbon group having 4 to 10 carbon atoms which may be substituted with a halogen atom, an oxo group, a hydroxyl group, a tri($C_1$–$C_7$) hydrocarbon silyloxy group, an acyloxy group having 2 to 7 carbon atoms, an alkoxycarbonyloxy group having 2 to 5 carbon atoms, an alkoxy group having 1 to 4 carbon atoms or an aromatic hydrocarbon group having 6 to 10 carbon atoms; an aromatic hydrocarbon group having 6 to 10 carbon atoms which may be substituted with a halogen atom, a hydroxyl group, a nitro group, a tri($C_1$–$C_7$) hydrocarbon silyloxy group, an acyloxy group having 2 to 7 carbon atoms, an alkoxycarbonyloxy group having 2 to 5 carbon atoms, an alkoxy group having 1 to 4 carbon atoms, an acyl group having 2 to 7 carbon atoms, a carboxyl group, an alkoxycarbonyl group having 2 to 5 carbon atoms or an alkyl group having 1 to 4 carbon atoms; or a group wherein 1 and $R^{810}$ are combined with each other to form a five- or six-membered ring); and (viii) —$NR^{91}R^{910}$ (wherein $R^{91}$ and $R^{910}$ which may be the same or different from each other stand for a hydrogen atom; an aliphatic hydrocarbon group having 1 to 10 carbon atoms or an alicyclic hydrocarbon group having 4 to 10 carbon atoms which may be substituted with a halogen atom, an oxo group, a hydroxyl group, a tri($C_1$–$C_7$) hydrocarbon silyloxy group, an acyloxy group having 2 to 7 carbon atoms, an alkoxycarbonyloxy group having 2 to 5 carbon atoms, an alkoxy group having 1 to 4 carbon atoms or an aromatic hydrocarbon group having 6 to 10 carbon atoms; an aromatic hydrocarbon group having 6 to 10 carbon atoms which may be substituted with a halogen atom, a hydroxyl group, a nitro group, a tri($C_1$–$C_7$) hydrocarbon silyloxy group, an acyloxy group having 2 to 7 carbon atoms, an alkoxycarbonyloxy group having 2 to 5 carbon atoms, an alkoxy group having 1 to 4 carbon atoms or an alkyl group having 1 to 4 carbon atoms; or a group wherein $R^{91}$ and $R^{910}$ are combined with each other to form a five- or six-membered ring).

Preferred examples of the halogen atom as the substituent (i) include fluorine, chlorine and bromine atoms.

Examples of the $R^{61}$ in the group represented by the formula —$COOR^{61}$ as the substituent (v) include a hydrogen atom; cations such as ammonium, tetramethylammonium, cyclohexylammonium, benzylammonium and phenetyl ammonium, a morpholinium cation, a piperidinium cation and one equivalent of cations such as $Na^+$, $K^+$, $\frac{1}{2}Ca^+$, $\frac{1}{2}Mg^{2+}$ and $\frac{1}{3}Al^{3+}$; residues of saccharides, for example, monosaccharides such as altrose, glucose, mannose, galactose, ribose, arabinose, xylose and fructose, or deoxy saccharides thereof; and aliphatic hydrocarbon groups having 1 to 10 carbon atoms, i.e., alkyl groups such as methyl, ethyl, propyl, isopropyl, butyl, isobutyl, s-butyl, t-butyl, pentyl, isopentyl, neopentyl, hexyl, octyl and decyl groups, alkenyl groups such as 2-propenyl, 2-butenyl, 2-pentenyl, 2-hexenyl and 5-hexenyl groups and alkynyl group such as 2-butynyl, 2-pentynyl and 3-hexynyl groups, which may be substituted with a halogen atom such as fluorine, chlorine or bromine, an oxy group, a hydroxyl group, a tri($C_1$–$C_7$) hydrocarbon silyloxy group such as a trimethylsilyloxy, triethylsilyloxy or t-butyldimethylsilyloxy group, an acyloxy group having 2 to 7 carbon atoms such as an acetoxy, propionyloxy, a butyryloxy, isobutyryloxy, valeryloxy or benzoyloxy group, an alkoxycarbonyloxy group having 2 to 5 carbon atoms such as a methoxycarbonyloxy, ethoxycarbonyloxy, propoxycarbonyloxy, isopropoxycarbonyloxy or butoxycarbonyloxy group, an alkoxy group having 1 to 4 carbon atoms such as a methoxy, ethoxy, propoxy, isopropoxy, butoxy, isobutoxy, s-butoxy or t-butoxy group an alicyclic hydrocarbon group having 4 to 10 carbon atoms such as a cyclobutyl, cyclopentyl or cyclohexyl group, or an aromatic hydrocarbon group having 6 to 10 carbon atoms such as a phenyl, 1-naphthyl or 2-naphthyl group.

Examples of the $R^{71}$ in the group represented by the formula —$OR^{71}$ as the substituent (iv) include a hydrogen atom; alkyl groups having 1 to 4 carbon atoms such as methyl, ethyl, propyl, isopropyl, butyl, isobutyl, s-butyl and t-butyl groups; acyl groups having 2 to 7 carbon atoms such as acetyl, propionyl, butyryl, isobutyryl, valeryl, isovaleryl, hexanoyl, heptanoyl and benzoyl groups; alkoxycarbonyl groups having 2 to 5 carbon atoms such as methoxycarbonyl, ethoxycarbonyl, propoxycarbonyl, isopropoxycarbonyl, butoxycarbonyl, isobutoxycarbonyl and t-butoxycarbonyl groups; tri($C_1$–$C_7$) hydrocarbon silyl groups such as trimethylsilyl, triethylsilyl, t-butyldimethylsilyl, t-butyldiphenylsilyl and tribenzylsilyl groups; a group capable of forming acetal bond together with the oxygen atom attached to the $R^{71}$, such as a methoxymethyl, 1-ethoxyethyl, 1-methoxy-1-methylethyl, 2-ethoxy-1-methylethyl, 2-methoxyethoxymethyl, tetrahydropyran-2-yl or tetrahydrofuran-2-yl, is attached; aliphatic hydrocarbon groups having 1 to 10 carbon atoms, i.e., alkyl groups such as methyl, ethyl, propyl, isopropyl, butyl, s-butyl, t-butyl, pentyl, isopentyl, neopentyl, t-pentyl, hexyl, heptyl, octyl, nonyl and decyl groups, alkenyl groups such as 2-propenyl, 2-butenyl, 3-butenyl and 3-hexenyl groups and alkynyl groups such as 2-propynyl, 2-butynyl and 3-hexynyl groups, or alicyclic hydrocarbon groups having 4 to 10 carbon atoms such as cyclobutyl, cyclopentyl, cyclohexyl, 3-cyclohexenyl, 4-cyclohexenyl, cyclooctyl and bicyclo[4.4.0]decan-2-yl groups, which may be substituted with a halogen atom such as fluorine, chlorine or bromine, an oxo group, a hydroxyl group, a carboxyl group, a tri($C_1$–$C_7$) hydrocarbon silyloxy group such as a trimethylsilyloxy, triethylsilyloxy or t-butyldimethylsilyloxy group, an acyloxy group having 2 to 7 carbon atoms such as an acetoxy, propionyloxy, butyryloxy, isobutyryloxy, valeryloxy, isovaleryloxy or benzoyloxy group, an alkoxycarbonyloxy group having 2 to 5 carbon atoms such as a methoxycarbonyloxy, ethoxycarbonyloxy, propoxycarbonyloxy, isopropoxycarbonyloxy or butoxycarbonyloxy group, an alkoxy group having 1 to 4 carbon atoms such as a methoxy, ethoxy propoxy, isopropoxy, butoxy, isobutoxy or t-butoxy group, an alkoxycarbonyl group having 2 to 5 carbon atoms such as a methoxycarbonyl, ethoxycarbonyl, isobutoxycarbonyl or t-butoxycarbonyl group, or an aromatic hydrocarbon group having 6 to 10 carbon atoms such as a phenyl, 1-naphthyl or 2-naphthyl group; and aromatic hydrocarbon groups having 6 to 10 carbon atoms such as phenyl, 1-naphthyl and 2-naphthyl groups, which may be substituted with a halogen atom such as fluorine, chlorine or bromine, an oxo group, a hydroxyl group, a nitro group, a tri($C_1$–$C_7$) hydrocarbon silyloxy group such as a trimethylsilyloxy, triethylsilyloxy or t-butyldimethylsilyloxy group, an alkoxy group having 1 to 4 carbon atoms such as a methoxy, ethoxy, propoxy, isopropoxy, butoxy, isobutoxy, s-butoxy or t-butoxy group, an acyloxy group having 2 to 7 carbon atoms such as an acetoxy, propionyloxy, butyryloxy, isobutyryloxy, valeryloxy, hexanoyloxy or benzoyloxy group, an alkoxycarbonyloxy group having 2 to 5 carbon atoms such as a methoxycarbonyloxy, ethoxycarbonyloxy, propoxycarbonyloxy, isopropoxycarbonyloxy, butoxycarbonyloxy group or t-butoxycarbonyloxy group, an acyl group having 2 to 7 carbon atoms such as an acetyl, propionyl, butyryl, isobutyryl, valeryl, hexanoyl, heptanoyl or benzoyl group, a carboxyl group, an alkoxycarbonyl group having 2 to 5 carbon atoms such as a methoxycarbonyl, ethoxycarbonyl, propoxycarbonyl, isopropoxycarbonyl, butoxycarbonyl, isobutoxycarbonyl or t-butoxycarbonyl group, or an alkyl group such as a methyl, ethyl, propyl, isopropyl, butyl, isobutyl, s-butyl or t-butyl group.

Examples of the $R^{81}$ and $R^{810}$ in the group represented by the formula —$CONR^{81}R^{810}$ as the substituent (vii) include a hydrogen atom; aliphatic hydrocarbon groups having 1 to 10 carbon atoms, i.e., alkyl groups such as methyl, ethyl, propyl, isopropyl, butyl, isobutyl, s-butyl, t-butyl, pentyl, isopentyl, neopentyl, t-pentyl, hexyl, heptyl, octyl, nonyl and decyl groups, alkenyl groups such as 2-propenyl, 2-butenyl, 2-pentenyl and 3-hexenyl groups and alkynyl groups such as 2-propynyl, 2-butynyl, 2-pentynyl and 3-hexynyl groups, or alicyclic hydrocarbon groups having 4 to 10 carbon atoms such as cyclobutyl, cyclopentyl, cyclohexyl, cyclooctyl and bicyclo[4.4.0]decan-2-yl groups, which may be substituted with a halogen atom such as fluorine, chlorine or bromine, an oxo group, a hydroxyl group, a tri($C_1$–$C_7$) hydrocarbon silyloxy group such as a trimethylsilyloxy, triethylsilyloxy or t-butyldimethylsilyloxy group, an acyloxy group having 2 to 7 carbon atoms such as an acetoxy, propionyloxy, butyryloxy, isobutyryloxy, valeryloxy, hexanoyloxy or benzoyloxy group, an alkoxycarbonyloxy group having 2 to 5 carbon atoms such as a methoxycarbonyloxy, ethoxycarbonyloxy, propoxycarbonyloxy, isopropoxycarbonyloxy, butoxycarbonyloxy group or t-butoxycarbonyloxy group, an alkoxy group having 1 to 4 carbon atoms such as a methoxy, ethoxy, propoxy, isopropoxy, butoxy, isobutoxy, s-butoxy or t-butoxy group, or an aromatic hydrocarbon group having 6 to 10 carbon atoms such as a phenyl, 1-naphthyl or 2-naphthyl group; aromatic hydrocarbon groups having 6 to 10 carbon atoms such as phenyl, 1-naphthyl and 2-naphthyl groups, which may be substituted with a halogen atom such as fluorine, chlorine or bromine, a hydroxyl group, a nitro group, a tri($C_1$–$C_7$) hydrocarbon silyloxy group such as a trimethylsilyloxy, triethylsilyloxy or t-butyldimethylsilyloxy group, an acyloxy group having 2 to 7 carbon atoms such as an acetoxy, propionyloxy, butyryloxy, isobutyryloxy, valeryloxy, hexanoyloxy or benzoyloxy group, an alkoxycarbonyloxy group having 2 to 5 carbon atoms such as a methoxycarbonyloxy, ethoxycarbonyloxy, propoxycarbonyloxy, isopropoxycarbonyloxy, butoxycarbonyloxy group or t-butoxycarbonyloxy group, an alkoxy group having 1 to 4 carbon atoms such as a methoxy, ethoxy, propoxy, isopropoxy, butoxy, isobutoxy, s-butoxy or t-butoxy group, an acyl group having 2 to 7 carbon atoms such as an acetyl, propionyl, butyryl, isobutyryl, valeryl, hexanoyl or benzoyl group, a carboxyl group, an alkoxycarbonyl group having 2 to 5 carbon atoms such as a methoxycarbonyl, ethoxycarbonyl, propoxycarbonyl, isopropoxycarbonyl, butoxycarbonyl, isobutoxycarbonyl or t-butoxycarbonyl group, or an alkyl group having 1 to 4 carbon atoms such as a methyl, ethyl, propyl, isopropyl, butyl, isobutyl, s-butyl or t-butyl group; or a group wherein the $R^{81}$ and $R^{810}$ are combined with each other to form a five- or six-membered ring together with a nitrogen atom intervening between the $R^{81}$ and the $R^{810}$, for example, 1-pyrrolidinyl, 1-piperidinyl, 1-imidazolidinyl, 1-piperazinyl, 4-morpholinyl and 2-thioxo-3-thiazolidinyl groups, which may be substituted with an alkoxy group having 1 to 4 carbon atoms such as methoxy, ethoxy, propoxy, isopropoxy, butoxy, isobutoxy, s-butoxy or t-butoxy group, or an alkyl group having 1 to 4 carbon atoms such as a methyl, ethyl, propyl, isopropyl, butyl, isobutyl, s-butyl or t-butyl group.

Examples of the $R^{91}$ and in the group represented by the formula —$NR^{91}R^{910}$ as the substituent (viii) include a hydrogen atom; aliphatic hydrocarbon groups having 1 to 10 carbon atoms, i.e., alkyl groups such as methyl, ethyl, propyl, isopropyl, butyl, isobutyl, s-butyl, t-butyl, pentyl, isopentyl, neopentyl, hexyl, octyl and decyl groups, alkenyl groups such as 2-propenyl, 2-butenyl, 2-pentenyl, 2-hexenyl and 5-hexenyl groups and alkynyl groups such as 2-butynyl, 2-pentynyl and 3-hexynyl groups, or alicyclic hydrocarbon groups having 4 to 10 carbon atoms such as cyclobutyl, cyclopentyl, cyclohexyl, cycloheptyl, cyclooctyl and bicyclo[4.4.0]decan-2-yl groups, which may be substituted with a halogen atom such as fluorine, chlorine or bromine, an oxo group, a hydroxyl group, a tri($C_1$–$C_7$) hydrocarbon silyloxy group such as a trimethylsilyloxy, triethylsilyloxy or t-butyldimethylsilyloxy group, an acyloxy group having 2 to 7 carbon atoms such as an acetoxy, propionyloxy, butyryloxy, isobutyryloxy, valeryloxy, hexanoyloxy or benzoyloxy group, an alkoxycarbonyloxy group having 2 to 5 carbon atoms such as a methoxycarbonyloxy, ethoxycarbonyloxy, propoxycarbonyloxy, isopropoxycarbonyloxy, butoxycarbonyloxy or t-butoxycarbonyloxy group, an alkoxy group having 1 to 4 carbon atoms such as a methoxy, ethoxy, propoxy, isopropoxy, butoxy, s-butoxy or t-butoxy group, or an aromatic hydrocarbon group having 6 to 10 carbon atoms such as a phenyl, 1-naphthyl or 2-naphthyl group; aromatic hydrocarbon groups having 6 to 10 carbon atoms such as phenyl, 1-naphthyl and 2-naphthyl groups, which may be substituted with a halogen atom such as fluorine, chlorine or bromine, a hydroxyl group, a nitro group, a tri($C_1$–$C_7$) hydrocarbon silyloxy group such as a trimethylsilyloxy, triethylsilyloxy or t-butyldimethylsilyloxy group, an acyloxy group having 2 to 7 carbon atoms such as an acetoxy, propionyloxy, butyryloxy, isobutyryloxy, valeryloxy, hexanoyloxy or benzoyloxy group, an alkoxycarbonyloxy group having 2 to 5 carbon atoms such as a methoxycarbonyloxy, ethoxycarbonyloxy, propoxycarbonyloxy, isopropoxycarbonyloxy or butoxycarbonyloxy group, an alkoxy group having 1 to 4 carbon atoms such as a methoxy, ethoxy, propoxy, isopropoxy, butoxy, isobutoxy or t-butoxy group, or an alkyl group such as a methyl, ethyl, propyl, isopropyl, butyl, isobutyl, s-butyl or t-butyl group; or a group wherein the $R^{91}$ and $R^{910}$ are combined with each other to form a five- or six-membered ring together with a nitrogen atom intervening between the $R^{91}$ and the $R^{910}$, for example, 1-pyrrolidinyl, 1-piperidinyl, 1-imidazolidinyl, 1-piperazinyl, 4-morpholinyl and 2-thioxo-3-thiazolidinyl groups, which may be substituted with an alkoxy group having 1 to 4 carbon atoms, such as methoxy, ethoxy, propoxy, isopropoxy, butoxy, isobutoxy or t-butoxy group, or an alkyl group having 1 to 4 carbon atoms such as a methyl, ethyl, propyl, isopropyl, butyl, isobutyl or t-butyl group.

Preferred examples of the $R^1$ include methyl, ethyl, propyl, 2-propenyl, isopropyl, butyl, isobutyl, s-butyl, t-butyl, hexyl, octyl, 2,3-dihydroxypropyl, 2,3-diacetoxypropyl, 3,4-dimethoxyphenylpropyl, 4-phenoxybutyl, carboxymethyl, methoxycarbonylmethyl, ethoxycarbonylmethyl, 2-carboxyethyl, 5-carboxypentyl, 5-methoxycarbonylpentyl, 5-butoxycarbonylpentyl, 5-decyloxycarbonylpentyl, 5-carboxy-4-pentenyl, 5-methoxycarbonyl-4-pentenyl, 5-methoxycarbonyl-5,5-difluoropentyl, 5-(2-thioxo-3-thiazolidinylcarbonyl)-pentyl, 5-(6-D-glucosylcarbonyl)pentyl, 5-(1-D-xylosylcarbonyl)pentyl, 5-(5-D-ribosylcarbonyl)pentyl, 2-(butylamino)ethyl, 2-(4-fluorophenylamino)ethyl, 2-(2-phenylethylamino)ethyl, cyclohexyl, phenyl, 3-methylphenyl, 4-methylphenyl, 3-methoxyphenyl, 4-methoxyphenyl, 4-fluorophenyl, 4-chlorophenyl, 4-bromophenyl, 2,5-dichlorophenyl, 4-bromo-3-methylphenyl, 2,3,5,6-tetrafluorophenyl, 2,4,5-trichlorophenyl, 3-aminophenyl, 4-aminophenyl, 4-nitrophenyl, 2-pyridinyl, 4-pyridinyl, 3-hydroxy-2-pyridinyl, 4-hydroxy-2-pyrimidinyl, 4,6-dimethyl-2-pyrimidinyl, 4,6-dichloro-2-pyrimidinyl, 4-hydroxy-6-propyl-2-pyrimidinyl, 4,5-diamino-2-pyrimidinyl, 4,6-diamino-2-pyrimidinyl, 4-amino-6-hydroxy-2-pyrimidinyl, 1-methyl-2-imidazolyl, 4-methyl-1,2,4-triazole-3-yl, 1-methyl-5-tetrazolyl, 2-benzimidazolyl, 2-benzoxazolyl, 2-benzothiazolyl, 5-chloro-2-benzothiazolyl, 6-ethoxy-2-benzothiazolyl, 2-quinolinyl, 4-hydroxy-pteridinyl, 6-hydroxy-8-purinyl, 6-purinyl, 4-pyrazolo[3,4-d]pyrimidinyl, 2-amino-6-purinyl, 6-hydroxy-2-purinyl, 2-hydroxy-6-purinyl, 3-cyclohexylpropyl, benzyl, (2-chlorophenyl)methyl, (4-chlorophenyl)methyl, 2-(3,4-dichlorophenyl)ethyl, (3-fluorophenyl)methyl, (4-methoxyphenyl)methyl, (3-trifluoromethylphenyl)-methyl and 3-phenylpropyl, 2-furanylmethyl, 3-(4-morpholinyl)propyl.

In the above-described formula (I), the $R^2$ stands for a substituted or unsubstituted aliphatic hydrocarbon group having 1 to 10 carbon atoms, alicyclic hydrocarbon group having 4 to 10 carbon atoms, aromatic hydrocarbon having 6 to 10 carbon atoms or heterocyclic group having 1 to 9 carbon atoms. Examples of the unsubstituted aliphatic hydrocarbon group having 1 to 10 carbon atoms in the $R^2$ include alkyl groups such as methyl, ethyl, propyl, isopropyl, butyl, isobutyl, s-butyl, t-butyl, pentyl, isopentyl, neopentyl, 4-methylpentyl, hexyl, heptyl, octyl, 3,7-dimethyloctyl-, nonyl and decyl groups; alkenyl groups such as vinyl, 1-methylvinyl, 1-ethylvinyl, 1-propenyl, 2-propenyl, 2-methyl-1-propenyl, 1-butenyl, 2-butenyl, 2-methyl-1-butenyl, 1,3-butadienyl, 1-pentenyl, 2-pentenyl, 4-methyl-1-pentenyl, 1-hexenyl, 2-hexenyl, 3-hexenyl, 5-hexenyl, 1,5-hexadienyl, 1-heptenyl, 1-octenyl, 6-methyl-1-heptenyl, 1-nonenyl and 1-decenyl groups; and alkynyl groups such as ethynyl, 1-propynyl, 2-propynyl, 1-butynyl, 3-methyl-1-butynyl, 3,3-dimethyl-1-butynyl, 1-pentynyl, 2-pentynyl, 1-hexynyl, 2-hexynyl, 5-hexen-1-yl, 1-heptynyl, 1-nonynyl and 1-decynyl groups.

Examples of the unsubstituted alicyclic hydrocarbon group having 4 to 10 carbon atoms in the $R^2$ include cyclobutyl, cyclopentyl, cyclohexyl, 1-cyclohexenyl, 3-cyclohexenyl, 4-cyclohexenyl, cycloheptyl, cyclooctyl and bicyclo[4.4.0]decan-2-yl. Examples of the unsubstituted aromatic hydrocarbon group having 6 to 10 carbon atoms in the $R^2$ include phenyl, 1-naphthyl and 2-naphthyl groups. Examples of the unsubstituted heterocyclic hydrocarbon group having 1 to 9 carbon atoms in the $R^2$ include monocyclic or bicyclic groups having an oxygen, nitrogen or sulfur atom, such as furyl, thienyl, pyrolyl, oxazolyl, isooxazolyl, thiazolyl, isothiazolyl, imidazolyl, pyrazolyl, triazolyl, tetrazolyl, pyranyl, pyridyl, pyrazinyl, pyrimidinyl, benzofuranyl, indolyl, benzimidazolyl, benzothiazolyl, benzoxazolyl, quinolyl, isoquinolyl, quinazolyl, purinyl, pteridinyl, morpholinyl and piperidinyl groups.

The $R^2$ may be a group comprising, attached to each other, any combination of the above-described aliphatic hydrocarbon group having 1 to 10 carbon atoms, alicyclic hydrocarbon group having 4 to 10 carbon atoms, aromatic hydrocarbon group having 6 to 10 carbon atoms and heterocyclic group having 1 to 9 carbon atoms. Among them, preferred examples of the $R^2$ include a substituted or unsubstituted (r2—a) aliphatic hydrocarbon group having 1 to 10 carbon atoms which may be substituted with one or a plurality of alkoxy groups having 1 to 4 carbon atoms;

(r2—b) alicyclic hydrocarbon group having 4 to 10 carbon atoms which may be substituted with one or a plurality of alkyl groups having 1 to 4 carbon atoms or alkoxy groups having 1 to 4 carbon atoms;

(r2—c) aromatic hydrocarbon group having 6 to 10 carbon atoms which may be substituted with one or a plurality of alkyl groups having 1 to 4 carbon atoms or alkoxy groups having 1 to 4 carbon atoms;

(r2—d) heterocyclic group having 1 to 9 carbon atoms which may be substituted with one or a plurality of alkyl groups having 1 to 4 carbon atoms or alkoxy groups having 1 to 4 carbon atoms;

(r2—e) aliphatic hydrocarbon group having 1 to 10 carbon atoms substituted with an alicyclic hydrocarbon group having 4 to 10 carbon atoms and which may be substituted with one or a plurality of alkyl groups having 1 to 4 carbon atoms or alkoxy groups having 1 to 4 carbon atoms;

(r2—f) aliphatic hydrocarbon group having 1 to 10 carbon atoms substituted with an aromatic hydrocarbon group having 6 to 10 carbon atoms and which may be substituted with one or a plurality of alkyl groups having 1 to 4 carbon atoms or alkoxy groups having 1 to 4 carbon atoms; and (r2—g) aliphatic hydrocarbon group having 1 to 10 carbon atoms substituted with a heterocyclic group having 1 to 9 carbon atoms and which may be substituted with one or a plurality of alkyl groups having 1 to 4 carbon atoms or alkoxy groups having 1 to 4 carbon atoms.

Preferred examples of the unsubstituted group ($r^2$—a) include methyl, ethyl, propyl, isopropyl, butyl, isobutyl, s-butyl, pentyl, hexyl, octyl, nonyl, decyl, vinyl, 1-propenyl, 1-pentenyl, 4-pentenyl, 6-methyl-1-heptenyl, ethynyl, 1-propynyl, 1-pentynyl, 3-methoxypropyl and 1-(2-methoxyethyl)vinyl groups. Preferred examples of the unsubstituted group ($r^2$—b) include cyclopentyl, cyclohexyl, cyclooctyl, 3-methylcyclopentyl, 4-methylcyclohexyl, 4-butylcyclohexyl, 3,4-dimethylcyclohexyl and 4-methoxycyclohexyl groups. Preferred examples of the unsubstituted group ($r^2$—c) include phenyl, 1-naphthyl, 2-methylphenyl, 3-methylphenyl, 4-methylphenyl, 2,4-dimethylphenyl, 3,5-dimethylphenyl, 4-ethylphenyl, 4-isobutylphenyl, 3-t-butylphenyl, 2-methoxyphenyl, 3-methoxyphenyl, 4-methoxyphenyl, 4-ethoxyphenyl, 6-methoxy-2-naphthyl, 7-methoxy-2-naphthyl and 6,7-dimethoxy-2-naphthyl groups. Preferred examples of the unsubstituted group ($r^2$—d) include 2-oxazolyl, 2-thiazolyl, 2-imidazolyl, 2-pyridyl, 4-pyridyl, 2-pyrimidinyl, 2-benzimidazolyl, 2-benzoxazolyl, 2-benzothiazolyl, 6-purinyl, 1-methylimidazol-2-yl, 4-methyl-1,2,4-triazol-3-yl, 1-methyl-5-tetrazolyl, 5-methyl-2-benzimidazolyl, 4-methyl-2-pyrimidinyl and 6-propyl-2-pyrimidinyl groups.

Preferred examples of the unsubstituted group ($r^2$—e) include cyclopentylmethyl, cyclohexylmethyl, 2-cyclohexylmethyl, 2-cyclohexylpropyl, 3-cyclohexylpropyl, 4-cyclohexylbutyl, (4-t-butylcyclohexyl)methyl and (4-methoxycyclohexyl)methyl groups. Preferred examples of the unsubstituted group ($r^2$—f) include benzyl, 2-phenylethyl, 3-phenylpropyl, 4-phenylbutyl, (1-naphthyl)methyl, (2-naphthyl)methyl, 2-phenylvinyl, 2-phenyl-1-propenyl, (4-methylphenyl)methyl, (3-methylphenyl)methyl, (4-ethylphenyl)methyl, (4-butylphenyl)methyl, (4-methoxyphenyl)methyl and 2-(3,4-dimethoxyphenyl)ethyl groups. Preferred examples of the unsubstituted group ($r^2$—g) include furfuryl and 3-(4-morpholinyl)propyl groups.

The above-described groups ($r^2$—a) to ($r^2$—g) may be substituted with a plurality of different groups, and examples of the substituent include (i) a halogen atom; (ii) an oxo group; (iii) a cyano group; (iv) a nitro group; (v) —COOR$^{62}$ (wherein R$^{62}$ stands for a hydrogen atom; one equivalent of cation; a residue of a saccharide; or an aliphatic hydrocarbon group having 1 to 10 carbon atoms which may be substituted with a halogen atom, an oxo group, a hydroxyl group, a nitro group, a tri($C_1$–$C_7$) hydrocarbon silyloxy group, an acyloxy group having 2 to 7 carbon atoms, an alkoxycarbonyloxy group having 2 to 5 carbon atoms, an alkoxy group having 1 to 4 carbon atoms, an alicyclic hydrocarbon group having 4 to 10 carbon atoms or an aromatic hydrocarbon group having 6 to 10 carbon atoms); (vi) —OR$^{72}$ (wherein R$^{72}$ stands for a hydrogen atom; an alkyl group having 1 to 4 carbon atoms; an acyl group having 2 to 7 carbon atoms; an alkoxycarbonyl group having 2 to 5 carbon atoms; a tri($C_1$–$C_7$) hydrocarbon silyl group; a group capable of forming an acetal bond together with the oxygen atom attached to the R$^{72}$; an aliphatic hydrocarbon group having 1 to 10 carbon atoms or an alicyclic hydrocarbon group having 4 to 10 carbon atoms which may be substituted with a halogen atom, an oxo group, a hydroxyl group, a carboxyl group, a tri($C_1$–$C_7$) hydrocarbon silyloxy group, an acyloxy group having 2 to 7 carbon atoms, an alkoxycarbonyloxy group having 2 to 5 carbon atoms, an alkoxy group having 1 to 4 carbon atoms, an alkoxycarbonyl group having 2 to 5 carbon atoms or an aromatic hydrocarbon group having 6 to 10 carbon atoms; or an aromatic hydrocarbon group having 6 to 10 carbon atoms which may be substituted with a halogen atom, hydroxyl group, a nitro group, a tri($C_1$–$C_7$) hydrocarbon silyloxy group, an alkoxycarbonyloxy group having 2 to 5 carbon atoms, an acyl group having 2 to 7 carbon atoms, a carboxyl group, an alkoxycarbonyl group having 2 to 5 carbon atoms or an alkyl group having 1 to 4 carbon atoms); (vii) —CONR$^{82}$R$^{820}$ (wherein R$^{82}$ and R$^{820}$ which may be the same or different from each other stand for a hydrogen atom; an aliphatic hydrocarbon group having 1 to 10 carbon atoms or an alicyclic hydrocarbon group having 4 to 10 carbon atoms which may be substituted with a halogen atom, an oxo group, a hydroxyl group, a tri($C_1$–$C_7$) hydrocarbon silyloxy group, an acyloxy group having 2 to 7 carbon atoms, an alkoxycarbonyloxy group having 2 to 5 carbon atoms, an alkoxy group having 1 to 4 carbon atoms or an aromatic hydrocarbon group having 6 to 10 carbon atoms; an aromatic hydrocarbon group having 6 to 10 carbon atoms which may be substituted with a halogen atom, a hydroxyl group, a nitro group, a tri($C_1$–$C_7$) hydrocarbon silyloxy group, an acyloxy group having 2 to 7 carbon atoms, an alkoxycarbonyloxy group having 2 to 5 carbon atoms, an alkoxy group having 1 to 4 carbon atoms, an acyl group having 2 to 7 carbon atoms, a carboxyl group, an alkoxycarbonyl group having 2 to 5 carbon atoms or an alkyl group having 1 to 4 carbon atoms; or a group wherein the R$^{82}$ and R$^{820}$ are combined with each other to form a five- or six-membered ring); (viii) —NR$^{92}$R$^{920}$ (wherein R$^{92}$ and R$^{920}$ which may be the same or different from each other stand for a hydrogen atom; an aliphatic hydrocarbon group having 1 to 10 carbon atoms or an alicyclic hydrocarbon group having 4 to 10 carbon atoms which may be substituted with a halogen atom, an oxo group, a hydroxyl group, a tri($C_1$–$C_7$) hydrocarbon silyloxy group, an acyloxy group having 2 to 7 carbon atoms, an alkoxycarbonyloxy group having 2 to 5 carbon atoms, an alkoxy group having 1 to 4 carbon atoms or an aromatic hydrocarbon group having 6 to 10 carbon atoms; an aromatic hydrocarbon group having 6 to 10 carbon atoms which may be substituted with a halogen atom, a hydroxyl group, a nitro group, a tri($C_1$–$C_7$) hydrocarbon silyloxy group, an acyloxy group having 2 to 7 carbon atoms, an alkoxycarbonyl group having 2 to 5 carbon atoms, an alkoxy group having 1 to 4 carbon atoms, an acyl group having 2 to 7 carbon atoms, a carboxyl group, an alkoxycarbonyl group having 2 to 5 carbon atoms or an alkyl group having 1 to 4 carbon atoms; or a group wherein the R$^{92}$ and R$^{920}$ are combined with each other to form a five- or six-membered ring); and (ix) —SR$^{76}$ (wherein R$^{76}$ stands for an aliphatic hydrocarbon group having 1 to 10 carbon atoms or an alicyclic hydrocarbon group having 4 to 10 carbon atoms which may be substituted with a halogen atom, an oxo group, a hydroxyl group, a carboxyl group, a tri($C_1$–$C_7$) hydrocarbon silyloxy group, an acyloxy group having 2 to 7 carbon atoms, an alkoxycarbonyloxy group having 2 to 5 carbon atoms, an alkoxy group having 1 to 4 carbon atoms, an alkylcarbonyl group having 2 to 5 carbon atoms or an aromatic hydrocarbon group having 6 to 10 carbon atoms; an aromatic hydrocarbon group having 6 to 10 carbon atoms which may be substituted with a halogen atom, a hydroxyl group, a tri($C_1$–$C_7$) hydrocarbon silyloxy group, a nitro group, an acyloxy group having 2 to 7 carbon atoms, an alkoxycarbonyl group having 2 to 5 carbon atoms, an alkoxy group having 1 to 4 carbon atoms, an acyl group having 2 to 7 carbon atoms, a carboxyl group, an alkoxycarbonyl group having 2 to 5 carbon atoms or an alkyl group having 1 to 4 carbon atoms.

Examples of the substituents (i) to (viii) of the groups ($r^2$—a) to ($r^2$—g) include the same substituents as those of the groups ($r^1$—a) to ($r^1$—g) described above in connection with the $R^1$. Examples of the —$SR^{76}$ in the substituent (ix) of the groups ($r^2$—a) to ($r^2$—g) include aliphatic hydrocarbon groups having 1 to 10 carbon atoms, i.e., alkyl groups such as methyl, ethyl, propyl, isopropyl, butyl, isobutyl, s-butyl, t-butyl, pentyl, isopentyl, neopentyl, t-pentyl, hexyl, heptyl, octyl and decyl groups, alkenyl groups such as 2-propenyl, 2-butenyl, 3-hexenyl and 5-hexenyl groups and alkynyl groups such as 2-propynyl, 2-butynyl and 3-hexynyl groups, or alicyclic hydrocarbon groups having 4 to 10 carbon atoms such as cyclobutyl, cyclopentyl, cyclohexyl and bicyclo[4.4.0]decan-2-yl groups, which may be substituted with a halogen atom such as fluorine, chlorine or bromine, an oxo group, a hydroxyl group, a carboxyl group, a tri($C_1$-$C_7$) hydrocarbon silyloxy group such as a trimethylsilyloxy, triethylsilyloxy, t-butyldimethylsilyloxy or t-butyldiphenylsilyloxy group, an acyloxy group having 2 to 7 carbon atoms such as an acetoxy, propionyloxy, butyryloxy, isobutyryloxy, valeryloxy, hexanoyloxy or benzoyloxy group, an alkoxycarbonyloxy group having 2 to 5 carbon atoms such as a methoxycarbonyloxy, ethoxycarbonyloxy, propoxycarbonyloxy, isopropoxycarbonyloxy, butoxycarbonyloxy group or t-butoxycarbonyloxy group, an alkoxy group having 1 to 4 carbon atoms such as a methoxy, ethoxy, propoxy, isopropoxy, butoxy, isobutoxy, or t-butoxy group, an alkoxycarbonyl group having 2 to 5 carbon atoms such as a methoxycarbonyl, ethoxycarbonyl, propoxycarbonyl, isopropoxycarbonyl, butoxycarbonyl or t-butoxycarbonyl group, or an aromatic hydrocarbon group having 6 to 10 carbon atoms such as a phenyl, 1-naphthyl or 2-naphthyl group; and aromatic hydrocarbon groups having 6 to 10 carbon atoms such as phenyl, 1-naphthyl and 2-naphthyl groups, which may be substituted with a halogen atom such as fluorine, chlorine or bromine, a hydroxyl group, a tri($C_1$-$C_7$) hydrocarbon silyloxy group such as a trimethylsilyloxy, triethylsilyloxy or t-butyldimethylsilyloxy group, a nitro group, an acyloxy group having 2 to 7 carbon atoms such as an acetoxy, propionyloxy, butyryloxy, isobutyryloxy, valeryloxy, hexanoyloxy, heptanoyloxy or benzoyloxy group, an alkoxycarbonyloxy group having 2 to 5 carbon atoms such as a methoxycarbonyloxy, ethoxycarbonyloxy, propoxycarbonyloxy, isopropoxycarbonyloxy, butoxycarbonyloxy or t-butoxycarbonyloxy group, an alkoxy group having 1 to 4 carbon atoms such as a methoxy, ethoxy, propoxy, isopropoxy, butoxy, isobutoxy, s-butoxy or t-butoxy group, an acyl group having 2 to 7 carbon atoms such as an acetyl, propionyl, butyryl, isobutyryl, valeryl, hexanoyl or benzoyl group, an alkoxycarbonyl group having 2 to 5 carbon atoms such as a carboxyl, methoxycarbonyl, ethoxycarbonyl, propoxycarbonyl, isopropoxycarbonyl, butoxycarbonyl, isobutoxycarbonyl or t-butoxycarbonyl group, or an alkyl group such as a methyl, ethyl, propyl, isopropyl, butyl, isobutyl, s-butyl or t-butyl group.

Preferred examples of the $R^2$ include methyl, ethyl, propyl, nonyl, 3-carboxypropyl, 3-methoxycarbonylpropyl, 3-(2-thioxo-3-thiazolidinylcarbonyl)propyl, 3-(6-D-glucosylcarbonyl)propyl, 5-carboxypentyl, 5-methoxycarbonylpentyl, 5-ethoxycarbonylpentyl, 5-butoxycarbonylpentyl, 5-decyloxycarbonylpentyl, 5-(2-thioxo-3-thiazolidinylcarbonyl)pentyl, 5-(6-D-glucosylcarbonyl)pentyl, 5-(1-D-xylosylcarbonyl)pentyl, 5-(5-D-ribosylcarbonyl)pentyl, 5-cyanopentyl, 5-methoxycarbonyl-5,5-difluoropentyl, 5-methoxycarbonyl-4-pentenyl, 3,6-dihydroxyhexyl, 3,6-dihydroxy-1-hexenyl, 3,6-diacetoxy-1-hexenyl, 3,6-bis-t-butyldimethylsilyloxy-1-hexenyl, 3,6-bismethoxycarbonyloxy-1-hexenyl, 3,5-diacetoxy-4-(1-methoxy-1-methylethoxy-1-pentenyl, 3,5-diacetoxy-4-hydroxy-1-hexenyl, 7-hydroxy-6-hydroxymethyl-1-heptenyl, 3,4,5-triacetoxy-1-pentenyl, 5-methoxycarbonyl-1-pentynyl, 3-methoxycarbonylpropylthiomethyl, cyclohexyl, phenyl, 4-dimethylaminophenyl, 4-methoxycarbonylphenyl, 4-(3-hydroxy-2-hydroxymethylpropyl)phenyl, 4-pyridinyl, 5-methyl-2-furanyl, 2-cyclohexylethyl, 4-oxo-4-phenylbutyl, 2-phenylvinyl, 2-(3,4-dimethoxyphenyl)ethyl, 2-(4-dimethylaminophenyl)vinyl, 2-(1-piperidinyl)ethyl, 2-(4-morpholinyl)ethyl and 2-(4-methyl-1-piperazinyl)ethyl.

In the above-described formula (I), the $R^5$ stands for a hydrogen atom or a substituted or unsubstituted aliphatic hydrocarbon group having 1 to 10 carbon atoms or alicyclic hydrocarbon group having 4 to 10 carbon atoms. Examples of the unsubstituted aliphatic hydrocarbon group having 1 to 10 carbon atoms in the $R^5$ include alkyl groups such as methyl, ethyl, propyl, isopropyl, butyl, isobutyl, s-butyl, t-butyl, pentyl, isopentyl, neopentyl, hexyl, heptyl, octyl, 3,7-dimethyloctyl, nonyl and decyl groups; alkenyl groups such as 2-propenyl, 2-butenyl, 3-butenyl and 3-hexenyl groups; and alkynyl groups such as 2-propynyl and 2-butynyl groups.

Examples of the unsubstituted alicyclic hydrocarbon group having 4 to 10 carbon atoms in the $R^5$ include cyclobutyl, cyclopentyl, cyclohexyl, 3-cyclohexenyl, cyclooctyl and bicyclo[4.4.0]decan-2-yl.

The $R^5$ may be a group comprising, attached to each other, any combination of the above-described aliphatic hydrocarbon group having 1 to 10 carbon atoms and alicyclic hydrocarbon group having 4 to 10 carbon atoms. Among them, preferred examples of the $R^5$ include a substituted or unsubstituted ($r^5$—a) aliphatic hydrocarbon group having 1 to 10 carbon atoms which may be substituted with one or a plurality of phenyl groups;

($r^5$—b) alicyclic hydrocarbon group having 4 to 10 carbon atoms which may be substituted with one or a plurality of alkyl groups having 1 to 4 carbon atoms, alkoxy groups having 1 to 4 carbon atoms or phenyl groups; and ($r^5$—c) aliphatic hydrocarbon group having 1 to 10 carbon atoms substituted with an alicyclic hydrocarbon group having 4 to 10 carbon atoms and which may be substituted with one or a plurality of alkyl groups having 1 to 4 carbon atoms, alkoxy groups having 1 to 4 carbon atoms or phenyl groups.

Preferred examples of the unsubstituted group ($r^5$—a) include methyl, ethyl, propyl, isopropyl, butyl, isobutyl, s-butyl, t-butyl, pentyl, hexyl, octyl, decyl, 3,7-dimethyloctyl, benzyl, 2-phenylethyl, 3-phenylpropyl, 4-phenylbutyl and 5-phenylpentyl groups. Preferred examples of the unsubstituted group ($r^5$—b) include cyclopentyl, cyclohexyl, cyclooctyl, 3-methylcyclopentyl, 4-methylcyclohexyl, 4-butylcyclohexyl, 3,4-dimethylcyclohexyl, 4-methoxycyclohexyl and 4-phenylcyclohexyl groups. Preferred examples of the unsubstituted group (r5—c) include 3-cyclopentylpropyl, 3-cyclohexylpropyl, 4-cyclopentylbutyl and 4-cyclohexylbutyl groups.

The above-described groups (r5-a) to (r5-c) may be substituted with a plurality of different groups, and examples of the substituent include (i) a halogen atom; (ii) an oxo group; (iii) a cyano group; (iv) a nitro group; (v)—COOR$^{65}$ (wherein R$^{65}$ stands for a hydrogen atom; one equivalent of cation; a residue of a saccharide; or an aliphatic hydrocarbon group having 1 to 10 carbon atoms which may be substituted with a halogen atom, an oxo group, a hydroxyl group, a nitro group, a tri($C_1$-$C_7$) hydrocarbon silyloxy group, an acyloxy group having 2 to 7 carbon atoms, an alkoxycarbonyloxy group having 2 to 5 carbon atoms, an alkoxy group having 1 to 4 carbon atoms, an alicyclic hydrocarbon group having 4 to 10 carbon atoms or an aromatic hydrocarbon group having 6 to 10 carbon atoms); (vi) —OR$^{75}$ (wherein R$^{75}$ stands for a hydrogen atom; an alkyl group having 1 to 4 carbon atoms; an acyl group having 2 to 7 carbon atoms; an alkoxycarbonyl group having 2 to 5 carbon atoms; a tri($C_1$-$C_7$) hydrocarbon silyl group; a group capable of forming an acetal bond together with the oxygen atom attached to the R$^{75}$; an aliphatic hydrocarbon group having 1 to 10 carbon atoms or an alicyclic hydrocarbon group having 4 to 10 carbon atoms which may be substituted with a halogen atom, an oxo group, a hydroxyl group, a carboxyl group, a tri($C_1$-$C_7$) hydrocarbon silyloxy group, an acyloxy group having 2 to 7 carbon atoms, an alkoxycarbonyloxy group having 2 to 5 carbon atoms, an alkoxy group having 1 to 4 carbon atoms, an alkoxycarbonyl group having 2 to 5 carbon atoms or an aromatic hydrocarbon group having 6 to 10 carbon atoms; or an aromatic hydrocarbon group having 6 to 10 carbon atoms which may be substituted with a halogen atom, hydroxyl group, a nitro group, a tri($C_1$-$C_7$) hydrocarbon silyloxy group, an alkoxy group having 1 to 4 carbon atoms, an acyloxy group having 2 to 7 carbon atoms, an alkoxycarbonyloxy group having 2 to 5 carbon atoms, an acyl group having 2 to 7 carbon atoms, a carboxyl group, an alkoxycarbonyl group having 2 to 5 carbon atoms or an alkyl group having 1 to 4 carbon atoms); (vii) —CONR$^{85}$R$^{850}$ (wherein R$^{85}$ and R$^{850}$ which may be the same or different from each other stand for a hydrogen atom; an aliphatic hydrocarbon group having 1 to 10 carbon atoms or an alicyclic hydrocarbon group having 4 to 10 carbon atoms which may be substituted with a halogen atom, an oxo group, a hydroxyl group, a tri($C_1$-$C_7$) hydrocarbon silyloxy group, an acyloxy group having 2 to 7 carbon atoms, an alkoxycarbonyloxy group having 2 to 5 carbon atoms, an alkoxy group having 1 to 4 carbon atoms or an aromatic hydrocarbon group having 6 to 10 carbon atoms; an aromatic hydrocarbon group having 6 to 10 carbon atoms which may be substituted with a halogen atom, a hydroxyl group, a nitro group, a tri($C_1$-$C_7$) hydrocarbon silyloxy group, an acryloxy group having 2 to 7 carbon atoms, an alkoxycarbonyloxy group having 2 to 5 carbon atoms, an alkoxy group having 1 to 4 carbon atoms, an acyl group having 2 to 7 carbon atoms, a carboxyl group, an alkoxycarbonyl group having 2 to 5 carbon atoms or an alkyl group having 1 to 4 carbon atoms; or a group wherein the and R$^{850}$ are combined with each other to form a five- or six-membered ring); (viii) —NR$^{95}$R$^{950}$ (wherein R$^{95}$ and R$^{950}$ which may be the same or different from each other stand for a hydrogen atom; an aliphatic hydrocarbon group having 1 to 10 carbon atoms or an alicyclic hydrocarbon group having 4 to 10 carbon atoms which may be substituted with a halogen atom, an oxo group, a hydroxyl group, a tri($C_1$-$C_7$) hydrocarbon silyloxy group, an acyloxy group having 2 to 7 carbon atoms, an alkoxycarbonyloxy group having 2 to 5 carbon atoms, an alkoxy group having 1 to 4 carbon atoms or an aromatic hydrocarbon group having 6 to 10 carbon atoms; and an aromatic hydrocarbon group having 6 to 10 carbon atoms which may be substituted with a halogen atom, a hydroxyl group, a nitro group, a tri($C_1$-$C_7$) hydrocarbon silyloxy group, an acyloxy group having 2 to 7 carbon atoms, an alkoxycarbonyloxy group having 2 to 5 carbon atoms, an alkoxy group having 1 to 4 carbon atoms, an acyl group having 2 to 7 carbon atoms, a carboxyl group, an alkoxycarbonyl group having 2 to 5 carbon atoms or an alkyl group having 1 to 4 carbon atoms; or a group wherein the R$^{95}$ and R$^{950}$ are combined with each other to form a five- or six-membered ring).

Examples of the substituents (i) to (viii) of the groups (r5—a) to (r5—c) include the same substituents as those of the groups (r1—a) to (r1—g) described above in connection with the R$^1$.

Preferred examples of the R$^5$ include methyl, ethyl, propyl, isopropyl, butyl, t-butyl, hexyl, octyl, 3,7-dimethyloctyl, 3,7-dimethyl-6-octenyl, benzyl, 3-(3,4-dimethoxyphenyl)propyl, 5-phenylpentyl, cyclohexyl, 3-cyclohexylpropyl, 4-cyclohexylbutyl, 6-hydroxyhexyl, 6-t-butyldimethylsilyloxyhexyl, 6-acetoxyhexyl, 6-(1-ethoxyethoxy)hexyl, 5-carboxypentyl, 5-methoxycarbonylpentyl, 5-(6-D-glucosylcarbonyl)pentyl and 4-phenoxybutyl.

In the above-described formula (I), the R$^3$ stands for a hydrogen atom, a substituted or unsubstituted aliphatic hydrocarbon group having 1 to 10 carbon atoms, alicyclic hydrocarbon group having 4 to 10 carbon atoms or aromatic hydrocarbon group having 6 to 10 carbon atoms. When the R$^3$ is attached to the carbon atom of the cyclopentene skeleton through a single bond, X stands for a hydrogen atom, —OR$^4$ (wherein R$^4$ stands for a hydrogen atom, an alkyl group having 1 to 4 carbon atoms, an acyl group having 2 to 7 carbon atoms, an alkoxycarbonyl group having 2 to 5 carbon atoms, a tri($C_1$-$C_7$) hydrocarbon silyl group or a group capable of forming an acetal bond together with the oxygen atom attached to the R$^4$) or is absent when the R$^3$ is attached to the carbon atom through a double bond. Specifically, when the R$^3$ is attached to the cyclopentene skeleton through a single bond, the above-described formula (I) represents 2-substituted-2-cyclopentenones represented by the following formula (I'):

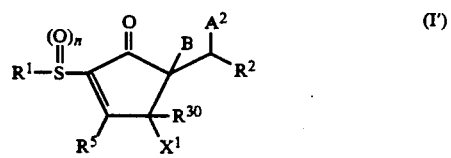

wherein
A, B, R$^1$, R$^2$, R$^5$ and n are as defined above;
R$^3$ stands for a hydrogen atom or a substituted or unsubstituted aliphatic hydrocarbon group having 1 to 10 carbon atoms, alicyclic hydrocarbon group having 4 to 10 carbon atoms or aromatic hydrocarbon group having 6 to 10 carbon atoms; and X¹ stands for a hydrogen atom or OR⁴ (wherein R⁴ is as defined above). When the R³ is attached to the carbon atom of the cyclopentene skeleton through a double bond and X is absent, the above-described formula (I) represents 2-substituted-2-cyclopentenones represented by the following formula (I''):

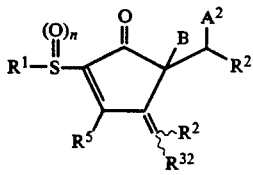

wherein A, B, R¹, R², R⁵, n and are as defined above;

R³¹ and R³² which may be the same or different from each other stand for a hydrogen atom, a substituted or unsubstituted aliphatic hydrocarbon group having 1 to 9 carbon atoms, alicyclic hydrocarbon group having 4 to 10 carbon atoms or aromatic hydrocarbon group having 6 to 10 carbon atoms, or a group wherein the R³¹ and R³² are combined with each other to form an alicyclic hydrocarbon group having 4 to 10 carbon atoms.

The R³⁰ in the above-described formula (I,) stands for a hydrogen atom, a substituted or unsubstituted aliphatic hydrocarbon group having 1 to 10 carbon atoms, alicyclic hydrocarbon group having 4 to 10 carbon atoms or aromatic hydrocarbon group having 6 to 10 carbon atoms. Examples of the unsubstituted aliphatic hydrocarbon group having 1 to 10 carbon atoms in the R³⁰ include alkyl groups such as methyl, ethyl, propyl, isopropyl, butyl, s-butyl, t-butyl, pentyl, isopentyl, neopentyl, hexyl, heptyl, octyl, 3,7-dimethyloctyl, nonyl and decyl groups; alkenyl groups such as vinyl, 1-methylvinyl, 1-propenyl, 2-propenyl, 2-methyl-1-propenyl, 1-butenyl, 2-butenyl, 2-methyl-1-butenyl, 1-pentenyl, 2-pentenyl, 1-hexenyl, 2-hexenyl, 3,3-dimethyl-1-butenyl, 5-hexenyl, 1,5-hexadienyl, 1-heptenyl, 1-octenyl, 3-methyl-1-octenyl, 4,4-dimethyl-1-octenyl, 1,7-octadienyl, 1-nonenyl, 5-methyl-1-nonenyl and 1-decenyl groups; and alkynyl groups such as ethynyl, 1-propynyl, 2-propynyl, 1-butynyl, 3-methyl-1-butynyl, 3,3-dimethyl-1-butynyl, 1-pentynyl, 2-pentynyl, 1-hexynyl, 2-hexynyl, 5-hexen-1-yl, 1-heptynyl, 1-nonynyl and 1-decynyl groups.

Examples of the unsubstituted alicyclic hydrocarbon groups having 4 to 10 carbon atoms in the R³⁰ include cyclobutyl, cyclopentyl, cyclohexyl, 1-cyclohexenyl, 3-cyclohexenyl, 4-cyclohexenyl, cycloheptyl, cyclooctyl and bicyclo[4.4.0]decan-2-yl groups.

Examples of the unsubstituted aromatic hydrocarbon group having 6 to 10 carbon groups in the R³⁰ include phenyl, 1-naphthyl and 2-naphthyl groups.

The R³⁰ may be a group comprising, attached to each other, any combination of the above-described aliphatic hydrocarbon group having 1 to 10 carbon atoms, alicyclic hydrocarbon group having 4 to 10 carbon atoms and aromatic hydrocarbon group having 6 to 10 carbon atoms. Among them, preferred examples of the R³⁰ include a substituted or unsubstituted (r³⁰—a) aliphatic hydrocarbon group having 1 to 10 carbon atoms which may be substituted with one or a plurality of alkoxy groups having 1 to 4 carbon atoms;

(r³⁰—b) alicyclic hydrocarbon group having 4 to 10 carbon atoms which may be substituted with one or a plurality of alkyl groups having 1 to 4 carbon atoms and alkoxy groups having 1 to 4 carbon atoms;

(r³⁰—c) aromatic hydrocarbon group having 6 to 10 carbon atoms which may be substituted with one or a plurality of alkyl groups having 1 to 4 carbon atoms and alkoxy groups having 1 to 4 carbon atoms;

(r³⁰—d) aliphatic hydrocarbon group having 1 to 10 carbon atoms substituted with an alicyclic hydrocarbon group having 4 to 10 carbon atoms and which may be substituted with one or a plurality of alkyl groups having 1 to 4 carbon atoms and alkoxy groups having 1 to 4 carbon atoms; and (r³⁰—e) aliphatic hydrocarbon group having 1 to 10 carbon atoms substituted with an aromatic hydrocarbon group having 6 to 10 carbon atoms and which may be substituted with one or a plurality of alkyl groups having 1 to 4 carbon atoms and alkoxy groups having 1 to 4 carbon atoms.

Preferred examples of the unsubstituted group (r³⁰—a) include methyl, ethyl, propyl, isopropyl, butyl, isobutyl, t-butyl, pentyl, hexyl, octyl, decyl, 3,7-dimethyloctyl, vinyl, 1-propenyl, 1-methylvinyl, 1-butenyl, 1-octenyl, 3,3-dimethyl-1-butenyl, 3-methyl-1-octenyl, 4,4-dimethyl-1-octenyl, nona-7-yne-1-enyl, 5-methyl-1-nonenyl, 1-propynyl, 3,3-dimethyl-1-butynyl, 1-pentynyl, 3,3-dimethyl-1-hexynyl and 2-hexenyl. Preferred examples of the unsubstituted group (r³⁰—b) include cyclopentyl, cyclohexyl, cyclooctyl, 3-methylcyclopentyl, 4-methylcyclohexyl, 4-butylcyclohexyl, 3,4-dimethylcyclohexyl and 4-methoxycyclohexyl groups. Preferred examples of the unsubstituted group (r³⁰—c) include phenyl, 1-naphthyl, 4-methylphenyl, 3,5-dimethylphenyl, 4-ethylphenyl, 4-butylphenyl, 4-methoxyphenyl, 4-ethoxyphenyl, 6-methoxy-2-naphthyl and 6,7-dimethoxy-2-naphthyl groups. Preferred examples of the unsubstituted group (r³⁰—d) include 3-cyclopentyl-1-propenyl, 3-cyclohexylpropyl, 3-cyclopentyl-3,3-dimethyl-1-propenyl, 4-cyclohexyl-1-propenyl and 3-(3-methylcyclopentyl)-1-propenyl groups. Preferred examples of the unsubstituted group (r³⁰—e) include benzyl, 2-phenylethyl, 3-phenylpropyl, 4-phenylbutyl, 1-naphthylmethyl, 2-naphthylmethyl, 4-butylbenzyl, 4-methoxybenzyl, 3,4-dimethoxybenzyl and 3,3-dimethyl-4-phenyl-1-butenyl groups.

The X¹ in the above-described formula (I') stands for a hydrogen atom or —OR⁴ wherein R⁴ stands for a hydrogen atom, an alkyl group having 1 to 4 carbon atoms, an acyl group having 2 to 7 carbon atoms, an alkoxycarbonyl group having 2 to 5 carbon atoms, a tri(C₁–C₇) hydrocarbon silyl group or a group combining with the oxygen atom attached to the R⁴ to form an acetal bond. Examples of the alkyl group having 1 to 4 carbon atoms in the R⁴ include methyl, ethyl, propyl, isopropyl, butyl, isobutyl and t-butyl groups. Examples of the acyl group having 2 to 7 carbon atoms include acetyl, propionyl, butyryl, isobutyryl, valeryl, hexanoyl and benzoyl groups. Examples of the alkoxycarbonyl group having 2 to 5 carbon atoms include methoxycarbonyl, ethoxycarbonyl, propoxycarbonyl, isopropoxycarbonyl, butoxycarbonyl and t-butoxycarbonyl groups. Examples of the tri(C₁–C₇) hydrocarbon silyl group include trimethylsilyl, triethylsilyl, t-butyldimethylsilyl, t-butyldiphenylsilyl and tribenzylsilyl groups. Examples of the group combining with an oxygen atom attached to the R⁴ to form an acetal bond include methoxymethyl, 1-ethoxyethyl, 1-methoxy-1-methylethyl, 2-ethoxy-1-methylethyl, 2-methoxyethoxymethyl, tetrahydropyran-2-yl, 6,6-dimethyl-3-oxa-2-oxobicyclo[3.1.0]hexane-4-yl groups.

Examples of the $X^1$ include a hydrogen atom and hydroxyl, methoxy, ethoxy, trimethylsilyloxy, acetoxy, methoxycarbonyloxy and isopropoxycarbonyloxy groups.

The $R^{31}$ and $R^{32}$ in the above-described formula (II,) each stand for a hydrogen atom, a substituted or unsubstituted aliphatic hydrocarbon group having 1 to 9 carbon atoms, alicyclic hydrocarbon group having 4 to 10 carbon atoms or aromatic hydrocarbon group having 6 to 10 carbon atoms, or a group wherein the $R^{31}$ and $R^{32}$ are combined with each other to form an alicyclic hydrocarbon group having a four to ten-membered ring. Examples of the unsubstituted aliphatic hydrocarbon group having 1 to 9 carbon atoms in the $R^{31}$ and $R^{32}$ include alkyl groups such as methyl, ethyl, isopropyl, butyl, pentyl, heptyl, octyl, nonyl and 2,6-dimethylheptyl groups; alkenyl groups such as vinyl, 1-propenyl, 1-pentenyl and 1-hexenyl groups; and alkynyl groups such as 1-propynyl and 1-pentynyl groups.

Examples of the unsubstituted alicyclic hydrocarbon group having 4 to 10 carbon atoms and aromatic hydrocarbon having 6 to 10 carbon atoms in the $R^{31}$ and $R^{32}$ include those described above in connection with the $R^{30}$. Examples of the unsubstituted group which is an alicyclic hydrocarbon group having a four to ten-membered ring formed by combining $R^{31}$ with $R^{32}$ to each other together with a carbon atom intervening between the $R^{31}$ and the $R^{32}$ include cyclobutylidene, cyclopentylidene, cyclohexylidene, 2-cyclohexenylidene and bicyclo[4.4.0]decan-2-ylidene groups. The $R^{31}$ and $R^{32}$ may also be one comprising, attached to each other, any combination of the above-described aliphatic hydrocarbon group having 1 to 9 carbon atoms, alicyclic hydrocarbon group having 4 to 10 carbon atoms and aromatic hydrocarbon group having 6 to 10 carbon atoms; or a group wherein the $R^{31}$ and $R^{32}$ are combined with each other to form an alicyclic hydrocarbon group having a four to ten-membered ring to which the above-described aliphatic hydrocarbon having 1 to 9 carbon atoms or aromatic hydrocarbon group having 6 to 10 carbon atoms is attached. Among them, preferred examples of the $R^{31}$ and $R^{32}$ include a substituted or unsubstituted ($r^{31}$—a) aliphatic hydrocarbon group having 1 to 10 carbon atoms which may be substituted with one or a plurality of alkoxy groups having 1 to 4 carbon atoms;

($r^{31}$—b) alicyclic hydrocarbon group having 4 to 10 carbon atoms which may be substituted with one or a plurality of alkyl groups having 1 to 4 carbon atoms and alkoxy groups having 1 to 4 carbon atoms;

($r^{31}$—c) aromatic hydrocarbon group having 6 to 10 carbon atoms which may be substituted with one or a plurality of alkyl groups having 1 to 4 carbon atoms and alkoxy groups having 1 to 4 carbon atoms;

($r^{31}$—d) aliphatic hydrocarbon group having 1 to 10 carbon atoms substituted with an alicyclic hydrocarbon group having 4 to 10 carbon atoms and which may be substituted with one or a plurality of alkyl groups having 1 to 4 carbon atoms and alkoxy groups having 1 to 4 carbon atoms;

($r^{31}$—e) aliphatic hydrocarbon group having 1 to 10 carbon atoms substituted with an aromatic hydrocarbon group having 6 to 10 carbon atoms and which may be substituted with one or a plurality of alkyl groups having 1 to 4 carbon atoms and alkoxy groups having 1 to 4 carbon atoms; and ($r^{31}$—f) group wherein $R^{31}$ and $R^{32}$ are combined with each other to form an alicyclic hydrocarbon having a four to ten-membered ring, which may be substituted with one or a plurality of alkyl groups having 1 to 4 carbon atoms and alkoxy groups having 1 to 4 carbon atoms.

Preferred examples of the unsubstituted group ($r^{31}$—a) include methyl, ethyl, propyl, isopropyl, butyl, isobutyl, t-butyl, pentyl, heptyl, nonyl, 2,6-dimethylheptyl, vinyl, 1-propenyl and 1-pentenyl groups. Preferred examples of the unsubstituted groups ($r^{31}$—b) and ($r^{31}$—c) include respectively those of the ($r^{30}$—b) and ($r^{30}$—c) described above in connection with the $R^{30}$. Preferred examples of the unsubstituted group ($r^{31}$—f) include cyclopentylidene and cyclohexylidene.

The above-described groups ($r^{30}$—a) to ($r^{30}$—e) or ($r^{31}$—a) to ($r^{31}$—f) may be substituted with a plurality of different groups, and examples of the substituent include (i) a halogen atom; (ii) an oxo group; (iii) a cyano group; (iv) a nitro group; (v) —COOR$^{63}$ (wherein R$^{63}$ stands for a hydrogen atom; one equivalent of cation; a residue of a saccharide; or an aliphatic hydrocarbon group having 1 to 10 carbon atoms which may be substituted with a halogen atom, an oxo group, a hydroxyl group, a nitro group, a tri($C_1$-$C_7$) hydrocarbon silyloxy group, an acyloxy group having 2 to 7 carbon atoms, an alkoxycarbonyloxy group having 2 to 5 carbon atoms, an alkoxy group having 1 to 4 carbon atoms, an alicyclic hydrocarbon group having 4 to 10 carbon atoms or an aromatic hydrocarbon group having 6 to 10 carbon atoms); (vi) —OR$^{73}$ (wherein R$^{73}$ stands for a hydrogen atom; an alkyl group having 1 to 4 carbon atoms; an acyl group having 2 to 7 carbon atoms; an alkoxycarbonyl group having 2 to 5 carbon atoms; a tri($C_1$-$C_7$) hydrocarbon silyl group; a group capable of forming an acetal bond together with the oxygen atom attached to the R$^{73}$; an aliphatic hydrocarbon group having 1 to 10 carbon atoms or an alicyclic hydrocarbon group having 4 to 10 carbon atoms which may be substituted with a halogen atom, an oxo group, a hydroxyl group, a carboxyl group, a tri($C_1$-$C_7$) hydrocarbon silyloxy group, an acyloxy group having 2 to 7 carbon atoms, an alkoxycarbonyloxy group having 2 to 5 carbon atoms, an alkoxy group having 1 to 4 carbon atoms, an alkoxycarbonyl group having 2 to 5 carbon atoms or an aromatic hydrocarbon group having 6 to 10 carbon atoms; or an aromatic hydrocarbon group having 6 to 10 carbon atoms which may be substituted with a halogen atom, hydroxyl group, a nitro group, a tri($C_1$-$C_7$) hydrocarbon silyloxy group, an alkoxy group having 1 to 4 carbon atoms, an acyloxy group having 2 to 7 carbon atoms, an alkoxycarbonyloxy group having 2 to 5 carbon atoms, an acyl group having 2 to 7 carbon atoms, a carboxyl group, an alkoxycarbonyl group having 2 to 5 carbon atoms or an alkyl group having 1 to 4 carbon atoms); (vii) —CONR$^{83}$R$^{830}$ (wherein R$^{83}$ and R$^{830}$ which may be the same or different from each other stand for a hydrogen atom; an aliphatic hydrocarbon group having 1 to 10 carbon atoms or an alicyclic hydrocarbon group having 4 to 10 carbon atoms which may be substituted with a halogen atom, an oxo group, a hydroxyl group, a tri($C_1$-$C_7$) hydrocarbon silyloxy group, an acyloxy group having 2 to 7 carbon atoms, an alkoxycarbonyloxy group having 2 to 5 carbon atoms, an alkoxy group having 1 to 4 carbon atoms or an aromatic hydrocarbon group having 6 to 10 carbon atoms;

an aromatic hydrocarbon group having 6 to 10 carbon atoms which may be substituted with a halogen atom, a hydroxyl group, a nitro group, a tri($C_1$-$C_7$) hydrocarbon silyloxy group, an acyloxy group having 2 to 7 carbon atoms, an alkoxycarbonyloxy group having 2 to 5 carbon atoms, an alkoxy group having 1 to 4 carbon atoms, an acyl group having 2 to 7 carbon atoms, a carboxyl group, an alkoxycarbonyl group having 2 to 5 carbon atoms or an alkyl group having 1 to 4 carbon atoms; or a group wherein $R^{83}$ and $R^{830}$ are combined with each other to form a five- or six-membered ring); and (viii) —$NR^{93}R^{930}$ (wherein $R^{93}$ and $R^{930}$ which may be the same or different from each other stand for a hydrogen atom; an aliphatic hydrocarbon group having 1 to 10 carbon atoms or an alicyclic hydrocarbon group having 4 to 10 carbon atoms which may be substituted with a halogen atom, an oxo group, a hydroxyl group, a tri($C_1$-$C_7$) hydrocarbon silyloxy group, an acyloxy group having 2 to 7 carbon atoms, an alkoxycarbonyloxy group having 2 to 5 carbon atoms, an alkoxy group having 1 to 4 carbon atoms or an aromatic hydrocarbon group having 6 to 10 carbon atoms; and an aromatic hydrocarbon group having 6 to 10 carbon atoms which may be substituted with a halogen atom, a hydroxyl group, a nitro group, a tri($C_1$-$C_7$) hydrocarbon silyloxy group, an acyloxy group having 2 to 7 carbon atoms, an alkoxycarbonyloxy group having 2 to 5 carbon atoms, an alkoxy group having 1 to 4 carbon atoms, an acyl group having 2 to 7 carbon atoms, a carboxyl group, an alkoxycarbonyl group having 2 to 5 carbon atoms or an alkyl group having 1 to 4 carbon atoms; or a group wherein $R^{93}$ and $R^{930}$ are combined with each other to form a five- or six-membered ring).

Examples of the substituents (i) to (viii) of the groups ($r^{30}$—a) to ($r^{30}$—e) or ($r^{31}$—a) to ($r^{31}$—f) include the same substituents as those of the groups ($r^1$—a) to ($r^1$—g) described above in connection with the R1.

Preferred examples of the $R^{30}$ include methyl, ethyl, propyl, isopropyl, butyl, isobutyl, butyl, t-butyl, octyl, 3,7-dimethyloctyl, 1-methylvinyl, 1-octenyl, 3,3-dimethyl-4-phenyl-1-butenyl, 3,3-dimethyl-1-butynyl, 1-pentynyl, 1-hexynyl, 3-t-butyldimethylsilyloxy-1-octenyl, 3-hydroxy-1-octenyl, 3-acetoxy-1-octenyl, 3-methoxycarbonyloxy-1-octenyl, 3-trimethylsilyloxy-3-methyl-1-octenyl, 3-hydroxy-3-methyl-1-octenyl, 3-t-butyldimethylsilyloxy-5-methyl-1-nonenyl, 3-hydroxy-5-methyl-1-nonenyl, 6-carboxyhexyl, 6-methoxycarbonylhexyl, 6-(2-thioxo-3-thiazolidinylcarbonyl)hexyl, 6-(6-D-glucosylcarbonyl)hexyl, 6-(1-D-xylosylcarbonyl)hexyl, 6-(5-D-ribosylcarbonyl)hexyl, 6-hydroxyhexyl, 6-t-butyldimethylsilyloxyhexyl, 6-acetoxyhexyl, 6-hydroxy-2-hexenyl, 6-carboxy-2-hexenyl, 6-methoxycarbonyl-2-hexenyl, 3-cyclohexylpropyl, 3-hydroxy-3-cyclopentyl-1-propenyl, 3-methoxycarbonyloxy-3-cyclopentyl-1-propenyl, 3-isopropoxycarbonyloxy-3-cyclopentyl-1-propenyl, 3-t-butyldimethylsilyloxy-3-cyclopentyl-1-propenyl, 3-hydroxy-3-cyclohexyl-1-propenyl, 3-t-butyldimethylsilyloxy-3-cyclohexyl-1-propenyl, 3-hydroxy-4-cyclohexyl-1-butenyl, 4-phenoxybutyl, 3-(3,4-dimethoxyphenyl) propyl, benzyl, 2-phenylethyl, 5-phenylpentyl, cyclohexyl and phenyl.

Preferred examples of the $R^{31}$ and $R^{310}$ include a hydrogen atom, methyl, ethyl, propyl, 1-heptenyl, 5-methoxycarbonylpentyl, 5-methoxycarbonyl-1-pentenyl and 3-phenoxypropyl.

Among the 2-substituted-2-cyclopentenone compounds represented by the above-described formula (I), a 2-substituted-2-cyclopentenone compound represented by the formula (I-b-1-1) can be produced through the following scheme 1 by subjecting a 2-cyclopentenone compound represented by the formula (III-b) to an epoxidation reaction to prepare a 2,3-epoxycyclopentanone compound represented by the formula (IV-b), reacting the 2,3-epoxycyclopentanone compound with a thiol compound represented by the formula (V) in the 2-cyclopentenone compound represented by the formula (I-b-10) and then subjecting the 2-substituted-2-cyclopentenone compound to the following optional reactions: an oxidation reaction; a deblocking reaction for a protecting group of a hydroxyl group; a protecting reaction for a hydroxyl group; a hydrolysis reaction of an ester; and an esterification reaction, an amidation reaction, a condensation reaction of a sugar residue and/or a salt forming reaction of a carboxyl group.

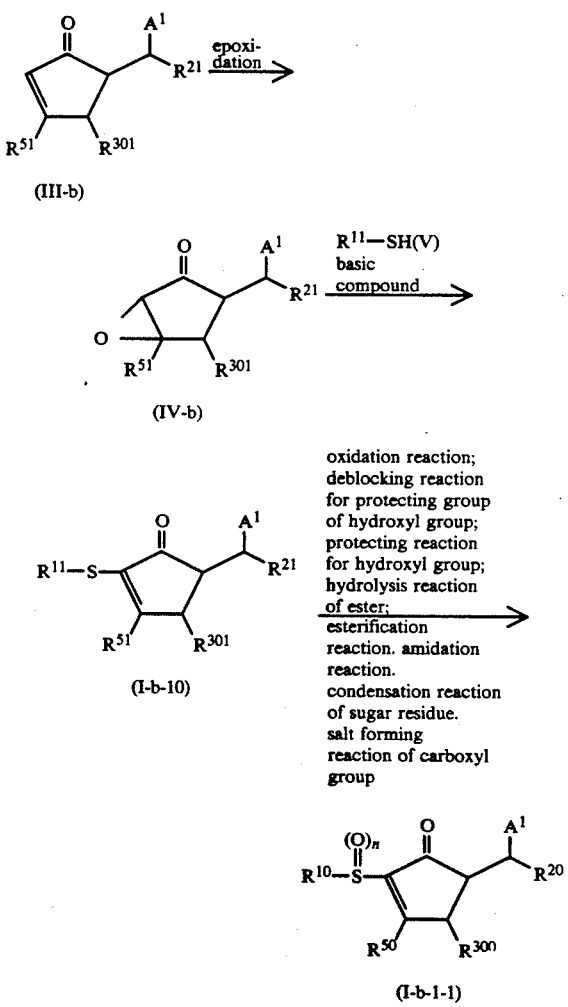

wherein $R^{10}$ and $R^{11}$ each stand for a substituted or unsubstituted aliphatic hydrocarbon group having 1 to 10 carbon atoms, alicyclic hydrocarbon group having 4 to 10 carbon atoms, aromatic hydrocarbon group having 6 to 10 carbon atoms or heterocyclic group having 1 to 9 carbon atoms;

$R^{20}$ and $R^{21}$ each stand for a substituted or unsubstituted aliphatic hydrocarbon group having 1 to 10 carbon atoms, alicyclic hydrocarbon group having 4 to 10 carbon atoms, aromatic hydrocarbon group having 6 to 10 carbon atoms or heterocyclic group having 1 to 9 carbon atoms;

$R^{300}$ and $R^{301}$ each stand for a hydrogen atom or a substituted or unsubstituted aliphatic hydrocarbon group having 1 to 10 carbon atoms, alicyclic hydrocarbon group having 4 to 10 carbon atoms or aromatic hydrocarbon group having 6 to 10 carbon atoms;

$R^{50}$ and $R^{51}$ each stand for a hydrogen atom or a substituted or unsubstituted aliphatic hydrocarbon group having 1 to 10 carbon atoms or alicyclic hydrocarbon group having 4 to 10 carbon atoms;

$A^1$ is a hydrogen atom or a hydroxyl group; and n is 0, 1 or 2.

Specific examples of the $R^{10}$ and $R^{11}$ include the groups referred to in the specific examples of the $R^1$ described above in connection with the above-described formula (I). Specific examples of the $R^{20}$ and $R^{21}$ include the groups referred to in the specific examples of the $R^2$ described above in connection with the above-described formula (I). Specific examples of the $R^{300}$ and $R^{301}$ include the groups referred to in the specific examples of the $R^3$ described above in connection with the above-described formula (I). Specific examples of the $R^{50}$ and $R^{51}$ include the groups referred to in the specific examples of the $R^5$ described above in connection with the above-described formula (I).

Preferred substituents of the $R^{10}$, $R^{20}$, $R^{300}$ and $R^{50}$ are respectively the same substituents as those of the $R^1$, $R^2$, $R^3$ and $R^5$, and preferred substituents of the $R^{11}$, $R^{21}$, $R^{301}$ and $R^{51}$ are respectively the same substituents as those of the $R^1$, $R^2$, $R^3$ and $R^5$, other than the salts of carboxylic acids.

The starting compound represented by the formula (III-b) can be prepared, for example, through the following scheme comprising a combination of processes described in Japanese Unexamined Patent Publication (Kokai) Nos. 59-164747 and 62-81344.

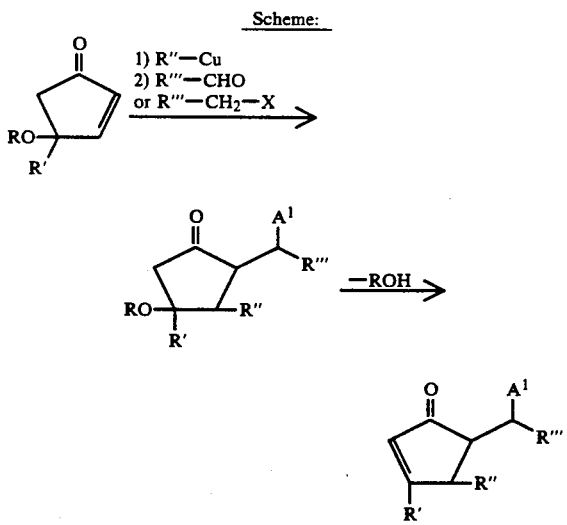

wherein $A^1$ is as defined above.

Among the 2-substituted-2-cyclopentenone compounds represented by the above-described formula (I), a 2-substituted-2-cyclopentenone compound represented by the formula (I-b-1-2) can be produced through the following scheme 2 by subjecting a 2-substituted-2-cyclopentenone compound represented by the formula (I-b-11) belonging to the 2-substituted-2-cyclopentenone compound represented by the above-described formula (I-b-10) to an acylation reaction or an alkoxycarbonylation reaction to prepare a 2-substituted-2-cyclopentenone compound represented by the formula (I-b-12) and then subjecting the 2-substituted-2-cyclopentenone compound to the following optional reactions: an oxidation reaction; a deblocking reaction for a protecting group of a hydroxyl group; a protecting reaction for a hydroxyl group; a hydrolysis reaction of an ester; and an esterification reaction, an amidation reaction, a condensation reaction of a sugar residue and/or a salt forming reaction of a carboxyl group.

Scheme 2:

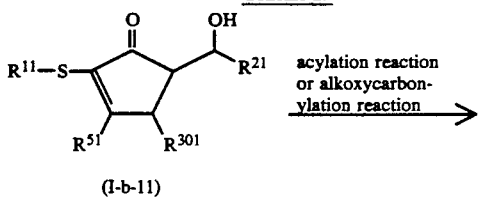

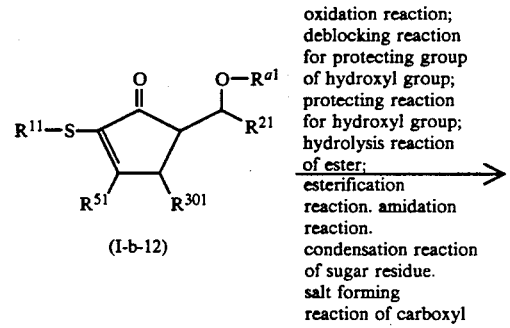

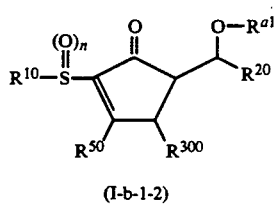

wherein $R^{10}$, $R^{11}$, $R^{20}$, $R^{21}$, $R^{300}$, $R^{301}$, $R^{50}$, $R^{51}$ and n are each as defined above; and $R^{a1}$ stands for an acyl group having 2 to 7 carbon atoms or an alkoxycarbonyl group having 2 to 5 carbon atoms.

Specific examples of the $R^{a1}$ in the form of —O—$R^{a1}$ include the groups referred to in the specific examples of the acyloxy group having 2 to 7 carbon atoms and alkoxycarbonyloxy group having 2 to 5 carbon atoms in the A described above in connection with the above-described formula (I).

Among the 2-substituted-2-cyclopentenone compounds represented by the above-described formula (I), a 2-substituted-2-cyclopentenone compound represented by the formula (I-a-1) can be produced through the following scheme 3 by subjecting a 2-substituted-2-cyclopentenone compound represented by the formula (I-b-11) to a sulfonylation reaction to prepare a 2-substituted-2-cyclopentenone compound represented by the formula (I-b-13), subjecting the 2-substituted-2- cyclopentenone compound to a desulfonation reaction to prepare a 2-substituted-2-cyclopentenone compound represented by the formula (I-a-10) and then subjecting the 2-substituted-2-cyclopentenone compound to the following optional reactions: an oxidation reaction; a deblocking reaction for a protecting group of a hydroxy group; a protecting reaction for a hydroxyl group; a hydrolysis reaction of an ester; and an esterification reaction, an amidation reaction, a condensation reaction of a sugar residue and/or a salt forming reaction of a carboxyl group.

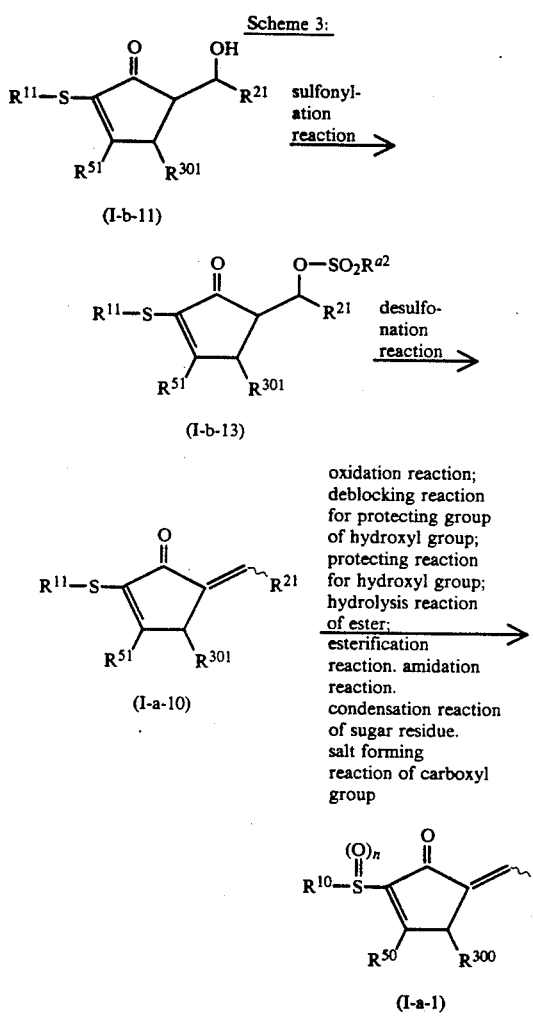

wherein
$R^{10}$, $R^{11}$, $R^{20}$, $R^{21}$, $R^{300}$, $R^{301}$, $R^{50}$, $R^{51}$ and n are each as defined above; represents that the substituent attached to the double bond is in an E-configuration or a Z-configuration or a mixture thereof in any proportion; and $R^{a2}$ stands for an alkyl group which may be substituted with a halogen atom, a substituted or unsubstituted phenyl group or a substituted or unsubstituted phenyl ($C_1$-$C_2$) alkyl group.

Specific examples of the $R^{a2}$ in the form of —O—$SO_2R^{a2}$ include the groups referred to in the specific examples of the alkylsulfonyloxy group having 1 to 4 carbon atoms which may be substituted with a halogen atom, the substituted or unsubstituted phenylsulfonyloxy group or the substituted or unsubstituted phenyl ($C_1$-$C_2$) alkylsulfonyloxy group in the A described above in connection with the above-described formula (I).

Among the 2-substituted-2-cyclopentenone compounds represented by the above-described formula (I), a 2-substituted-2-cyclopentenone compound represented by the formula (I-b-1-3) and a 2-substituted-2-cyclopentenone compound represented by the formula (I-a-1) can be produced through the following scheme 4 by reacting a 2,3-epoxycyclopentanone compound represented by the formula (IV-a-1) with a thiol compound represented by the formula (V) in the presence of a basic compound to prepare 2-substituted-2-cyclopentenone compounds respectively represented by the formula (I-b-14) and (I-a-10) and then subjecting the 2-substituted-2-cyclopentenone compounds to the following optional reactions: an oxidation reaction; a deblocking reaction for a protecting group of a hydroxyl group; a protecting reaction for a hydroxyl group; a hydrolysis reaction of an ester; and an esterification reaction, an amidation reaction, a condensation reaction of a sugar residue and/or a salt forming reaction of a carboxyl group.

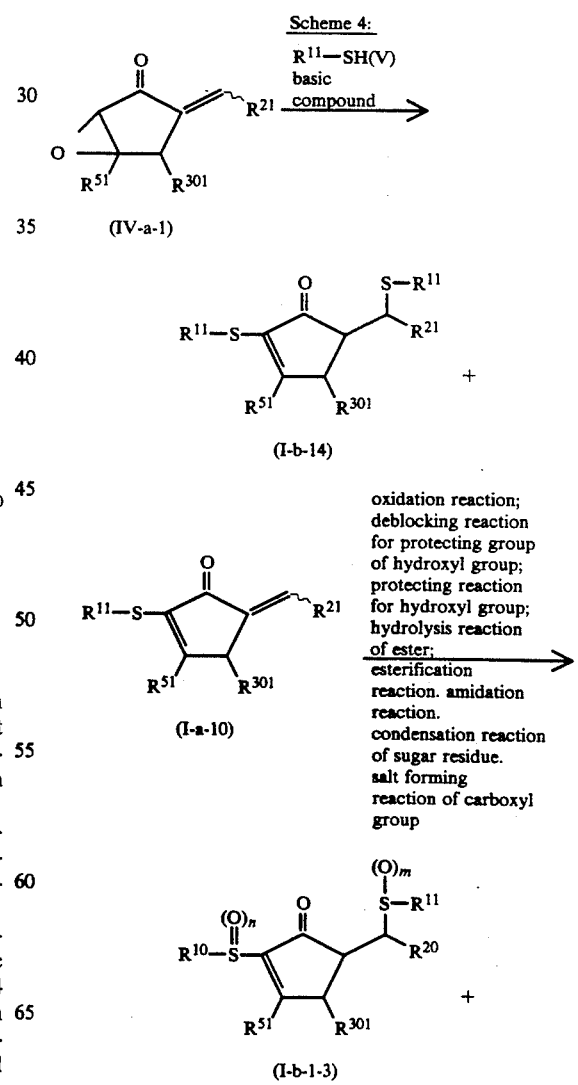

-continued
Scheme 4:

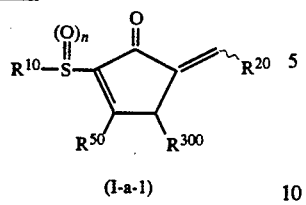

(I-a-1)

wherein
$R^{10}$, $R^{11}$, $R^{20}$, $R^{21}$, $R^{300}$, $R^{301}$, $R^{50}$, $R^{51}$ and n are each as defined above; and
m is 0, 1 or 2.

The starting compound represented by the formula (IV-a-1) can be prepared, for example, through the following scheme in the same manner as that described in Japanese Unexamined Patent Publication (Kokai) Nos. 61-47437.

Scheme:

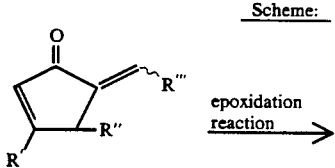  epoxidation reaction →

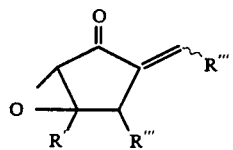

Among the 2-substituted-2-cyclopentenone compounds represented by the above-described formula (I), a 2-substituted-2-cyclopentenone compound represented by the formula (I-c-1) can be produced through the following scheme 5 by subjecting a 2-cyclopentenone compound represented by the formula (III-a) to an epoxidation reaction to prepare a 2,3-epoxycyclopentanone compound represented by the formula (IV-a-2), reacting the 2,3-epoxycyclopentanone compound with a thiol compound in the presence of a basic compound represented by the formula (V) to prepare a 2-substituted-2-cyclopentenone compound represented by the formula (I-c-2) and then subjecting the 2-substituted-2-cyclopentenone compound to the following optional reactions: an oxidation reaction; a deblocking reaction for a protecting group of a hydroxyl group; a protecting reaction for a hydroxyl group; a hydrolysis reaction of an ester; and an esterification reaction, an amidation reaction, a condensation reaction of a sugar residue and/or a salt forming reaction of a carboxyl group.

Scheme 5:

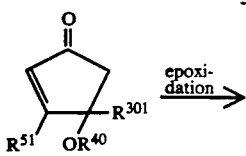  epoxidation →

-continued
Scheme 5:

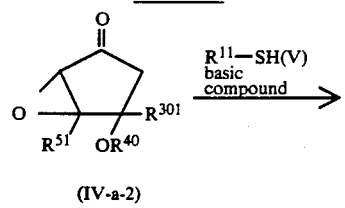  $R^{11}$—SH(V) basic compound →

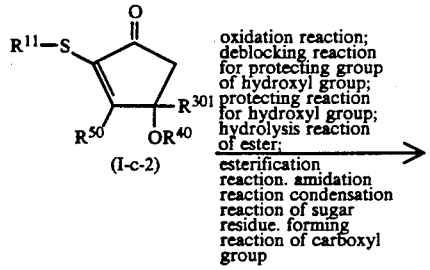

oxidation reaction; deblocking reaction for protecting group of hydroxyl group; protecting reaction for hydroxyl group; hydrolysis reaction of ester; esterification reaction. amidation reaction condensation reaction of sugar residue. forming reaction of carboxyl group →

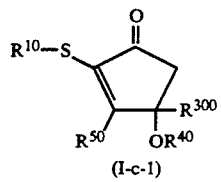

(I-c-1)

wherein
$R^{10}$, $R^{11}$, $R^{300}$, $R^{301}$, $R^{50}$ and $R^{51}$ are each as defined above; and
$R^{40}$ stands for a hydrogen atom, an alkyl group having 1 to 4 carbon atoms, an acyl group having 2 to 7 carbon atoms, an alkoxycarbonyl group having 2 to 5 carbon atoms, a tri($C_1$–$C_7$) hydrocarbon silyl group or a group capable of forming an acetal bond together with an oxygen atom attached to the $R^{40}$.

Specific examples of the $R^{40}$ include the groups referred to in the specific examples of the $R^4$ described above in connection with the above-described formula (I).

The starting compound represented by the formula (III-a) can be prepared, for example, by a process represented by the following scheme.

Scheme:

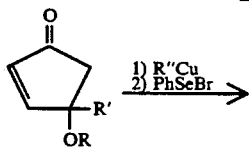  1) R"Cu  2) PhSeBr →

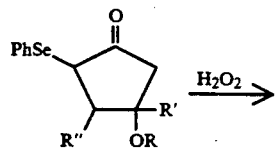  $H_2O_2$ →

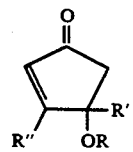

Among the 2-substituted-2-cyclopentenone compounds represented by the above-described formula (I), a 2-substituted-2-cyclopentenone compound represented by the formula (I-b-2-1) can be produced through the following scheme 6 by subjecting a 2-cyclopentenone compound represented by the formula (I-c-21) belonging to the 2-substituted-2-cyclopentenone compound represented by the above-described formula (I-c-2) to an aldol condensation reaction with an aldehyde compound represented by the formula (II-a) in the presence of a lithium amide compound or (a tertiary amine compound and a dialkylborontrifluoromethanesulfonic acid) to prepare a 2-substituted-2-cyclopentenone compound represented by the formula (I-b-21) and then subjecting the 2-substituted-2-cyclopentenone compound to the following optional reactions: an oxidation reaction; a deblocking reaction for a protecting group of a hydroxyl group; a protecting reaction for a hydroxyl group; a hydrolysis reaction of an ester; and an esterification reaction, an amidation reaction, a condensation reaction of a sugar residue and/or a salt forming reaction of a carboxyl group.

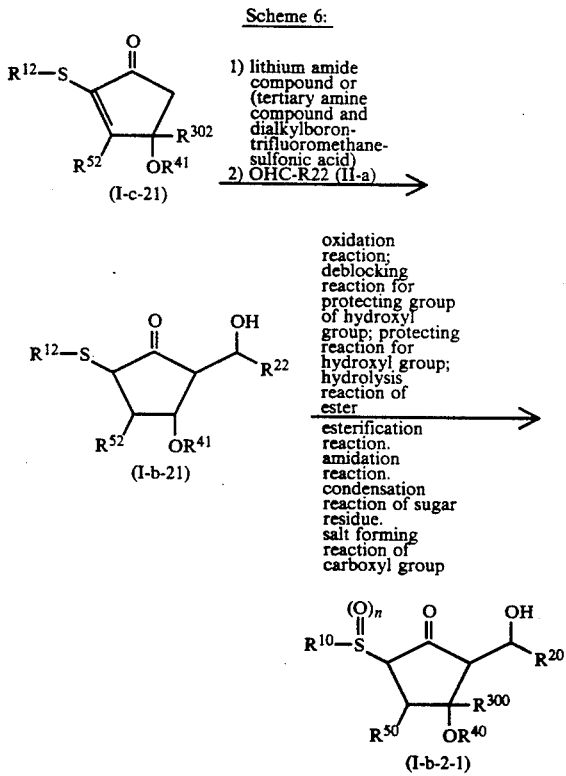

wherein
$R^{10}$, $R^{20}$, $R^{300}$, $R^{40}$, $R^{50}$ and n are each as defined above;

$R^{12}$ stands for a substituted or unsubstituted aliphatic hydrocarbon group having 1 to 10 carbon atoms, alicyclic hydrocarbon group having 4 to 10 carbon atoms, aromatic hydrocarbon group having 6 to 10 carbon atoms or heterocyclic group having 1 to 9 carbon atoms;

$R^1$ stands for a substituted or unsubstituted aliphatic hydrocarbon group having 1 to 10 carbon atoms, alicyclic hydrocarbon group having 4 to 10 carbon atoms, aromatic hydrocarbon group having 6 to 10 carbon atoms or heterocyclic group having 1 to 9 carbon atoms;

$R^{302}$ stands for a hydrogen atom or a substituted or unsubstituted aliphatic hydrocarbon group having 1 to 10 carbon atoms, alicyclic hydrocarbon group having 4 to 10 carbon atoms or aromatic hydrocarbon group having 6 to 10 carbon atoms;

$R^{41}$ stands for an alkyl group having 1 to 4 carbon atoms, an acyl group having 2 to 7 carbon atoms, an alkoxycarbonyl group having 2 to 5 carbon atoms, a tri($C_1$-$C_7$) hydrocarbon silyl group or a group capable of forming an acetal bond together with an oxygen atom attached to the $R^{41}$; and $R^{52}$ stands for a hydrogen atom or a substituted or unsubstituted aliphatic hydrocarbon group having 1 to 10 carbon atoms or alicyclic hydrocarbon group having 4 to 10 carbon atoms.

Specific examples of the $R^{12}$ include the groups referred to in the specific examples of the $R^1$ described above in connection with the above-described formula (I).

Specific examples of the $R^{22}$ include the groups referred to in the specific examples of the $R^2$ described above in connection with the above-described formula (I).

Specific examples of the $R^{302}$ include the groups referred to in the specific examples of the $R^3$ described above in connection with the above-described formula (I).

Specific examples of the $R^{52}$ include the groups referred to in the specific examples of the $R^5$ described above in connection with the above-described formula (I).

Preferred substituents of the $R^{12}$, $R^{22}$, $R^{302}$ and $R^{52}$ are respectively the groups described as the substituents of the $R^1$, $R^2$, $R^3$ and $R^5$ exclusive of the groups having a carboxylic acid, a salt of a carboxylic acid and a hydroxyl group.

Among the 2-substituted-2-cyclopentenone compounds represented by the above-described formula (I), a 2-substituted-2-cyclopentenone compound represented by the formula (I-b-2-2) can be produced through the following scheme 7 by subjecting a 2-cyclopentenone compound represented by the formula (I-b-21) to an acylation reaction or an alkoxycarbonylation reaction to prepare a 2-substituted-2-cyclopentenone compound represented by the formula (I-b-22) and then subjecting the 2-substituted-2-cyclopentenone compound to the following optional reactions: an oxidation reaction; a deblocking reaction for a protecting group of a hydroxyl group; a protecting reaction for a hydroxyl group; a hydrolysis reaction of an ester; and an esterification reaction, an amidation reaction, a condensation reaction of a sugar residue and/or a salt forming reaction of a carboxyl group.

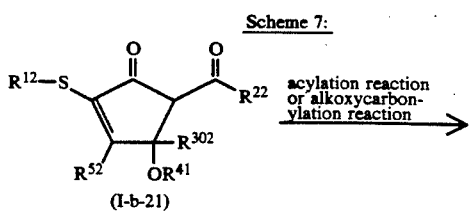

Scheme 7:

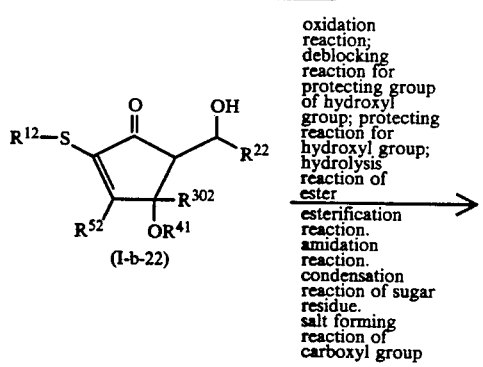
(I-b-22)

oxidation reaction; deblocking reaction for protecting group of hydroxyl group; protecting reaction for hydroxyl group; hydrolysis reaction of ester esterification reaction. amidation reaction. condensation reaction of sugar residue. salt forming reaction of carboxyl group
→

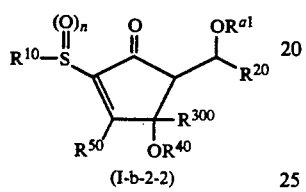
(I-b-2-2)

wherein $R^{10}$, $R^{12}$, $R^{20}$, $R^{22}$, $R^{300}$, $R^{302}$, $R^{40}$, $R^{41}$, $R^{50}$, $R^{52}$, $R^{a1}$ and n are each as defined above.

Among the 2-substituted-2-cyclopentenone compounds represented by the above-described formula (I), a 2-substituted-2-cyclopentenone compound represented by the formula (I-b-2-3) can be produced through the following scheme 8 by subjecting a 2-substituted-2-cyclopentenone compound represented by the formula (I-c-21) to an enolation with a lithium amide compound, reacting the enolation product with an organoiodide represented by the formula (II-b) in the presence of an organotin compound to prepare a 2-substituted-2-cyclopentenone compound represented by the formula (I-b-23) and then subjecting the 2-substituted-2-cyclopentenone compound to the following optional reactions: an oxidation reaction; a deblocking reaction for a protecting group of a hydroxyl group; a protecting reaction for a hydroxyl group; a hydrolysis reaction of an ester; and an esterification reaction, an amidation reaction, a condensation reaction of a sugar residue and/or a salt forming reaction of a carboxyl group.

Scheme 8:

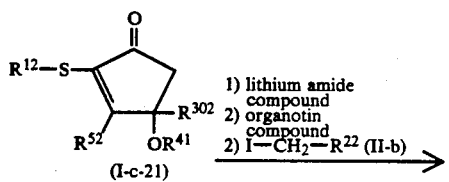
(I-c-21)

1) lithium amide compound
2) organotin compound
2) I—CH$_2$—R$^{22}$ (II-b)
→

Scheme 8:

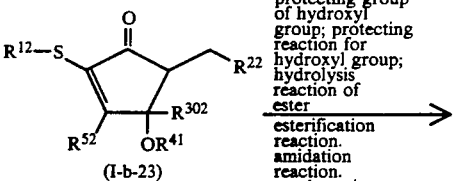
(I-b-23)

oxidation reaction; deblocking reaction for protecting group of hydroxyl group; protecting reaction for hydroxyl group; hydrolysis reaction of ester esterification reaction. amidation reaction. condensation reaction of sugar residue. salt forming reaction of carboxyl group
→

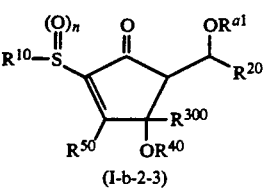
(I-b-2-3)

wherein $R^{10}$, $R^{12}$, $R^{20}$, $R^{22}$, $R^{300}$, $R^{302}$, $R^{40}$, $R^{41}$, $R^{50}$, $R^{52}$, and n are each as defined above.

Among the 2-substituted-2-cyclopentenone compounds represented by the above-described formula (I), a 2-substituted-2-cyclopentenone compound represented by the formula (I-a-2) can be produced through the following scheme 9 by subjecting a 2-substituted-2-cyclopentenone compound represented by the formula (I-b-21) to a sulfonylation reaction to prepare a 2-substituted-2-cyclopentenone compound represented by the formula (I-b-24), subjecting the 2-substituted-2-cyclopentenone compound to a desulfonation reaction to prepare a 2-substituted-2-cyclopentenone compound represented by the formula (I-a-20) and then subjecting the 2-substituted-2-cyclopentenone compound to the following optional reactions: an oxidation reaction; a deblocking reaction for a protecting group of a hydroxyl group; a protecting reaction for a hydroxyl group; a hydrolysis reaction of an ester; and an esterification reaction, an amidation reaction, a condensation reaction of a sugar residue and/or a salt forming reaction of a carboxyl group.

Scheme 9:

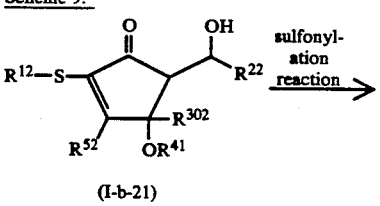
(I-b-21)

sulfonylation reaction →

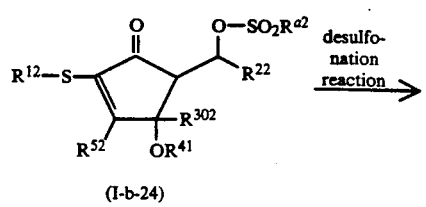
(I-b-24)

desulfonation reaction →

Scheme 9:

-continued

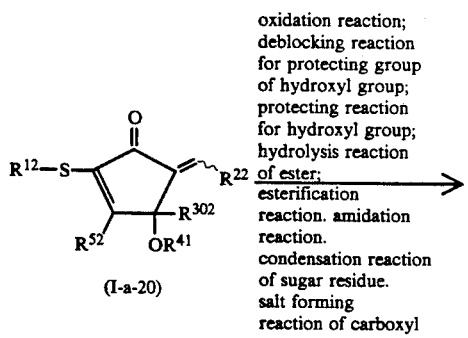

(I-a-20)

oxidation reaction;
deblocking reaction
for protecting group
of hydroxyl group;
protecting reaction
for hydroxyl group;
hydrolysis reaction
of ester;
esterification
reaction. amidation
reaction.
condensation reaction
of sugar residue.
salt forming
reaction of carboxyl
group

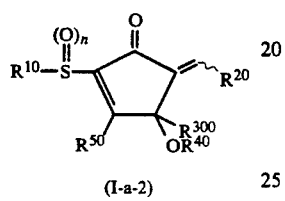

(I-a-2)

wherein $R^{10}$, $R^{12}$, $R^{20}$, $R^{22}$, $R^{300}$, $R^{302}$, $R^{40}$, $R^{41}$, $R^{50}$, $R^{52}$, n, $R^{a2}$ and are each as defined above.

Among the 2-substituted-2-cyclopentenone compounds represented by the above-described formula (I), a 2-substituted-2-cyclopentenone compound represented by the formula (I-a-3) can be produced through the following scheme 10 by subjecting a 2-substituted-2-cyclopentenone compound represented by the formula (I-a-21) belonging to the 2-substituted-2-cyclopentenone compounds represented by the above-described formula (I-a-2) to an elimination reaction under an acidic condition to prepare a 2-substituted-2-cyclopentenone compound represented by the formula (I-a-22) and then subjecting the 2-substituted-2-cyclopentenone compound to the following optional reactions: an oxidation reaction; a deblocking reaction for a protecting group of a hydroxyl group; a protecting reaction for a hydroxyl group, a hydrolysis reaction of an ester; and an esterification reaction, an amidation reaction, a condensation reaction of a sugar residue and/or a salt forming reaction of a carboxyl group.

Scheme 10:

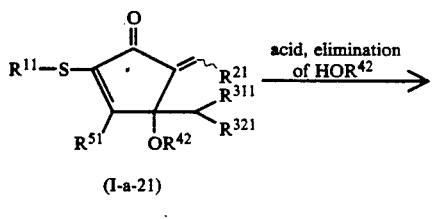

(I-a-21)

Scheme 10:

-continued

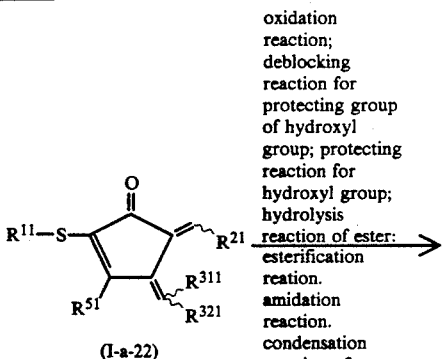

(I-a-22)

oxidation
reaction;
deblocking
reaction for
protecting group
of hydroxyl
group; protecting
reaction for
hydroxyl group;
hydrolysis
reaction of ester;
esterification
reation.
amidation
reaction.
condensation
reaction of sugar
residue.
salt forming
reaction of
carboxyl group

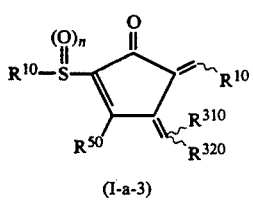

(I-a-3)

wherein $R^{10}$, $R^{11}$, $R^{20}$, $R^{21}$, $R^{50}$, $R^{51}$, and are each as defined above;

$R^{310}$ and $R^{320}$, or $R^{311}$ and $R^{321}$ which may be the same or different from each other stand for a hydrogen atom, a substituted or unsubstituted aliphatic hydrocarbon group having 1 to 9 carbon atoms, alicyclic hydrocarbon group having 4 to 10 carbon atoms or aromatic hydrocarbon group having 6 to 10 carbon atoms or a group wherein $R^{310}$ and $R^{320}$, or $R^{311}$ and $R^{321}$ are combined with each other to form an alicyclic hydrocarbon group having a four to ten-membered ring; and $R^{42}$ stands for a hydrogen atom or a tri($C_1$–$C_7$) hydrocarbon silyloxy group.

Specific examples of the $R^{310}$ and $R^{320}$, or $R^{311}$ and $R^{321}$ include the groups referred to in the specific examples of the $R^{31}$ and $R^{32}$ described above in connection with the above-described formula (I).

Specific examples of the $R^{42}$ include the groups referred to in the specific examples of the $R^4$ described above in connection with the above-described formula (I).

Preferred substituents of the $R^{310}$ and $R^{320}$ are respectively the same substituents as those of the $R^{31}$ and $R^{32}$, and preferred substituents of the $R^{311}$ and $R^{321}$ are respectively the groups described as the substituents of the $R^{31}$ and $R^{32}$ exclusive of the salt of a carboxylic acid.

The compounds of the present invention are administered to patients by methods such as oral administration, suppository administration, dermal administration, nasal administration, subcutaneous administration, intramuscular administration, intravenous injection and intra-arterial injection.

In the case of the oral administration, the compounds of the present invention may be in the form of a solid preparation or a liquid preparation. Examples of the dosage form include tablets, pills, powders, granules, solutions, suspensions and capsules.

Pharmaceutical preparations in the form of a tablet are prepared by a conventional procedure through the use of additives, for example, excipients such as lactose, starch, calcium carbonate, crystalline cellulose and silicic acid; binders such as carboxymethyl cellulose, methyl cellulose, calcium phosphate and polyvinyl pyrrolidone; disintegrators such as sodium alginate, sodium bicarbonate, sodium laurylsulfate and monoglyceride stearate; lubricants such as glycerin; absorbers such as kaolin and colloidal silica; and lubricants such as talc and granular boric acid.

Pharmaceutical preparations in the form of a pill, powder or granule also may be prepared by a conventional procedure through the use of the same additives as those described above.

Liquid preparations, such as a solution and a suspension, also may be prepared by a conventional procedure. Examples of the carrier used include glycerol esters such as tricaprylin, triacetin and iodided poppy seed oil fatty acid esters; water; alcohols such as ethanol; and oleaginous bases such as liquid paraffin, coconut oil, soybean oil, sesame oil and corn oil.

The above-described powders, granules and liquid preparations may be encapsulated in a gelatin or the like.

In the present invention, the pharmaceutically acceptable carrier includes, besides the above-described carriers, auxiliary substances, perfuming agents, stabilizers and preservatives commonly used in the art, according to need.

Examples of the dosage form in the case of the dermal administration include ointments, creams, lotions and solutions.

Examples of the base for the ointment include fatty oils such as castor oil, olive oil, sesame oil and safflower oil; lanolin; white, yellow or hydrophilic petrolatum; wax; higher alcohols such as oleyl alcohol, isostearyl alcohol, octyldodecanol and hexyldecanol; and glycols such as glycerin, diglycerin, ethylene glycol, propylene glycol, sorbitol and 1,3-butanediol. Ethanol, dimethylsulfoxide, polyethylene glycol, etc. may be used as a solubilizing agent for the compound of the present invention. If necessary, it is also possible to use preservatives such as p-oxybenzoates, sodium benzoate, salicylic acid, sorbic acid and boric acid; and antioxidants such as butylhydroxyanisole and dibutylhydroxytoluene.

Absorbefacients, such as diisopropyl adipate, diethyl sebacate, ethyl caproate and ethyl laurate, may be added to thereby promote the percutaneous absorption. Further, to enhance the stabilization, the compounds of the present invention can be used in the form of a compound included in an $\alpha$, $\beta$ or $\gamma$-cyclodextrin.

The ointment can be prepared by a conventional procedure. The cream is preferably in an oil-in-water cream form from the viewpoint of stabilizing the compounds of the present invention. The above-described fatty oils, higher alcohols and glycols are used as the base, and use is made of emulsifiers such as diethylene glycol, propylene glycol, sorbitan monofatty acid ester, polysorbate 80 and sodium laurylsulfate. Further, if necessary, the above-described preservatives, antioxidants, etc. may be added. As with the ointment, in the case of the cream, the compound of the present invention may be used in the form of a compound included in a cyclodextrin or a methylated cyclodextrin. The cream can be prepared by a conventional procedure.

Examples of the lotion include lotions in the form of a suspension, an emulsion and a solution. The lotion in the form of a suspension is prepared through the use of a suspending agent, such as sodium alginate, tragacanth or sodium carboxymethylcellulose, and antioxidants, preservatives, etc. are added thereto according to need.

The lotion in the form of an emulsion is prepared through the use of an emulsifier, such as sorbitan monofatty acid ester, polysorbate 80 or sodium laurylsulfate, by a conventional procedure.

The lotion in the form of a solution is preferably an alcoholic lotion, and the alcoholic lotion is prepared through the use of an alcohol, such as ethanol, by a conventional procedure. Examples of the preparation in the form of a solution include that prepared by dissolving the compound of the present invention in ethanol, and optionally, adding an antioxidant or a preservative, etc. to the solution.

Examples of other dosage forms include dermatologic pastes, cataplasms and aerosols. These preparations can be prepared by a conventional procedure.

The preparation for nasal administration is provided in the form of a liquid or powdery composition. Water, a saline solution, a phosphate buffer and an acetate buffer are used as a base for the liquid formulation, and the liquid formulation may contain surfactants, antioxidants, stabilizers, preservatives and tackifiers. Water absorbing bases are preferred as a base for the powder formulation, and examples thereof include bases easily soluble in water, for example, polyacrylates such as sodium polyacrylate, potassium polyacrylate and ammonium polyacrylate, cellulose lower alkyl ethers, such as methyl cellulose, hydroxyethyl cellulose, hydroxypropyl cellulose and sodium carboxymethyl cellulose, polyethylene glycol polyvinyl pyrrolidone, amylose and pullulan, and bases hardly soluble in water, for example, celluloses such as crystalline cellulose, $\alpha$-cellulose and crosslinked carboxymethyl cellulose, starches such as hydroxypropyl starch, carboxymethyl starch, crosslinked starch, amylose, amylopectin and pectin, proteins such as gelatin, casein, sodium casein, gums such as gum arabic, tragacanth gum and glucomannan, and crosslinked vinyl polymers such as polyvinyl polypyrrolidone, crosslinked polyacrylic acid and its salts, crosslinked polyvinyl alcohol and polyhydroxyethyl methacrylate, which may be used in the form of a mixture thereof. Further, the powder formulation may contain antioxidants, colorants, preservatives, antiseptics, and corrigents, etc. The above-described liquid and powder formulations may be administered by, for example, a spray.

The preparation for injection administration is provided in the form of an aseptic aqueous or non-aqueous solution, suspension or emulsion. In the non-aqueous solution or suspension, propylene glycol, polyethylene glycol, vegetable oils such as olive oil and injectable organic esters such as ethyl oleate and iodided poppy seed oil fatty acid ester are used as a pharmaceutically acceptable carrier. These preparations may contain auxiliary agents such as antiseptics, wetting agents, emulsifiers, dispersants and stabilizers, and may be in a sustained release form. The above-described solutions, suspensions and emulsions can be made aseptic through a proper filtration whereby they are passed through a bacteria retaining filter, incorporation of a germicide, or treatments such as irradiation. Further, an aseptic solid preparation may be prepared and dissolved in an aseptic water or an aseptic solvent for injection immediately before use.

Further, it is also possible to use the compound of the present invention in the form of a compound included in an α, β or γ-cyclodextrin or a methylated cyclodextrin. Further, the compound of the present invention may be used in the form of an injection wherein a fat is bonded to the compound.

Although the effective dose of the compound of the present invention varies depending upon the administration method, age, sex and condition of patients, it is generally 1 to $10^5$ μg/kg/day, preferably about 10 to $10^4$ μg/kg/day.

The 2-substituted-2-cyclopentenone compound of the present invention exhibits, at a low concentration thereof, a strong effect of inhibiting the growth of L1210 leukemia cells and therefore, can be considered for use as an anticancer agent. Moreover, this compound enhances the alkaline phosphatase activity of human osteoblasts, and further, enhances the content of calcium and phosphorus in the human osteoblasts. Therefore, the compound of the present invention is useful as a bone formation accelerator and is effective for the treatment or prevention of osteoporosis and osteomalalacia. Further, the compound of the present invention can be expected to have an antiviral activity and an antimicrobial activity, which renders the compound of the present invention very useful as a pharmaceutical.

EXAMPLES

The present invention will now be described in more detail by way of the following Examples, but is not limited to these Examples.

REFERENCE EXAMPLE 1

First, 10 g of a starting 2-cyclopentenone compound as given in the following Table 1 was dissolved in 10 ml of dichloromethane, 5.71 ml of pyridine was added to the solution and 10.8 g of phenylselenenyl chloride was then added and the mixture stirred for 5 hr. The stirred mixture was poured in an aqueous potassium hydrogen sulfate solution and extracted with ethyl acetate, and the resultant organic phase was washed with an aqueous sodium bicarbonate and a saline solution, and then dried over magnesium sulfate. The dried organic phase was filtered, concentrated, and then subjected to silica gel chromatography to obtain a 2-cyclopentenone compound as given in Table 1. Spectral data ($^1$H-NMR (δ, CDCl$_3$)) are also given in Table 1.

REFERENCE EXAMPLE 2

First, 1.56 g of 1-pentynyl copper was weighed and purged with nitrogen, 5.4 ml of hexamethylphosphoric triamide was added thereto, the mixture was stirred for 20 min, 15 ml of tetrahydrofuran and 40 ml of an ether were added thereto, and the mixture was cooled to −70° C. Then, 7.86 ml of a 1.52M pentane solution of a starting organolithium reagent as given in the following Table 2 was added thereto, the mixture was stirred for 20 min, a solution of 4.0 g of a starting 2-cyclopentenone compound as given in Table 2 in 20 ml of tetrahydrofuran was added thereto, and the mixture was again stirred at −70° to −50° C. for 2 hr. The stirred mixture was poured in an acetate buffer having a pH value of 4, and hexane was added thereto for extraction. The resultant organic phase was washed with a saline solution, dried over magnesium sulfate, and filtered and concentrated to obtain an oily residue. The oily residue was dissolved in 50 ml of dichloromethane, 1 ml of pyridine was added to the solution, then 5 ml of a 30% aqueous hydrogen peroxide was added thereto with stirring and cooling on ice, and the mixture was stirred for 30 min. The stirred mixture was poured in an aqueous potassium hydrogensulfate and extracted with hexane. The resultant organic phase was washed with a saline solution, dried over magnesium sulfate, filtered, concentrated, and then subjected to silica gel chromatography to obtain a 2-cyclopentenone compound (an intended product) as given in the following Table 2.

REFERENCE EXAMPLE 3

First, 157 mg of 1-pentynyl copper was weighed and purged with nitrogen, 545 μl of hexamethylphosphoric triamide was added thereto, and the mixture was stirred for 20 min. Then 5 ml of tetrahydrofuran was added thereto, and the mixture was cooled to −70° C. and added to 1.2 mmol of a starting organolithium compound as given in the following Table 2. The mixture was stirred at −70° C. for 20 min, a solution of 318 mg of a starting 2-cyclopentenone compound given in Table 2 in 10 ml of tetrahydrofuran was added thereto, and the mixture was again stirred for 2 hr. A solution of 283 mg of phenylselenenyl bromide in 10 ml of tetrahydrofuran was added thereto, and the mixture was stirred for 1 hr, and the stirred mixture was poured in an aqueous ammonium chloride and extracted with ethyl acetate. The resultant organic phases were combined with each other, washed with a saline solution, and dried over magnesium sulfate. The dried organic phase was filtered, concentrated, and then subjected to silica gel chromatography to obtain an intermediate. The intermediate was dissolved in 20 ml of dichloromethane, 500 μl of pyridine was added thereto, 2 ml of a 30% aqueous hydrogen peroxide was added thereto, and the mixture was stirred for 1.5 hr. The stirred mixture was poured in potassium hydrogensulfate and extracted with ethyl acetate. The resultant organic phases were combined with each other, washed with an aqueous sodium carbonate solution and a saline solution, in that order, and then dried over magnesium sulfate. The dried organic phase was filtered, concentrated, and then subjected to silica gel chromatography to obtain a 2-cyclopentenone compound as given in Table 2.

REFERENCE EXAMPLES 4 AND 5

The 2-cyclopentenone compounds (intended products) as given in the following Table 2 were prepared in the same manner as that of Reference Example 3.

REFERENCE EXAMPLE 6

First, 61 mg of copper (II) chloride dihydrate and 30 mg of lithium chloride were weighed and heat-dried under a reduced pressure, 5 ml of tetrahydrofuran was added thereto, and the mixture was cooled to −70° C. Then a solution of 955 mg of a starting 2-cyclopentenone as given in the following Table 3 in 10 ml of tetrahydrofuran was added thereto, 3.6 mmol of a Grignard's reagent as given in Table 3 was added thereto, and the mixture was stirred at −70° to −30° C. for 2.5 hr. Then a solution of 944 mg of phenylselenenyl bromide in 10 ml of tetrahydrofuran was added thereto, the mixture was stirred at −30° C. for 1 hr, an aqueous ammonium chloride solution was added thereto, and the mixture was extracted with ethyl acetate. The resultant organic phase was washed with a saline solution, the washed organic layer was concentrated, the resultant oil residue containing an intermediate was dissolved in 40 ml of dichloromethane, 1 ml of pyridine was added thereto, and then 4 ml of a 30% aqueous hydrogen peroxide was added thereto with stirring and cooling on ice, and the mixture was stirred for 1 hr. An aqueous potassium hydrogensulfate solution was added thereto, and the mixture was extracted with ethyl acetate. The resultant organic layer was washed with an aqueous sodium bicarbonate solution and a saline solution and dried over magnesium sulfate. The dried organic phase was filtered, concentrated and then subjected to silica gel chromatography to obtain a 2-cyclopentenone compound (an intended product) given in Table 3.

REFERENCE EXAMPLES 7 TO 13

The 2-cyclopentenone compounds as given in the following Table 3 were prepared in the same manner as that of Reference Example 6.

REFERENCE EXAMPLE 14

First, 1.3 ml of hexamethylphosphorous triamide was added to 313 mg of 1-pentynyl copper, the mixture was stirred for 20 min, 5 ml of an ether was added thereto, and the mixture was cooled to $-70°$ C. and added to 2.5 mmol of a starting organolithium compound as given in the following Table 4. Then the mixture was stirred at $-70°$ C. for 15 min, a solution of 453 mg of a starting 2-cyclopentenone compound given in Table 4 in 10 ml of an ether was added thereto, 300 µl of a boron trifluoride-ether complex was further added thereto, and the mixture was stirred at $-70°$ to $-30°$ C. for 1 hr. Then a solution of 375 mg of an aldehyde compound given in Table 1 in 10 ml of an ether was added thereto, the mixture was stirred at $-30°$ C. for 1 hr, an aqueous ammonium chloride was added thereto, and the mixture was extracted with ethyl acetate. The resultant organic phase was washed with a saline solution and dried over magnesium sulfate, the dried organic phase was filtered and concentrated, the resultant oily residue was dissolved in 40 ml of dichloromethane, 400 µl of 1,8-diazabicyclo[5.4.0.]-7-undecene was added thereto, and the mixture was stirred for 5 hr. Then an aqueous potassium hydrogensulfate solution was added thereto, and the mixture was extracted with ethyl acetate. The resultant organic phase was washed with a saline solution and then dried over magnesium sulfate. The dried organic phase was filtered, concentrated and then subjected to silica gel chromatography to obtain a 2-cyclopentenone compound as given in Table 4.

REFERENCE EXAMPLES 15 TO 17

The 2-cyclopentenone compounds as given in the following Table 4 were prepared in the same manner as that of Reference Example 14.

EXAMPLE 1

First, 3.3 g of a starting 2-cyclopentenone compound as given in the following Table 5 was dissolved in 50 ml of methanol, 5.0 ml of a 30% aqueous hydrogen peroxide was added thereto with stirring and cooling on ice, and 500 µl of a 1N aqueous sodium hydroxide solution was added thereto. Then the mixture was stirred for 3.5 hr, an aqueous ammonium chloride solution was added thereto, and the mixture was extracted with ethyl acetate. The resultant organic phase was washed with a saline solution and dried over magnesium sulfate, and the dried organic phase was filtered, concentrated and then subjected to silica gel chromatography to obtain a 2,3-epoxycyclopentanone compound as given in Table 5.

EXAMPLES 2 TO 39

The 2,3-cyclopentanone compounds as given in the following Table 5 were prepared in the same manner as that of Example 1.

EXAMPLE 40

First, 9.2 mg of sodium thiomethoxide was dissolved in 2 ml of methanol, 11.2 µl of acetic acid was added thereto with stirring and cooling on ice, 36.4 µl of triethylamine was added thereto, 19 mg of a 2,3-epoxycyclopentanone compound as given in the following Table 6 was added, and the mixture was stirred for 5 hr. Then an aqueous ammonium chloride solution was added thereto, and the mixture was extracted with ethyl acetate, and the resultant organic phase was washed with a saline solution and dried over magnesium sulfate, and the dried organic phase was filtered, concentrated and then subjected to silica gel chromatography to obtain a 2-substituted-2-cyclopentenone compound as given in Table 6.

EXAMPLE 41

A 2-substituted-2-cyclopentenone compound as given in the following Table 6 was prepared in the same manner as that of Example 40.

REFERENCE EXAMPLES 18 TO 20

The 2-Substituted-2-cyclopentenone compounds as given in the following Table 7 were prepared in the same manner as that of Example 40.

EXAMPLE 42

First, 1.5 g of sodium thiomethoxide was dissolved in 80 ml of methanol, 1.8 ml of acetic acid was added thereto with cooling on ice, the mixture was stirred for 5 min, 4.8 ml of triethylamine was added thereto, and a solution of 1.38 g of a starting 2,3-epoxycyclopentanone compound as given in the following Table 6 in 20 ml of methanol was added thereto. Then the mixture was stirred for 4 hr, water was added thereto, and the mixture was extracted with ethyl acetate. The resultant organic phases were combined with each other, washed with a saline solution and dried over magnesium sulfate. The dried organic phase was filtered and concentrated, the resultant oily residue was dissolved in 15 ml of dimethylformamide, 1.15 g of imidazole and 1.04 ml of chlorotrimethylsilane were added thereto with stirring and cooling on ice, and the mixture was stirred at 0° C. for 3 hr. Water and hexane were added thereto for extraction, and the resultant organic phase was washed with a saline solution. The organic phase was dried over sodium sulfate, filtered, concentrated and then subjected to a silica gel chromatography to obtain a 2-substituted-2-cyclopentenone compound as given in Table 6.

EXAMPLES 43 TO 45

The 2-Substituted-2-cyclopentenone compounds as given in the following Table 6 were prepared in the same manner as that of Example 42.

REFERENCE EXAMPLES 21 TO 23

The 2-Substituted-2-cyclopentenone compounds as given in the following Table 7 were prepared in the same manner as that of Example 42.

EXAMPLE 46

First, 5 g of a starting 2,3-epoxycyclopentanone compound as given in the following Table 8 was dissolved in 100 ml of methanol, 10 ml of triethylamine was added thereto, 1.2 g of a thiol compound was added thereto, and the mixture was stirred for 2 hr. The reaction mixture was poured in an aqueous potassium hydrogensulfate solution and extracted with ethyl acetate, and the extract was washed with a saline solution and dried over magnesium sulfate, and the dried extract was filtered, concentrated and then subjected to silica gel chromatography to obtain a 2-substituted-2-cyclopentenone compound as given in Table 8.

EXAMPLES 47 TO 76

The 2-Substituted-2-cyclopentenone compounds as given in the following Table 8 were prepared in the same manner as that of Example 46.

REFERENCE EXAMPLES 24 TO 32

The 2-Substituted-2-cyclopentenone compounds as given in the following Table 9 were prepared in the same manner as that of Example 46.

REFERENCE EXAMPLES 33 TO 40

The 2-Substituted-2-cyclopentenone compounds as given in the following Table 11 were prepared in the same manner as that of Example 77.

EXAMPLE 77

First, 1.8 g of a starting 2,3-epoxycyclopentanone compound as given in the following Table 10 was dissolved in 15 ml of methanol, 1.0 ml of triethylamine was added thereto, 790 mg of a thiol compound was added thereto, and the mixture was stirred for 1.5 hr. The reaction mixture was poured in an aqueous potassium hydrogensulfate solution and extracted with ethyl acetate, and the resultant organic phase was washed with a saline solution and dried over magnesium sulfate. The dried organic phase was filtered and concentrated, the resultant crude oily residue was dissolved in 20 ml of dimethylformamide, and 1.5 g of imidazole was added thereto with stirring and cooling on ice. Then 1.4 g of chlorotrimethylsilane was added thereto, the mixture was stirred at 0° C. for 5 hr, and water and hexane were added thereto for extraction. The resultant organic phase was washed with a saline solution, dried over sodium sulfate, filtered, concentrated and then subjected to silica gel chromatography to obtain a 2-substituted-2-cyclopentenone compound as given in Table 10.

EXAMPLES 78 TO 113

The 2-Substituted-2-cyclopentenone compounds as given in the following Table 10 were prepared in the same manner as that of Example 77.

EXAMPLE 114

First, 65 mg of a starting 2,3-epoxycyclopentanone compound as given in the following Table 12 was dissolved in 2 ml of methanol, 150 μl of triethylamine and 25 mg of cyclohexanethiol were added thereto, the mixture was stirred for 4 hr, an aqueous ammonium chloride solution was added thereto, and the mixture was extracted with ethyl acetate. The resultant organic phase was washed with a saline solution and dried over magnesium sulfate, and the dried organic phase was filtered, concentrated and then subjected to silica gel chromatography to obtain two 2-substituted-2-cyclopentenone compounds as given in Table 12.

EXAMPLE 115

First, 216 mg of a starting 2-substituted-2-cyclopentenone compound as given in the following Table 13 was weighed, 2.5 ml of an ether and 2.5 ml of hexane were added thereto, 157 μl of diisopropylethylamine was added thereto, and the mixture was cooled to −70° C. Then, 750 μl of a 1M dichloromethane solution of dibutylboron trifluoromethanesulfonate was added thereto, the mixture was stirred for 1 hr, a solution of 373 mg of a starting aldehyde compound in 10 ml of an ether was cooled to −70° C. and added thereto, and the mixture was stirred at −70° to −25° C. for 4 hr. Then the stirred mixture was dried over magnesium sulfate, filtered, concentrated and then subjected to silica gel chromatography to obtain a 2-substituted-2-cyclopentenone compound (an intended product) as given in Table 13.

EXAMPLES 116 TO 202

The 2-Substituted-2-cyclopentenone compounds (intended products) as given in the following Table 13 were prepared in the same manner as that of Example 115.

REFERENCE EXAMPLES 41 TO 45

The 2-Substituted-2-cyclopentenone compounds (intended products) as given in the following Table 14 were prepared in the same manner as that of Example 115.

EXAMPLE 203

First, 861 mg of a starting 2-substituted-2-cyclopentenone compound as given in the following Table 15 was dissolved in 5 ml of tetrahydrofuran, the solution was cooled to −70° C., 1.67 ml of a 1.5M tetrahydrofuran solution of lithium diisopropylamide was added thereto, and the mixture was stirred for 30 min. Then a solution of 526 mg of a starting aldehyde compound in 5 ml of tetrahydrofuran was added thereto, the mixture was stirred at −70° to −40° C. for 3 hr, the reaction mixture was poured in an aqueous ammonium chloride solution, and the mixture was extracted with ethyl acetate. The resultant organic phase was washed with a saline solution and dried over magnesium sulfate, and the dried organic phase was filtered, concentrated and then subjected to silica gel chromatography to obtain a 2-substituted-2-cyclopentenone compound (an intended product) as given in Table 15.

EXAMPLES 204 TO 207

The 2-Substituted-2-cyclopentenone compounds as given in the following Table 15 were prepared in the same manner as that of Example 203.

EXAMPLE 208

First, 60 mg of a starting 2-substituted-2-cyclopentenone compound as given in the following Table 16 was dissolved in 3 ml of dichloromethane, 200 μl of pyridine was added thereto, 100 μl of acetyl chloride was added thereto, and the mixture was stirred for 16 hr. Then the mixture was poured in an aqueous potassium hydrogensulfate solution, the mixture was extracted with ethyl acetate, and the resultant organic phase was washed with an aqueous sodium bicarbonate solution and a saline solution and then dried over magnesium sulfate. The dried organic phase was filtered, concentrated and then subjected to silica gel chromatography to obtain a 2-substituted-2-cyclopentenone compound (an intended product) as given in Table 16.

EXAMPLES 209 TO 219

The 2-Substituted-2-cyclopentenone compounds as given in the following Table 16 were prepared in the same manner as that of Example 208.

EXAMPLE 220

First, 60 mg of a starting 2-substituted-2-cyclopentenone compound as given in the following Table 16 was dissolved in 3 ml of dichloromethane, 500 μl of pyridine was added thereto, 300 μl of methoxycarbonyl chloride was added thereto, and the mixture was stirred for 16 hr. Then the mixture was poured in an aqueous potassium hydrogensulfate solution, the mixture was extracted with ethyl acetate, and the resultant organic phases were combined with each other, washed with an aqueous sodium bicarbonate solution and a saline solution and then dried over magnesium sulfate. The dried organic phase was filtered, concentrated and then subjected to silica gel chromatography to obtain a 2-substituted-2-cyclopentenone compound (an intended product) as given in Table 16.

EXAMPLES 221 TO 222

The 2-Substituted-2-cyclopentenone compounds as given in the following Table 16 were prepared in the same manner as that of Example 220.

EXAMPLE 223

First, 60 mg of a starting 2-substituted-2-cyclopentenone compound as given in the following Table 16 was dissolved in 3 ml of dichloromethane, 200 μl of pyridine was added thereto, 300 μl of isopropoxycarbonyl chloride was added thereto, and the mixture was stirred for 16 hr. Then the mixture was poured in an aqueous potassium hydrogensulfate solution, the mixture was extracted with ethyl acetate and the resultant organic phases were combined with each other, washed with an aqueous sodium bicarbonate solution and a saline solution and then dried over magnesium sulfate. The dried organic phase was filtered, concentrated and then subjected to silica gel chromatography to obtain a 2-substituted-2-cyclopentenone compound (an intended product) as given in Table 16.

EXAMPLES 224 TO 231

The 2-Substituted-2-cyclopentenone compounds as given in the following Table 16 were prepared in the same manner as that of Example 223.

EXAMPLE 232

First, 182 mg of a starting 2-substituted-2-cyclopentenone compound as given in the following Table 17 was weighed and purged with nitrogen, 15 ml of tetrahydrofuran was added thereto, the mixture was cooled to $-70°$ C., 600 μl of a 1.5M cyclohexane solution of lithium diisopropylamide was added thereto, and the mixture was stirred at $-70°$ C. for 40 min. Then 1 ml of N-methyl pyrrolidone was added thereto, a solution of 251 mg of triphenyltin chloride in 10 ml of tetrahydrofuran was added thereto, the mixture was stirred at $-70°$ C. for 1 hr, a solution of 400 mg of a starting organoiodide in 10 ml of tetrahydrofuran was added thereto, the mixture was stirred at $-40°$ to $-10°$ C. for 19 hr and poured in an aqueous potassium hydrogensulfate solution, and the mixture was extracted with ethyl acetate. The resultant organic phases were combined with each other, washed with an aqueous sodium bicarbonate solution and a saline solution and then dried over magnesium sulfate, and the dried organic phase was filtered, concentrated and then subjected to silica gel chromatography to obtain a 2-substituted-2-cyclopentenone compound (an intended product) as given in Table 17.

EXAMPLES 233 TO 237

The 2-Substituted-2-cyclopentenone compounds as given in the following Table 17 were prepared in the same manner as that of Example 232.

EXAMPLE 238

First, Dimethylaminopyridine (1.5 g) was added to a solution of 3.5 g of a starting 2-substituted-2-cyclopentenone compound as given in the following Table 18 in dichloromethane (30 ml), the mixture was cooled to 0° C., 0.6 ml of methanesulfonyl chloride was dropwise added thereto, and the mixture was stirred at room temperature for 13 hr. Then ethyl acetate and an aqueous potassium hydrogensulfate were added to the reaction mixture to extract the product into an organic phase, the extract was washed with an aqueous sodium bicarbonate solution and a saline solution, dried over magnesium sulfate, filtered and concentrated, and the concentrate was subjected to silica gel chromatography to obtain a 2-substituted-2-cyclopentenone compound (an intended product) as given in Table 18.

EXAMPLES 239 TO 348

The 2-Substituted-2-cyclopentenone compounds as given in the following Table 18 were prepared in the same manner as that of Example 238.

EXAMPLE 349

First, 300 mg of a starting 2-substituted-2-cyclopentenone compound as given in the following Table 19 was dissolved in 15 ml of acetonitrile, 2 ml of pyridine was added thereto, 1 ml of a hydrogen fluoride-pyridine solution was added thereto with stirring and cooling on ice, and the mixture was stirred at 0° C. to room temperature for 16 hr. Then the stirred mixture was poured in an aqueous potassium hydrogensulfate solution, the mixture was extracted with ethyl acetate, and the resultant organic phases were combined with each other, washed with a saline solution and then dried over magnesium sulfate. The dried organic phase was filtered, concentrated and then subjected to silica gel chromatography to obtain a 2-substituted-2-cyclopentenone compound (an intended product) as given in Table 19.

EXAMPLES 350 TO 511

The 2-Substituted-2-cyclopentenone compounds as given in the following Table 19 were prepared in the same manner as that of Example 349.

EXAMPLES 512 AND 513

The Two 2-substituted-2-cyclopentenone compounds as given in the following Table 20 were prepared in the same manner as that of Example 349.

EXAMPLE 514

First, 50 mg of a starting 2-substituted-2-cyclopentenone compound as given in the following Table 20 was dissolved in 5 ml of a mixed solvent comprising acetic acid, tetrahydrofuran and water in a ratio of 2:1:1, and the mixture was stirred for 5 hr. Then the the solution was neutralized with sodium bicarbonate and extracted with ethyl acetate, and the resultant organic phases were combined with each other, washed with a saline solution, dried over magnesium sulfate, filtered, concentrated, and then subjected to silica gel chromatography to obtain a 2-substituted-2-cyclopentenone compound (an intended product) as given in Table 20.

EXAMPLES 515

A 2-substituted-2-cyclopentenone compound as given in the following Table 20 was prepared in the same manner as that of Example 514.

EXAMPLE 516

First, 5 mg of a starting 2-substituted-2-cyclopentenone compound as given in the following Table 20 was dissolved in 1 ml of methanol, 0.5 $\mu$l of acetic acid was added thereto, and the mixture was stirred for 24 hr. Then an aqueous sodium bicarbonate solution was added thereto, and the mixture was extracted with ethyl acetate. The extract was dried over magnesium sulfate, filtered, concentrated and then subjected to a silica gel chromatography to obtain a 2-substituted-2-cyclopentenone compound (an intended product) as given in Table 20.

EXAMPLE 517

First, 30 mg of a starting 2-substituted-2-cyclopentenone compound as given in the following Table 20 was dissolved in 5 ml of ethanol, 5 $\mu$l of acetic acid was added thereto, and the mixture was stirred for 40 hr. Then an aqueous sodium bicarbonate solution was added thereto, the mixture was extracted with ethyl acetate, and the extract was dried over magnesium sulfate, filtered, concentrated and then subjected to silica gel chromatography to obtain a 2-substituted-2-cyclopentenone compound (an intended product) as given in Table 20.

EXAMPLE 518

First, 36 mg of the 2-substituted-2-cyclopentenone compound as given in the following Table 20 was dissolved in 2 ml of dichloromethane, 200 $\mu$l of triethylamine was added thereto, 20 $\mu$l of acetyl chloride was added while stirring and cooling on ice, and the mixture was stirred at 0° C. for 2 hr. Then a saline solution was added thereto, the mixture was extracted with ethyl acetate, and the extract was dried over magnesium sulfate, filtered, concentrated and then subjected to silica gel chromatography to obtain two 2-substituted-2-cyclopentenone compounds (intended products) as given in Table 20.

EXAMPLE 519

First, 500 mg of a starting 2-substituted-2-cyclopentenone compound as given in the following Table 20 was dissolved in 20 ml of acetone, 220 ml of a 0.1M phosphate buffer having a pH value of 8 was added to the solution, 24 mg of pig liver esterase was added thereto with stirring, and the mixture was stirred at 30° to 35° C. for 6 days. Then a 0.1N hydrochloric acid was added to adjust the pH value to 4, ammonium sulfate was added to saturate the solution, ethyl acetate was added thereto, and the mixture was filtered. The filtrate was extracted with ethyl acetate and the resultant organic phases were combined with each other and then washed with a saline solution, and the washed organic phase was dried over magnesium sulfate, filtered, concentrated and then subjected to silica gel chromatography to obtain an 2-substituted-2-cyclopentenone compound (an intended product) as given in Table 20.

EXAMPLE 520

A 2-substituted-2-cyclopentenone compound as given in the following Table 20 was prepared in the same manner as that of Example 519.

EXAMPLE 521

First, 70 mg of a starting 2-substituted-2-cyclopentenone compound as given in the following Table 20 was dissolved in 5 ml of dichloromethane, and the solution was cooled to −70° C., 15 $\mu$l of triethylamine was added, and 10 $\mu$l of isobutoxycarbonyl chloride was then added thereto. Then the mixture was stirred at room temperature for 10 min, the temperature of the mixture was returned to room temperature, 500 $\mu$l of an aqueous ammonia was added thereto, the mixture was stirred for 30 min, an aqueous ammonium chloride solution was added thereto, and the mixture was extracted with dichloromethane. The organic phase was dried over magnesium sulfate, filtered and concentrated, the resultant oily residue was dissolved in a mixed solvent comprising 3 ml of acetic acid, 2 ml of tetrahydrofuran and 2 ml of water, and the mixture was stirred for 24 hr. The mixture was concentrated and extracted with an aqueous sodium hydrogencarbonate solution and ethyl acetate, and the resultant organic phases were combined with each other and washed with a saline solution. The washed organic phase was dried over magnesium sulfate, filtered, concentrated and then subjected to silica gel chromatography to obtain a 2-substituted-2-cyclopentenone compound (an intended product) as given in Table 20.

EXAMPLE 522

First, 90 mg of a starting 2-substituted-2-cyclopentenone compound as given in the following Table 20 was dissolved in 3 ml of dichloromethane, 45 mg of 1-methyl-2-fluoropyridinium methylsulfate, 15 mg of cyclohexylmethylamine and 20 mg of triethylamine were added to the solution, and the mixture was stirred for 18 hr. Then water was added, the mixture was extracted with dichloromethane and dried over magnesium sulfate, the dried extract was filtered and concentrated, the resultant oily residue was dissolved in 2 ml of acetonitrile, 200 $\mu$l of pyridine was added thereto, 200 $\mu$l of a hydrogen fluoride-pyridine solution was added thereto, and the mixture was stirred for 16 hr. An aqueous potassium hydrogensulfate solution was added thereto, the mixture was extracted with ethyl acetate, and the resultant organic phase was washed with an aqueous sodium hydrogencarbonate and a saline solution, dried over magnesium sulfate, filtered, and then subjected to silica gel chromatography to obtain a 2-substituted-2-cyclopentenone compound (an intended product) as given in Table 20.

EXAMPLE 523

A solution of 30 mg of a starting 2-substituted-2-cyclopentenone compound as given in the following Table 20 in dichloromethane (4 ml) was cooled to 0° C., a solution of 3-chloroperbenzoic acid (13 mg) in dichloromethane (3 ml) was dropwise added thereto, the mixture was stirred at 0° C. for 1 hr, and ethyl acetate and an aqueous sodium hydrogen carbonate solution were added thereto to extract the product into an organic phase. The extract was successively washed with a saline solution, an aqueous ammonium chloride and a saline solution, dried over magnesium sulfate, filtered and then concentrated, and the concentrate was subjected to silica gel chromatography to obtain a 2-substituted-2-cyclopentenone compound (an intended product) as given in Table 20.

EXAMPLE 524

A 2-substituted-2-cyclopentenone compound as given in the following Table 20 was prepared in the same manner as that of Example 523.

EXAMPLE 525

A solution of 20 mg of a starting 2-substituted-2-cyclopentenone compound as given in the following Table 20 in dichloromethane (1.5 ml) was cooled to 0° C., a solution of 3-chloroperbenzoic acid (15.7 mg) in dichloromethane (1 ml) was dropwise added thereto, the mixture was stirred at 0° C. for 2 hr, and ethyl acetate and an aqueous sodium hydrogen carbonate solution were added thereto to extract the product into an organic phase. The extract was successively washed with an aqueous ammonium chloride and a saline solution, dried over magnesium sulfate, filtered and then concentrated, and the concentrate was subjected to silica gel chromatography to obtain a 2-substituted-2-cyclopentenone compound (an intended product) as given in Table 20.

EXAMPLE 526

A 2-substituted-2-cyclopentenone compound as given in the following Table 20 was prepared in the same manner as that of Example 525.

EXAMPLE 527

First, 320 mg of a starting 2-substituted-2-cyclopentenone compound as given in the following Table 20 was dissolved in 25 ml of dichloromethane, 120 μl of triethylamine was added to the solution, the mixture was cooled to −20° C., 110 μl of pivaloyl chloride was added thereto, the mixture was stirred for 2 hr, 95 mg of 2-mercaptothiazoline and 9 mg of 4-dimethylaminopyridine were added thereto, and the mixture was again stirred for 2 hr. Then an aqueous sodium hydrogen carbonate solution was added thereto, the mixture was extracted with ethyl acetate, the resultant organic phase was washed with an aqueous potassium hydrogensulfate solution, an aqueous sodium hydrogen carbonate solution, and a saline solution, and dried over magnesium sulfate. The dried organic phase was filtered, concentrated and then subjected to silica gel chromatography to obtain a 2-substituted-2-cyclopentenone compound (an intended product) as given in Table 20.

EXAMPLE 528

First, 85 mg of a starting 2-substituted-2-cyclopentenone compound as given in the following Table 20 was dissolved in 4 ml of pyridine, 85 mg of D-glucose was added thereto. 3 mg of sodium hydride (60% in oil) and 3 mg of 4-dimethylaminopyridine was added thereto, and the mixture was stirred for 16 hr. Then 5 ml of a 0.1 M phosphate buffer having a pH value of 7 was added thereto, and mixture was extracted with butanol, and the organic layer was washed with a saline solution, concentrated and then subjected to silica gel chromatography to obtain a 2-substituted-2-cyclopentenone compound (an intended product) as given in Table 20.

EXAMPLE 529

First, 63 mg of a starting 2-substituted-2-cyclopentenone compound as given in the following Table 20 was dissolved in 4 ml of pyridine, and 70 mg of D-xylose was added thereto, 2.5 mg of sodium hydride (60% in oil) was added thereto, and the mixture was stirred for 16 hr. Then 5 ml of a 0.1M phosphate buffer having a pH value of 7 was added thereto, the mixture was extracted with butanol, and the organic layer was washed with a saline solution, concentrated and then subjected to silica gel chromatography to obtain a 2-substituted-2-cyclo-pentenone compound (an intended product) as given in Table 20.

TABLE 1

| Ref. Ex. No. | Starting Compd. (2-Cyclopentenones) | 2-Cyclopentenones | Yield (%) | NMR(δ, CDCl₃) |
|---|---|---|---|---|
| 1 | 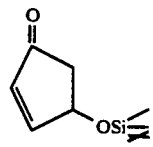 | 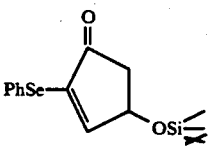 | 100 | 0.04(s, 3H), 0.05(s, 3H), 2.40(dd, 1H, J=18.3, 2.2Hz), 2.84(dd, 1H, J=18.3, 5.9Hz), 4.86(dt, 1H, J=5.7, 2.4Hz), 6.73(d, 1H, J=2.4Hz), 7.1–7.8(m, 6H) |

TABLE 2

| Ref. Ex. No. | Starting Compd. 2-Cyclopentenones | Organolithium reagent | 2-Cyclopentenones | Yield (%) | NMR (δ, CDCl₃) |
|---|---|---|---|---|---|
| 2 | PhSe-substituted 2-cyclopentenone with OSi group | t-BuLi | 2-cyclopentenone with OSi group | 81 | 0.12(s, 3H), 0.16(s, 3H), 0.91(s, 9H), 1.26(s, 9H), 2.31(dd, 1H, J=7.9, 2.6Hz), 2.70(dd, 1H, J=7.9, 5.8Hz), 5.04(ddd, 1H, J=5.8, 2.6, 1.0Hz), 5.96(d, 1H, J=1.0Hz) |
| 3 | 2-cyclopentenone with OSi and (CH₂)₄OPh | n-BuLi | 2-cyclopentenone with OSi, (CH₂)₄OPh, and n-Bu | 53 | 0.10(s, 9H), 0.7–1.05(m, 3H), 1.05–2.8 (m, 12H), 2.56(s, 2H), 3.93(t, 2H, J=5.8Hz), 5.90(t, 1H, J=1.5Hz), 6.7–7.05(m, 3H), 7.1–7.5 (m, 2H) |
| 4 | 2-cyclopentenone with OSi and 3,4-dimethoxyphenylpropyl | MeLi | 2-cyclopentenone with OSi, Me, and 3,4-dimethoxyphenylpropyl | 68 | 0.08(s, 9H), 1.5–2.0(m, 4H), 2.19(d, 3H, J=13Hz), 2.3–2.8(m, 4H), 3.80(s, 6H), 5.93(brs, 1H), 6.4–6.9 (m, 3H) |
| 5 | 2-cyclopentenone with Me and OSi | t-BuLi | 2-cyclopentenone with Me and OSi | 33 | 0.07(s, 9H), 1.26(s, 12H), 2.57(s, 2H), 5.94(d, 1H, J=1.0Hz) |

TABLE 3

| Ref. Ex. No. | Starting Compd. 2-Cyclopentenones | Grignard's reagent | 2-Cyclopentenones | Yield (%) | NMR(δ, CDCl₃) |
|---|---|---|---|---|---|
| 6 | [cyclopentenone with OSi≡X and (CH₂)₃OPh substituent] | EtMgBr | [4-ethyl-4-OSi-5-(CH₂)₃OPh cyclopentenone] | 31 | 0.10(s, 9H), 1.17(t, 3H, J=7.5Hz), 2.57(s, 2H), 3.93(t, 2H, J=5.8Hz), 5.90(brs, 1H), 6.7-7.1(m, 3H), 7.1-7.5(m, 2H) |
| 7 | Same as above | Ph(CH₂)₅MgBr | [cyclopentenone with Ph(CH₂)₅ group and (CH₂)₃OPh] | 47 | 0.08(s, 9H), 1.1-3.1(m, 19H), 2.55(s, 2H), 3.93(t, 2H, J=5.8Hz), 5.92(brs, 1H),6.7-7.5(m, 10H) |
| 8 | Same as above | [prenyl MgBr structure] | [cyclopentenone with prenyl chain and (CH₂)₃OPh] | 38 | 0.08(s, 9H), 0.85(brd, 3H, J=4.3Hz), (1.0-2.7(m, 21H), 2.55(s, 2H), 3.91(t, 2H, J=6.0Hz), 4.8-5.2(m, 1H), 5.90(brs, 1H), 6.7-7.1(m, 3H), 7.1-7.5(m, 2H) |
| 9 | [cyclopentenone with OSi and propyl] | EtMgBr | [cyclopentenone with ethyl, propyl, OSi] | 61 | 0.09(s, 9H), 0.7-1.0(m, 3H), 1.18(t, 3H, J=7.6Hz), 1.2-1.9(m, 6H), 2.57(s, 2H), 2.4-2.7(m, 2H), 5.91(brs, 1H) |
| 10 | Same as above | [cyclohexyl MgBr] | [cyclopentenone with cyclohexyl and propyl, OSi] | 32 | 0.09(s, 9H), 0.7-1.0(m, 3H), 1.1-1.9(m, 16H), 2.55(s, 2H), 2.4-2.7(m, 1H), 5.90(brs, 1H) |

TABLE 3-continued

| Ref. Ex. No. | Starting Compd. 2-Cyclopentenones | Grignard's reagent | 2-Cyclopentenones | Yield (%) | NMR(δ, CDCl₃) |
|---|---|---|---|---|---|
| 11 | (structure) | PrMgBr | (structure) | 42 | 0.07(s, 9H), 0.7–1.0(m, 6H), 1.1–2.0 (m, 6H), 2.2–2.8(m, 6H), 5.90(brs, 1H) |
| 12 | (structure) | (cyclohexylpropyl)MgBr | (structure) | 39 | 0.0–0.1(m, 15H), 0.89(s, 9H), 1.0–2.0 (m, 26H), 2.4–2.8(m, 4H), 5.4–6.1 (m, 3H) |
| 13 | (structure) | i-PrMgBr | (structure) | 27 | 0.09(s, 9H), 0.7–1.2(m, 15H), 1.2–2.1 (m, 12H), 2.53(s, 2H), 2.4–2.7 (m, 1H), 5.88(s, 1H) |

TABLE 4

| Ref. Ex. No. | Starting Compd. 2-Cyclopentenones | Organolithium reagent | Aldehydes | 2-Cyclopentenones | Yield (%) | NMR (δ, CDCl₃) |
|---|---|---|---|---|---|---|
| 14 | [cyclopentenone with propyl and OSi group] | [Li-vinyl with pentyl and OSi group] | [aldehyde with CO₂Me] | [cyclopentenone product with OH, CO₂Me, OSi, propyl] | 35 | 0–0.1(m, 6H), 0.89(s, 9H), 0.7–1.1 (m, 6H), 1.1–2.7(m, 26H), 3.0–3.3 (m, 1H), 3.60(s, 3H), 3.6–4.1(m, 2H), 5.4–5.8(m, 2H), 5.92(brs, 1H) |
| 15 | Same as above | [Li with cyclopentyl and OSi group] | [alkyne aldehyde with CO₂Me] | [product with OH, cyclopentyl, CO₂Me, OSi, propyl] | 28 | 0.0–0.1(m, 6H), 0.88(s, 9H), 0.7–1.0 (m, 3H), 1.0–2.9(m, 23H), 3.1–3.3 (m, 1H), 3.69(s, 3H), 3.5–3.8 (m, 1H), 4.6–5.0(m, 1H), 5.4–5.9 (m, 3H) |
| 16 | [cyclopentenone with PhO-propyl and OSi group] | MeLi | [PhCH₂CH₂CHO] | [cyclopentenone product with OH, Ph, Me, PhO-propyl] | 26 | 0.86(d, 1H, J=6.5Hz), 1.3–2.1(m, 6H), 2.5–3.0(m, 7H), 3.5–4.1(m, 3H), 5.9(brs, 1H), 6.7–7.5(m, 10H) |
| 17 | [cyclopentenone with Me, OSi group] | t-BuLi | [nonanal] | [cyclopentenone product with OH, nonyl, X, Me] | 16 | 0.7–1.1(m, 3H), 0.88(s, 9H), 1.1–1.9 (m, 16H), 2.18(d, 3H, J=1.5Hz), 2.6–2.9(m, 3H), 3.5–3.8(m, 1H), 5.9 (m, 1H) |

TABLE 5

| Ex. No. | Starting Compd. (2-Cyclopentenones) | 2,3-Epoxycyclopentanones | Yield (%) | NMR(δ, CDCl₃) |
|---|---|---|---|---|
| 1 | | | 74 | −0.03(3H, s), 0.00(3H, s), 0.84 (9H, s), 0.7–1.1(3H, brt), 1.1–2.3 (20H, m), 3.4–3.5(1H, m), 3.61(3H, s), 3.68(1H, brs), 3.6–4.1(2H, m), 5.5–5.7(2H, m) |
| 2 | | | 51 | 0.00(3H, s), 0.05(3H, s), 0.89(9H, s), 1.2–2.0(11H, m), 2.0–2.6(5H, m), 3.1–3.3(1H, m), 3.50(1H, d, J=2.5Hz), 3.69(3H, s), 3.77(1H, d, J=2.5Hz), 3.8–4.05(1H, m), 4.6–4.9 (1H, m), 5.3–5.9(2H, m) |
| 3 | | | 63 | 0.01(3H, s), 0.06(3H, s), 0.89(9H, s), 0.7–1.1(6H, m), 1.1–2.7(17H, m), 3.0–3.3(1H, m), 3.49(1H, d, J=2.5Hz), 3.68(3H, s), 3.79(1H, d, J=2.5Hz), 3.6–4.6(2H, m), 5.4–5.9 (2H, m), 5.87(1H, d, J=16.0Hz), 7.03(1H, dt, J=16.0, 7.2Hz) |
| 4 | | | 43 | 1.1–2.7(29H, m), 2.9–3.3(1H, m), 3.3–4.4(5H, m), 3.69(3H, s), 4.5–5.0(2H, m), 5.3–5.8(2H, m) |
| 5 | | | 69 | 0.7–1.1(3H, m), 1.1–3.1(9H, m), 3.3–3.6(1H, m), 3.49(1H, d, J=2.6 Hz), 3.76(1H, d, J=2.6Hz), 4.3–4.7 (1H, m), 6.4–6.8(1H, m), 7.0–8.0 (5H, m) |

TABLE 5-continued
| Ex. No. | Starting Compd. (2-Cyclopentenones) | 2,3-Epoxycyclopentanones | Yield (%) | NMR(δ, CDCl₃) |
|---|---|---|---|---|
| 6 | 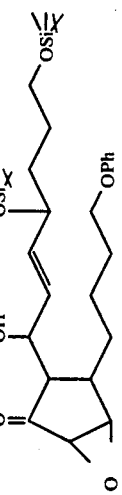 | 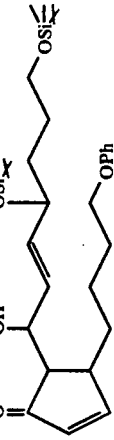 | 36 | 0.03(s, 12H), 0.88(s, 18H), 1.1–2.9(m, 13H), 3.2–3.5(m, 1H), 3.4–3.7(m, 2H), 3.6–3.8(m, 1H), 3.8–4.1(m, 2H), 4.0–4.3(m, 2H), 4.3–4.6(m, 1H), 5.3–5.9(m, 2H), 6.7–7.1(m, 3H), 7.1–7.6(m, 2H) |
| 7 |  | 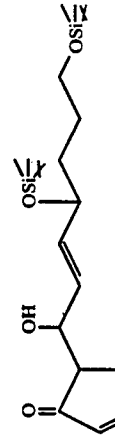 | 53 | 0–0.15(12H, m), 0.84(9H, s), 0.86 (9H, s), 1.3–1.7(4H, m), 2.4–2.7 (1H, m), 3.5–3.7(2H, m), 3.7–3.9 (1H, m), 3.78(1H, d, J=2.4Hz), 3.90 (1H, t, J=2.2Hz), 4.0–4.3(1H, m), 4.3–4.7(1H, m), 5.4–5.9(2H, m), 7.0–7.4(5H, m) |
| 8 | 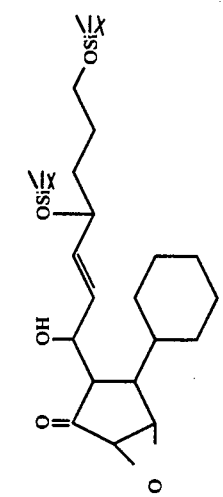 | 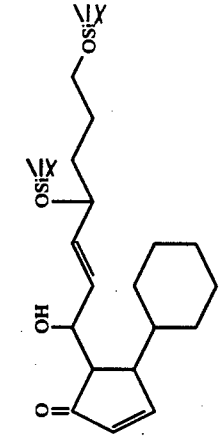 | 48 | 0.08(s, 12H), 0.89(s, 18H), 1.1–2.9(m, 17H), 3.2–3.5(m, 1H), 3.4–3.7(m, 3H), 3.6–3.8(m, 1H), 4.0–4.3(m, 1H), 4.3–4.6(m, 1H), 5.3–5.9 (m, 2H) |
| 9 | 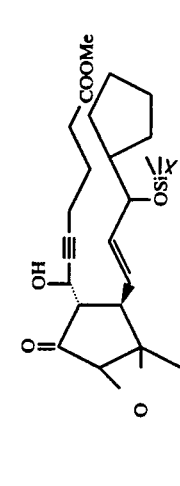 | 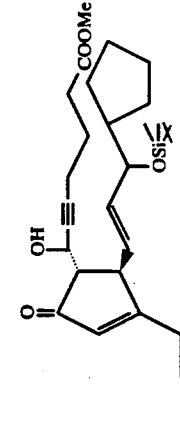 | 27 | 0.0–0.1(m, 6H), 0.90(s, 9H), 0.7–1.0(m, 3H), 1.2–2.0(m, 17H), 2.0–2.6(m, 5H), 3.1–3.3(m, 1H), 3.40 (s, 1H), 3.69(s, 3H), 3.8–4.1(m, 1H), 4.4–4.9(m, 2H), 5.3–5.9(m, 2H) |
| 10 | 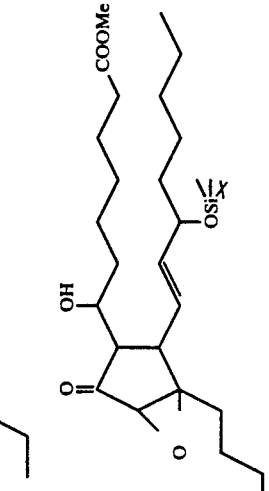 | 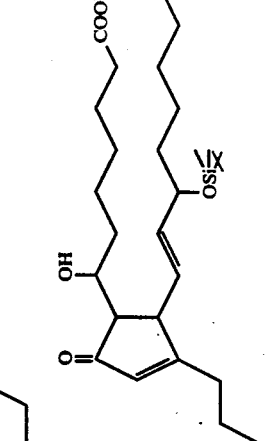 | 33 | 0–0.1(s, 6H), 0.86(s, 9H), 0.7–1.1 (m, 6H), 1.1–2.7(m, 26H), 3.0–3.3 (m, 1H), 3.60(s, 3H), 3.5–4.1(m, 3H), 5.4–5.8(m, 2H) |

TABLE 5-continued

| Ex. No. | Starting Compd. (2-Cyclopentenones) | 2,3-Epoxycyclopentanones | Yield (%) | NMR(δ, CDCl₃) |
|---|---|---|---|---|
| 11 | | | 28 | 0.86(d, 1H, J=6.6Hz), 1.3–2.1(m, 8H), 2.3–3.0(m, 4H), 3.41(s, 1H), 3.5–4.1(m, 3H), 6.7–7.5(m, 10H) |
| 12 | | | 39 | 0.7–1.1(m, 3H), 0.88(s, 9H), 1.30 (s, 3H), 1.1–1.9(m, 16H), 2.3–2.8 (m, 3H), 3.35(s, 1H), 3.5–3.8(m, 1H) |
| 13 | | | 57 | 0–0.1(m, 6H), 0.89(s, 9H), 0.7–1.1 (m, 6H), 1.27(s, 3H), 1.1–2.8(m, 21H), 3.41(s, 1H), 3.6–4.6(m, 4H), 5.4–6.1(m, 3H), 7.0(dt, 1H, J=16.0, 7.4Hz) |
| 14 | | | 69 | 0–0.2(m, 6H), 0.89(s, 9H), 0.7–1.0 (m, 3H), 1.1–2.4(m, 22H), 3.45(d, 1H, J=2.1Hz), 3.69(s, 3H), 3.73(d, 1H, J=2.1Hz), 4.0–4.1(m, 1H), 5.5–5.8(m, 2H) |
| 15 | | | 46 | 0.0(s, 3H), 0.03(s, 3H), 0.87(s, 9H), 0.7–1.0(m, 3H), 1.2–2.6(m, 19H), 2.9–3.2(m, 1H), 3.50(d, 1H, J=2.3Hz), 3.73(s, 3H), 3.79(d, 1H, J=2.3Hz), 4.0–4.3(m, 1H), 4.7–5.0 (m, 2H), 5.5–5.8(m, 2H) |

TABLE 5-continued

| Ex. No. | Starting Compd. (2-Cyclopentenones) | 2,3-Epoxycyclopentanones | Yield (%) | NMR(δ, CDCl₃) |
|---|---|---|---|---|
| 16 | | | 58 | 0.7–1.0(m, 3H), 1.2–2.0(m, 14H), 2.33(d, 1H, J=16.0Hz), 2.42(d, 1H, J=16.0Hz), 2.4–2.8(m, 1H), 3.3–3.6(m, 1H), 3.7–3.9(m, 1H) |
| 17 | | | 49 | 0.7–1.2(m, 9H), 1.2–2.0(m, 12H), 2.35(d, 1H, J=16.2Hz), 2.43(d, 1H, J=16.2Hz), 2.4–2.8(m, 1H), 3.3–3.5(m, 1H), 3.6–3.9(m, 1H) |
| 18 | | | 53 | 1.1–2.0(m, 10H), 2.1–2.9(m, 5H), 3.3–3.5(m, 1H), 3.68(s, 3H), 3.6–3.8(m, 1H) |
| 19 | | | 79 | 1.4–2.1(6H, m), 2.31(1H, d, J=16.3 Hz), 2.4(1H, d, J=16.3Hz), 2.4–2.8 (1H, m), 3.35–3.6(1H, m), 3.65–4.2 (3H, m), 6.7–7.05(3H, m), 7.1–7.45 (2H, m) |
| 20 | | | 63 | 1.4–1.9(m, 4H), 2.3–2.9(m, 5H), 3.3–3.5(m, 1H), 3.6–3.8(m, 1H), 3.80(s, 6H), 6.4–6.9(m, 3H) |
| 21 | | | 42 | 0.7–1.0(m, 3H), 1.1–2.8(m, 9H), 3.3–3.5(m, 1H), 3.7–3.9(m, 1H) |

TABLE 5-continued

| Ex. No. | Starting Compd. (2-Cyclopentenones) | 2,3-Epoxycyclopentanones | Yield (%) | NMR(δ, CDCl₃) |
|---|---|---|---|---|
| 22 | | | 47 | 0–0.1(m, 6H), 0.89(s, 9H), 1.0–2.0 (m, 11H), 2.3–2.8(m, 3H), 3.3–3.6 (m, 1H), 3.6–3.8(m, 1H), 4.6–4.9 (m, 1H), 5.4–5.9(m, 2H) |
| 23 | | | 63 | 1.24(s, 3H), 2.44(s, 2H), 2.5–2.8 (m, 1H), 3.3–3.6(m, 1H), 3.7–3.9 (m, 1H) |
| 24 | | | 49 | 1.08(s, 9H), 2.51(s, 2H), 2.5–2.8 (m, 1H), 3.3–3.6(m, 1H), 3.7–3.9 (m, 1H) |
| 25 | | | 54 | 1.68(s, 6H), 2.49(s, 2H), 2.5–2.8 (m, 1H), 3.3–3.6(m, 1H), 3.6–3.8 (m, 1H), 5.4–5.9(m, 2H), 7.0–7.5 (m, 5H) |
| 26 | | | 47 | 0.7–1.1(m, 6H), 1.1–2.0(m, 8H), 2.45(s, 2H), 2.5–2.8(m, 1H), 3.40 (s, 1H) |

TABLE 5-continued

| Ex. No. | Starting Compd. (2-Cyclopentenones) | 2,3-Epoxycyclopentanones | Yield (%) | NMR(δ, CDCl$_3$) |
|---|---|---|---|---|
| 27 | | | 16 | 0.7–1.0(m, 3H), 1.1–2.0(m, 17H), 2.44(s, 2H), 2.5–2.8(m, 1H), 3.37 (s, 1H) |
| 28 | | | 39 | 0.7–1.0(m, 6H), 1.1–2.7(m, 13H), 3.39(s, 1H) |
| 29 | | | 21 | 0–0.1(m, 6H), 0.88(s, 9H), 1.0–2.0 (m, 28H), 2.3–2.8(m, 3H), 3.38(s, 1H), 4.6–4.9(m, 1H), 5.4–5.8(m, 2H) |
| 30 | | | 30 | 0.7–1.2(m, 15H), 1.2–2.0(m, 13H), 2.1–2.6(m, 3H), 3.35(s, 1H) |

TABLE 5-continued

| Ex. No. | Starting Compd. (2-Cyclopentenones) | 2,3-Epoxycyclopentanones | Yield (%) | NMR(δ, CDCl₃) |
|---|---|---|---|---|
| 31 | (structure) | (structure) | 13 | 1.18(s, 9H), 1.22(s, 3H), 2.42(s, 2H), 2.5–2.8(m, 1H), 3.36(s, 1H) |
| 32 | (structure) | (structure) | 42 | 1.28(s, 3H), 1.4–1.9(m, 4H), 2.3–2.8(m, 5H), 3.38(s, 1H), 3.80(s, 6H), 6.4–6.9(m, 3H) |
| 33 | (structure) | (structure) | 33 | 0.7–1.2(m, 6H), 1.3–1.9(m, 7H), 2.39(s, 2H), 2.4–2.8(m, 1H), 6.7–7.1(m, 3H), 7.1–7.5(m, 2H) |
| 34 | (structure) | (structure) | 55 | 0.7–1.05(m, 3H), 1.05–2.7(m, 13H), 2.42(s, 2H), 3.38(s, 1H), 3.97(t, 2H, J=6.0Hz), 6.7–7.1(m, 3H), 7.1–7.4(m, 2H) |

TABLE 5-continued

| Ex. No. | Starting Compd. (2-Cyclopentenones) | 2,3-Epoxycyclopentanones | Yield (%) | NMR(δ, CDCl₃) |
|---|---|---|---|---|
| 35 | (structure with OSi, OPh, ethyl substituents on cyclopentenone) | (structure with O, OH, OPh, ethyl on cyclopentanone) | 43 | 0.7–1.1(m, 3H), 1.1–2.7(m, 9H), 2.43(s, 2H), 3.39(s, 1H), 3.98(t, 2H, J=6.0Hz), 6.7–7.1(m, 3H), 7.1–7.4(m, 2H) |
| 36 | (structure with OSi, OPh, CH₂Ph chain on cyclopentenone) | (structure with O, OH, OPh, CH₂Ph chain on cyclopentanone) | 29 | 1.0–3.0(m, 17H), 2.41(s, 2H), 3.40(s, 1H), 3.96(t, 2H, J=6.0Hz), 6.7–7.4(m, 10H) |
| 37 | (structure with OSi, OPh, prenyl chain on cyclopentenone) | (structure with O, OH, OPh, prenyl chain on cyclopentanone) | 31 | 0.85(brd, 3H, J=4.3Hz), 1.0–2.7(m, 24H), 3.37(s, 1H), 3.93(t, 2H, J=5.8Hz), 4.8–5.2(m, 1H), 6.7–7.1(m, 3H), 7.1–7.4(m, 2H) |
| 38 | (cyclopentenone with OSi) | (cyclopentanone with OSi and epoxide) | 89 | 0.12(s, 6H), 0.88(s, 9H), 1.93(d, 1H, J=18.0Hz), 2.53(dd, 1H, J=18.0, 6.0Hz), 3.36(d, 1H, J=2.4Hz), 3.75(d, 1H, J=2.4Hz), 4.57(d, 1H, J=6.0Hz) |

TABLE 5-continued
| Ex. No. | Starting Compd. (2-Cyclopentenones) | 2,3-Epoxycyclopentanones | Yield (%) | NMR(δ, CDCl₃) |
|---|---|---|---|---|
| 39 | 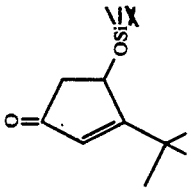 | 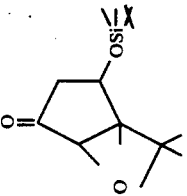 | 67 | 0.09(s, 3H), 0.14(s, 3H), 0.92(s, 9H), 1.10(s, 9H), 1.93(d, 1H, J=17.6Hz), 2.70(dd, 1H, J=17.6, 5.9 Hz), 3.30(d, 1H, J=0.7Hz), 4.72(d, 1H, J=5.9Hz) |

TABLE 6

| Ex. No. | Starting Compd. (2,3-Epoxycyclopentanones) | 2-substituted-2-cyclopentenones | Yield (%) | NMR(δ, CDCl₃) |
|---|---|---|---|---|
| 40 | | | 74 | 0–0.1(m, 6H), 0.89(s, 9H), 0.7–1.1 (m, 6H), 1.1–2.7(m, 26H), 2.34(s, 3H), 3.1–3.3(m, 1H), 3.61(s, 3H), 3.6–4.1(m, 2H), 5.4–5.7(m, 2H) |
| 41 | | | 63 | 0–0.2(m, 6H), 0.90(s, 9H), 0.7–1.0 (m, 3H), 1.1–2.3(m, 21H), 2.35(s, 3H), 3.0–3.4(m, 1H), 3.68(s, 3H), 3.8–4.1(m, 1H), 5.5–5.8(m, 2H), 7.18(d, 1H, J=2.7Hz) |
| 42 | | | 67 | 0.11(s, 9H), 0.7–1.1(m, 3H), 1.1–2.0 (m, 10H), 2.36(s, 3H), 2.56(s, 2H), 2.3–2.9(m, 2H), 3.93(t, 3H, J=6.2Hz), 6.8–7.1(m, 5H), 7.1–7.4(m, 2H) |
| 43 | | | 48 | 0.08(s, 9H), 0.7–1.0(m, 3H), 1.1–1.9 (m, 16H), 2.53(s, 2H), 2.4–2.8 (m, 1H) |

TABLE 6-continued

| Ex. No. | Starting Compd. (2,3-Epoxycyclopentanones) | 2-substituted-2-cyclopentenones | Yield (%) | NMR(δ, CDCl₃) |
|---|---|---|---|---|
| 44 | (structure with Me, OH, O, epoxide, t-Bu) | (structure with Me, OSi, O, MeS, t-Bu) | 59 | 0.07(s, 9H), 1.26(s, 3H), 1.33(s, 9H), 2.34(s, 3H), 2.53(s, 2H) |
| 45 | (structure with alkynyl-pentyl, OH, O, epoxide, butyl) | (structure with alkynyl-pentyl, OSi, O, MeS, butyl) | 47 | 0.06(s, 9H), 0.7–1.1(m, 6H), 1.1–2.0 (m, 6H), 2.2–2.8(m, 6H), 2.36(s, 3H) |

TABLE 7

| Ex. No. | Starting Compd. (2,3-Epoxycyclopentanones) | 2-substituted-2-cyclopentenones | yield (%) | NMR(δ, CDCl₃) |
|---|---|---|---|---|
| 18 | | | 70 | 0.03(s, 12H), 0.88(s, 18H), 1.1–2.0 (m, 10H), 2.32(s, 3H), 2.2–3.0 (m, 3H), 3.4–3.7(m, 2H), 3.8–4.1 (m, 2H), 4.0–4.7(m, 2H), 5.5–5.8 (m, 2H), 6.7–7.1(m, 4H), 7.1–7.5 (m, 2H) |
| 19 | | | 27 | 0–0.1(12H, m), 0.85(9H, s), 0.88 (9H, s), 1.3–1.6(4H, m), 2.35(3H, s), 2.6–2.8(1H, m), 3.4–3.7(2H, m), 3.9–4.2(2H, m), 4.6–4.8(1H, m), 5.6–5.8(2H, m), 6.95(1H, d, J=3.1, Hz), 7.1–7.5(5H, m) |
| 20 | | | 89 | 0.12(s, 6H), 0.91(s, 9H), 2.34(s, 3H), 2.38(dd, 1H, J=18.3, 2.2Hz), 2.83 (dd, 1H, J=18.3, 5.7Hz), 4.95(dt, 1H, J=5.7, 2.5Hz), 6.73(d, 1H, J=2.6Hz) |
| 21 | | | 72 | 0.11(s, 9H), 1.3–1.9(m, 6H), 2.35 (s, 3H), 2.66(s, 2H), 3.95(t, 2H, J=5.9Hz), 6.80(s, 1H), 6.8–7.45(m, 5H) |
| 22 | | | 67 | 0.09(s, 9H), 1.4–1.9(m, 4H), 2.3–2.9 (m, 4H), 2.35(s, 3H), 3.82(s, 6H), 6.6–7.1(m, 4H) |
| 23 | | | 49 | 0.01–0.08(m, 15H), 0.89(s, 9H), 1.0–2.0(m, 11H), 2.39(s, 3H), 2.68 (s, 2H), 4.6–4.85(m, 1H), 5.4–5.8 (m, 2H), 6.85(s, 1H) |

TABLE 8

| Ex. No. | Starting Material 2,3-Epoxycyclopentanones | Thiols | 2-Substituted-2-cyclopentenones | Yield (%) | NMR (δ, CDCl$_3$) |
|---|---|---|---|---|---|
| 46 | (structure: epoxycyclopentanone with OH, COOMe chain, OSi group) | cyclohexyl-SH | (structure: 2-cyclopentenone with S-cyclohexyl, OH, COOMe, OSi) | 75 | −0.03–0.06(6H, m), 0.85(9H, s), 0.7–1.1(3H, brt), 1.1–2.6(31H, m), 3.1–3.3(1H, m), 3.64(3H, s), 3.69(1H, brs), 3.9–4.2(1H, m), 5.5–5.7(2H, m), 6.80(1H, d, J=3Hz) |
| 47 | Same as above | (pyridine-SH) | (structure with S-pyridyl) | 53 | 0–0.1(6H, m), 0.89(9H, s), 0.7–1.1(3H, brt), 1.1–2.4(20H, m), 3.1–3.3(1H, m), 3.67(3H, s), 3.6–3.8(1H, m), 3.9–4.2(1H, m), 5.5–5.7(2H, m), 6.77(1H, d, J=2.8Hz), 7.2–8.1(4H, m) |
| 48 | Same as above | (N-methyl tetrazole-SH) | (structure with S-tetrazolyl-Me) | 29 | 0–0.1(6H, s), 0.90(9H, s), 0.7–1.1(3H, brt), 1.1–2.4(20H, m), 3.1–3.3(1H, m), 3.68(3H, s), 3.6–3.8(1H, m), 3.9–4.2(1H, m), 4.1(3H, s), 5.5–5.8(2H, m), 6.8(1H, d, J=2.8Hz) |
| 49 | (structure: epoxycyclopentanone with OH, COOMe, OSi chain) | (benzoxazole-SH) | (structure with S-benzoxazolyl) | 68 | 0–0.1(6H, m), 0.89(9H, s), 0.7–1.1(6H, m), 1.1–2.7(17H, m), 3.1–3.3(1H, m), 3.68(3H, s), 3.6–3.9(1H, m), 3.8–4.3(1H, m), 5.4–5.8(2H, m), 5.89(1H, d, J=16Hz), 6.8–7.2(2H, m), 7.2–7.8(4H, m) |
| 50 | (structure: epoxycyclopentanone with OH, OSi, OPh chains) | (N-methyl imidazole-SH) | (structure with S-imidazolyl-Me, OSi, OPh) | 57 | 0.02(s, 12H), 0.89(s, 18H), 1.1–2.0(m, 10H), 2.2–3.0(m, 3H), 3.4–3.7(m, 2H), 3.66(s, 3H), 3.8–4.1(m, 2H), 4.0–4.7(m, 2H), 5.5–5.8(m, 2H), 6.7–7.1(m, 5H), 7.1–7.5(m, 2H) |

TABLE 8-continued

| Ex. No. | Starting Material 2,3-Epoxycyclopentanones | Thiols | 2-Substituted-2-cyclopentenones | Yield (%) | NMR (δ, CDCl₃) |
|---|---|---|---|---|---|
| 51 | (structure) | 2-aminothiophenol | (structure) | 31 | 0–0.2(m, 6H), 0.89(s, 9H), 1.1–2.1 (m, 11H), 2.1–3.2(m, 6H), 3.4–4.0 (m, 4H), 3.67(s, 3H), 4.6–4.9(m, 1H), 5.4–5.8(m, 2H), 6.5–7.6(m, 5H) |
| 52 | Same as above | (pyrimidine thiol) | (structure) | 29 | 0–0.2(m, 6H), 0.88(s, 9H), 1.1–2.1 (m, 11H), 2.1–3.2(m, 6H), 3.4–3.6 (m, 1H), 3.68(s, 3H), 3.9–4.3(m, 1H), 4.6–5.0(m, 1H), 5.4–5.8(m, 1H), 6.9–7.2(m, 1H), 8.21(s, 1H), 8.55(s, 1H) |
| 53 | Same as above | furfuryl mercaptan | (structure) | 65 | 0–0.1(6H, m), 0.89(9H, s), 1.0–2.1 (11H, m), 2.1–3.2(6H, m), 3.4–3.7 (1H, m), 3.67(3H, s), 3.7–4.3(3H, m), 4.6–4.9(1H, m), 5.4–5.8(2H, m), 6.0–6.5(2H, m), 7.12(1H, d, J=3Hz), 7.25–7.4(1H, m) |
| 54 | (structure) | N-methyl imidazole thiol | (structure) | 47 | 0.09(s, 12H), 0.89(s, 18H), 1.1–2.0(m, 16H), 2.2–3.0(m, 3H), 3.4–3.7(m, 2H), 3.67(s, 3H), 3.8–4.1 (m, 2H), 4.0–4.7(m, 2H), 5.5–5.8 (m, 2H), 6.7–7.2(m, 3H) |
| 55 | (structure) | i-PrSH | (structure) | 37 | 0–0.1(m, 6H), 0.87(s, 9H), 0.7–1.1 (m, 6H), 1.1–3.0(m, 33H), 3.3–3.6 (m, 1H), 3.68(s, 3H), 3.6–4.2(m, 2H), 5.4–5.7(m, 2H) |

TABLE 8-continued
| Ex. No. | Starting Material | | 2-Substituted-2-cyclopentenones | Yield (%) | NMR (δ, CDCl₃) |
|---|---|---|---|---|---|
| | 2,3-Epoxycyclopentanones | Thiols | | | |
| 56 | Same as above | EtSH | 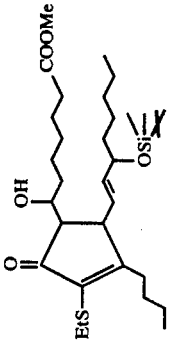 | 41 | 0–0.1(m, 6H), 0.85(s, 9H), 0.7–1.0 (m, 6H), 1.0–3.0(m, 31H), 3.3–3.6 (m, 1H), 3.67(s, 3H), 3.6–4.1(m, 2H), 5.4–5.7(m, 2H) |
| 57 | Same as above | t-BuSH | 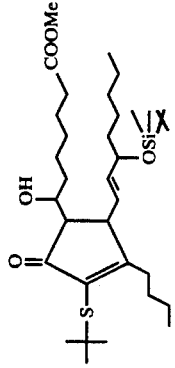 | 23 | 0–0.1(m, 6H), 0.87(s, 9H), 0.7–1.0 (m, 6H), 1.38(s, 9H), 1.0–3.0(m, 26H), 3.3–3.7(m, 1H), 3.68(s, 3H), 3.6–4.2(m, 2H), 5.4–5.7(m, 2H) |
| 58 | Same as above | cyclohexyl-SH | 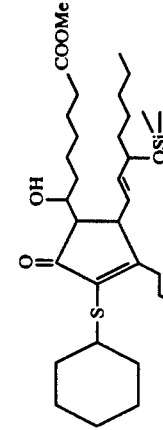 | 38 | 0–0.1(m, 6H), 0.90(s, 9H), 0.7–1.1 (m, 6H), 1.1–2.7(m, 37H), 3.1–3.3 (m, 1H), 3.62(s, 3H), 3.6–4.1(m, 2H), 5.4–5.8(m, 2H) |
| 59 | Same as above | pyridyl-SH | 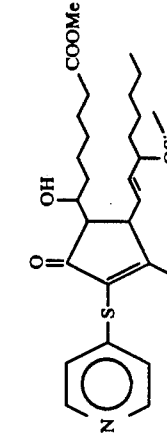 | 27 | 0–0.1(m, 6H), 0.89(s, 9H), 0.7–1.1 (m, 6H), 1.1–3.0(m, 26H), 3.1–3.3 (m, 1H), 3.68(s, 3H), 3.6–3.8(m, 1H), 3.9–4.2(m, 1H), 5.5–5.7(m, 2H), 7.2–8.1(m, 4H) |
| 60 | Same as above | N-methylimidazolyl-SH | 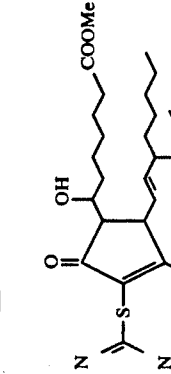 | 31 | 0–0.1(m, 6H), 0.87(s, 9H), 0.7–1.1 (m, 6H), 1.1–3.0(m, 26H), 3.1–3.3 (m, 1H), 3.66(s, 3H), 3.68(s, 3H), 3.6–3.8(m, 1H), 3.9–4.2(m, 1H), 5.5–5.7(m, 2H), 7.0–7.3(m, 2H) |

TABLE 8-continued

| Ex. No. | Starting Material | | Yield | |
|---|---|---|---|---|
| | 2,3-Epoxycyclopentanones | Thiols | 2-Substituted-2-cyclopentenones | (%) | NMR (δ, CDCl₃) |
| 61 | Same as above | Me-pyrimidine-SH | (structure with pyrimidinyl-S, OH, COOMe, OSi) | 28 | 0–0.1(m, 6H), 0.89(s, 9H), 0.7–1.1 (m, 6H), 1.1–3.0(m, 26H), 2.43(s, 3H), 3.1–3.3(m, 1H), 3.67(s, 3H), 3.6–3.8(m, 1H), 3.9–4.2(m, 1H), 5.4–5.8(m, 2H), 6.87(d, 1H, J=5.1 Hz), 8.32(d, 1H, J=5.1Hz) |
| 62 | (epoxycyclopentanone structure with COOMe, OSi) | PhSH | (structure with PhS, OH, COOMe, OSi) | 55 | 0.06(s, 6H), 0.89(s, 9H), 0.7–1.0 (m, 3H), 1.1–2.9(m, 22H), 3.0–3.3 (m, 1H), 3.4–3.6(m, 1H), 3.69(s, 3H), 3.8–4.0(m, 1H), 4.7–4.9(m, 1H), 5.4–5.8(m, 2H), 7.2–7.7(m, 5H) |
| 63 | Same as above | Ph-(CH₂)₃-SH | (structure with PhCH₂CH₂CH₂S, COOMe, OSi) | 49 | 0.07(s, 6H), 0.90(s, 9H), 0.7–1.0 (m, 3H), 1.0–3.1(m, 29H), 3.3–3.7 (m, 1H), 3.69(s, 3H), 3.8–4.0(m, 1H), 4.6–4.9(m, 1H), 5.4–5.7(m, 2H), 7.0–7.4(m, 5H) |
| 64 | Same as above | MeOOC-(CH₂)ₙ-SH | (structure with MeOOC(CH₂)ₙS, OH, COOMe, OSi) | 26 | 0.05(s, 6H), 0.89(s, 9H), 0.7–1.0 (m, 3H), 1.1–3.1(m, 33H), 3.4–3.8 (m, 1H), 3.68(s, 6H), 3.8–4.0(m, 1H), 4.6–4.9(m, 1H), 5.4–5.8(m, 2H) |

TABLE 8-continued

| Ex. No. | Starting Material | | Yield | |
|---|---|---|---|---|
| | 2,3-Epoxycyclopentanones | Thiols | 2-Substituted-2-cyclopentenones | (%) | NMR (δ, CDCl₃) |
| 65 | Same as above | HS—C₁₀H₆—OMe (6-methoxy-2-naphthalenethiol) | (product with 6-methoxynaphthalen-2-ylthio group) | 43 | 0.08(s, 6H), 0.88(s, 9H), 0.7–1.0 (m, 3H), 1.1–2.9(m, 23H), 3.3–3.5 (m, 1H), 3.69(s, 3H), 3.8–4.1(m, 1H), 3.97(s, 3H), 4.6–4.8(m, 1H), 5.4–5.9(m, 2H), 7.0–8.1(m, 5H) |
| 66 | Same as above | Me—C₆H₄—SH (p-toluenethiol) | (product with p-tolylthio group) | 29 | 0.08(s, 6H), 0.89(s, 9H), 0.7–1.0 (m, 3H), 1.1–2.9(m, 23H), 2.3(s, 3H), 3.3–3.5(m, 1H), 3.68(s, 3H), 3.8–4.1(m, 1H), 4.6–4.8(m, 1H), 5.4–5.9(m, 2H), 6.9–7.5(m, 4H) |
| 67 | Same as above | furfuryl mercaptan | (product with furfurylthio group) | 26 | 0.0–0.1(m, 6H), 0.89(s, 9H), 0.7–1.0(m, 3H), 1.0–3.2(m, 23H), 3.4–3.7(m, 1H), 3.68(s, 3H), 3.7–4.3 (m, 3H), 4.6–4.9(m, 1H), 5.4–5.8 (m, 2H), 6.0–6.5(m, 2H), 7.3–7.6 (m, 1H) |
| 68 | Same as above | HOCH₂CH(OH)CH₂SH (1-thioglycerol) | (product with 2,3-dihydroxypropylthio group) | 35 | 0–0.1(m, 6H), 0.89(s, 9H), 0.7–1.0 (m, 3H), 1.1–2.8(m, 23H), 2.8–3.4 (m, 5H), 3.68(s, 3H), 3.4–4.0(m, 4H), 4.5–4.9(m, 1H), 5.4–5.8(m, 2H) |

TABLE 8-continued

| Ex. No. | Starting Material 2,3-Epoxycyclopentanones | Thiols | 2-Substituted-2-cyclopentenones | Yield (%) | NMR (δ, CDCl₃) |
|---|---|---|---|---|---|
| 69 | [structure with OH, Ph, Me, PhO] | cyclopentyl-SH | [structure with OH, Ph, Me, S-cyclopentyl, PhO] | 44 | 0.86(d, 3H, J=6.5Hz), 1.3-2.1(m, 14H), 2.2-3.0(m, 8H), 3.5-4.1(m, 3H), 6.7-7.5(m, 10H) |
| 70 | [structure with OH, X, Me] | F₃C-benzyl-SH | [structure with OH, Me, S-CH₂-Ar(CF₃)] | 51 | 0.7-1.1(m, 3H), 0.89(s, 9H), 1.0-2.0(m, 13H), 2.27(s, 3H), 2.4-2.8 (m, 2H), 4.12(d, 2H, J=3.0Hz), 4.20 (s, 2H), 6.9-7.1(m, 1H), 7.3-7.7 (m, 3H) |
| 71 | [structure with OH, COOEt, X, Me] | Cl-benzyl-SH | [structure with OH, COOEt, Me, S-CH₂-Ar(Cl)] | 59 | 0.7-1.1(m, 6H), 1.1-2.8(m, 21H), 2.25(s, 3H), 3.1-3.3(m, 1H), 3.6-4.0(m, 4H), 4.05(s, 2H), 5.4-5.8 (m, 2H), 5.89(d, 1H, J=16.0Hz), 6.92(dt, 1H, J=16.0, 6.8Hz), 7.1-7.4(m, 4H) |
| 72 | [structure with OH, COOMe, OSi, Me] | PhSH | [structure with COOMe, OSi, PhS] | 82 | 0-0.2(m, 6H), 0.89(s, 9H), 0.7-1.0 (m, 3H), 1.1-2.3(m, 21H), 3.0-3.4 (m, 1H), 3.70(s, 3H), 3.9-4.1(m, 1H), 5.4-5.8(m, 2H), 7.1-7.4(m, 6H) |
| 73 | Same as above | cyclohexyl-SH | [structure with COOMe, OSi, S-cyclohexyl] | 70 | 0-0.2(m, 6H), 0.89(s, 9H), 0.7-1.0 (m, 3H), 1.1-2.5(m, 32H), 3.0-3.4 (m, 1H), 3.69(s, 3H), 3.9-4.1(m, 1H), 5.4-5.7(m, 2H), 7.18(d, 1H, J=2.3Hz) |

TABLE 8-continued

| Ex. No. | Starting Material | | 2-Substituted-2-cyclopentenones | Yield (%) | NMR (δ, CDCl₃) |
|---|---|---|---|---|---|
| | 2,3-Epoxycyclopentanones | Thiols | | | |
| 74 | Same as above | [structure: N-methylimidazole-2-thiol, SH] | [structure: 2-substituted cyclopentenone with COOMe chain, OSi group, and N-methylimidazolyl-thio substituent] | 76 | 0–0.2(m, 6H), 0.88(s, 9H), 0.7–1.0 (m, 3H), 1.1–2.2(m, 21H), 3.0–3.4 (m, 1H), 3.66(s, 3H), 3.70(s, 3H), 3.9–4.2(m, 1H), 5.4–5.8(m, 2H), 6.7–7.2(m, 3H) |
| 75 | [structure: epoxycyclopentanone with COOMe chain and OSi group] | [structure: HOCH₂CH(OH)CH₂SH] | [structure: 2-substituted cyclopentenone with COOMe chain, OSi, and S-CH₂CH(OH)CH₂OH substituent] | 68 | 0.0(s, 6H), 0.88(s, 9H), 0.7–1.0 (m, 3H), 1.1–2.8(m, 21H), 2.8–3.3 (m, 3H), 3.67(s, 3H), 3.6–4.2(m, 4H), 4.80(brs, 2H), 5.4–5.7(m, 2H), 7.16(d, 1H, J=2.9Hz) |
| 76 | [structure: epoxy bicyclic ketone with OSi and gem-dimethyl] | PhSH | [structure: 2-phenylthio cyclopentenone with OSi substituent] | 72 | 0.13(s, 3H), 0.17(s, 3H), 0.92(s, 9H), 1.46(s, 9H), 2.33(dd, 1H, J = 18.2, 1.5Hz), 2.69(dd, 1H, J = 18.2, 5.7Hz), 5.11(dd, 1H, J=5.5, 1.5Hz), 7.2(s, 5H) |

TABLE 9

| Ex. No. | Starting Material | | Yield (%) | NMR (δ, CDCl₃) |
|---|---|---|---|---|
| | 2,3-Epoxycyclopentanones | Thiols 2-Substituted-2-cyclopentenones | | |
| 24 | [structure: epoxycyclopentanone with COOMe, OSi side chain] | HOCH₂CH(OH)CH₂SH / [structure: 2-substituted-2-cyclopentenone with S-CH₂CH(OH)CH₂OH, COOMe, OSi side chain] | 62 | 0.05(3H, s), 0.09(3H, s), 0.89(9H, s), 1.1–2.0(11H, m), 2.0–2.7(6H, m), 2.7–3.4(6H, m), 3.67(3H, s), 3.4–4.0(3H, m), 4.5–4.9(1H, m), 5.4–5.8(2H, m), 7.1–7.3(1H, m) |
| 25 | Same as above | Ph(CH₂)₃SH / [structure: 2-substituted-2-cyclopentenone with S(CH₂)₃Ph side chain] | 74 | 0.04(6H, s), 0.90(9H, s), 1.0–3.0 (23H, m), 3.35–3.7(1H, m), 3.68 (3H, s), 3.8–4.0(1H, m), 4.6–4.8 (1H, m), 5.4–5.7(2H, m), 6.89(1H, d, J=2.8Hz), 7.0–7.4(5H, m) |
| 26 | Same as above | PhSH / [structure with PhS] | 91 | 0.07(6H, s), 0.89(9H, s), 1.1–2.0 (11H, m), 2.0–2.7(5H, m), 3.0–3.3 (1H, m), 3.4–3.6(1H, m), 3.7(3H, s), 3.8–4.0(1H, m), 4.7–4.9(1H, m), 5.4–5.8(2H, m), 6.85(1H, d, J=2.7Hz), 7.2–7.7(5H, m) |
| 27 | [structure: epoxycyclopentanone] | PhSH / [structure: 2-PhS-cyclopentenone] | 52 | 2.5–2.7(m, 4H), 6.95(t, 1H, J=2.6Hz), 7.2–7.6(m, 5H) |
| 28 | [structure: epoxycyclopentanone with OSi] | benzoxazole-2-thiol / [structure: 2-(benzoxazol-2-ylthio)-cyclopentenone with OSi] | 21 | 0.16(s, 3H), 0.17(s, 3H), 0.93(s, 9H), 2.44(dd, 1H, J=18.2, 2.4Hz) 2.95(dd, 1H, J=18.2, 5.8Hz), 5.0–5.2 (m, 1H), 7.2–7.8(m, 4H), 8.03 (d, 1H, J=2.6Hz) |

TABLE 9-continued

| Ex. No. | Starting Material | | 2-Substituted-2-cyclopentenones | Yield (%) | NMR(δ, CDCl₃) |
|---|---|---|---|---|---|
| | 2,3-Epoxycyclopentanones | Thiols | | | |
| 29 | Same as above | Me-pyrimidine-SH (2-mercapto-4-methylpyrimidine) | cyclopentenone-S-(4-methylpyrimidin-2-yl), OSi | 77 | 0.15(s, 6H), 0.93(s, 9H), 2.43(dd, 1H, J=18.0, 2.4Hz), 2.44(s, 3H), 2.93(dd, 1H, J=18.0, 5.9Hz), 5.0–5.1 (m, 1H), 6.88(d, 1H, J=5.1Hz), 7.89(d, 1H, J=2.6Hz), 8.33(d, 1H, J=5.1Hz) |
| 30 | Same as above | 1-methyl-tetrazole-5-thiol | cyclopentenone-S-(1-methyltetrazol-5-yl), OSi | 79 | 0.13(s, 6H), 0.90(s, 9H), 2.38(dd, 1H, J=18.5, 2.2Hz), 2.90(dd, 1H, J=18.5, 5.8Hz), 4.10(s, 3H), 4.9–5.1 (m, 1H), 7.73(d, 1H, J=2.6Hz) |
| 31 | Same as above | PhSH | cyclopentenone-SPh, OSi | 63 | 0.14(s, 6H), 0.92(s, 9H), 2.45(dd, 1H, J=18.0, 2.1Hz), 2.94(dd, 1H, J=18.0, 5.7Hz), 5.0–5.2(m, 1H), 7.2–7.7 (m, 6H) |
| 32 | Same as above | cyclohexyl-SH | cyclopentenone-S-cyclohexyl, OSi | 68 | 0.11(s, 6H), 0.90(s, 9H), 1.1–2.0 (m, 10H), 2.44(dd, 1H, J=18.3, 2.2Hz), 2.3–2.8(m, 1H), 2.91(dd, 1H, J=18.3, 6.0Hz), 5.0–5.2(m, 1H), 7.19(d, 1H, J=2.1Hz) |

TABLE 10

| Ex. No. | Starting Material 2,3-Epoxycyclopentanones | Thiols | 2-Substituted-2-cyclopentenones | Yield (%) | NMR (δ, CDCl₃) |
|---|---|---|---|---|---|
| 77 | (structure: 2,3-epoxycyclopentanone with OH, OPh side chain) | cyclohexyl-SH | (cyclopentenone with S-cyclohexyl, OSi, OPh side chain) | 84 | 0.11(s,9H), 1.3–2.0(16H,m), 2.3–2.7(3H,m), 3.95(t,2H,J=5.9 Hz), 6.80–7.6(m,6H) |
| 78 | Same as above | cyclopentyl-SH | (cyclopentenone with S-cyclopentyl, OSi, OPh side chain) | 77 | 0.09(s,9H), 1.3–2.0(m,14H), 2.3–2.7(m, 3H), 3.96(t,2H, J=6.0Hz), 6.8–7.6(m,6H) |
| 79 | Same as above | cyclohexyl-CH₂CH₂-SH | (cyclopentenone with S-CH₂CH₂-cyclohexyl, OSi, OPh side chain) | 83 | 0.10(s,9H), 1.2–2.1(m,21H), 2.3–2.7(m,4H), 3.94(t,2H,J=6.2 Hz), 6.8–7.6(m,6H) |
| 80 | Same as above | 2-mercaptopyridine | (cyclopentenone with S-pyridyl, OSi, OPh side chain) | 77 | 0.08(s,9H), 1.1–1.9(m,6H), 2.56(s,2H), 3.84(t,2H, J=5.9Hz), 6.6–7.5(m,8H), 7.55 (s,1H), 8.1–8.4(m,1H) |
| 81 | Same as above | 2-mercapto-6-ethoxybenzothiazole | (cyclopentenone with S-(6-ethoxybenzothiazolyl), OSi, OPh side chain) | 72 | 0.06(s,9H), 1.37(t,3H,J=7.0 Hz), 1.2–1.9(m,6H), 2.62(s, 2H), 3.88(t,2H,J=6.9Hz), 3.99 (q,2H,J=7.0Hz), 6.6–7.4(m,7H), 7.68(s,1H), 7.75(d,1H,J=9.0Hz) |

TABLE 10-continued

| Ex. No. | Starting Material | | Yield (%) | NMR (δ, CDCl₃) |
|---|---|---|---|---|
| | 2,3-Epoxycyclopentanones | Thiols | | |
| | | | | 2-Substituted-2-cyclopentenones |

| Ex. No. | 2,3-Epoxycyclopentanones | Thiols | 2-Substituted-2-cyclopentenones | Yield (%) | NMR (δ, CDCl₃) |
|---|---|---|---|---|---|
| 82 | Same as above | imidazole-2-thiol (N-Me) | cyclopentenone with OSi, OPh chain, S-S-imidazole(N-Me) | 62 | 0.0(s,9H), 1.1–2.2(m,6H), 2.58(s,2H), 3.67(s,3H), 3.90(t,2H, J=5.9Hz), 6.83(s,1H), 6.6–7.4(m,7H) |
| 83 | Same as above | thiazoline-2-thiol | cyclopentenone with OSi, OPh chain, S-thiazoline | 6 | 0.08(s,9H), 1.3–2.1(m,7H), 2.6–2.7(m,2H), 3.2–3.8(m,2H), 3.8–4.4(m,4H), 6.7–7.0(m,3H), 7.1–7.4(m,2H), 7.84(s,1H) |
| 84 | hydroxyl epoxide | cyclopentanethiol | cyclopentenone with OSi, alkyl chain, S-cyclopentyl | 61 | 0.08(9H,s), 0.83(9H,d,J=4.4Hz), 0.9–2.1(20H,m), 2.3–2.7(3H,m), 6.85(1H,s) |
| 85 | Same as above | 2-cyclohexylethanethiol | cyclopentenone with OSi, alkyl chain, S-CH₂CH₂-cyclohexyl | 59 | 0.10(9H,s), 0.84(9H,d,J=4.6Hz), 0.9–2.8(31H,m), 6.80(1H,s) |
| 86 | Same as above | benzoxazole-2-thiol | cyclopentenone with OSi, alkyl chain, S-benzoxazole | 46 | 0.09(s,9H), 0.84(d,9H,J=4.6Hz), 0.9–2.1(m,12H), 2.60(s,2H), 6.84(s,1H), 7.2–7.8(m,4H) |

TABLE 10-continued

| Ex. No. | Starting Material | | 2-Substituted-2-cyclopentenones | Yield (%) | NMR (δ, CDCl₃) |
|---|---|---|---|---|---|
| | 2,3-Epoxycyclopentanones | Thiols | | | |
| 87 | (structure: cyclopentanone with OH, heptyl, epoxide) | cyclohexyl-SH | (cyclopentenone with OSi, heptyl, S-cyclohexyl) | 54 | 0.09(s,9H), 0.7–1.0(m,3H), 1.1–2.0(m,24H), 2.3–2.9(m,3H), 6.75(s,1H) |
| 88 | Same as above | N-methylimidazole-2-thiol | (cyclopentenone with OSi, heptyl, S-(N-methylimidazolyl)) | 49 | 0.06(9H,s), 0.89(3H,brt), 1.1–1.9(14H,m), 2.59(2H,s), 3.69(3H,s), 6.6–6.9(3H,m) |
| 89 | (structure: cyclopentanone with OH, CH₂CH₂-3,4-dimethoxyphenyl, epoxide) | cyclohexyl-SH | (cyclopentenone with OSi, CH₂CH₂-3,4-dimethoxyphenyl, S-cyclohexyl) | 69 | 0.10(s,9H), 1.2–2.1(m,14H), 2.3–2.9(m,5H), 3.79(s,6H), 6.4–6.9(m,4H) |
| 90 | Same as above | N-methylimidazole-2-thiol | (cyclopentenone with OSi, CH₂CH₂-3,4-dimethoxyphenyl, S-(N-methylimidazolyl)) | 44 | 0.09(s,9H), 1.3–2.1(m,4H), 2.2–2.6(m,2H), 2.60(s,2H), 3.66(s,3H), 3.78(s,6H), 6.4–7.2(m,6H) |
| 91 | Same as above | 4-pyridinethiol | (cyclopentenone with OSi, CH₂CH₂-3,4-dimethoxyphenyl, S-(4-pyridyl)) | 53 | 0.08(s,9H), 1.3–2.1(m,4H), 2.2–2.6(m,2H), 2.58(s,2H), 3.80(s,6H), 6.4–6.9(m,4H), 7.2–8.1(m,4H) |

TABLE 10-continued

| Ex. No. | Starting Material | | 2-Substituted-2-cyclopentenones | Yield (%) | NMR (δ, CDCl₃) |
|---|---|---|---|---|---|
| | 2,3-Epoxycyclopentanones | Thiols | | | |
| 92 | Same as above | benzoxazole-2-thiol | 2-(benzoxazol-2-ylthio)-4-[2-(3,4-dimethoxyphenyl)ethyl]-4-trimethylsilyloxy-2-cyclopentenone | 51 | 0.09(s,9H), 1.4–1.9(m,4H), 2.3–2.9(m,4H), 3.84(s,6H), 6.4–6.9(m,3H), 7.2–7.8(m,4H) |
| 93 | Same as above | furfuryl mercaptan | 2-(furfurylthio)-4-[2-(3,4-dimethoxyphenyl)ethyl]-4-trimethylsilyloxy-2-cyclopentenone | 47 | 0.08(s,9H), 1.4–1.9(m,4H), 2.3–2.9(m,4H), 3.85(s,6H), 4.03(s,2H), 6.0–6.5(m,2H), 6.84(s,1H), 7.3–7.6(m,1H) |
| 94 | 2,3-epoxy-3-methyl-4-hydroxycyclopentanone derivative | benzothiazole-2-thiol | 2-(benzothiazol-2-ylthio)-4-methyl-4-trimethylsilyloxy-2-cyclopentenone | 58 | 0.09(s,9H), 1.25(s,3H), 2.57(s,2H), 7.2–7.9(m,5H) |
| 95 | Same as above | furfuryl mercaptan | 2-(furfurylthio)-4-methyl-4-trimethylsilyloxy-2-cyclopentenone | 49 | 0.08(s,9H), 1.27(s,3H), 2.56(s,2H), 4.03(s,2H), 6.0–6.5(m,2H), 6.85(m,1H), 7.2–7.4(m,1H) |
| 96 | 2,3-epoxy-4-hydroxy-4-(5-methoxycarbonylpentyl)cyclopentanone | 1-methylimidazole-2-thiol | 2-(1-methylimidazol-2-ylthio)-4-(5-methoxycarbonylpentyl)-4-trimethylsilyloxy-2-cyclopentenone | 73 | 0.04(s,9H), 1.0–2.0(m,10H), 2.1–2.4(m,2H), 2.56(s,2H), 3.68(s,3H), 6.6–6.9(m,3H) |

TABLE 10-continued

| Ex. No. | Starting Material | | 2-Substituted-2-cyclopentenones | Yield (%) | NMR (δ, CDCl₃) |
|---|---|---|---|---|---|
| | 2,3-Epoxycyclopentanones | Thiols | | | |
| 97 | (cyclohexyl-CH(OH)-CH=CH-substituted epoxycyclopentanone) | 4-Me-pyrimidine-2-thiol | (corresponding 2-substituted cyclopentenone with OSi(Me)₃ groups) | 42 | 0–0.15(m,15H), 0.89(s,9H), 1.1–2.1(m,11H), 2.45(s,3H), 2.60(s,2H), 4.6–4.9(m,1H), 5.4–5.8(m,2H), 6.6–7.0(m,2H), 8.32(d,1H,J=5.1Hz) |
| 98 | Same as above | 6-chloro-benzothiazole-2-thiol | (corresponding product) | 32 | 0–0.2(m,15H), 0.90(s,9H), 1.1–2.1(m,11H), 2.59(s,2H), 4.6–4.9(m,1H), 5.4–5.8(m,2H), 7.0–7.8(m,4H) |
| 99 | (Ph-C(Me)₂-CH=CH-substituted epoxycyclopentanone) | 1-methylimidazole-2-thiol | (corresponding product) | 52 | 0.08(s,9H), 1.66(s,6H), 2.60(s,2H), 3.66(s,3H), 5.4–5.9(m,2H), 6.6–7.5(m,8H) |
| 100 | (pentynyl-substituted epoxycyclopentanone) | 4-mercaptopyridine | (corresponding product) | 51 | 0.08(s,9H), 0.7–1.0(m,3H), 1.2–1.9(m,4H), 2.2–2.6(m,2H), 2.61(s,2H), 7.10(s,3H), 7.4–7.9(m,4H) |

TABLE 10-continued

| Ex. No. | Starting Material | | Thiols | 2-Substituted-2-cyclopentenones | Yield (%) | NMR (δ, CDCl₃) |
|---|---|---|---|---|---|---|
| | 2,3-Epoxycyclopentanones | | | | | |
| 101 | Same as above | | (6-ethoxybenzothiazole-2-thiol) | cyclopentenone with benzothiazolyl-S, alkynyl-OSi substituents | 41 | 0.04(s,9H), 0.7–1.0(m,3H), 1.40(t,3H,J=7.0Hz), 1.3–2.1(m,4H), 2.2–2.8(m,4H), 4.01(q,2H,J=7.0Hz), 6.8–7.4(m,3H), 7.63(s,1H) |
| 102 | (hydroxy epoxycyclopentanone with t-Bu alkynyl) | | 1-methylimidazole-2-thiol | cyclopentenone with imidazolyl-S, t-Bu-alkynyl-OSi | 40 | 0.09(s,9H), 1.05(s,9H), 2.58(s,2H), 3.67(s,3H), 6.6–7.1(m,3H) |
| 103 | (hydroxy epoxycyclopentanone with OPh-propyl, propyl) | | PhSH | cyclopentenone with PhS, propyl, OPh-propyl-OSi | 63 | 0.04(s,9H), 0.7–1.0(m,3H), 1.1–1.9(m,13H), 2.63(s,2H), 2.4–2.8(m,2H), 3.95(t,2H, J=6.0Hz), 6.8–7.7(m,11H) |
| 104 | same as above | | t-BuSH | cyclopentenone with t-BuS, propyl, OPh-propyl-OSi | 39 | 0.07(s,9H), 0.7–1.0(m,3H), 1.1–2.0(m,10H), 1.36(s,9H), 2.4–2.9(m,4H), 3.95(t,2H, J=5.8Hz), 6.8–7.1(m,3H), 7.1–7.5(m,2H) |
| 105 | Same as above | | cyclohexyl-SH | cyclopentenone with cyclohexyl-S, propyl, OPh-propyl-OSi | 53 | 0.10(s,9H), 0.7–1.0(m,3H), 1.3–2.0(m,20H), 2.3–2.8(m,5H), 3.93(t,2H,J=5.9Hz), 6.7–7.5(m,5H) |

TABLE 10-continued

| Ex. No. | Starting Material | | Yield (%) | NMR (δ, CDCl₃) |
|---|---|---|---|---|
| | 2,3-Epoxycyclopentanones | Thiols | 2-Substituted-2-cyclopentenones | |
| 106 | Same as above | (thiol: 2-mercapto-1-methylimidazole, SH on imidazole N-Me) | (cyclopentenone with OSi, OPh side chain, S-linked N-methylimidazole, propyl) | 68 | 0.08(s,9H), 0.8–1.1(m,3H), 1.1–2.3(m,10H), 2.56(s,2H), 2.3–2.9(m,2H), 3.81(s,3H), 3.92(t,2H,J=6.2Hz), 6.8–7.1(m,5H), 7.1–7.4(m,2H) |
| 107 | (epoxycyclopentanone with OPh, OH, Et) | pyridine-SH | (cyclopentenone with OSi, OPh, S-pyridyl, Et) | 49 | 0.10(s,9H), 0.8–1.1(m,3H), 1.1–2.3(m,6H), 2.60(s,2H), 2.3–2.8(m,2H), 3.93(t,2H, J=6.2Hz), 7.2–8.1(m,4H) |
| 108 | (epoxycyclopentanone with OPh, OH, CH₂Ph) | cyclopentyl-SH | (cyclopentenone with OSi, OPh, S-cyclopentyl, CH₂Ph) | 53 | 0.09(s,9H), 1.1–3.1(m,27H), 3.95(t,2H,J=6.1Hz), 6.7–7.5(m,10H) |
| 109 | (epoxycyclopentanone with OPh, OH, prenyl chain) | MeOOOC-(CH₂)ₙ-SH | (cyclopentenone with OSi, OPh, S-(CH₂)ₙ-COOMe, prenyl) | 47 | 0.07(s,9H), 0.85(brd,3H, J=4.5Hz), 1.0–2.7(m,33H), 3.67(s,3H), 3.95(t,2H,J=5.9Hz), 4.8–5.2(m,1H), 6.7–7.1(m,3H), 7.1–7.4(m,2H) |
| 110 | (epoxycyclopentanone with OPh, OH, butyl) | 3-CF₃-benzyl-SH | (cyclopentenone with OSi, OPh, S-CH₂-(3-CF₃-C₆H₄), butyl) | 68 | 0.09(s,9H), 0.7–1.1(m,6H), 1.1–2.0(m,6H), 2.4–2.9(m,4H), 4.15(s,2H), 6.99(s,1H), 7.3–7.7(m,3H) |

TABLE 10-continued
| Ex. No. | Starting Material 2,3-Epoxycyclopentanones | Thiols | 2-Substituted-2-cyclopentenones | Yield (%) | NMR (δ, CDCl₃) |
|---|---|---|---|---|---|
| 111 | 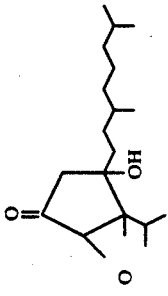 | 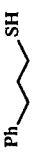 | 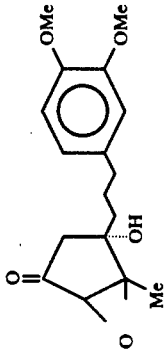 | 64 | 0.07(s,9H), 0.7-1.2(m,15H), 1.2-2.0(m,14H), 2.1-3.0(m,7H), 7.0-7.4(m,5H) |
| 112 |  | 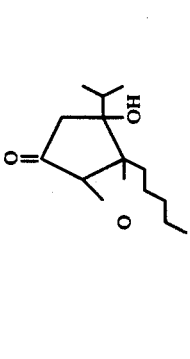 |  | 68 | 0.08(s,9H), 1.5-2.0(m,4H), 2.31(s,3H), 2.58(s,2H), 2.4-2.9(m,2H), 3.81(s,6H), 6.4-6.9(m,3H), 7.2-7.8(m,4H) |
| 113 | | | | 33 | 0.08(s,9H), 0.7-1.2(m,6H), 1.3-1.8(m,5H), 2.3-2.8(m,4H), 3.77(s,3H), 3.95(t,2H,J=6.1 Hz), 6.6-7.5(m,9H) |

TABLE 11

| Ex. No. | Starting Material 2,3-Epoxycyclopentanones | Thiols | 2-substituted-2-cyclopentenones | Yield (%) | NMR (δ.CDCl₃) |
|---|---|---|---|---|---|
| 33 | (cyclopentanone with OH, hexyl, epoxide) | EtSH | (cyclopentenone with EtS, OSi, hexyl) | 41 | 0.09(s, 9H), 0.7–1.0(m, 6H), 1.1–2.1(m, 14H), 2.2–2.8(m, 4H), 6.84(s, 1H) |
| 34 | (cyclopentanone with OH, isobutyl chain, epoxide) | i-PrSH | (cyclopentenone with i-PrS, OSi, isobutyl chain) | 44 | 0.08(s, 9H), 0.7–1.3(m, 15H), 1.2–2.8(m, 15H), 6.73(s, 1H) |
| 35 | (cyclopentanone with OH, cyclohexyl-CH=CH-OSi, epoxide) | MeOOC(CH₂)ₙSH | (cyclopentenone with MeOOC-S, SiO, cyclohexyl-CH=CH-OSi) | 28 | 0–0.1(m, 15H), 0.90(s, 9H), 1.0–2.0(m, 17H), 2.1–2.9(m, 6H), 3.69(s, 3H), 4.6–4.8(m, 1H), 5.4–5.8(m, 2H), 6.90(s, 1H) |
| 36 | (cyclopentanone with OH, (CH₂)₃OPh, epoxide) | PhSH | (cyclopentenone with PhS, OSi, (CH₂)₃OPh) | 37 | 0.05(s, 9H), 1.1–1.9(m, 6H), 2.63(s, 2H), 3.95(t, 2H, J=6.0Hz), 6.8–7.7(m, 11H) |
| 37 | Same as above | (4-Cl-C₆H₄-CH₂-SH) | (cyclopentenone with 4-Cl-benzyl-S, OSi, (CH₂)₃OPh) | 32 | 0.08(s, 9H), 1.1–2.0(m, 6H), 2.59(s, 2H), 3.92(t, 2H, J=6.1Hz), 4.04(s, 2H), 6.8–7.7 (m, 10H) |

TABLE 11-continued
| Ex. No. | Starting Material | | 2-substituted-2-cyclopentenones | Yield (%) | NMR (δ.CDCl₃) |
|---|---|---|---|---|---|
| | 2,3-Epoxycyclopentanones | Thiols | | | |
| 38 | 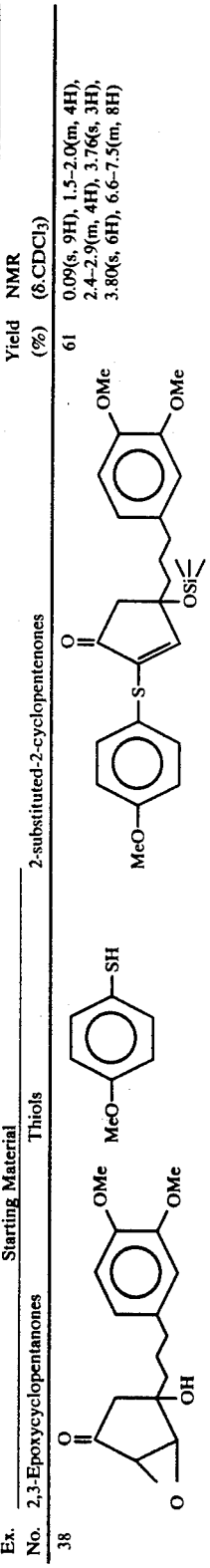 | 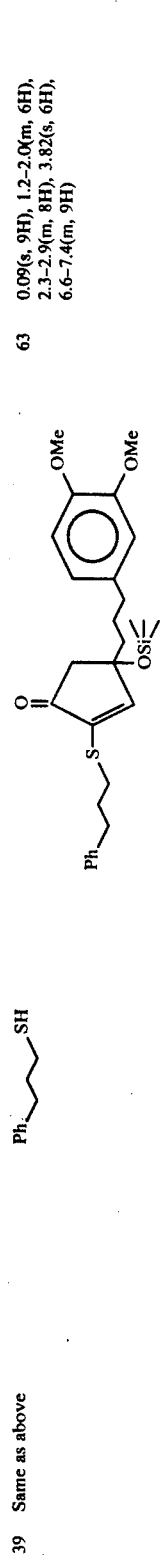 | 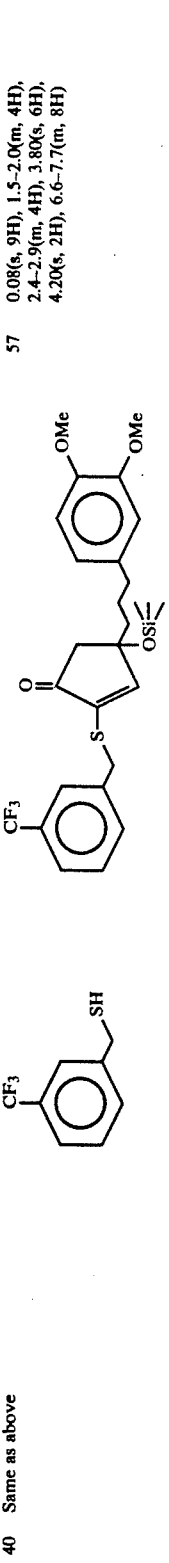 | 61 | 0.09(s, 9H), 1.5–2.0(m, 4H), 2.4–2.9(m, 4H), 3.76(s, 3H), 3.80(s, 6H), 6.6–7.5(m, 8H) |
| 39 | Same as above | 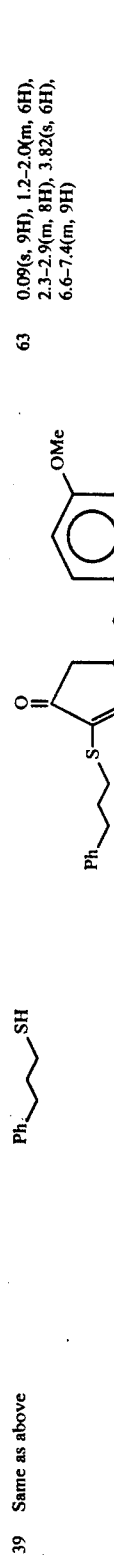 | 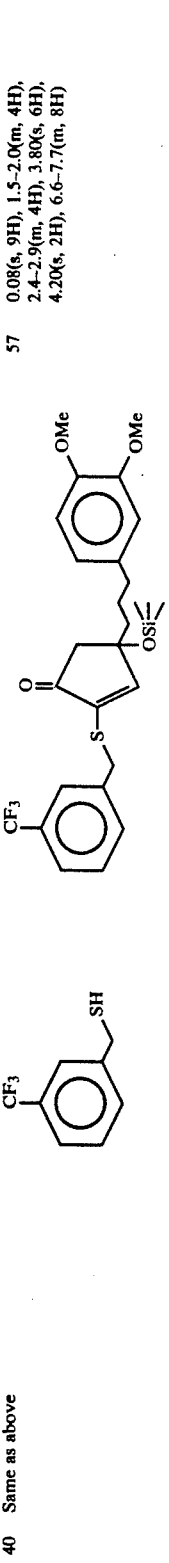 | 63 | 0.09(s, 9H), 1.2–2.0(m, 6H), 2.3–2.9(m, 8H), 3.82(s, 6H), 6.6–7.4(m, 9H) |
| 40 | Same as above | 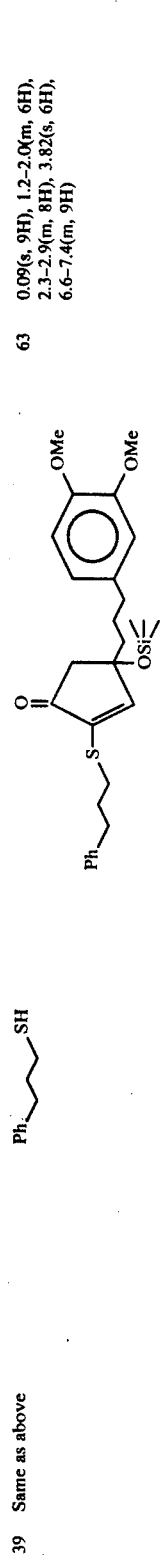 | 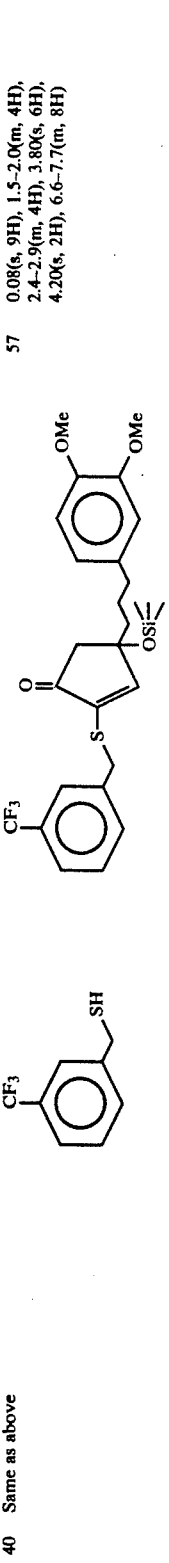 | 57 | 0.08(s, 9H), 1.5–2.0(m, 4H), 2.4–2.9(m, 4H), 3.80(s, 6H), 4.20(s, 2H), 6.6–7.7(m, 8H) |

TABLE 12

| Ex. No. | Starting Material (2,3-Epoxycyclopentanones) | 2-Substituted-2-cyclopentenones | Yield (%) | NMR($\delta$, CDCl$_3$) |
|---|---|---|---|---|
| 114 | (structure) | (structure) | 20 | 0.89(3H, brt, J=5.5Hz), 1.0–2.6(31H, m), 3.68 (3H, s), 3.7–4.1(1H, m), 5.20(1H, dd, J=15.0, 8.5Hz), 5.67(1H, dt, J=15.0, 6.4Hz), 6.5–6.8 (2H, m) |
| | | (structure) | 14 | 0.89(3H, brt, J=5.0Hz), 1.1–2.7(43H, m), 3.0–3.3(1H, m), 3.4–3.6(1H, m), 3.69(3H, s), 5.36(1H, dd, J=15.5, 7.8Hz), 5.61(1H, dt, J=15.5, 7.8Hz), 6.87–6.90(1H, d, J=3.0Hz) |

TABLE 13

| Ex. No. | Starting Material 2-Substituted-2-cyclopentenones | Aldehydes | 2-Substituted-2-cyclopentenones |
|---|---|---|---|
| 115 | (structure shown) | (structure shown) | (structure shown) |
| 116 | Same as above | (structure shown) | (structure shown) |
| 117 | Same as above | (structure shown) | (structure shown) |
| 118 | Same as above | (structure shown) | (structure shown) |
| 119 | Same as above | (structure shown) | (structure shown) |

TABLE 13-continued
| | | | |
|---|---|---|---|
| 120 | Same as above |  |  |
| 121 | |  |  |
| 122 | |  |  |
| 123 | |  |  |
| 124 | Same as above |  |  |

TABLE 13-continued

TABLE 13-continued

TABLE 13-continued

| | | |
|---|---|---|
| 135 | Same as above | (structure) |
| 136 | Same as above | (structure) |
| 137 | Same as above | (structure) |
| 138 | Same as above | (structure) |
| 139 | Same as above | (structure) |

TABLE 13-continued

| | | |
|---|---|---|
| 140 | Same as above | (structure) |
| 141 | Same as above | (structure) |
| 142 | Same as above | (structure) |
| 143 | Same as above | (structure) |
| 144 | Same as above | (structure) |

TABLE 13-continued
| | | |
|---|---|---|
| 145 | Same as above 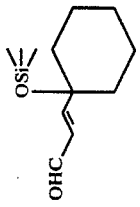 | 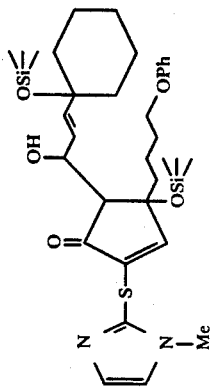 |
| 146 | Same as above 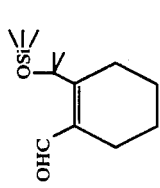 | 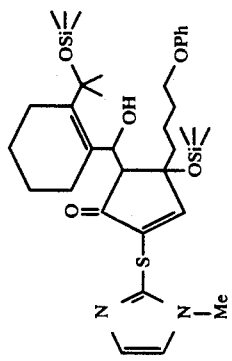 |
| 147 | Same as above 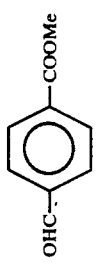 | 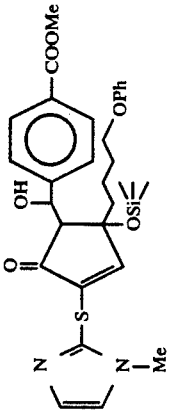 |
| 148 | Same as above 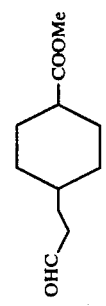 | 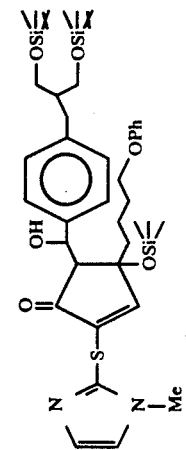 |
| 149 | 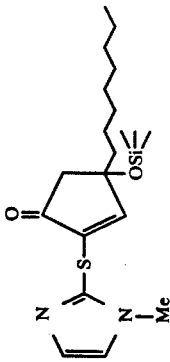 | |

TABLE 13-continued
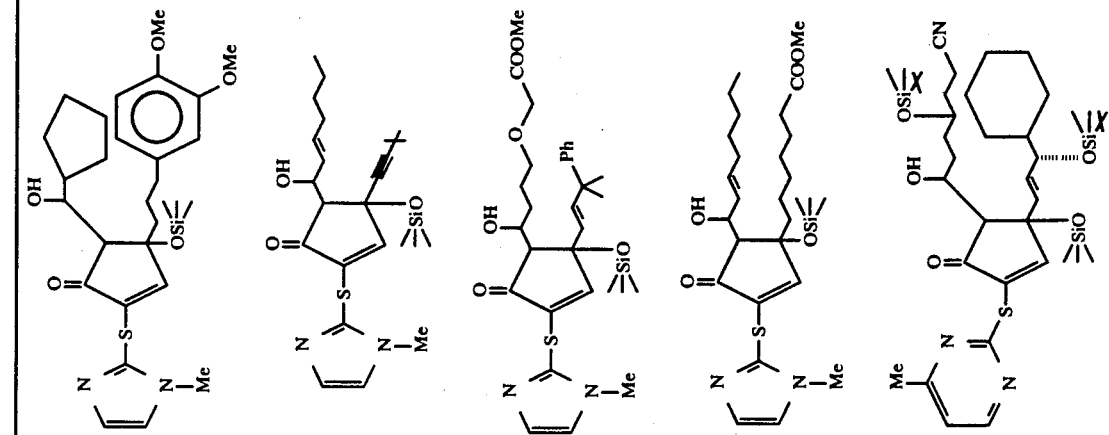
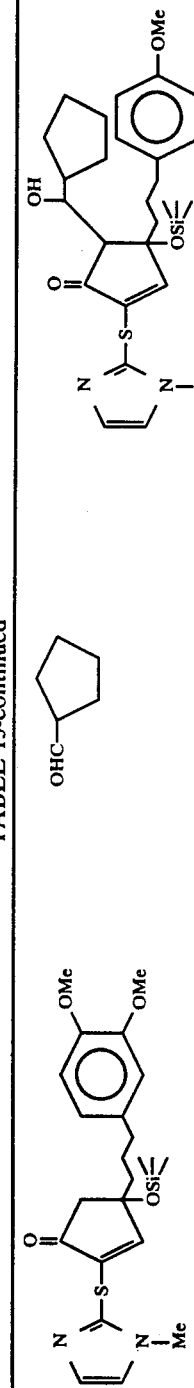
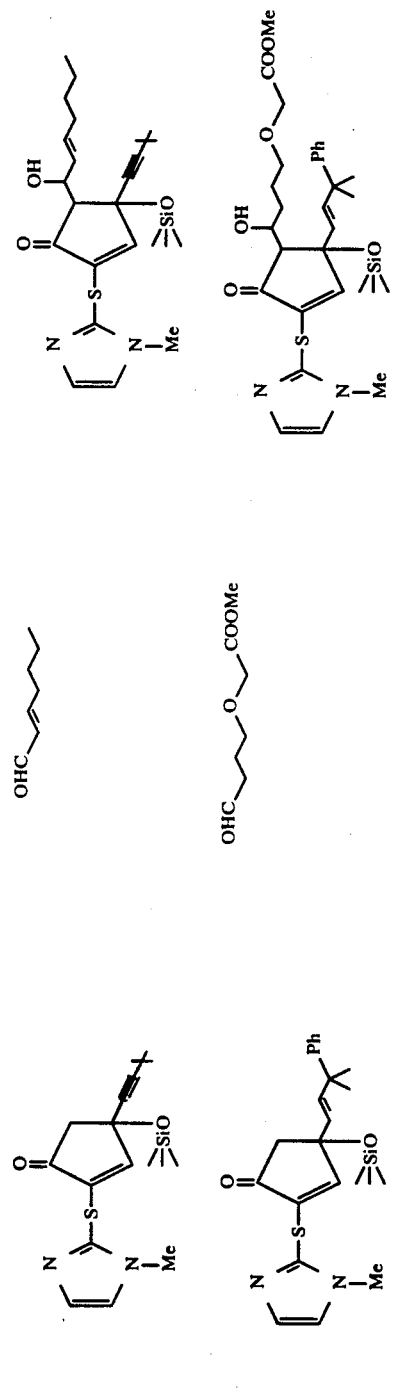
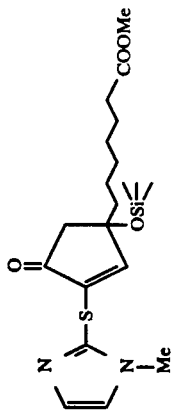

TABLE 13-continued

TABLE 13-continued

TABLE 13-continued
| | | |
|---|---|---|
| 165 | Same as above | 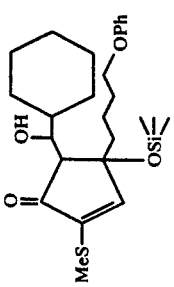 |
| 166 | 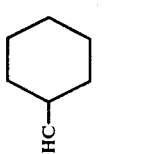 | 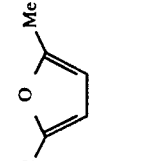 |
| 167 | 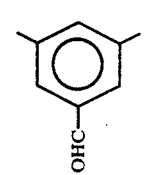 | 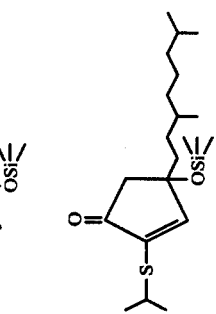 |
| 168 | 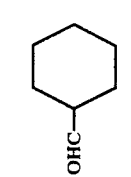 | 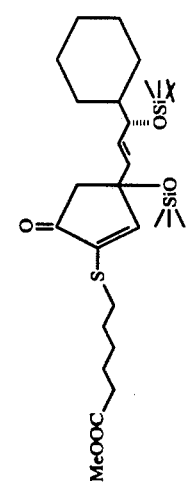 |
| 169 | Same as above |  |

TABLE 13-continued

| 170 | 171 | 172 | 173 |

TABLE 13-continued

| | | | |
|---|---|---|---|
| 174 | | | |
| 175 | | | |
| 176 | | Same as above | |
| 177 | | | |
| 178 | | | Same as above |

TABLE 13-continued

TABLE 13-continued

| | EtCHO | |
|---|---|---|
| 184 | | |
| 185 | | |
| 186 | | |
| 187 | | |
| 188 | | |

TABLE 13-continued

TABLE 13-continued
| | | | |
|---|---|---|---|
| 195 | 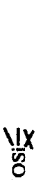 | Same as above |  |
| 196 | 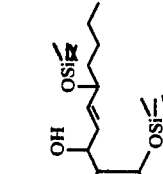 | Same as above | 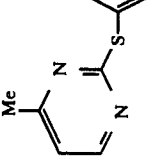 |
| 197 | 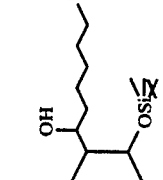 | 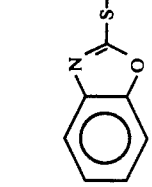 | 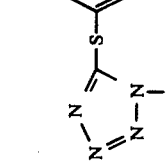 |
| 198 | 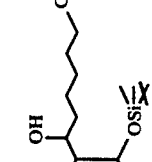 | Same as above | 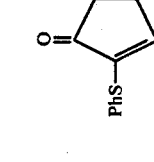 |
| 199 | 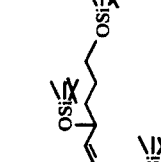 | 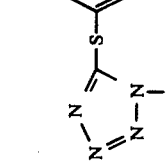 | 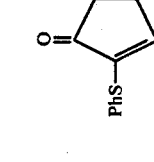 |
| 200 | 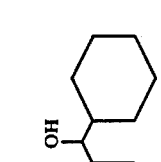 | 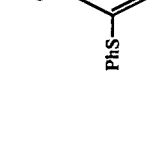 | |

TABLE 13-continued

| 201 | Same as above | (structure: cyclopentenone with cyclohexylmethyl-CH(OH)- substituent and PhS group) |
|---|---|---|
| 202 | Same as above | (structure: cyclopentenone with (5-methylfuran-2-yl)methylene substituent and PhS group) |

| Ex. No. | Yield (%) | NMR (δ, CDCl₃) |
|---|---|---|
| 115 | 82 | 0–0.2(21H, m), 0.85(18H, s), 1.0–2.9(20H, m), 3.0–3.4(1H, m), 3.4–3.7(2H, m), 3.7–4.3(3H, m), 4.3–4.8(1H, m), 5.4–6.0(2H, m), 6.6–7.6(6H, m) |
| 116 | 72 | 0.03(9H, s), 1.1–2.5(30H, m), 2.6–2.9(1H, m), 3.68(3H, s), 3.6–4.1(3H, m), 6.7–7.4(6H, m) |
| 117 | 14 | 0.09(s, 9H), 1.2–2.0(m, 19H), 2.0–2.7(m, 7H), 2.8–3.0(m, 1H), 3.5–4.0(m, 3H), 3.76(s, 3H), 6.7–7.1(m, 4H), 7.1–7.5(m, 2H) |
| 118 | 61 | 0.08(s, 9H), 1.2–2.0(m, 21H), 2.2–2.4(m, 1H), 2.8–3.0(m, 1H), 3.4–4.0(m, 5H), 3.73(s, 3H), 4.09(s, 2H), 6.8–7.1(m, 4H), 7.1–7.5(m, 2H) |
| 119 | 70 | 0.07(s, 9H), 1.1–2.9(m, 33H), 3.67(s, 3H), 3.5–4.1(m, 3H), 6.7–7.4(m, 6H) |
| 120 | 83 | 0.03(s, 9H), 1.0–2.4(m, 17H), 3.0–3.3(m, 1H), 3.75(s, 3H), 3.94(t, 2H, J=5.4Hz), 4.3–4.5(m, 1H), 4.57(s, 2H), 4.9–5.1(m, 1H), 6.5–7.4(m, 10H) |
| 121 | 83 | 0.10(s, 9H), 0.7–1.0(m, 6H), 1.1–2.0(m, 41H), 2.3–2.6(m, 1H), 2.9–3.1(m, 1H), 3.5–3.9(m, 1H), 6.77(s, 1H) |
| 122 | 39 | 0.10(s, 9H), 1.2–2.1(m, 21H), 2.1–3.0(m, 8H), 3.83(s, 6H), 3.9–4.2(m, 1H), 5.2–5.5(m, 1H), 6.4–6.9(m, 4H) |
| 123 | 75 | 0.09(s, 3H), 0.7–1.0(m, 3H), 1.2–2.5(m, 20H), 2.8–3.0(m, 3H), 3.5–4.0(m, 3H), 6.7–7.4(m, 6H) |
| 124 | 49 | 0.06(s, 3H), 1.1–2.9(m, 22H), 3.74(s, 3H), 3.5–4.1(m, 3H), 6.6–7.5(m, 10H) |
| 125 | 50 | 0.09(s, 3H), 0.83(d, 9H, J=4.7Hz), 0.9–2.1(m, 21H), 2.3–2.9(m, 2H), 4.9–5.1(m, 1H), 6.7–7.4(m, 5H) |
| 126 | 40 | 0.13(s, 9H), 1.2–2.6(m, 30H), 2.8–3.0(m, 1H), 3.67(s, 3H), 3.8–4.1(m, 2H), 4.6–4.9(m, 1H), 6.8–7.1(m, 4H), 7.1–7.5(m, 2H) |
| 127 | 61 | 0.10(s, 9H), 0.85(d, 9H, J=4.7Hz), 0.9–3.0(m, 36H), 3.5–3.8(m, 1H), 6.80(s, 1H), 7.1–7.5(m, 5H) |
| 128 | 39 | 0.07(s, 9H), 0.7–1.0(m, 3H), 1.1–1.9(m, 19H), 2.9–3.1(m, 1H), 3.5–4.0(m, 3H), 6.6–7.8(m, 8H), 7.80(s, 1H), 8.2–8.4(m, 1H) |
| 129 | 54 | 0.08(s, 21H), 0.85(s, 18H), 1.1–2.9(m, 12H), 3.4–3.7(m, 2H), 3.8–4.3(m, 3H), 4.4–4.6(m, 1H), 5.5–6.1(m, 2H), 6.7–7.9(m, 8H), 7.79(s, 1H) |
| 130 | 60 | 0.08(s, 9H), 0.88(s, 18H), 1.3–2.1(m, 6H), 2.4–2.7(m, 4H), 3.0–3.3(m, 1H), 3.56(d, 4H, J=5.5Hz), 3.75(s, 6H), 5.0–5.1(m, 1H), 6.4–7.0(m, 4H), 7.2–8.1(m, 8H) |
| 131 | 43 | 0.09(s, 9H), 0.7–1.0(m, 6H), 1.2–1.9(m, 7H), 2.2–2.6(m, 2H), 2.9–3.1(m, 1H), 3.5–3.7(m, 1H), 7.02(s, 1H), 7.4–7.9(m, 4H) |
| 132 | 60 | –0.2(m, 9H), 0.7–1.1(m, 3H), 1.1–2.2(m, 13H), 2.6–2.8(m, 1H), 3.68(s, 3H), 3.8–4.1(m, 2H), 4.3–4.6(m, 1H), 5.5–5.8(m, 2H), 6.7–7.45(m, 8H) |
| 133 | 22 | –0.2(m, 15H), 0.89(s, 9H), 1.1–2.0(m, 7H), 2.7–2.9(m, 1H), 3.65(s, 3H), 3.7–4.3(m, 3H), 4.5–4.7(m, 1H), 5.6–5.9(m, 2H), 6.8–7.5(m, 8H) |
| 134 | 48 | 0.03(s, 12H), 0.07(s, 9H), 0.88(s, 18H), 1.1–2.0(m, 14H), 2.3–2.6(m, 1H), 3.54(d, 4H, J=5Hz), 3.69(s, 3H), 3.6–3.8(m, 1H), 3.8–4.0(m, 2H), 6.8–7.4(m, 8H) |
| 135 | 46 | 0.015(21H, m), 0.85(18H, s), 1.1–2.1(10H, m), 2.3–2.9(1H, m), 3.3–3.8(2H, m), 3.66(3H, s), 3.75–4.1(2H, m), 4.0–4.3(1H, m), 4.3–4.6(1H, m), 5.5–6.1(2H, m), 6.7–7.4(8H, m) |
| 136 | 42 | 0.03(s, 12H), 0.06(s, 9H), 0.88(s, 18H), 1.1–2.5(m, 14H), 2.5–2.8(m, 1H), 3.54(d, 4H, J=5Hz), 3.68(s, 3H), 3.8–4.0(m, 2H), 4.2–4.4(m, 1H), 5.6–5.8(m, 2H), 6.8–7.4(m, 8H) |
| 137 | 69 | 0.13(s, 9H), 1.1–2.0(m, 14H), 2.1–2.7(m, 4H), 3.2–3.5(m, 1H), 3.65(s, 3H), 3.71(s, 3H), 3.8–4.1(m, 2H), 6.7–7.5(m, 8H) |
| 138 | 70 | 0.12(s, 9H), 1.3–2.1(m, 8H), 2.1–2.6(m, 5H), 2.8–3.0(m, 1H), 3.67(s, 3H), 3.70(s, 3H), 3.8–4.1(m, 1H), 4.6–4.9(m, 1H), 6.7–7.5(m, 8H) |
| 139 | 63 | 0.09(s, 9H), 1.2–2.0(m, 11H), 2.8–3.1(m, 1H), 3.4–4.1(m, 5H), 3.65(s, 3H), 3.70(s, 3H), 4.10(s, 2H), 6.7–7.5(m, 8H) |
| 140 | 36 | 0.07(s, 9H), 1.0–2.2(m, 7H), 2.2–3.1(m, 3H), 3.3–4.6(m, 5H), 3.70(s, 3H), 3.74(s, 3H), 4.10(s, 2H), 5.0–5.3(m, 2H), 6.7–7.5(m, 8H) |
| 141 | 23 | 0.07(s, 9H), 1.0–2.2(m, 7H), 2.2–3.0(m, 3H), 3.49(s, 3H), 3.74(s, 3H), 3.7–4.1(m, 2H), 4.10(s, 2H), 4.07(s, 3H), 4.1–4.6(m, 3H), 5.0–5.1(m, 1H), 5.1–5.3(m, 1H), 6.7–7.5(m, 8H) |
| 142 | 10 | 0.08(s, 9H), 1.1–2.0(m, 8H), 2.0–3.3(m, 4H), 3.4–3.7(m, 1H), 3.67(s, 3H), 3.8–4.1(m, 2H), 5.2–5.7(m, 1H), 6.7–7.6(m, 10H), 7.7–7.9(m, 2H) |
| 143 | 35 | 0.06(s, 9H), 1.0–2.1(m, 10H), 2.2–2.9(m, 2H), 3.74(s, 3H), 3.89(s, 3H), 3.91(s, 3H), 3.7–4.1(m, 1H), 6.7–7.4(m, 11H) |
| 144 | 37 | –0.04(s, 9H), 1.2–2.0(m, 13H), 2.1–2.5(m, 4H), 2.7–3.0(m, 1H), 3.69(s, 3H), 3.71(s, 3H), 3.7–4.2(m, 3H), 5.2–5.5(m, 1H), 6.8–7.4(m, 8H) |
| 145 | 33 | 0.11(s, 9H), 0.15(s, 9H), 1.2–2.0(m, 16H), 2.77(d, 1H, J=7.0Hz), 3.71(s, 3H), 3.99(t, 2H, J=7.0Hz), 4.56(d, 1H, J=7.0Hz), 5.7–6.1(m, 2H), 6.8–7.5(m, 18H) |
| 146 | 9 | 0.04(s, 18H), 1.07(s, 3H), 1.12(s, 3H), 1.0–2.1(m, 15H), 2.58(d, 1H, J=1.8Hz), 3.71(s, 3H), 3.97(t, 2H, J=5.9Hz), 4.8–5.0(m, 1H), 6.7–7.4(m, 8H) |
| 147 | 76 | –0.02(s, 9H), 1.4–2.0(m, 10H), 2.2–2.9(m, 2H), 3.74(s, 3H), 3.89(s, 3H), 3.7–4.1(m, 2H), 3.91(s, 3H), 3.7–4.1(m, 2H), 5.11(d, 1H, J=7.2Hz), 6.75–7.4(m, 8H), 7.45(d, 2H, J=8.6Hz), 8.01(d, 2H, J=8.1Hz) |
| 148 | 42 | –0.05(s, 9H), 0.0(s, 12H), 0.88(s, 18H), 1.1–2.1(m, 7H), 2.64(d, 2H, J=2.0Hz), 3.22(d, 1H, J=7.8Hz), 3.56(d, 4H, J=5.3Hz), 3.73(s, 3H), 3.92(t, 2H, J=5.8Hz), 5.01(d, 1H, J=7.8Hz), 6.8–7.5(m, 12H) |
| 149 | 69 | 0.06(s, 9H), 0.7–1.0(m, 3H), 1.1–2.4(m, 29H), 2.8–3.0(m, 1H), 3.4–3.8(m, 1H), 3.69(s, 3H), 3.76(s, 3H), 6.6–6.9(m, 3H) |
| 150 | 40 | 0.05(s, 9H), 1.1–2.1(m, 12H), 2.3–2.6(m, 2H), 2.9–3.1(m, 1H), 3.65(s, 3H), 3.80(s, 6H), 3.5–3.9(m, 1H), 6.4–7.2(m, 6H) |

TABLE 13-continued

| | | |
|---|---|---|
| 151 | 37 | 0.08(s, 9H), 0.7-1.0(m, 3H), 1.05(s, 9H), 1.2-2.0(m, 5H), 2.2-2.5(m, 2H), 3.0-3.2(m, 1H), 3.67(s, 3H), 3.8-4.1(m, 1H), 6.6-7.1(m, 3H) |
| 152 | 50 | 0.10(s, 9H), 1.68(s, 6H), 1.5-1.9(m, 5H), 2.8-3.0(m, 1H), 3.4-4.0(m, 3H), 3.66(s, 3H), 3.71(s, 3H), 4.10(s, 2H), 5.4-5.9(m, 2H), 6.6-7.5(m, 8H) |
| 153 | 68 | 0.08(s, 9H), 0.7-1.0(m, 3H), 1.0-2.1(m, 17H), 2.2-2.5(m, 4H), 2.8-3.0(m, 1H), 3.68(s, 3H), 3.70(s, 3H), 3.7-4.0(m, 1H), 5.4-5.9(m, 2H), 6.7-7.3(m, 3H) |
| 154 | 54 | 0-0.2(m, 21H), 0.88(s, 9H), 0.90(s, 9H), 1.1-2.1(m, 18H), 2.40(t, 2H, J=7.5Hz), 2.47(s, 3H), 2.9-3.1(m, 1H), 3.5-4.0(m, 2H), 4.6-4.9(m, 1H), 5.4-5.8(m, 2H), 6.6-7.0(m, 2H), 8.33(d, 1H, J=5.0Hz) |
| 155 | 75 | 0.09(s, 9H), 0.7-1.1(m, 18H), 1.1-2.0(m, 23H), 2.8-3.0(m, 1H), 3.5-3.9(m, 1H), 6.86(s, 1H), 7.2-7.8(m, 4H) |
| 156 | 59 | 0.09(s, 9H), 0.7-1.0(m, 3H), 1.2-1.9(m, 13H), 2.3-3.0(m, 3H), 3.5-3.9(m, 1H), 3.85(s, 6H), 6.4-6.9(m, 4H), 7.2-7.8(m, 4H) |
| 157 | 38 | 0.07(s, 9H), 0.95(d, 6H, J=6.4Hz), 1.23(s, 3H), 1.2-1.8(m, 3H), 2.0-2.3(m, 1H), 2.8-3.1(m, 1H), 3.4-3.9(m, 1H), 7.2-7.9(m, 5H) |
| 158 | 54 | 0-0.2(m, 15H), 0.90(s, 9H), 0.7-1.0(m, 3H), 1.1-2.1(m, 16H), 2.8-3.0(m, 1H), 3.5-3.9(m, 1H), 4.6-4.9(m, 1H), 5.4-5.8(m, 2H), 7.0-7.8(m, 4H) |
| 159 | 60 | 0.10(s, 21H), 0.85(s, 18H), 1.40(t, 3H, J=6.9Hz), 1.1-2.9(m, 11H), 3.4-3.7(m, 2H), 3.7-4.3(m, 5H), 4.53(t, 1H, J=5.4Hz), 5.5-6.1(m, 2H), 6.7-7.4(m, 7H), 7.6-7.9(m, 1H), 7.90(s, 1H) |
| 160 | 70 | 0.08(s, 9H), 0.7-1.1(m, 6H), 1.1-2.9(m, 14H), 3.5-4.3(m, 7H), 5.88(d, 1H, J=16.0Hz), 6.7-7.9(m, 10H) |
| 161 | 71 | 0.05(s, 9H), 0.7-1.0(m, 3H), 1.40(t, 3H, J=7.0Hz), 1.1-2.1(m, 9H), 2.2-3.0(m, 5H), 3.74(s, 3H), 3.6-3.9(m, 1H), 4.01(q, 2H, J=7.0Hz), 6.6-7.4(m, 7H), 7.60(s, 1H) |
| 162 | 44 | 0.08(s, 9H), 1.3-1.9(m, 9H), 2.0-3.0(m, 7H), 3.74(s, 3H), 3.84(s, 6H), 3.8-4.2(m, 3H), 6.0-6.5(m, 2H), 6.85(s, 1H), 7.3-7.6(m, 1H) |
| 163 | 70 | 0.09(s, 9H), 1.07(s, 3H), 1.3-1.7(m, 3H), 2.3-2.6(m, 2H), 2.9-3.1(m, 1H), 3.7-3.9(m, 1 H), 3.90(s, 6H), 4.07(s, 2H), 6.0-6.9(m, 6H), 7.2-7.4(m, 1H) |
| 164 | 87 | 0.03(9H, s), 1.0-2.0(6H, m), 2.31(1H, d, J=7.5Hz), 3.18(1H, d, J=7.5Hz), 3.75(3H, s), 3.92(2H, t, J=5.0Hz), 4.3-4.5(1H, m), 4.58(2H, s), 4.9-5.1(1H, m), 6.5-7.4(10H, m) |
| 165 | 70 | 0.08(s, 9H), 1.1-2.0(m, 18H), 2.34(s, 3H), 2.8-3.1(m, 1H), 3.4-3.7(m, 1H), 3.94(t, 2H, J=6.0Hz), 6.7-7.1(m, 4H), 7.1-7.4(m, 2H) |
| 166 | 18 | 0.08(s, 9H), 0.7-1.0(m, 6H), 1.1-2.1(m, 14H), 2.2-2.6(m, 2H), 2.35(s, 3H), 3.0-3.3(m, 3H), 6.14(d, 1H, J=3.4Hz), 6.63(d, 1H, J=3.4Hz), 6.85(s, 1H), 7.35(s, 1H) |
| 167 | 72 | 0.08(s, 9H), 0.7-1.3(m, 15H), 1.2-2.8(m, 14H), 2.25(s, 6H), 3.0-3.3(m, 1H), 4.9-5.1(m, 2H), 6.6-7.1(m, 4H) |
| 168 | 44 | 0-0.1(m, 15H), 0.90(s, 9H), 0.7-1.0(m, 29H), 2.1-3.0(m, 5H), 3.4-3.7(m, 1H), 3.69(s, 3H), 4.6-4.8(m, 1H), 5.4-5.8(m, 2H), 6.90(s, 1H) |
| 169 | 42 | 0.08(s, 9H), 1.1-2.0(m, 18H), 2.8-3.1(m, 1H), 3.4-3.7(m, 1H), 3.95(t, 2H, J=6.0Hz), 6.8-7.7(m, 11H) |
| 170 | 65 | 0-0.2(m, 21H), 0.89(s, 18H), 1.1-2.1(m, 7H), 2.66(d, 2H, J=2.2Hz), 3.24(d, 1H, J=7.6Hz), 3.55(d, 4H, J=5.0Hz), 3.94(t, 2H, J=6.0Hz), 5.03(d, 1H, J=7.6Hz), 6.8-7.5(m, 15H) |
| 171 | 63 | 0.08(s, 9H), 1.1-2.0(m, 14H), 2.4-3.0(m, 3H), 3.4-3.7(m, 1H), 3.76(s, 3H), 3.79(s, 6H), 6.6-7.4(m, 13H) |
| 172 | 69 | 0.09(s, 9H), 1.30(s, 9H), 1.2-2.9(m, 13H), 3.0-3.3(m, 1H), 3.80(s, 6H), 6.6-7.4(m, 13H) |
| 173 | 49 | 0.06(s, 9H), 1.2-1.9(m, 7H), 3.1-3.4(m, 1H), 3.7-4.1(m, 2H), 3.92(s, 3H), 4.18(s, 2H), 5.00(d, 1H, J=7.0Hz), 6.8-7.7(m, 14H) |
| 174 | 50 | 0.09(s, 9H), 0.7-1.0(m, 3H), 1.2-2.1(m, 9H), 2.4-2.9(m, 2H), 3.80(s, 6H), 3.75-4.20(m, 3H), 6.6-7.7(m, 12H) |
| 175 | 56 | 0-0.2(m, 21H), 0.90(s, 18H), 0.7-1.0(m, 3H), 1.0-2.1(m, 14H), 2.35(s, 3H), 2.2-2.9(m, 4H), 3.4-3.7(m, 2H), 3.98(t, 2H, J=5.4Hz), 4.0-4.3(m, 1H), 4.3-4.8(m, 1H), 5.5-6.2(m, 2H), 6.7-7.1(m, 3H), 7.1-7.5(m, 2H) |
| 156 | 41 | 0.04(s, 9H), 0.7-1.0(m, 3H), 1.0-2.1(m, 14H), 2.1-2.9(m, 6H), 2.34(s, 3H), 3.67(s, 3H), 3.6-4.1(m, 3H), 6.7-7.1(m, 3H), 7.1-7.5(m, 2H) |
| 177 | 46 | 0.06(s, 9H), 1.29(s, 3H), 1.34(s, 9H), 1.1-2.3(m, 9H), 2.34(s, 3H), 2.6-3.0(m, 2H), 3.67(s, 3H), 3.7-4.0(m, 1H) |
| 178 | 37 | 0.07(s, 9H), 0.7-1.1(m, 6H), 1.1-2.0(m, 14H), 2.34(s, 3H), 2.1-2.8(m, 11H), 3.54(s, 3H), 3.68(s, 3H), 3.7-4.0(m, 1H) |
| 179 | 40 | 0.07(s, 9H), 0.7-1.0(m, 6H), 1.1-1.9(m, 32H), 2.36(s, 3H), 2.4-2.9(m, 3H), 3.7-4.0(m, 1H) |
| 180 | 26 | 0-0.1(m, 15H), 0.89(s, 9H), 1.0-2.0(m, 31H), 2.1-3.0(m, 10H), 3.67(s, 3H), 3.8-4.0(m, 1H), 4.6-4.8(m, 1H), 5.3-5.9(m, 2H) |
| 181 | 38 | 0.05(s, 9H), 0.7-1.0(m, 3H), 1.1-2.3(m, 9H), 1.31(s, 9H), 2.4-2.9(m, 2H), 2.34(s, 3H), 2.6-3.0(m, 2H), 3.67(s, 3H), 3.86(m, 2H, J=5.7Hz), 4.0-4.4(m, 1H), 4.6-5.0(m, 1H), 6.7-7.6(m, 10H) |
| 182 | 21 | 0.06(s, 9H), 0.7-1.1(m, 36H), 1.1-2.0(m, 14H), 2.34(s, 3H), 2.1-2.8(m, 11H), 3.67(s, 3H), 3.68(s, 3H), 3.8-4.3(m, 3H), 4.8-5.2(m, 1H), 6.7-7.1(m, 3H), 7.1-7.4(m, 2H) |
| 183 | 52 | 0.07(s, 9H), 0.7-1.0(m, 6H), 1.1-1.9(m, 23H), 2.1-2.9(m, 4H), 3.6-4.2(m, 3H), 6.7-7.5(m, 10H) |
| 184 | 29 | 0.07(s, 9H), 0.7-1.2(m, 9H), 1.3-1.9(m, 7H), 2.3-2.8(m, 4H), 3.78(s, 3H), 3.67(s, 3H), 3.6-4.1(m, 3H), 6.6-7.5(m, 9H) |
| 185 | 40 | 0.08(s, 9H), 0.7-1.2(m, 15H), 1.2-2.0(m, 22H), 2.1-3.0(m, 9H), 3.67(s, 3H), 3.7-4.0(m, 1H), 7.0-7.4(m, 5H) |
| 186 | 34 | 0.06(s, 9H), 0.7-1.1(m, 15H), 1.1-2.0(m, 16H), 2.4-2.9(m, 4H), 3.6-3.9(m, 2H), 6.69(s, 1H), 7.3-7.7(m, 3H) |
| 187 | 42 | 0.07(s, 9H), 1.1-2.0(m, 28H), 2.1-2.9(m, 7H), 3.68(s, 3H), 3.6-4.1(m, 3H), 6.7-7.0(m, 3H), 7.1-7.4(m, 2H) |
| 188 | 20 | 0.07(s, 9H), 1.1-2.0(m, 24H), 2.1-2.9(m, 9H), 3.72(s, 3H), 3.7-4.3(m, 3H), 6.6-7.5(m, 14H) |
| 189 | 39 | 0.09(s, 9H), 0.7-1.0(m, 3H), 1.1-2.2(m, 18H), 2.3-2.9(m, 3H), 3.3-3.7(m, 1H), 3.93(t, 2H, J=6.1Hz), 6.7-7.1(m, 3H), 7.1-8.1(m, 6H) |
| 190 | 11 | 0-0.1(m, 21H), 0.91(s, 18H), 0.8-1.1(m, 3H), 1.1-2.3(m, 15H), 2.4-2.8(m, 3H), 3.4-4.3(m, 3H), 3.70(s, 3H), 4.3-4.6(m, 1H), 5.6-5.8(m, 2H), 6.7-7.1(m, 3H), 7.1-7.4(m, 2H) |
| 191 | 33 | 0.06(s, 9H), 1.2-2.1(m, 11H), 2.40(s, 3H), 2.2-3.0(m, 6H), 3.80(s, 6H), 3.6-4.0(m, 3H), 5.89(d, 1H, J=16Hz), 6.4-7.1(m, 4H), 7.2-7.8(m, 4H) |
| 192 | 24 | 0.04(s, 12H), 0.15(s, 6H), 0.89(s, 18H), 0.91(s, 9H), 1.4-1.8(m, 4H), 2.32(s, 9H), 2.6-2.8(m, 1H), 3.5-3.8(m, 2H), 4.0-4.2(m, 1H), 4.4-4.7(m, 1H), 4.8-4.95(m, 1H) |
| 193 | 27 | 0.08(s, 6H), 0.88(s, 9H), 1.1-2.2(m, 11H), 2.34(s, 3H), 2.5-2.8(m, 1H), 3.68(s, 3H), 3.7-4.0(m, 1H), 6.79(d, 1H, J=2.4Hz) |
| 194 | 26 | 0-0.2(m, 18H), 0.89(s, 18H), 0.92(s, 9H), 1.1-2.0(m, 15H), 2.2-2.8(m, 2H), 3.5-3.8(m, 2H), 4.0-4.2(m, 1H), 4.4-4.7(m, 1H), 4.8-4.95(m, 1H), 5.6-5.8(m, 2H), 6.70(d, 1H, J=2.3Hz) |
| 195 | 18 | 0-0.2(m, 18H), 0.89(s, 18H), 0.90(s, 9H), 1.1-1.8(m, 5H), 2.4-2.7(m, 1H), 4.0-4.7(m, 7H), 4.8-5.0(m, 1H), 5.6-5.9(m, 2H), 6.75(d, 1H, J=1.4Hz) |
| 196 | 20 | 0-0.2(m, 18H), 0.88(s, 18H), 0.90(s, 9H), 1.1-1.9(m, 5H), 2.46(s, 3H), 2.5-2.8(m, 1H), 3.5-3.8(m, 2H), 4.0-4.7(m, 2H), 4.8-5.0(m, 1H), 5.6-5.8(m, 2H), 6.88(d, 1H, J=5.1Hz), 7.89(d, 1H, J=2.6Hz), 8.32(d, 1H, J=5.1Hz) |

TABLE 13-continued

| | | |
|---|---|---|
| 197 | 21 | 0.08(s, 6H), 0.87(s, 9H), 1.1–2.2(m, 11H), 2.5–2.8(m, 1H), 3.69(s, 3H), 3.7–4.0(m, 1H), 5.0–5.2(m, 1H), 7.2–7.8(m, 4H), 8.03(d, 1H, J=2.6Hz) |
| 198 | 6 | 0.09(s, 6H), 0.89(s, 9H), 1.0–2.2(m, 11H), 2.5–2.9(m, 1H), 3.68(s, 3H), 3.7–4.0(m, 1H), 4.10(s, 3H), 4.9–5.1(m, 1H), 7.73(d, 1H, J=2.6Hz) |
| 199 | 85 | 0–0.25(m, 18H), 0.89(s, 18H), 0.90(s, 9H), 1.44(s, 9H), 1.3–1.8(m, 5H), 2.4–2.7(m, 1H), 3.5–3.8(m, 2H), 4.0–4.7(m, 2H), 4.99(s, 1H), 5.6–5.9(m, 2H), 7.0(s, 5H) |
| 200 | 20 | 1.0–1.9(m, 11H), 2.1–2.9(m, 3H), 3.4–3.7(m, 1H), 6.99(t, 1H, J=2.9Hz), 7.2–7.7(m, 5H) |
| 201 | 9 | 0.9–1.9(m, 15H), 2.1–2.9(m, 3H), 3.5–3.9(m, 1H), 6.98(t, 1H, J=2.9Hz), 7.2–7.7(m, 5H) |
| 202 | 23 | 2.35(s, 3H), 3.4–3.6(m, 2H), 6.12(d, 1H, J=3.3Hz), 6.61(d, 1H, J=3.5Hz), 6.86(t, 1H, J=2.8Hz), 7.2–7.6(m, 6H) |

TABLE 14

| Ref. Ex. No. | Starting Material | | 2-Substituted-2-cyclopentenones | Yield (%) | NMR (δ,CDCl₃) |
|---|---|---|---|---|---|
| | 2-Substituted-2-cyclopentenones | Aldehydes | | | |
| 41 | [structure: MeS-cyclopentenone with OPh and OSi side chain] | OHC-CH=CH-CH₂CH₂CH₂CH₃ | [structure] | 50 | 0.10(s, 9H), 0.7-1.0(m, 3H), 1.1-2.1(m, 14H), 2.33(s, 3H), 2.5-2.8(m, 1H), 3.8-4.1(m, 3H), 5.6-5.9(m, 2H), 6.7-7.1(m, 4H), 7.1-7.5(m, 2H) |
| 42 | Same as above | OHC-C≡C-CH₂CH₂-COOMe | [structure] | 59 | 0.14(s, 9H), 1.3-2.1(m, 8H), 2.1-2.6(m, 5H), 2.34(s, 3H), 2.8-3.0(m, 1H), 3.66(s, 3H), 3.8-4.1(m, 2H), 4.6-4.9(m, 1H), 6.8-7.1(m, 4H), 7.1-7.45(m, 2H) |
| 43 | Same as above | OHC-CH=CH-CH₂CH(OSi)- | [structure] | 75 | 0-0.2(m, 21H), 0.90(s, 18H), 1.0-2.1(m, 10H), 2.34(s, 3H), 2.74(d, 1H, J=7.0Hz), 3.5-3.7(m, 2H), 3.98(t, 2H, J=5.4Hz), 4.05-4.35(m, 1H), 4.35-4.7(m, 1H), 5.5-6.2(m, 2H), 6.7-7.1(m, 4H), 7.1-7.5(m, 2H) |
| 44 | [structure: iPr-cyclopentenone with OPh and OSi side chain] | Same as above | [structure] | 82 | 0-0.2(m, 21H), 0.85(s, 18H), 1.1-2.2(m, 12H), 2.3-2.9(m, 1H), 3.1-3.7(m, 3H), 3.8-4.3(m, 3H), 4.4-4.8(m, 1H), 5.5-6.1(m, 2H), 6.7-7.6(m, 6H) |
| 45 | [structure: PhS-cyclopentenone with OPh and OSi side chain] | Same as above | [structure] | 66 | 0-0.1(m, 21H), 0.87(s, 18H), 1.1-2.1(m, 10H), 2.6-2.8(m, 1H), 3.3-3.7(m, 2H), 3.7-4.0(m, 3H), 4.0-4.3(m, 1H), 4.4-4.7(m, 1H), 5.5-6.1(m, 2H), 6.3-6.7(m, 1H), 6.7-7.05(m, 3H), 7.05-7.8(m, 7H) |

TABLE 15

| Ex. No. | Starting Material | | | Yield (%) | NMR (δ, CDCl₃) |
|---|---|---|---|---|---|
| | 2-Substituted-2-cyclopentenones | Aldehydes | 2-Substituted-2-cyclopentenones | | |
| 203 | (structure) | (structure) | (structure) | 42 | 0.09(s, 9H), 1.2–2.0(m, 6H), 2.3–2.8(m, 2H), 2.95(s, 6H), 3.68(s, 3H), 3.90(t, 2H, J=6.1Hz), 4.7–5.0(m, 1H), 5.98(dd, 1H, J=15.4, 6.3Hz), 6.4–7.4(m, 13H) |
| 204 | (structure) | (structure) | (structure) | 24 | 0.09(s, 9H), 1.2–1.9(m, 7H), 2.9–3.2(m, 1H), 3.90(t, 2H, J=5.9Hz), 5.0–5.2(m, 1H), 6.7–7.4(m, 11H), 8.2–8.4(m, 2H) |
| 205 | (structure) | (structure) | (structure) | 36 | 0.09(s, 9H), 1.2–2.0(m, 6H), 2.3–3.0(m, 10H), 3.55(s, 2H), 3.68(s, 3H), 3.9–4.2(m, 3H), 5.2–5.5(m, 1H), 6.7–7.1(m, 6H), 7.1–7.5(m, 7H) |
| 206 | (structure) | (structure) | (structure) | 32 | 0.07(s, 9H), 0.7–1.0(m, 3H), 1.1–2.0(m, 10H), 2.34(s, 3H), 2.2–2.8(m, 4H), 2.95(s, 6H), 3.95(t, 2H, J=5.8Hz), 4.7–5.0 (m, 1H), 6.00(dd, 1H, J=15.7, 6.7Hz), 6.4–6.8(m, 3H), 6.8–7.5(m, 7H) |
| 207 | (structure) | (structure) | (structure) | 32 | 0.08(s, 3H), 0.12(s, 3H), 0.87 (s, 9H), 2.34(s, 3H), 2.6–2.8 (m, 2H), 2.95(s, 6H), 4.7–5.0 (m, 2H), 6.00(dd, 1H, J=15.7, 6.7Hz), 6.4–6.8(m, 4H), 7.2–7.3(m, 2H) |

TABLE 16

| Ex. No. | Starting compd. (2-Substituted-2-cyclopentenones) | 2-Substituted-2-cyclopentenones | Yield (%) | NMR (δ, CDCl₃) |
|---|---|---|---|---|
| 208 | | | 47 | 0.03(s, 12H), 0.89(s, 18H), 1.1–2.3(m, 11H), 1.94(s, 3H), 2.33(s, 3H), 2.5–2.8(s, 1H), 3.5–3.8(m, 2H), 3.8–4.2(m, 3H), 5.5–6.0(m, 3H), 6.7–7.1 (m, 4H), 7.1–7.4(m, 2H) |
| 209 | | | 37 | 0–0.15(s, 12H), 0.87(s, 18H), 1.2–1.7(m, 4H), 1.93(s, 3H), 2.36(s, 3H), 2.6–2.9(m, 1H), 3.4–3.7(m, 2H), 4.0–4.2(m, 2H), 4.6–4.8(m, 1H), 5.5–6.0 (m, 3H), 6.97(d, 1H, J=2.7Hz), 7.1–7.5(m, 5H) |
| 210 | | | 24 | 0–0.1(m, 6H), 0.98(s, 9H), 1.0–2.8(m, 18H), 2.07(s, 9H), 3.10(d, 1H, J=6.5Hz), 3.67(s, 3H), 3.8–4.0(m, 1H), 4.1–4.5 (m, 2H), 5.0–5.3(m, 1H), 5.4–5.9(m, 3H), 7.26(d, 1H, J=7.0 Hz) |
| 211 | | | 43 | 0.0–0.1(m, 12H), 0.87(s, 18H), 1.1–2.3(m, 11H), 1.96(s, 3H), 2.5–2.8(m, 1H), 3.5–3.8(m, 2H), 3.72(s, 3H), 3.8–4.2(m, 3H), 5.5–6.0(m, 3H), 6.7–7.5 (m, 8H) |
| 212 | | | 44 | 0.09(s, 9H), 0.7–1.0(m, 3H), 1.2–2.1(m, 12H), 1.95(s, 3H), 2.35(s, 3H), 2.6–2.9(m, 1H), 3.7–4.0(m, 2H), 5.5–6.0(m, 3H), 6.7–7.1(m, 4H), 7.1–7.4 (m, 2H) |

TABLE 16-continued

| Ex. No. | Starting compd. (2-Substituted-2-cyclopentenones) | 2-Substituted-2-cyclopentenones | Yield (%) | NMR (δ, CDCl₃) |
|---|---|---|---|---|
| 213 | | | 48 | 0–0.15(m, 21H), 0.88(s, 18H), 1.0–2.4(m, 10H), 1.93(s, 3H), 2.32(s, 3H), 2.8–2.9(m, 1H), 3.4–3.7(m, 2H), 3.8–4.3(m, 3H), 5.4–6.1(m, 3H), 6.7–7.1(m, 4H), 7.1–7.4(m, 2H) |
| 214 | | | 40 | 0.09(s, 9H), 1.1–2.3(m, 12H), 1.98(s, 3H), 2.34(s, 3H), 2.6–2.8(m, 3H), 3.69(s, 3H), 5.4–5.8(m, 1H), 6.7–7.1(m, 4H), 7.1–7.4(m, 2H) |
| 215 | | | 52 | 0–0.2(m, 21H), 0.89(s, 18H), 1.1–2.2(m, 11H), 1.97(s, 3H), 2.3–2.9(m, 1H), 3.1–3.7(m, 3H), 3.8–4.3(m, 3H), 5.4–6.1(m, 3H), 6.7–7.1(m, 4H), 7.1–7.4(m, 2H) |
| 216 | | | 52 | 0–0.2(m, 21H), 0.89(s, 18H), 1.1–2.3(m, 10H), 1.95(s, 3H), 2.8–3.0(m, 1H), 3.5–3.7(m, 2H), 3.8–4.2(m, 3H), 5.4–6.1(m, 3H), 6.7–7.1(m, 4H), 7.1–7.5(m, 7H) |

TABLE 16-continued

| Ex. No. | Starting compd. (2-Substituted-2-cyclopentenones) | 2-Substituted-2-cyclopentenones | Yield (%) | NMR (δ, CDCl₃) |
|---|---|---|---|---|
| 217 | | | 39 | 0-0.2(m, 21H), 0.88(s, 18H), 1.1–2.4(m, 21H), 1.93(s, 3H), 2.8–3.0(m, 1H), 3.4–3.7(m, 2H), 3.8–4.2(m, 3H), 5.4–6.1(m, 3H), 6.7–7.1(m, 4H), 7.1–7.4(m, 2H) |
| 218 | | | 68 | 0.10(s, 21H), 0.94(s, 18H), 1.1–2.4(m, 10H), 2.4–3.0(m, 1H), 3.5–3.8(m, 2H), 3.75(s, 3H), 3.8–4.4(m, 3H), 5.5–6.1(m, 3H), 6.8–7.5(m, 8H) |
| 219 | | | 55 | 0-0.2(m, 21H), 0.90(s, 18H), 0.7–1.0(m, 3H), 1.1–2.4(m, 16H), 2.4–3.0(m, 1H), 3.5–3.8(m, 2H), 3.77(s, 3H), 3.8–4.4(m, 3H), 5.5–6.0(m, 3H), 6.8–7.5(m, 7H) |
| 220 | | | 31 | 0–0.1(m, 6H), 0.86(s, 9H), 1.0–2.0(m, 11H), 2.0–2.9(m, 6H), 3.66(s, 3H), 3.77(s, 3H), 3.6–4.0(m, 1H), 5.4–5.8(m, 3H), 6.83(d, 1H, J=2.8Hz), 7.1–7.7(m, 5H) |

TABLE 16-continued

| Ex. No. | Starting compd. (2-Substituted-2-cyclopentenones) | 2-Substituted-2-cyclopentenones | Yield (%) | NMR (δ, CDCl₃) |
|---|---|---|---|---|
| 221 | | | 28 | 0–0.2(m, 21H), 0.89(s, 18H), 1.0–2.0(m, 10H), 2.37(s, 3H), 2.5–3.0(m, 1H), 3.5–3.7(m, 2H), 3.78(s, 3H), 3.8–4.2(m, 3H), 5.3–6.1(m, 3H), 6.6–7.1 (m, 4H), 7.1–7.4(m, 2H) |
| 222 | | | 25 | 0–0.2(m, 21H), 1.0–2.0(m, 10H), 2.5–3.0(m, 1H), 3.5–3.7 (m, 2H), 3.74(s, 3H), 3.77(s, 3H), 3.8–4.3(m, 3H), 5.3–6.2 (m, 3H), 6.7–8.5(m, 8H), 0.88 (s, 18H) |
| 223 | | | 76 | 0–0.1(m, 6H), 0.89(s, 9H), 1.0–3.0(m, 29H), 3.64(s, 3H), 3.7–4.0(m, 1H), 4.6–5.1(m, 1H), 5.3–5.9(m, 3H), 6.94(d, 1H, J = 2.8Hz), 7.1–7.5(m, 5H) |
| 224 | | | 53 | 0–0.2(m, 12H), 0.88(s, 18H), 1.22(d, 1H, J=5.9Hz), 1.1–2.3 (m, 12H), 2.33(s, 3H), 2.5–3.0 (m, 1H), 3.4–3.7(m, 2H), 3.8–4.2(m, 3H), 4.4–5.0(m, 1H), 5.3–6.0(m, 3H), 6.7–7.1(m, 4H), 7.1–7.4(m, 2H) |
| 225 | | | 59 | 0–0.2(m, 12H), 0.89(s, 18H), 1.23(d, 1H, J=6.1Hz), 1.1–2.3 (m, 12H), 2.5–3.0(m, 1H), 3.4–3.7(m, 2H), 3.76(s, 3H), 3.8–4.2(m, 3H), 5.4–6.1(m, 3H), 6.7–7.4(m, 8H) |

TABLE 16-continued

| Ex. No. | Starting compd. (2-Substituted-2-cyclopentenones) | 2-Substituted-2-cyclopentenones | Yield (%) | NMR (δ, CDCl₃) |
|---|---|---|---|---|
| 226 | | | 43 | 0–0.2(m, 12H), 0.87(s,9H), 0.90(s, 9H), 1.23(d, 1H, J=6.0 Hz), 1.3–1.6(m, 4H), 2.35(s, 3H), 2.6–3.0(m, 1H), 3.4–3.7 (m, 2H), 4.0–4.2(m, 1H), 4.4–4.9(m, 1H), 5.4–5.9(m, 3H), 6.97(d, 1H, J=3.3Hz), 7.1–7.5 (m, 5H) |
| 227 | | | 80 | 0–0.15(m, 21H), 0.89(s, 18H), 1.21(d, 1H, J=6.4Hz), 1.1–2.1 (m, 10H), 2.29(s, 3H), 2.5–3.0 (m, 1H), 3.4–3.7(m, 2H), 3.8–4.2(m, 3H), 4.4–5.0(m, 1H), 5.3–6.1(m, 3H), 6.7–7.1(m, 4H), 7.1–7.4(m, 2H) |
| 228 | | | 77 | 0–0.2(m, 21H), 0.90(s, 18H), 1.24(d, 1H, J=6.1Hz), 1.1–2.3 (m, 10H), 2.5–3.0(m, 1H), 3.4–3.7(m, 2H), 3.8–4.2(m, 3H), 4.5–5.0(m, 1H), 5.4–6.0(m, 3H), 6.7–7.1(m, 4H), 7.1–7.4 (m, 7H) |
| 229 | | | 63 | 0–0.2(m, 21H), 0.89(s, 18H), 1.25(d, 6H, J=6.4Hz), 1.1–2.4 (m, 21H), 2.5–3.0(m, 1H), 3.4–3.7(m, 2H), 3.8–4.2(m, 3H), 4.5–5.0(m, 1H), 5.3–6.0(m, 3H), 6.7–7.1(m, 4H), 7.1–7.4 (m, 2H) |

TABLE 16-continued

| Ex. No. | Starting compd. (2-Substituted-2-cyclopentenones) | 2-Substituted-2-cyclopentenones | Yield (%) | NMR (δ, CDCl₃) |
|---|---|---|---|---|
| 230 | (structure) | (structure) | 90 | 0–0.2(m, 21H), 0.91(s, 18H), 1.28(d, 6H, J=6.2Hz), 1.0–2.4 (m, 10H), 2.5–3.0(m, 1H), 3.5–3.8(m, 2H), 3.73(s, 3H), 3.74 (s, 3H), 3.8–4.3(m, 3H), 4.4–5.1(m, 1H), 5.3–6.2(m, 3H), 6.8–7.5(m, 8H) |
| 231 | (structure) | (structure) | 69 | 0–0.2(m, 21H), 0.90(s, 18H), 0.7–1.0(m, 3H), 1.25(d, 6H, J=6.0Hz), 1.0–2.3(m, 16H), 2.5–3.0(m, 1H), 3.5–3.8(m, 2H), 3.75(s, 3H), 3.77(s, 3H), 3.8–4.3(m, 3H), 4.5–5.1(m, 1H), 5.3–6.1(m, 3H), 6.8–7.5(m, 7H) |

TABLE 17

| Ex. No. | Starting Material | | 2-Substituted-2-cyclopentenones | Yield (%) | NMR(δ, CDCl₃) |
|---|---|---|---|---|---|
| | 2-Substituted-2-cyclopentenones | organic iodides | | | |
| 232 | [MeS-cyclopentenone with OSi and OPh sidechain] | [iodide with OSi groups and alkene] | [product structure] | 31 | 0–0.15(m, 21H) 0.89(s, 18H), 1.1–2.0(m, 10H), 2.0–2.8(m, 3H), 2.33(s, 3H), 3.4–3.7(m, 2H), 3.8–4.2(m, 3H), 5.4–5.8(m, 2H), 6.7–7.1(m, 4H), 7.1–7.4(m, 2H) |
| 233 | Same as above | [iodide with alkyne and COOMe] | [MeS product with COOMe] | 56 | 0.12(s, 9H), 1.3–2.9(m, 15H), 2.33(s, 3H), 3.66(s, 3H), 3.97 (t, 2H, J=5.8Hz), 6.7–7.1(m, 4H), 7.1–7.4(m, 2H) |
| 234 | [PhS-cyclopentenone with OSi and OPh] | Same as above | [PhS product with COOMe] | 49 | 0.10(s, 9H), 1.3–2.9(m, 15H), 3.69(s, 3H), 3.95(t, 2H, J=6.0Hz), 6.7–7.1(m, 4H), 7.1–7.6(m, 7H) |
| 235 | [cyclohexyl-S cyclopentenone] | Same as above | [product with cyclohexyl-S and COOMe] | 53 | 0.11(s, 9H), 1.3–2.9(m, 26H), 3.68(s, 3H), 3.96(t, 2H, J=6.1Hz), 6.7–7.1(m, 4H), 7.1–7.4(m, 2H) |
| 236 | [N-Me imidazolyl-S cyclopentenone] | Same as above | [product with imidazolyl-S and COOMe] | 36 | 0.10(s, 9H), 1.3–2.9(m, 15H), 3.65(s, 3H), 3.69(s, 3H), 3.95 (t, 2H, J=6.2Hz), 6.7–7.4(m, 8H) |

TABLE 17-continued
| Ex. No. | Starting Material | | Yield (%) | NMR(δ, CDCl₃) |
|---|---|---|---|---|
| | 2-Substituted-2-cyclopentenones | organic iodides | 2-Substituted-2-cyclopentenones | |
| 237 | 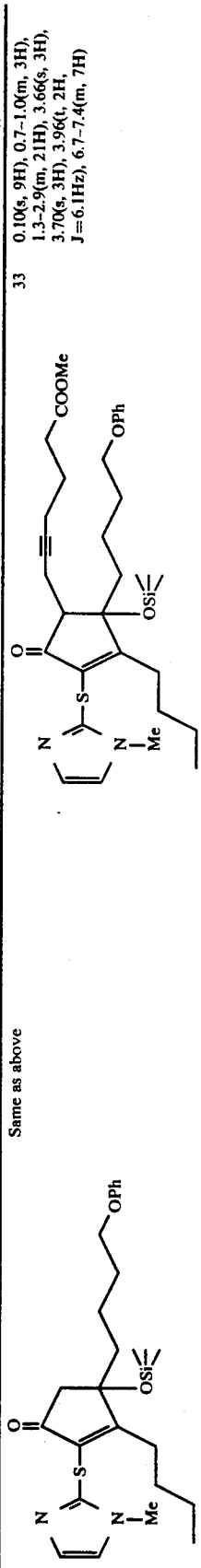 | Same as above | 33 | 0.10(s, 9H), 0.7–1.0(m, 3H), 1.3–2.9(m, 21H), 3.66(s, 3H), 3.70(s, 3H), 3.96(t, 2H, J=6.1Hz), 6.7–7.4(m, 7H) |

TABLE 18

| Ex. No. | Starting compd. (2-Substituted-2-cyclopentenones) | 2-Substituted-2-cyclopentenones | Yield (%) | NMR(δ, CDCl₃) |
|---|---|---|---|---|
| 238 | | | 78 | 0(3H, s), 0.02(3H, s), 0.87 (9H, s), 0.7 −1.1(3H, brt), 1.1−2.5(29H, m), 3.65(3H, s), 3.9−4.1(2H, m), 5.38(1H, dd, J=7.5 Hz), 5.65(1H, dd, J=15.6Hz), 6.5−6.8(2H, m) |
| 239 | | | 75 | 0−0.1(6H, m), 0.89(9H, s), 0.7−1.1(3H, brt), 1.1−2.6(18H, m), 3.68(3H, s), 3.9−4.1(2H, m), 5.3−5.8(2H, m), 6.5−6.9 (2H, m), 7.2−8.1(4H, m) |
| 240 | | | 52 | 0−0.1(6H, m), 0.90(9H, s), 0.7−1.1(3H, brt), 1.1−2.5(18H, m), 3.69(3H, s), 3.9−4.1(2H, m), 4.1(3H, s), 5.5−5.9(2H, m), 6.5−7.0(2H, m) |
| 241 | | | 67 | 0−0.3(m, 12H), 0.90(s, 18H), 1.1−2.0(m, 10H), 3.4−3.8(m, 3H), 3.70(s, 3H), 3.8−4.1(m, 2H), 4.1−4.5(m, 1H), 6.0−6.8 (m, 2H), 6.8−7.5(m, 9H) |
| 242 | | | 71 | 0−0.1(6H, m), 0.88(9H, s), 1.0−2.0(11H, m), 2.0−3.0(4H, m), 3.67(3H, s), 3.8−4.3(3H, m), 4.6−4.9(1H, m), 5.3−5.8(2H, m), 6.0−6.5(2H, m), 6.6−7.1 (2H, m), 7.2−7.4(1H, m) |

TABLE 18-continued

| | | | |
|---|---|---|---|
| 243 | (structure) | (structure) | 68 | 0-0.1(6H, m), 0.89(9H, s), 0.7-1.1(6H, m), 1.1-1.9(11H, m), 1.9-2.5(4H, m), 3.67(3H, s), 3.7-4.4(2H, m), 5.1-6.0(3H, m), 6.5-7.2(3H, m), 7.2-7.8 (4H, m) |
| 244 | (structure) | (structure) | 52 | 0-0.2(m, 12H), 0.89(s, 18H), 1.0-2.1(m, 15H), 3.4-3.8(m, 3H), 3.68(s, 3H), 4.1-4.5(m, 1H), 6.0-6.8(m, 2H), 6.8-7.4 (m, 4H) |
| 245 | (structure) | (structure) | 89 | 0-0.1(m, 6H), 0.90(s, 9H), 0.7-1.1(m, 6H), 1.1-2.8(m, 24H), 2.33(s, 3H), 3.63(s, 3H), 3.8-4.1(m, 2H), 5.3-5.9(m, 2H), 6.6-6.8(m, 1H) |
| 246 | (structure) | (structure) | 75 | 0-0.1(m, 6H), 0.89(s, 9H), 0.7-1.1(m, 6H), 1.1-2.9(m, 29H), 3.67(s, 3H), 3.7-4.1(m, 2H), 5.4-5.7(m, 2H), 6.6-6.9(m, 1H) |
| 247 | (structure) | (structure) | 78 | 0-0.1(m, 6H), 0.88(s, 9H), 0.7-1.1(m, 6H), 1.1-3.0(m, 31H), 3.67(s, 3H), 3.7-4.1(m, 2H), 5.4-5.8(m, 2H), 6.6-6.9(m, 1H) |

TABLE 18-continued

| | | | |
|---|---|---|---|
| 248 | [structure] | 68 | 0-0.1(m, 6H), 0.88(s, 9H), 0.7-1.0(m, 6H), 1.38(s, 9H), 1.0-3.0(m, 24H), 3.69(s, 3H), 3.7-4.2(m, 2H), 5.4-5.7(m, 2H), 6.6-6.9(m, 1H) |
| 249 | [structure] | 57 | 0.0-0.1(m, 6H), 0.89(s, 9H), 0.7-1.0(m, 3H), 1.1-3.0(m, 31H), 3.69(s, 6H), 3.7-4.1(m, 2H), 5.4-5.8(m, 2H), 6.5-6.8(m, 1H) |
| 250 | [structure] | 58 | 0.06(s, 6H), 0.89(s, 9H), 0.7-1.0(m, 3H), 1.1-2.9(m, 21H), 3.69(s, 3H), 3.7-4.2(m, 2H), 5.4-5.8(m, 2H), 6.5-6.8(m, 1H), 7.0-7.5(m, 5H) |
| 251 | [structure] | 63 | 0.08(s, 6H), 0.89(s, 9H), 0.7-1.0(m, 3H), 1.1-2.9(m, 23H), 2.32(s, 3H), 3.69(s, 3H), 3.7-4.1(m, 2H), 5.4-5.8(m, 1H), 6.5-6.8(m, 1H), 6.9-7.5(m, 4H) |

TABLE 18-continued

| | | |
|---|---|---|
| 252 | [structure] | 49 | 0.07(s, 6H), 0.88(s, 9H), 0.7–1.0(m, 3H), 1.1–2.9(m, 21H), 3.69(s, 3H), 3.7–4.2(m, 2H), 3.98(s, 3H), 5.4–5.8(m, 2H), 6.5–6.8(m, 1H), 7.0–8.1(m, 5H) |
| 253 | [structure] | 72 | 0–0.1(m, 6H), 0.89(s, 9H), 0.7–1.1(m, 6H), 1.1–2.7(m, 18H), 2.26(s, 3H), 3.6–4.1(m, 4H), 4.05(s, 2H), 5.4–5.8(m, 2H), 5.88(d, 1H, J=15.8Hz), 6.6–7.1(m, 2H), 7.2–7.7(m, 4H) |
| 254 | [structure] | 73 | 0.7–1.1(m, 3H), 0.93(s, 9H), 1.0–1.9(m, 10H), 2.30(s, 3H), 2.0–2.4(m, 2H), 4.23(s, 2H), 6.6–7.1(m, 2H), 7.3–7.7(m, 3H) |
| 255 | [structure] | 51 | 0.07(s, 6H), 0.89(s, 9H), 0.7–1.0(m, 3H), 1.0–3.1(m, 27H), 3.69(s, 3H), 3.7–4.1(m, 2H), 5.4–5.7(m, 2H), 6.5–6.8(m, 1H), 7.0–7.5(m, 5H) |
| 256 | [structure] | 76 | 0–0.1(m, 6H), 0.89(s, 9H), 0.7–1.1(m, 6H), 1.1–2.7(m, 35H), 3.67(s, 3H), 3.7–4.1(m, 2H), 5.4–5.8(m, 2H), 6.6–6.9(m, 1H) |

TABLE 18-continued

| # | Structure (left) | # | Structure (right) | NMR |
|---|---|---|---|---|
| 257 | (cyclopentenone with S-cyclopentyl, Me, CH(OH)-CH2CH2-Ph, and -(CH2)4-OPh chain) | 73 | (cyclopentadienone with S-cyclopentyl, Me, =CH-CH2-Ph, and -(CH2)4-OPh chain) | 0.93(d, 3H, J=7.8Hz), 1.3–3.0 (m, 19H), 3.1–3.5(m, 1H), 3.5–4.0(m, 2H), 6.6–7.5(m, 11H) |
| 258 | (cyclopentenone with S-pyridyl, butyl, CH(OH)-CH=CH-CH(OSi)-hexyl, and -(CH2)6-COOMe chain) | 59 | (cross-conjugated dienone with S-pyridyl, butyl, =CH-CH=CH-CH(OSi)-hexyl, and -(CH2)6-COOMe chain) | 0–0.1(m, 6H), 0.88(s, 9H), 0.7–1.0(m, 6H), 1.0–3.0(m, 24H), 3.68(s, 3H), 3.7–4.2(m, 2H), 5.4–5.8(m, 2H), 6.6–6.9(m, 1H), 7.2–8.1(m, 4H) |
| 259 | (cyclopentenone with S-(N-Me-imidazolyl), butyl, CH(OH)-CH=CH-CH(OSi)-hexyl, and -(CH2)6-COOMe chain) | 72 | (cross-conjugated dienone with S-(N-Me-imidazolyl), butyl, =CH-CH=CH-CH(OSi)-hexyl, and -(CH2)6-COOMe chain) | 0–0.1(m, 6H), 0.87(s, 9H), 0.7–1.0(m, 6H), 1.0–3.0(m, 24H), 3.67(s, 3H), 3.68(s, 3H), 3.6–4.2(m, 2H), 5.4–5.8(m, 2H), 6.6–6.9(m, 1H), 7.0–7.3(m, 2H) |
| 260 | (cyclopentenone with S-(methylpyrimidinyl), butyl, CH(OH)-CH=CH-CH(OSi)-hexyl, and -(CH2)6-COOMe chain) | 71 | (cross-conjugated dienone with S-(methylpyrimidinyl), butyl, =CH-CH=CH-CH(OSi)-hexyl, and -(CH2)6-COOMe chain) | 0–0.1(m, 6H), 0.88(s, 9H), 0.7–1.1(m, 6H), 1.1–2.9(m, 24H), 2.45(s, 3H), 3.68(s, 3H), 3.6–4.2(m, 2H), 5.4–5.8(m, 2H), 6.6–7.1(m, 2H), 8.30(d, 1H, J=5.0Hz) |

TABLE 18-continued

| | | NMR |
|---|---|---|
| 261 → 65 | | 0–0.1(m, 6H), 0.88(s, 9H), 0.7–1.0(m, 3H), 1.0–3.1(m, 21H), 3.69(s, 3H), 3.7–4.3(m, 4H), 5.4–5.8(m, 2H), 6.0–6.5(m, 1H), 6.5–6.8(m, 1H), 7.3–7.6 (m, 1H) |
| 262 → 76 | | 0.04(9H, s), 1.1–2.2(6H, m), 2.36(3H, s), 3.6–4.1(2H, m), 3.77(3H, s), 4.61(2H, s), 6.6–7.1(5H, m), 7.1–7.7(5H, m), 8.0(1H, m) |
| 263 → 63 | | 0.09(s, 9H), 1.1–2.0(m, 16H), 2.1–2.4(m, 1H), 2.36(s, 3H), 3.90(t, 2H, J=6.0Hz), 6.6–7.1 (m, 5H), 7.1–7.4(m, 2H) |
| 264 → 70 | | 0.05(s, 9H), 0.7–1.3(m, 15H), 1.2–2.0(m, 12H), 2.27(s, 6H), 2.2–2.5(m, 1H), 6.6–7.0(m, 2H) |

TABLE 18-continued

| # | Structure | Yield | NMR |
|---|---|---|---|
| 265 | (structures shown) | 76 | 0-0.2(m, 15H), 0.88(s, 9H), 1.0-2.1(m, 27H), 2.1-2.5(m, 5H), 3.69(s, 3H), 4.6-4.8(m, 1H), 5.4-5.8(m, 2H), 6.6-7.0(m, 2H) |
| 266 | (structures shown) | 53 | 0.08(s, 9H), 1.1-2.0(m, 16H), 2.1-2.5(m, 1H), 3.89(t, 2H, J=5.8Hz), 6.5-7.1(m, 5H), 7.1-7.5(m, 7H) |
| 267 | (structures shown) | 70 | 0-0.2(m, 21H), 0.89(s, 18H), 1.2-2.0(m, 7H), 2.68(d, 2H, J=6.8Hz), 3.55(d, 4H, J=5.0Hz), 3.90(t, 2H, J=6.0Hz), 6.6-7.5(m, 14H), 7.8-8.1(m, 2H) |
| 268 | (structures shown) | 63 | 0.09(s, 9H), 1.1-1.8(m, 6H), 3.90(s, 3H), 3.7-4.1(m, 4H), 6.6-7.7(m, 14H), 7.9-8.1(m, 1H) |

TABLE 18-continued

| | | | |
|---|---|---|---|
| 269 | [structure with CF₃-benzyl-S, cyclopentenone, OSi, butoxy-phenyl, dimethoxyphenyl, OH] | 68 | 0.09(s, 9H), 0.7–1.0(m, 3H), 1.1–2.1(m, 8H), 2.4–2.9(m, 2H), 3.79(s, 6H), 3.7–4.25(m, 4H), 6.5–7.8(m, 13H) |
| 270 | [structure with phenylpropyl-S, cyclopentenone, OSi, dimethoxyphenyl, OH] | 51 | 0.09(s, 9H), 1.37(s, 9H), 1.2–2.0(m, 6H), 2.2–2.7(m, 6H), 3.80(s, 6H), 6.5–7.5(m, 14H) |
| 271 | [structure with cyclohexyl-S, cyclopentenone, OSi, OPh, OSi sidechain, OH] | 95 | 0–0.2(21H, m), 0.89(18H, s), 1.0–2.3(20H, m), 2.3–2.8(1H, m), 3.4–3.7(2H, m), 3.7–4.1(2H, m), 4.1–4.5(1H, m), 5.6–6.3(2H, m), 6.3–7.1(4H, m), 7.1–8.0(3H, m) |
| 272 | [structure with cyclohexyl-S, cyclopentenone, OSi, OPh, COOMe sidechain, OH] | 74 | 0.03(9H, s), 1.1–2.5(27H, m), 3.68(3H, s), 3.9(2H, t, J=6.0 Hz), 6.4–6.7(2H, m), 6.7–7.0(3H, m), 7.1–7.4(2H, m) |

TABLE 18-continued

| No. | Structure (left) | Structure (right) | Yield | NMR |
|---|---|---|---|---|
| 273 | (hydroxy intermediate with S-cyclohexyl, OSi, OPh, COOMe-thioether chain) | (enone with S-cyclohexyl, OSi, OPh, COOMe-thioether chain) | 59 | 0.08(s, 9H), 1.1–2.0(m, 18H), 2.1–2.8(m, 5H), 3.1–3.3(m, 1H), 3.69(s, 3H), 3.96(t, 2H, J=6.0Hz), 6.4–6.7(m, 1H), 6.7–7.0(m, 4H), 7.1–7.4(m, 2H) |
| 274 | (hydroxy intermediate with S-cyclohexyl, OSi, OPh, COOMe-ether chain) | (enone with S-cyclohexyl, OSi, OPh, COOMe-ether chain) | 79 | 0.09(s, 9H), 1.1–2.0(m, 18H), 2.2–2.6(m, 3H), 3.4–4.0(m, 4H), 3.76(s, 3H), 4.08(s, 2H), 6.4–6.7(m, 1H), 6.7–7.1(m, 4H), 7.1–7.4(m, 2H) |
| 275 | (hydroxy intermediate with S-cyclohexyl, OSi, OPh, cyclohexyl-COOMe chain) | (enone with S-cyclohexyl, OSi, OPh, cyclohexyl-COOMe chain) | 71 | 0.05(s, 9H), 1.1–2.1(m, 27H), 2.2–2.7(m, 4H), 3.68(s, 3H), 3.95(t, 2H, J=5.8Hz), 6.4–6.7(m, 1H), 6.7–7.1(m, 4H), 7.1–7.4(m, 2H) |
| 276 | (hydroxy intermediate with S-cyclohexyl, OSi, OPh, aryl-OCH2COOMe chain) | (enone with S-cyclohexyl, OSi, OPh, aryl-OCH2COOMe chain) | 79 | 0.09(s, 9H), 1.0–2.0(m, 16H), 2.3–2.7(m, 1H), 3.70(s, 3H), 3.94(t, 2H, J=5.8Hz), 4.60(s, 2H), 6.6–7.7(m, 10H), 8.0–8.1(m, 1H) |
| 277 | (hydroxy intermediate with OSi, long alkyl chains) | (enone with OSi, long alkyl chains) | 69 | 0.10(s, 9H), 0.7–1.0(m, 6H), 1.1–2.0(m, 38H), 2.1–2.6(m, 3H), 6.4–6.8(m, 2H) |

TABLE 18-continued

| | | |
|---|---|---|
| 278 | | 73 | 0.04(s, 9H), 1.2–2.0(m, 20H), 2.1–2.5(m, 5H), 3.83(s, 6H), 6.3–7.3(m, 6H) |
| 279 | | 89 | 0.5(s, 9H), 0.7–1.0(m, 3H), 1.1–2.0(m, 16H), 2.1–2.5(m, 3H), 3.95(t, 2H, J=6.0Hz), 6.4–7.1(m, 5H), 7.1–7.4(m, 2H) |
| 280 | | 60 | 0.10(s, 9H), 1.1–2.0(m, 16H), 2.1–2.6(m, 5H), 3.75(s, 3H), 3.93(t, 2H, J=6.2Hz), 6.3–7.5(m, 11H) |
| 281 | | 63 | 0.09(s, 3H), 0.83(d, 9H, J=4.7 Hz), 0.9–2.1(m, 20H), 2.1–2.5(m, 1H), 6.6–7.5(m, 5H), 8.0–8.1(m, 1H) |

TABLE 18-continued

| | | | |
|---|---|---|---|
| 282 | [structure with cyclopentenone, OH, alkyne, COOMe, OPh, S-CH2CH2-cyclohexyl] | [structure with cyclopentenone, OSi, alkyne, COOMe, OPh, S-CH2CH2-cyclohexyl] | 70   0.09(s, 9H), 1.2–2.5(m, 29H), 3.68(s, 3H), 3.8–4.1(m, 2H), 6.10(t, 1H, J=2.0Hz), 6.69(s, 1H), 6.8–7.1(m, 3H), 7.1–7.4 (m, 2H) |
| 283 | [structure with cyclopentenone, OH, Ph, cyclohexyl branched chain, S-CH2CH2-cyclohexyl] | [structure with cyclopentenone, OSi, Ph, branched chain, S-CH2CH2-cyclohexyl] | 78   0.10(s, 9H), 0.85(d, 9H, J=4.7 Hz), 0.9–2.0(m, 27H), 2.1–2.6 (m, 6H), 6.5–6.7(m, 1H), 6.8–7.5(m, 6H) |
| 284 | [structure with cyclopentenone, OH, OSi, OPh, pyridyl-S] | [structure with cyclopentenone, OSi, OSi, OPh, pyridyl-S] | 39   0–0.2(m, 2H), 0.89(s, 18H), 1.0–2.2(m, 9H), 2.4–2.8(m, 1H), 3.4–3.8(m, 2H), 3.8–4.1 (m, 2H), 4.1–4.5(m, 1H), 5.8–6.3(m, 2H), 6.3–8.0(m, 10H), 8.3–8.6(m, 1H) |
| 285 | [structure with cyclopentenone, OH, alkyl chain, OPh, pyridyl-S] | [structure with cyclopentenone, OSi, alkyl chain, OPh, pyridyl-S] | 72   0.09(s, 9H), 0.7–1.0(m, 3H), 1.1–2.1(m, 14H), 2.2–2.5(m, 2H), 3.96(t, 2H, J=5.9Hz), 6.3–7.9(m, 10H), 8.2–8.5(m, 1H) |

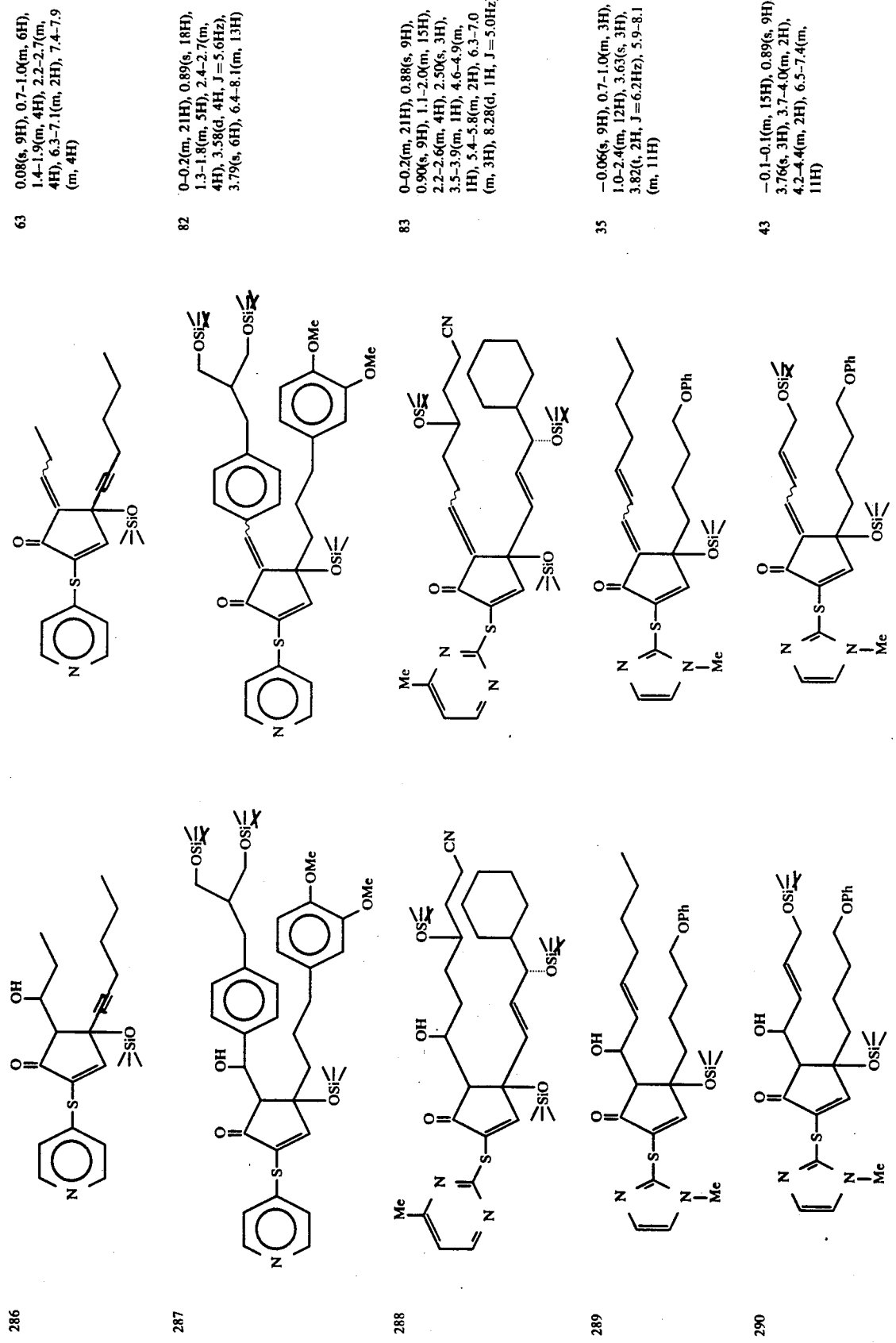

| | | | |
|---|---|---|---|
| 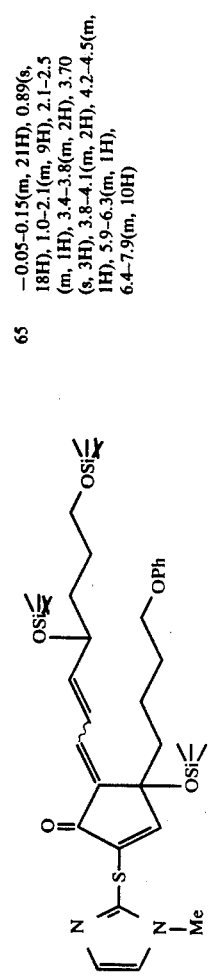 | 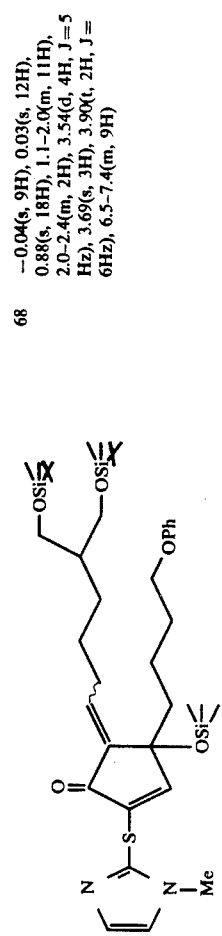 | 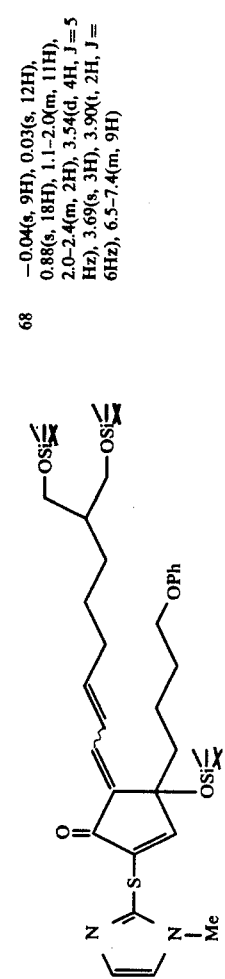 | 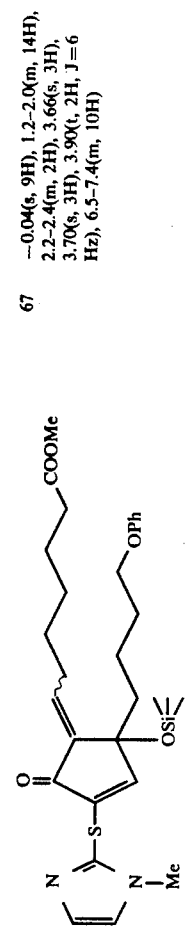 |
| 65 | 68 | 68 | 67 |
| −0.05–0.15(m, 21H), 0.89(s, 18H), 1.0–2.1(m, 9H), 2.1–2.5 (m, 1H), 3.4–3.8(m, 2H), 3.70 (s, 3H), 3.8–4.1(m, 2H), 4.2–4.5(m, 1H), 5.9–6.3(m, 1H), 6.4–7.9(m, 10H) | −0.04(s, 9H), 0.03(s, 12H), 0.88(s, 18H), 1.1–2.0(m, 11H), 2.0–2.4(m, 2H), 3.54(d, 4H, J=5 Hz), 3.69(s, 3H), 3.90(t, 2H, J=6Hz), 6.5–7.4(m, 9H) | −0.04(s, 9H), 0.03(s, 12H), 0.88(s, 18H), 1.1–2.0(m, 11H), 2.0–2.4(m, 2H), 3.54(d, 4H, J=5 Hz), 3.69(s, 3H), 3.90(t, 2H, J=6Hz), 6.5–7.4(m, 9H) | −0.04(s, 9H), 1.2–2.0(m, 14H), 2.2–2.4(m, 2H), 3.66(s, 3H), 3.70(s, 3H), 3.90(t, 2H, J=6 Hz), 6.5–7.4(m, 10H) |
| 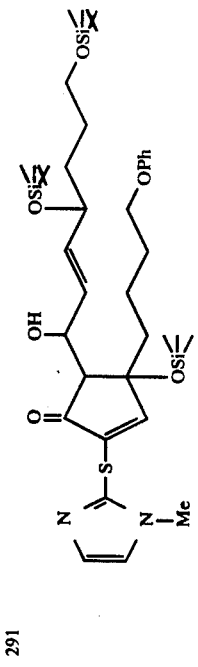 | 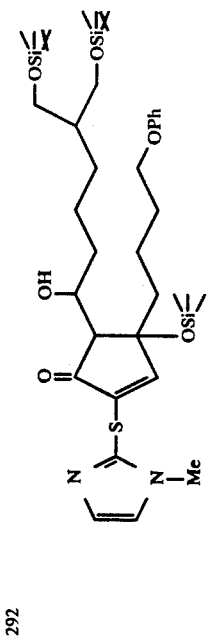 | 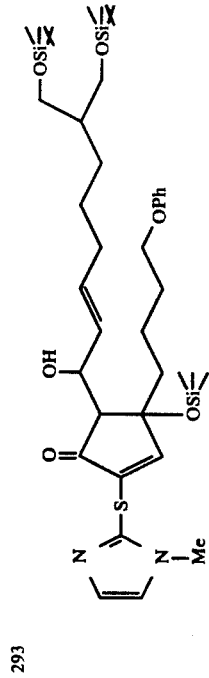 | 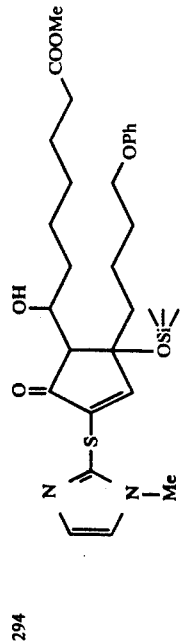 |
| 291 | 292 | 293 | 294 |

| | |
|---|---|
| 73 | 0.10(s, 9H), 1.1–2.3(m, 8H), 2.3–2.6(m, 4H), 3.70(s, 3H), 3.72(s, 3H), 3.96(t, 2H, J=6.2 Hz), 6.4–6.6(m, 1H), 6.70(s, 1H), 6.8–7.4(m, 7H) |
| 89 | 0.10(s, 9H), 1.1–2.0(m, 8H), 2.2–2.5(m, 2H), 3.4–4.1(m, 4H), 3.67(s, 3H), 3.70(s, 3H), 4.11(s, 2H), 6.4–7.5(m, 9H) |
| 27 | 0.0(s, 9H), 1.1–2.2(m, 6H), 2.65(t, 2H, J=6.8Hz), 3.4–3.8(m, 2H), 3.73(s, 3H), 3.76(s, 3H), 3.91(t, 2H, J=6.2Hz), 4.08(s, 2H), 5.5–5.7(m, 1H), 6.03(brs, 1H), 6.5–7.5(m, 9H) |
| 46 | 0.0(s, 9H), 1.0–2.2(m, 6H), 2.68(t, 2H, J=6.6Hz), 3.45(s, 3H), 3.73(s, 3H), 3.91(t, 2H, J=6.2Hz), 4.28(t, 2H, J=6.7Hz), 5.4–5.7(m, 1H), 6.05(brs, 1H), 6.4–7.5(m, 9H) |
| 61 | 0.04(s, 9H), 1.2–2.1(m, 6H), 2.6–2.9(m, 4H), 3.80(s, 3H), 3.95(s, 3H), 3.7–4.1(m, 2H), 6.2–7.5(m, 12H) |
-continued
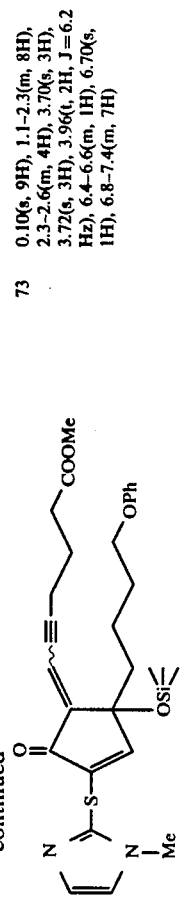 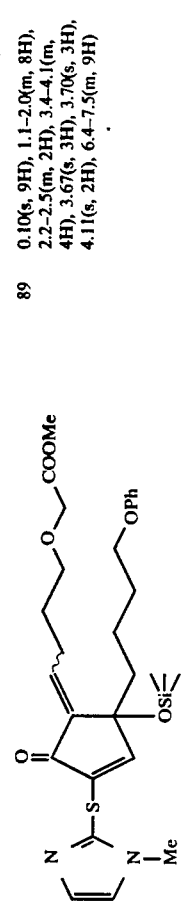 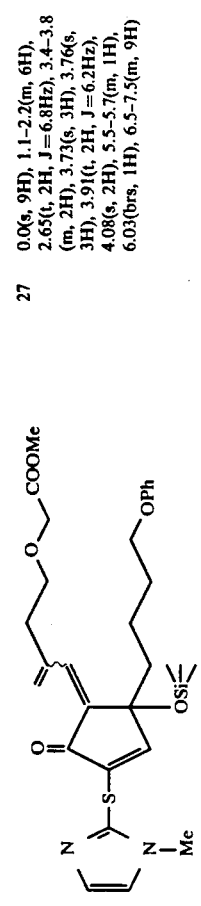 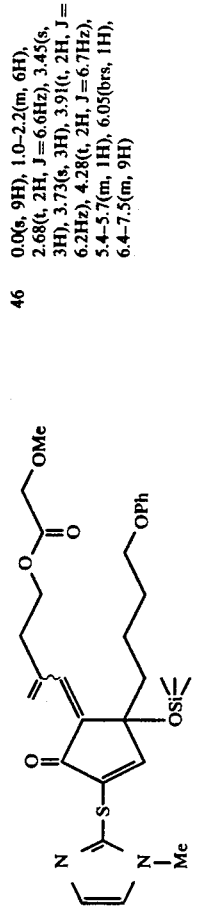 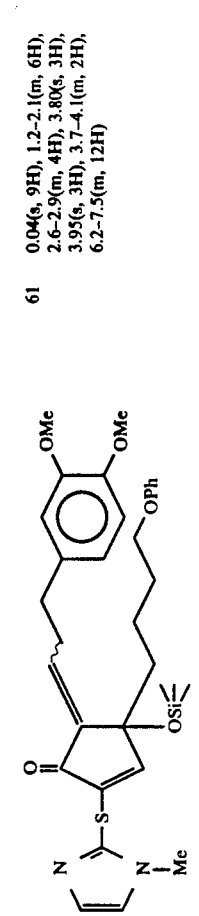
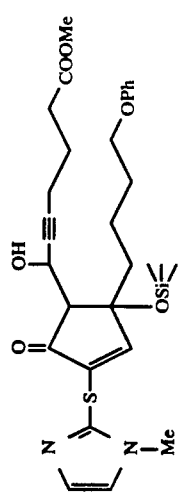 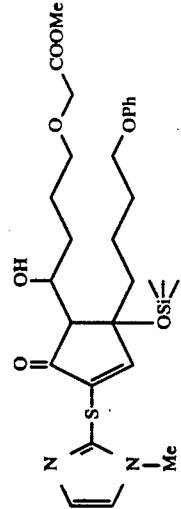 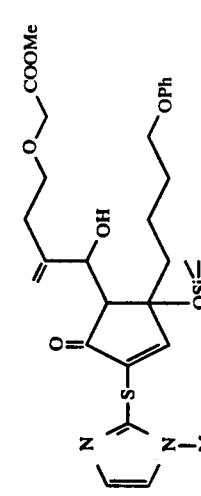 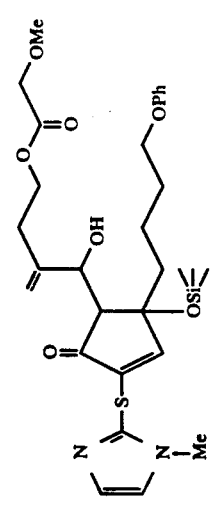 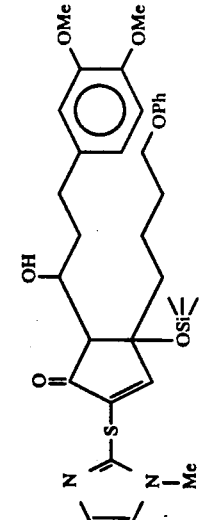
295  296  297  298  299

| | | | |
|---|---|---|---|
| 0.10(s, 9H), 1.2–1.9(m, 6H), 2.97(s, 6H), 3.68(s, 3H), 3.94(t, 2H, J=5.9Hz), 6.0–7.7(m, 15H) | −0.05(s, 9H), 1.1–2.0(m, 16H), 3.74(s, 3H), 3.8–4.0(m, 2H), 6.1–7.8(m, 11H) | −0.04(s, 9H), 1.2–2.0(m, 12H), 2.1–2.5(m, 4H), 3.72(s, 3H), 3.8–4.0(m, 2H), 6.3–7.4(m, 10H) | 0.09(s, 9H), 1.2–2.0(m, 6H), 2.2–2.6(m, 8H), 3.56(s, 2H), 3.69(s, 3H), 3.96(t, 2H, J=5.9 Hz), 6.4–7.4(m, 14H), 7.5–7.8 (m, 1H) |
| 61 | 81 | 48 | 48 |
| 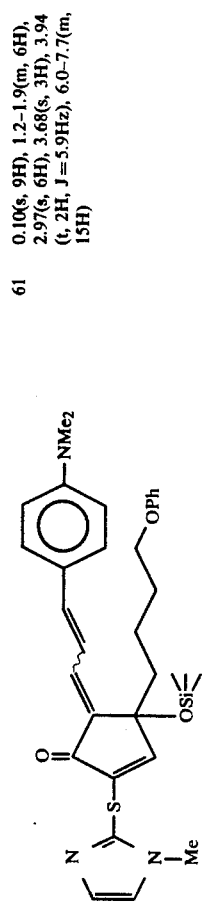 | 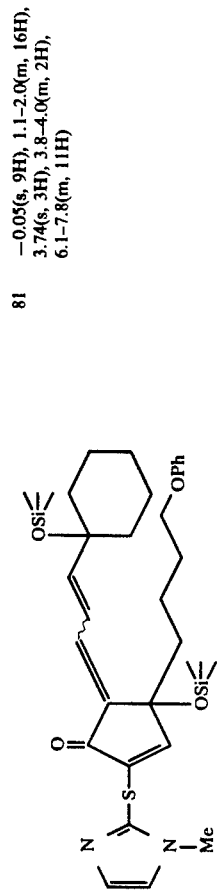 | 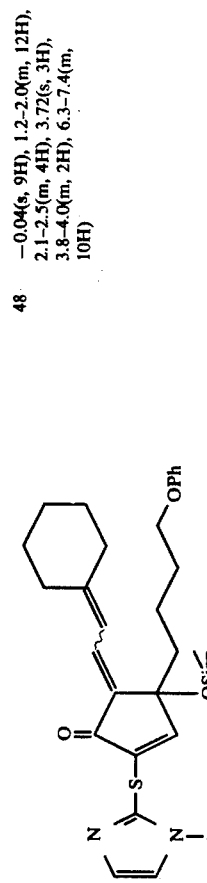 | 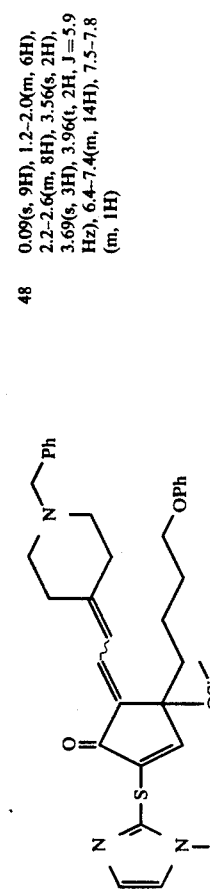 |
| 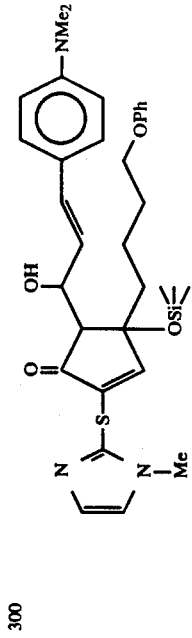 | 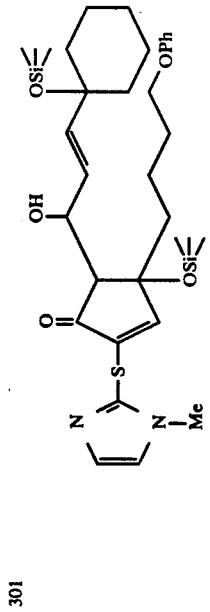 | 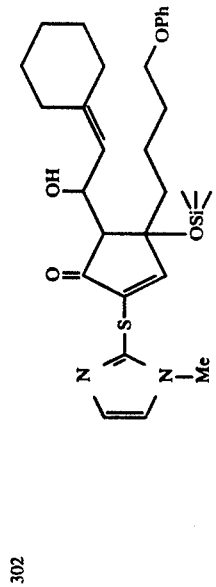 | 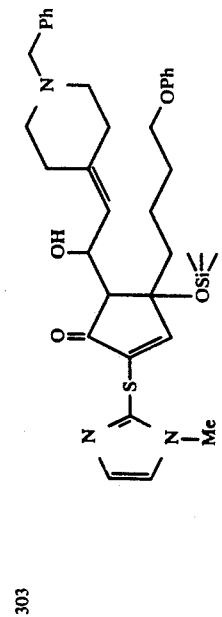 |
| 300 | 301 | 302 | 303 |

| | |
|---|---|
| 59 | 0.0(s, 9H) 1.4–1.8(m, 6H), 3.73(s, 3H), 3.94(s, 3H), 3.6–3.8(m, 2H), 6.6–7.0(m, 4H), 7.0–7.5(m, 5H), 8.03(s, 4H) |
| 82 | 0.04(s, 12H), 0.01(s, 9H), 0.89(s, 18H), 1.2–2.2(m, 7H), 2.64(d, 2H, J=7.3Hz), 3.53(d, 4H, J=5.3Hz), 3.71(s, 3H), 3.7–4.0(m, 2H), 6.6–7.5(m, 11H), 7.8–8.1(m, 2H) |
| 73 | 0.09(s, 9H), 0.7–1.0(m, 3H), 1.2–2.0(m, 16H), 2.1–2.5(m, 4H), 3.67(s, 3H), 3.68(s, 3H), 5.9–8.0(m, 6H) |
| 83 | 0.04(s, 9H), 0.7–1.0(m, 3H), 1.1–2.0(m, 25H), 2.2–2.5(m, 3H), 3.69(s, 3H), 3.72(s, 3H), 6.4–6.9(m, 4H) |
| 71 | 0.08(s, 9H), 1.2–2.1(m, 12H), 2.2–2.5(m, 3H), 3.67(s, 3H), 3.79(s, 6H), 6.4–7.2(m, 7H) |
-continued
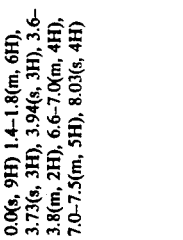
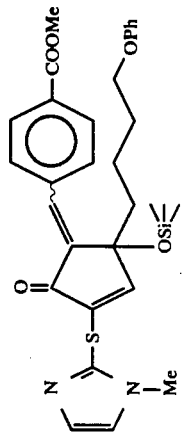
304
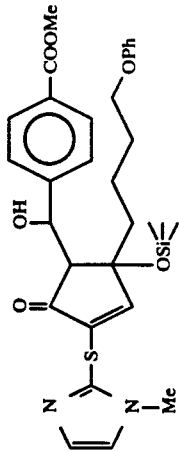
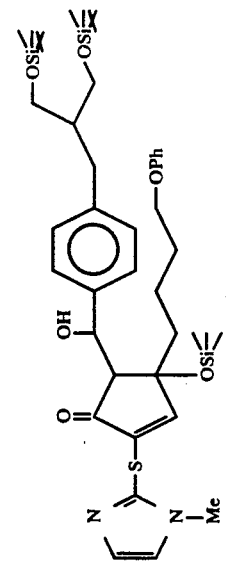
305
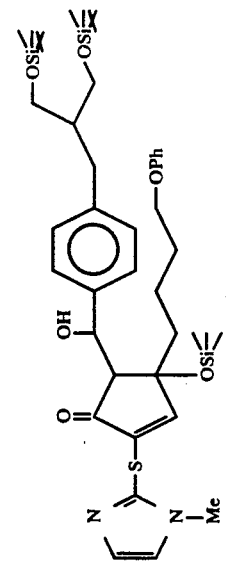
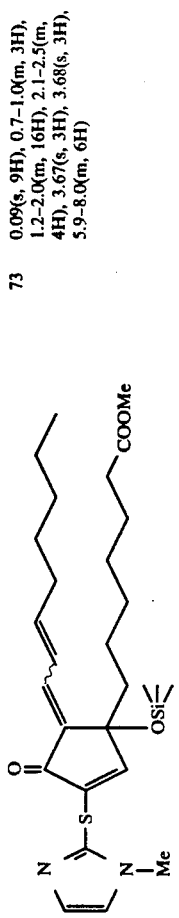
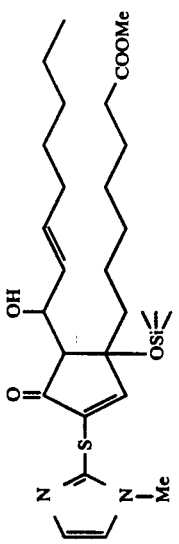
306
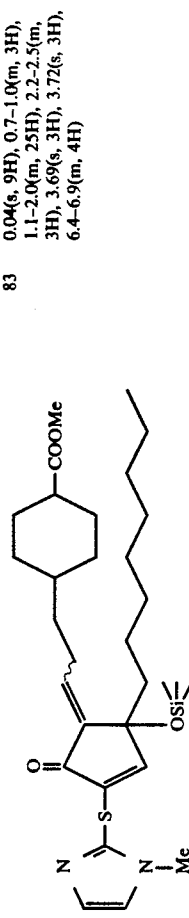
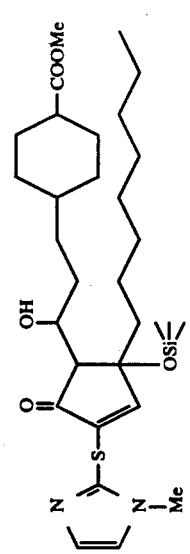
307
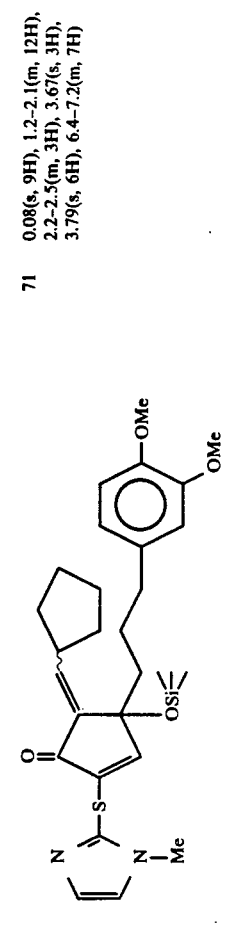
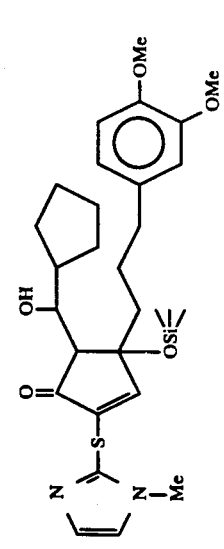
308

| # | Product | Yield | NMR |
|---|---|---|---|
| 309 | | 59 | 0.09(s, 9H), 0.7-1.0(m, 3H), 1.06(s, 9H), 1.2-1.8(m, 4H), 2.1-2.3(m, 2H), 3.69(s, 3H), 6.0-7.4(m, 6H) |
| 310 | | 72 | 0.10(s, 9H), 1.69(s, 6H), 1.5-1.9(m, 2H), 2.1-2.4(m, 2H), 3.4-3.9(m, 2H), 3.68(s, 3H), 3.73(s, 3H), 4.10(s, 2H), 5.4-5.9(m, 2H), 6.5-7.5(m, 9H) |
| 311 | | 72 | 0.10(s, 9H), 0.7-1.1(m, 18H), 1.1-2.0(m, 20H), 2.1-2.4(m, 2H), 6.4-6.7(m, 1H), 6.7-7.1(m, 9H), 7.2-7.8(m, 4H) |
| 312 | | 58 | 0.10(s, 9H), 0.7-1.0(m, 3H), 1.2-2.0(m, 10H), 2.1-2.5(m, 4H), 3.84(s, 6H), 6.3-7.0(m, 5H), 7.2-7.8(m, 4H) |
| 313 | | 43 | 0.08(s, 9H), 0.97(d, 6H, J=6.4 Hz), 1.23(s, 3H), 1.5-1.7(m, 1H), 2.0-2.4(m, 2H), 6.4-6.7(m, 1H), 6.9-7.9(m, 5H) |

| | | |
|---|---|---|
| 314 | [structure] | 33 | 0.05(s, 9H), 0.7–1.0(m, 3H), 1.1–2.0(m, 11H), 2.1–2.4(m, 2H), 4.6–4.9(m, 1H), 5.4–5.8(m, 2H), 6.3–6.6(m, 1H), 6.9–7.8(m, 4H) |
| 315 | [structure] | 70 | 0.03(s, 21H), 0.88(s, 18H), 1.1–2.2(m, 12H), 2.4–2.8(m, 1H), 3.4–3.8(m, 2H), 3.75–4.5(m, 5H), 5.8–6.5(m, 2H), 6.5–7.4(m, 7H), 7.4–7.9(m, 3H) |
| 316 | [structure] | 79 | 0.08(s, 9H), 0.7–1.1(m, 6H), 1.1–2.1(m, 8H), 2.2–2.7(m, 4H), 3.5–4.3(m, 6H), 5.90(d, 1H, J=16.0Hz), 6.4–7.9(m, 11H) |
| 317 | [structure] | 70 | 0.09(s, 9H), 0.7–1.0(m, 3H), 1.40(t, 3H, J=7.0Hz), 1.1–2.0(m, 6H), 2.2–2.6(m, 6H), 3.74(s, 3H), 4.03(q, 2H, J=7.0Hz), 6.3–7.5(m, 9H) |
| 318 | [structure] | 63 | 0.08(s, 9H), 1.3–2.0(m, 6H), 2.2–2.6(m, 6H), 3.69(s, 3H), 3.80(s, 6H), 4.03(s, 2H), 6.0–6.6(m, 3H), 6.70(s, 1H), 7.3–7.6(m, 1H) |

| | | |
|---|---|---|
| 319 | 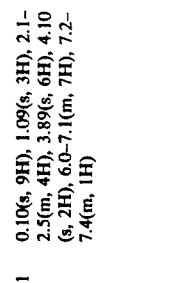<br>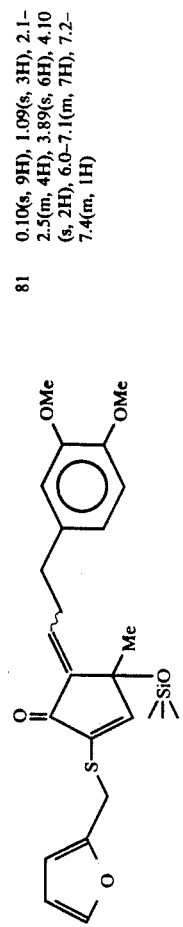 | 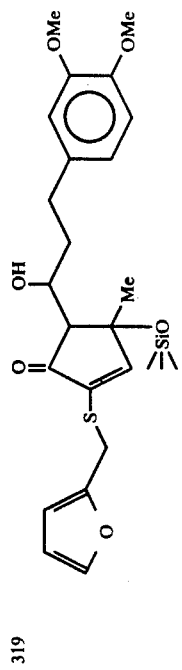81 | 0.10(s, 9H), 1.09(s, 3H), 2.1-2.5(m, 4H), 3.89(s, 6H), 4.10(s, 2H), 6.0-7.1(m, 7H), 7.2-7.4(m, 1H) |
| 320 | 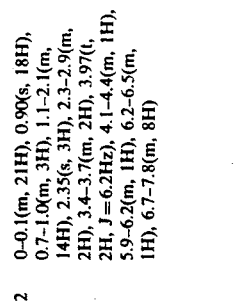<br>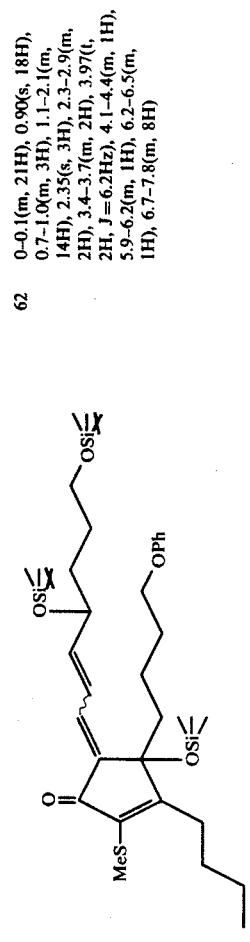 | 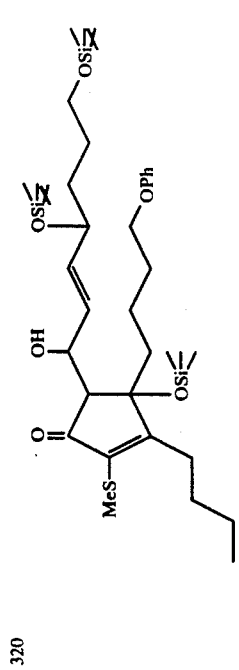62 | 0-0.1(m, 21H), 0.90(s, 18H), 0.7-1.0(m, 3H), 1.1-2.1(m, 14H), 2.35(s, 3H), 2.3-2.9(m, 2H), 3.4-3.7(m, 2H), 3.97(t, 2H, J=6.2Hz), 4.1-4.4(m, 1H), 5.9-6.2(m, 1H), 6.2-6.5(m, 1H), 6.7-7.8(m, 8H) |
| 321 | 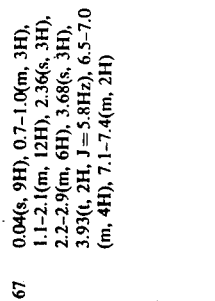<br>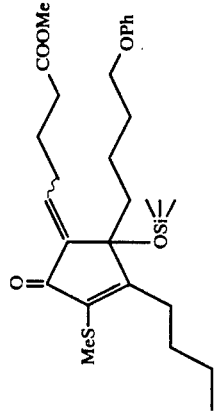 | 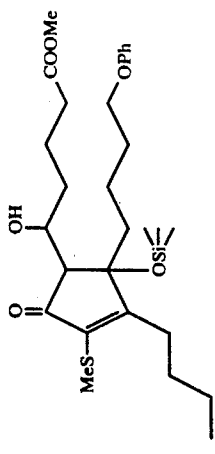67 | 0.04(s, 9H), 0.7-1.0(m, 3H), 1.1-2.1(m, 12H), 2.36(s, 3H), 2.2-2.9(m, 6H), 3.68(s, 3H), 3.93(t, 2H, J=5.8Hz), 6.5-7.0(m, 4H), 7.1-7.4(m, 2H) |
| 322 | 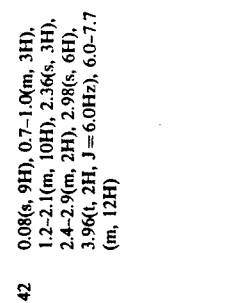<br>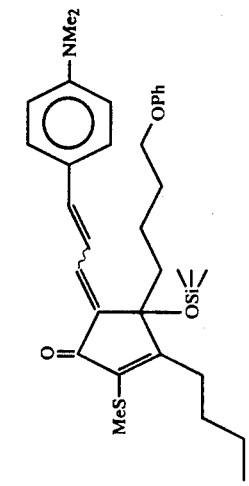 | 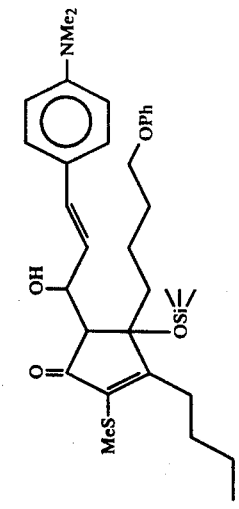42 | 0.08(s, 9H), 0.7-1.0(m, 3H), 1.2-2.1(m, 10H), 2.36(s, 3H), 2.4-2.9(m, 2H), 2.98(s, 6H), 3.96(t, 2H, J=6.0Hz), 6.0-7.7(m, 12H) |

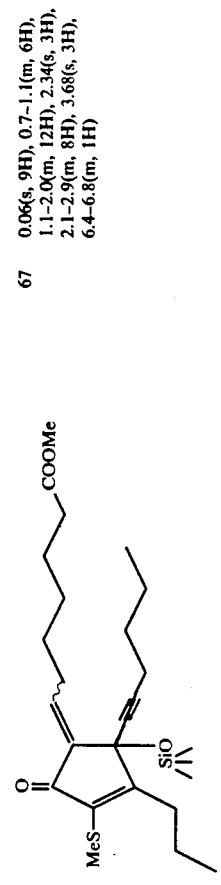
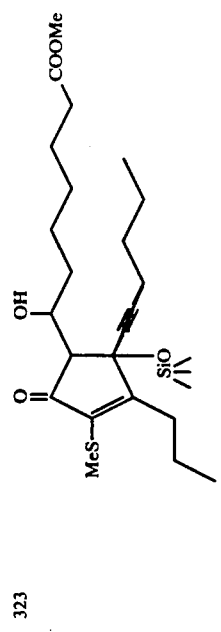
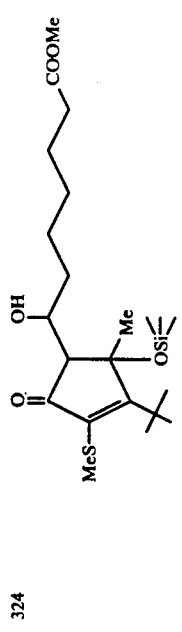
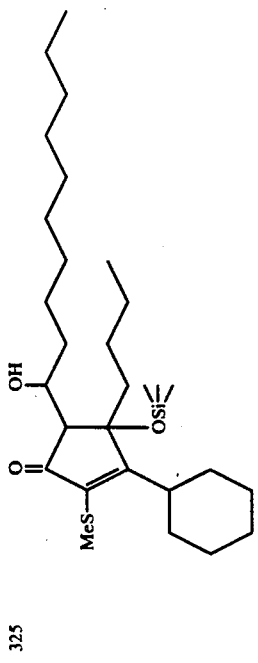
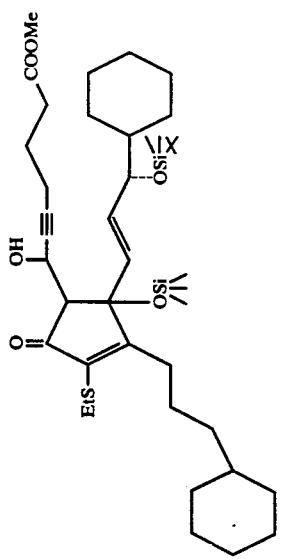

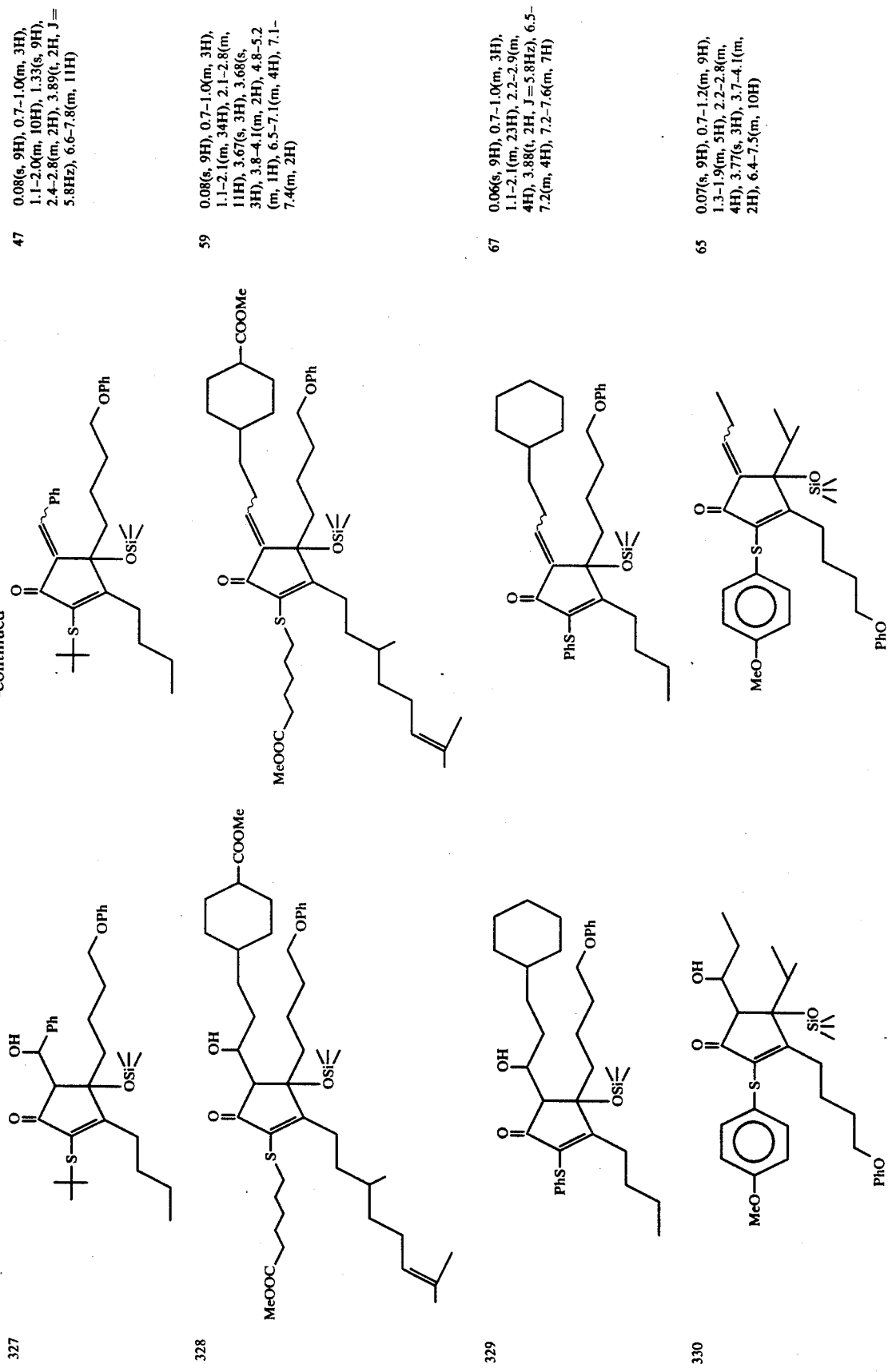

| | | |
|---|---|---|
| 331 | 58 | 0.07(s, 9H), 0.7-1.1(m, 15H), 1.1-2.0(m, 14H), 2.3-2.9(m, 4H), 4.20(s, 2H), 6.4-6.8(m, 2H), 7.3-7.8(m, 3H) |
| 332 | 72 | 0.08(s, 9H), 0.7-1.2(m, 15H), 1.2-2.0(m, 20H), 2.1-3.0(m, 9H), 3.68(s, 3H), 6.4-6.8(m, 1H), 7.0-7.4(m, 5H) |
| 333 | 68 | 0.08(s, 9H), 0.7-1.0(m, 3H), 1.1-2.0(m, 26H), 2.1-2.9(m, 7H), 3.67(s, 3H), 3.88(t, 2H, J=5.8Hz), 6.5-7.5(m, 6H) |
| 334 | 62 | 0.06(s, 9H), 1.1-2.0(m, 22H), 2.1-2.9(m, 9H), 3.74(s, 3H), 3.89(t, 2H, J=6.0Hz), 6.5-7.6(m, 15H) |

| | | |
|---|---|---|
| 335 | 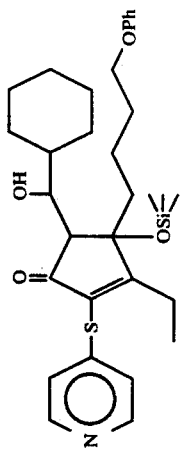 | 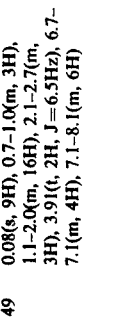 49 — 0.08(s, 9H), 0.7–1.0(m, 3H), 1.1–2.0(m, 16H), 2.1–2.7(m, 3H), 3.91(t, 2H, J=6.5Hz), 6.7–7.1(m, 4H), 7.1–8.1(m, 6H) |
| 336 | 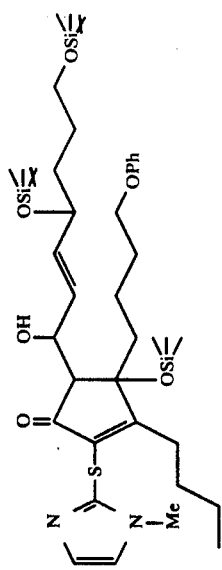 | 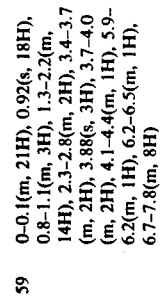 59 — 0–0.1(m, 21H), 0.92(s, 18H), 0.8–1.1(m, 3H), 1.3–2.2(m, 14H), 2.3–2.8(m, 2H), 3.4–3.7(m, 2H), 3.88(s, 3H), 3.7–4.0(m, 2H), 4.1–4.4(m, 1H), 5.9–6.2(m, 1H), 6.2–6.5(m, 1H), 6.7–7.8(m, 8H) |
| 337 | 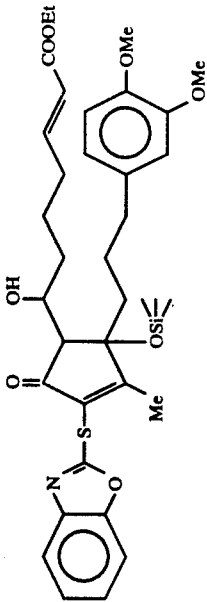 | 56 — 0.06(s, 9H), 1.2–2.1(m, 9H), 2.1–3.0(m, 6H), 2.42(s, 3H), 3.81(s, 6H), 3.7–4.0(m, 2H), 5.7–6.2(m, 2H), 6.4–7.1(m, 4H), 7.2–7.8(m, 4H) |
| 338 | 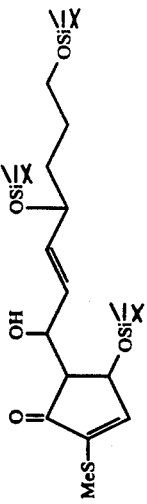 | 80 — 0–0.2(m, 18H), 0.88(s, 27H), 1.4–1.7(m, 4H), 2.36(s, 3H), 3.4–3.8(m, 2H), 4.1–4.5(m, 1H), 5.1–5.5(m, 1H), 5.8–7.8(m, 4H) |
| 339 | 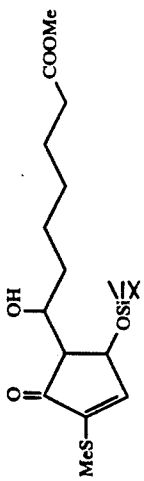 | 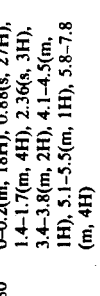 36 — 0.09(s, 6H), 0.89(s, 9H), 1.1–2.5(m, 10H), 2.37(s, 3H), 3.68(s, 3H), 4.8–5.2(m, 1H), 6.5–7.1(m, 2H) |
-continued
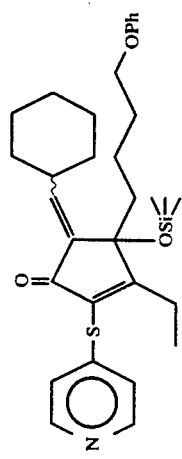
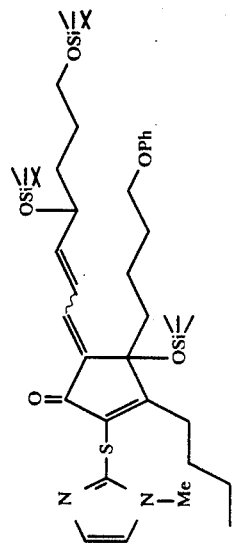
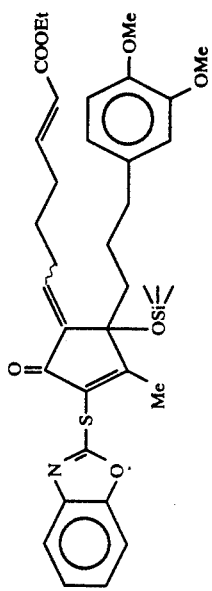
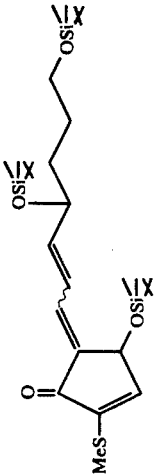
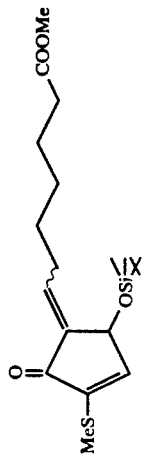

| | | |
|---|---|---|
| 53 | 0.09(s, 6H), 0.89(s, 9H), 2.34 (s, 3H), 2.99(s, 6H), 5.0–5.4 (m, 1H), 6.0–7.7(m, 8H) | 340 |
| 58 | 0–0.2(m, 18H), 0.89(s, 18H), 0.92(s, 9H), 1.2–1.8(m, 4H), 3.4–3.8(m, 2H), 4.1–4.5(m, 1H), 5.2–5.6(m, 1H), 6.0–7.5 (m, 10H) | 341 |
| 70 | 0–0.3(m, 18H), 0.88(s, 18H), 0.90(s, 9H), 1.1–1.8(m, 14H), 2.2–2.6(m, 1H), 3.5–3.8(m, 2H), 4.1–4.4(m, 1H), 5.1–5.5 (m, 1H), 5.9–7.6(m, 4H) | 342 |
| 66 | 0–0.2(m, 18H), 0.88(s, 18H), 0.89(s, 9H), 1.2–1.8(m, 4H), 2.47(s, 3H), 3.4–3.8(m, 2H), 4.1–4.4(m, 1H), 5.2–5.6(m, 1H), 5.9–8.4(m, 6H) | 343 |
| 44 | 0.08(s, 6H), 0.88(s, 9H), 1.0–2.4(m, 10H), 3.70(s, 3H), 4.13 (s, 3H), 4.9–5.3(m, 1H), 6.7–7.1(m, 1H), 7.76(d, 1H, J=2.0 Hz) | 344 |
| 59 | 0.04(s, 6H), 0.87(s, 9H), 1.1–2.4(m, 10H), 3.68(s, 3H), 4.9–5.4(m, 1H), 6.8–8.1(m, 6H) | 345 |

-continued
| | | |
|---|---|---|
| 346 | 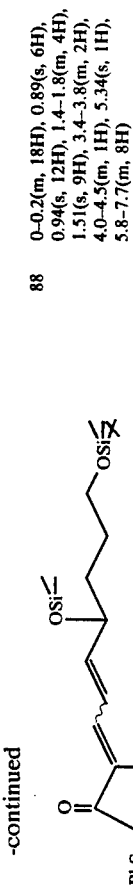 | 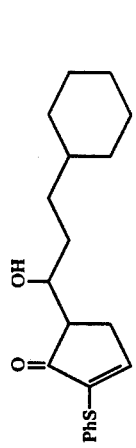 88 | 0-0.2(m, 18H), 0.89(s, 6H), 0.94(s, 12H), 1.4-1.8(m, 4H), 1.51(s, 9H), 3.4-3.8(m, 2H), 4.0-4.5(m, 1H), 5.34(s, 1H), 5.8-7.7(m, 8H) |
| 347 | 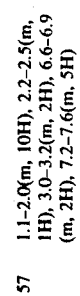 | 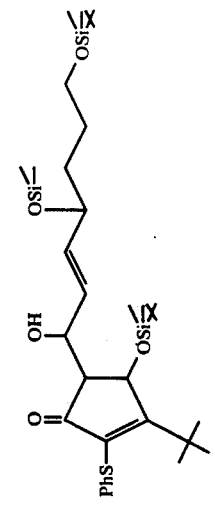 57 | 1.1-2.0(m, 10H), 2.2-2.5(m, 1H), 3.0-3.2(m, 2H), 6.6-6.9 (m, 2H), 7.2-7.6(m, 5H) |
| 348 | 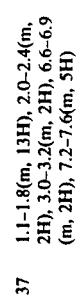 | 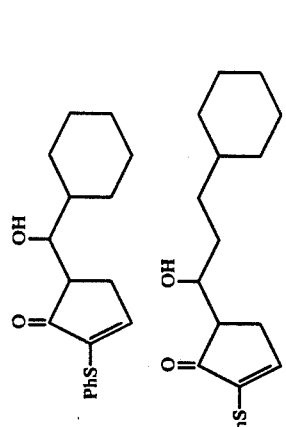 37 | 1.1-1.8(m, 13H), 2.0-2.4(m, 2H), 3.0-3.2(m, 2H), 6.6-6.9 (m, 2H), 7.2-7.6(m, 5H) |

TABLE 19

| Ex. No. | Starting compd. (2-Substituted-2-cyclopentenones) | 2-Substituted-2-cyclopentenones | Yield (%) | NMR(δ, CDCl₃) |
|---|---|---|---|---|
| 349 | | | 67 | 0.7–1.1(m, 3H), 1.1–2.6(m, 32H), 3.0–3.3(m, 1H), 3.67(s, 3H), 3.7–3.9(m, 1H), 3.9–4.3 (m, 1H), 5.5–5.7(m, 2H), 6.82 (d, 1H, J=2.8Hz) |
| 350 | | | 58 | 0.7–1.0(m, 3H), 1.1–2.4(m, 21H), 3.1–3.3(m, 1H), 3.69(s, 3H), 3.7–3.9(m, 1H), 3.9–4.3 (m, 1H), 5.5–5.8(m, 2H), 6.78 (d, 1H, J=2.4Hz), 7.2–8.1(m, 4H) |
| 351 | | | 54 | 0.7–1.0(m, 3H), 1.1–2.4(m, 21H), 3.1–3.4(m, 1H), 3.69(s, 3H), 3.7–4.3(m, 2H), 4.12(s, 3H), 5.4–5.7(m, 2H), 6.82(d, 1H, J=2.7Hz) |
| 352 | | | 41 | 0.7–1.1(m, 6H), 1.1–2.7(m, 18H), 3.1–3.3(m, 1H), 3.68(s, 3H), 3.7–4.0(m, 1H), 4.0–4.3 (m, 1H), 5.4–5.8(m, 2H), 5.88 (d, 1H, J=16.0Hz), 6.7–7.2(m, 2H), 7.2–7.8(m, 4H) |
| 353 | | | 71 | 1.1–2.9(m, 15H), 3.4–3.7(m, 2H), 3.67(s, 3H), 3.8–4.2(m, 2H), 4.2–4.7(m, 2H), 5.5–5.8 (m, 2H), 6.7–7.1(m, 5H), 7.1–7.5(m, 2H) |

TABLE 19-continued

| | | |
|---|---|---|
| 354 | [structure with COOMe, OH, cyclopentane, furan, S] | 39 — 1.1–2.1(m, 11H), 2.1–3.0(m, 7H), 3.2–3.5(m, 1H), 3.68(s, 3H), 3.7–4.3(m, 3H), 4.6–4.9 (m, 1H), 5.4–5.8(m, 2H), 6.0–6.5(m, 2H), 7.08(d, 1H, J=3.0 Hz), 7.2–7.4(m, 1H) |
| 355 | [structure with COOMe, MeS, OSi] | 57 — 0.7–1.1(m, 6H), 1.1–2.8(m, 27H), 2.35(s, 3H), 3.0–3.3(m, 1H), 3.66(s, 3H), 3.6–3.9(m, 1H), 3.9–4.2(m, 1H), 5.2–5.9 (m, 2H) |
| 356 | [structure with COOMe, cyclopentane, OSi, HO] | 56 — 0.7–1.0(m, 3H), 1.1–2.7(m, 23H), 2.9–3.4(m, 6H), 3.69(s, 3H), 3.4–4.2(m, 4H), 4.5–4.9 (m, 1H), 5.3–5.9(m, 2H) |
| 357 | [structure with COOMe, PhS, OSi] | 63 — 0.7–1.0(m, 3H), 1.1–3.0(m, 23H), 3.0–3.3(m, 1H), 3.4–3.6 (m, 1H), 3.68(s, 3H), 3.8–4.1 (m, 1H), 4.7–4.9(m, 1H), 5.3–5.9(m, 2H), 7.2–7.7(m, 5H) |
| 358 | [structure with COOEt, OH, Me, OSi, chlorobenzyl] | 59 — 0.7–1.1(m, 6H), 1.1–2.9(m, 24H), 3.1–3.3(m, 1H), 3.6–4.1 (m, 5H), 5.3–5.9(m, 2H), 5.86 (d, 1H, J=15.8Hz), 6.90(dt, 1H, J=15.8, 7.1Hz), 7.2–7.7(m, 4H) |

TABLE 19-continued

| | | | |
|---|---|---|---|
| 359 | [structure with cyclopentenone, OH, COOMe, OSi, S-cyclohexyl] | [structure with cyclopentenone, OH, COOMe, OH, S-cyclohexyl] | 67 | 0.7-1.1(m, 6H), 1.1-2.9(m, 38H), 3.1-3.3(m, 1H), 3.67(s, 3H), 3.6-4.2(m, 2H), 5.3-5.9 (m, 2H) |
| 360 | [structure with cyclopentenone, OH, COOMe, OSi, S-imidazole-Me] | [structure with cyclopentenone, OH, COOMe, OH, S-imidazole-Me] | 47 | 0.7-1.1(m, 6H), 1.1-3.0(m, 27H), 3.1-3.3(m, 1H), 3.67(s, 3H), 3.68(s, 3H), 3.6-3.9(m, 1H), 3.9-4.2(m, 1H), 5.5-5.7 (m, 2H), 7.0-7.3(m, 2H) |
| 361 | [structure with cyclopentenone, OAc, OSi, OPh, MeS] | [structure with cyclopentenone, OAc, OH, OPh, MeS] | 52 | 1.1-2.3(m, 11H), 2.00(s, 3H), 2.34(s, 3H), 2.5-2.8(m, 1H), 3.5-3.8(m, 2H), 3.8-4.2(m, 3H), 5.5-6.4(m, 3H), 6.7-7.1 (m, 4H), 7.1-7.4(m, 2H) |
| 362 | [structure with cyclopentenone, OAc, OSi, Ph, MeS] | [structure with cyclopentenone, OAc, OH, Ph, MeS] | 27 | 1.1-2.2(m, 6H), 2.03(s, 3H), 2.35(s, 3H), 2.6-2.9(m, 1H), 3.5-3.8(m, 2H), 4.0-4.2(m, 2H), 4.6-4.8(m, 1H), 5.5-6.0 (m, 1H), 6.0-6.5(m, 2H), 6.95 (d, 1H, J=2.5Hz), 7.1-7.5(m, 5H) |
| 363 | [structure with cyclopentenone, OAc, cyclopentyl, OSi, COOMe, S-CH2CH(OAc)CH2OAc] | [structure with cyclopentenone, OAc, cyclopentyl, OH, COOMe, S-CH2CH(OAc)CH2OAc] | 40 | 1.0-3.0(m, 19H), 2.11(s, 9H), 3.0-3.3(m, 1H), 3.67(s, 3H), 3.8-4.0(m, 1H), 4.1-4.5(m, 2H), 5.0-5.4(m, 1H), 5.4-6.0 (m, 3H), 7.25(d, 1H, J=7.0Hz) |

TABLE 19-continued
| | | | | |
|---|---|---|---|---|
| 364 | 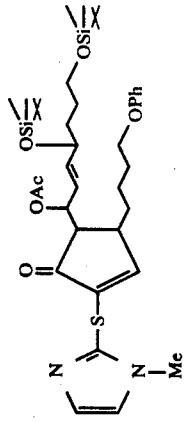 | 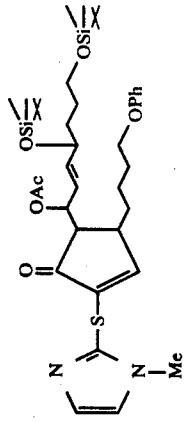 | 49 | 1.1–2.5(m, 13H), 2.02(s, 3H), 2.5–2.8(m, 1H), 3.5–3.8(m, 2H), 3.8–4.2(m, 3H), 5.5–6.3 (m, 3H), 6.7–7.4(m, 8H) |
| 365 | 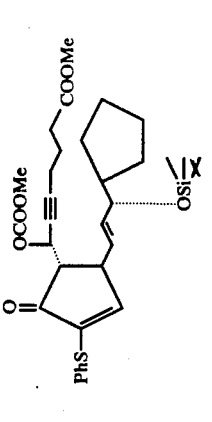 | 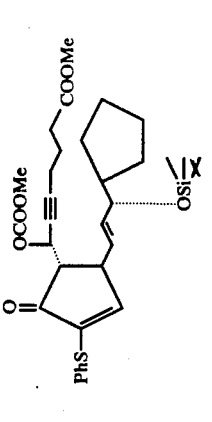 | 61 | 1.0–2.0(m, 11H), 2.0–3.1(m, 7H), 3.67(s, 3H), 3.78(s, 3H), 3.6–4.0(m, 1H), 5.4–5.9(m, 3H), 6.83(d, 1H, J=2.6Hz) |
| 366 | 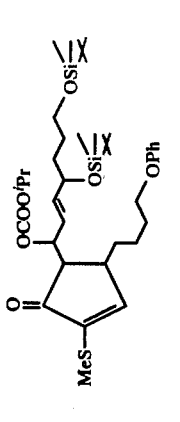 | 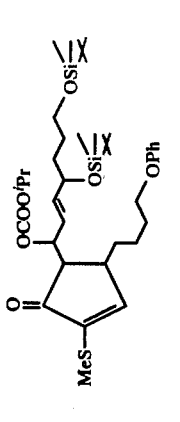 | 38 | 1.24(d, 1H, J=5.9Hz), 1.1–2.3 (m, 14H), 2.35(s, 3H), 2.5–3.0 (m, 1H), 3.4–3.7(m, 2H), 3.8–4.2(m, 3H), 4.4–5.0(m, 1H), 5.3–6.0(m, 3H), 6.7–7.1(m, 4H), 7.1–7.4(m, 2H) |
| 367 | 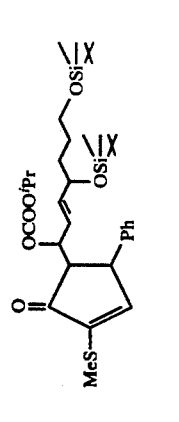 | 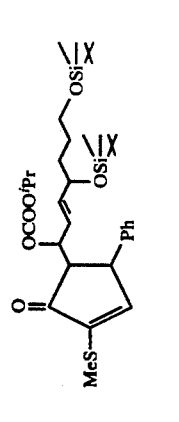 | 32 | 1.24(d, 1H, J=6.0Hz), 1.3–1.7 (m, 4H), 2.35(s, 3H), 2.7–3.1 (m, 1H), 3.4–3.7(m, 2H), 4.0–4.2(m, 1H), 4.4–4.9(m, 1H), 5.4–5.9(m, 3H), 6.95(d, 1H, J=3.3Hz), 7.1–7.5(m, 5H) |
| 368 | 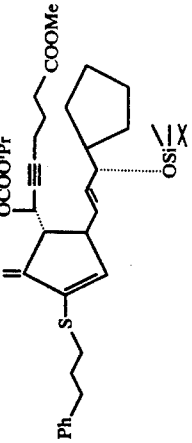 | 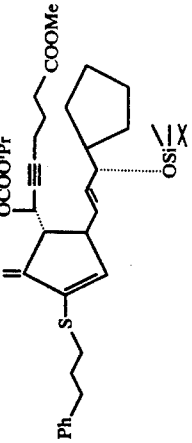 | 47 | 1.0–3.1(m, 30H), 3.68(s, 3H), 3.8–4.1(m, 1H), 4.6–5.1(m, 1H), 5.4–6.1(m, 3H), 6.95(d, 1H, J=2.8Hz), 7.1–7.5(m, 5H) |

TABLE 19-continued

| | | | | |
|---|---|---|---|---|
| 369 | [structure] | 40 | [structure] | 1.25(d, 1H, J=6.1Hz), 1.2–2.3 (m, 14H), 2.5–3.0(m, 1H), 3.4–3.7(m, 2H), 3.75(s, 3H), 3.8–4.2(m, 3H), 4.5–5.0(m, 1H), 5.4–6.1(m, 3H), 6.7–7.4(m, 8H) |
| 370 | [structure] | 64 | [structure] | 0.7–1.0(m, 3H), 1.2–2.5(m, 30H), 3.67(s, 3H), 3.9–4.1(m, 2H), 5.4–5.8(m, 2H), 6.5–6.8 (m, 2H) |
| 371 | [structure] | 77 | [structure] | 0.7–1.1(m, 3H), 1.1–2.6(m, 19H), 3.69(s, 3H), 3.8–4.1(m, 2H), 5.3–5.8(m, 2H), 6.5–6.8 (m, 2H) |
| 372 | [structure] | 73 | [structure] | 0.7–1.1(m, 3H), 1.1–2.5(m, 19H), 3.68(s, 3H), 3.9–4.1(m, 2H), 4.1(s, 3H), 5.4–5.8(m, 2H), 6.5–7.0(m, 2H) |
| 373 | [structure] | 69 | [structure] | 0.7–1.1(m, 6H), 1.1–2.0(m, 12H), 2.0–2.5(m, 4H), 3.69(s, 3H), 3.7–4.4(m, 2H), 5.1–6.0 (m, 3H), 6.5–7.2(m, 3H), 7.2–7.8(m, 4H) |

TABLE 19-continued

| | | | |
|---|---|---|---|
| 374 | (structure with OSiX groups, OPh, cyclopentenone, thiazole) | 76 | 1.1–2.2(m, 12H), 3.4–3.8(m, 3H), 3.70(s, 3H), 3.8–4.2(m, 2H), 4.1–4.5(m, 1H), 6.0–6.8(m, 2H), 6.8–7.5(m, 9H) |
| 375 | (structure with COOMe, cyclopentyl, OSiX, alkyne, cyclopentenone, furan-S) | 53 | 1.0–2.0(m, 12H), 2.0–3.0(m, 4H), 3.68(s, 3H), 3.8–4.3(m, 3H), 4.6–4.9(m, 1H), 5.3–5.8(m, 2H), 6.0–6.5(m, 2H), 6.6–7.1(m, 2H), 7.2–7.4(m, 1H) |
| 376 | (structure with OSiX, cyclohexyl, cyclopentenone, thiazole) | 39 | 1.0–2.2(m, 17H), 3.4–3.8(m, 3H), 3.69(s, 3H), 3.8–4.2(m, 2H), 4.2–4.6(m, 1H), 6.0–6.8(m, 2H), 6.8–7.4(m, 4H) |
| 377 | (structure with COOMe, OSiX, MeS, cyclopentenone) | 83 | 0.7–1.1(m, 6H), 1.1–2.8(m, 25H), 2.35(s, 3H), 3.64(s, 3H), 3.9–4.2(m, 2H), 5.2–5.9(m, 2H), 6.6–6.8(m, 1H) |
| 378 | (structure with COOMe, OSiX, EtS, cyclopentenone) | 72 | 0.7–1.1(m, 6H), 1.1–2.9(m, 30H), 3.68(s, 3H), 3.7–4.2(m, 2H), 5.3–5.9(m, 2H), 6.6–6.9(m, 1H) |

TABLE 19-continued

| | | | | |
|---|---|---|---|---|
| 379 | [structure with OSi≡X, COOMe, isopropyl-S] | | [structure with OH, COOMe, isopropyl-S] | 63 | 0.7-1.1(m, 6H), 1.1-3.0(m, 32H), 3.68(s, 3H), 3.7-4.2(m, 2H), 5.3-5.9(m, 2H), 6.6-6.9 (m, 1H) |
| 380 | [structure with OSi≡X, COOMe, S+] | | [structure with OH, COOMe, S+] | 59 | 0.7-1.0(m, 6H), 1.37(s, 9H), 1.0-3.0(m, 24H), 3.67(s, 3H), 3.7-4.2(m, 2H), 5.3-5.8(m, 2H), 6.6-6.9(m, 1H) |
| 381 | [structure with OSi≡X, COOMe, MeOOC-S] | | [structure with OH, COOMe, MeOOC-S] | 48 | 0.7-1.0(m, 3H), 1.1-3.0(m, 32H), 3.68(s, 6H), 3.7-4.2(m, 2H), 5.3-5.9(m, 2H), 6.5-6.9 (m, 1H) |
| 382 | [structure with OSi≡X, COOMe, PhS] | | [structure with OH, COOMe, PhS] | 43 | 0.7-1.0(m, 3H), 1.1-3.0(m, 22H), 3.68(s, 3H), 3.7-4.2(m, 2H), 5.3-5.9(m, 2H), 6.5-6.9 (m, 1H), 7.0-7.5(m, 5H) |
| 383 | [structure with OSi≡X, COOMe, tolyl-S] | | [structure with OH, COOMe, tolyl-S] | 53 | 0.7-1.0(m, 3H), 1.1-2.9(m, 24H), 2.33(s, 3H), 3.69(s, 3H), 3.7-4.2(m, 2H), 5.3-5.9 (m, 2H), 6.5-6.9(m, 1H), 6.9-7.5(m, 4H) |

TABLE 19-continued

| | | | | |
|---|---|---|---|---|
| 384 | [structure with naphthyl-OMe thioether, COOMe, OH/OSi-X variants] | 56 | 0.7–1.0(m, 3H), 1.1–3.0(m, 22H), 3.68(s, 3H), 3.7–4.2(m, 2H), 3.97(s, 3H), 5.4–5.9(m, 2H), 6.5–6.9(m, 1H), 7.0–8.1(m, 5H) |
| 385 | [structure with Ph(CH₂)₃S-, COOMe, OH/OSi-X] | 56 | 0.7–1.0(m, 3H), 1.0–3.1(m, 28H), 3.68(s, 3H), 3.7–4.2(m, 2H), 5.3–5.9(m, 2H), 6.5–6.9(m, 1H), 7.0–7.5(m, 5H) |
| 386 | [structure with 4-Cl-benzylthio, Me, COOEt, OH/OSi-X] | 57 | 0.7–1.1(m, 6H), 1.1–2.8(m, 22H), 3.6–4.1(m, 6H), 5.3–5.9(m, 2H), 5.88(d, 1H, J = 16Hz), 6.6–7.1(m, 2H), 7.2–7.7(m, 4H) |
| 387 | [structure with cyclohexylthio, COOMe, OH/OSi-X] | 68 | 0.7–1.1(m, 6H), 1.1–2.9(m, 36H), 3.68(s, 3H), 3.7–4.2(m, 2H), 5.3–5.9(m, 2H), 6.6–6.9(m, 1H) |
| 388 | [structure with pyridylthio, COOMe, OH/OSi-X] | 55 | 0.7–1.1(m, 6H), 1.0–3.0(m, 25H), 3.68(s, 3H), 3.7–4.2(m, 2H), 5.3–5.9(m, 2H), 6.6–6.9(m, 1H), 7.2–8.1(m, 4H) |

TABLE 19-continued

| | | | |
|---|---|---|---|
| 389 | (structure) | (structure) | 63 | 0.7-1.1(m, 6H), 1.0-3.0(m, 25H), 3.67(s, 3H), 3.69(s, 3H), 3.6-4.2(m, 2H), 5.3-5.8 (m, 2H), 6.6-6.9(m, 1H), 7.0-7.3(m, 2H) |
| 390 | (structure) | (structure) | 58 | 0.7-1.1(m, 6H), 1.1-3.0(m, 25H), 2.47(s, 3H), 3.69(s, 3H), 3.6-4.2(m, 2H), 5.3-5.9 (m, 2H), 6.6-7.1(m, 2H), 8.30 (d, 1H, J=5.0Hz) |
| 391 | (structure) | (structure) | 47 | 0.7-1.0(m, 3H), 1.0-3.1(m, 22H), 3.69(s, 3H), 3.7-4.3 (m, 4H), 5.3-5.9(m, 2H), 6.1-6.5(m, 1H), 6.5-6.8(m, 1H), 7.3-7.6(m, 1H) |
| 392 | (structure) | (structure) | 76 | 0.7-1.0(m, 3H), 1.1-2.3(m, 22H), 2.34(s, 3H), 3.0-3.4 (m, 1H), 3.69(s, 3H), 3.8-4.1 (m, 1H), 5.5-5.8(m, 2H), 7.18 (d, 1H, J=2.5Hz) |
| 393 | (structure) | (structure) | 92 | 0.7-1.0(m, 3H), 1.1-2.8(m, 22H), 2.8-3.3(m, 3H), 3.67(s, 3H), 3.4-4.2(m, 4H), 4.81 (brs, 1H), 5.3-5.7(m, 2H), 7.16(d, 1H, J=2.8Hz) |

| # | Structure (starting) | # | Structure (product) | Yield | NMR |
|---|---|---|---|---|---|
| 394 | | 69 | | | 0.7–1.0(m, 3H), 1.1–2.3(m, 22H), 3.0–3.3(m, 1H), 3.70(s, 3H), 3.8–4.1(m, 1H), 5.5–5.8 (m, 2H), 7.1–7.4(m, 6H) |
| 395 | | 71 | | | 0.7–1.0(m, 3H), 1.1–2.5(m, 33H), 3.0–3.3(m, 1H), 3.68(s, 3H), 3.9–4.1(m, 1H), 5.5–5.8 (m, 2H), 7.17(d, 1H, J=2.0Hz) |
| 396 | | 58 | | | 0.7–1.0(m, 3H), 1.1–2.2(m, 22H), 3.0–3.4(m, 1H), 3.68(s, 3H), 3.71(s, 3H), 3.9–4.2(m, 1H), 5.4–5.8(m, 2H), 6.7–7.2 (m, 3H) |
| 397 | | 70 | | | 1.0–2.1(m, 8H), 2.33(s, 3H), 3.2–3.4(m, 1H), 3.70(s, 3H), 3.94(t, 2H, J=5.0Hz), 4.3–4.5 (m, 1H), 4.60(s, 2H), 4.9–5.2 (m, 1H), 6.5–7.4(m, 10H) |
| 398 | | 60 | | | 1.1–2.4(m, 10H), 2.5–2.7(m, 2H), 3.1–3.4(m, 1H), 3.4–4.2 (m, 5H), 5.0–5.2(m, 1H), 6.8–7.5(m, 15H) |

TABLE 19-continued

| # | Product | Starting material | Yield |
|---|---|---|---|
| 399 / 40 | cyclopentenone with S-cyclohexyl, OH groups, CH=CH-CH(OH)-CH₂-CH₂OH side chain, and CH₂-CH₂-CH₂-OPh side chain | silyl-protected analog | 1.1–2.2(m, 20H), 2.3–3.4(m, 6H), 3.5–3.8(m, 2H), 3.8–4.1(m, 2H), 4.1–4.8(m, 2H), 5.5–6.5(m, 2H), 6.7–7.1(m, 3H), 7.1–7.7(m, 3H) |
| 400 / 69 | cyclopentenone with S-cyclohexyl, OH, (CH₂)₄-COOMe side chain, CH₂-CH₂-CH₂-OPh side chain | silyl-protected analog | 1.1–2.6(m, 31H), 2.7–3.0(m, 1H), 3.67(s, 3H), 3.6–4.1(m, 3H), 6.7–7.4(m, 6H) |
| 401 / 48 | cyclopentenone with S-(pyridyl), OH groups, CH(CH₂OH)- linker to 3,4-dimethoxyphenyl, and biphenyl | silyl-protected analog | 1.2–2.9(m, 13H), 3.0–3.3(m, 1H), 3.5–3.7(m, 4H), 3.77(s, 6H), 5.0–5.2(m, 2H), 6.4–7.0(m, 4H), 7.2–8.1(m, 8H) |
| 402 / 65 | cyclopentenone with S-(N-methylimidazolyl), OH groups, CH=CH-CH(OH)-CH₂-CH₂OH side chain, CH₂-CH₂-CH₂-OPh side chain | silyl-protected analog | 1.0–2.1(m, 10H), 2.5–2.8(m, 1H), 3.0–4.3(m, 8H), 4.4–4.75(m, 1H), 5.5–6.35(m, 2H), 6.5–7.6(m, 8H) |
| 403 / 83 | cyclopentenone with S-(N-methylimidazolyl), OH, C≡C-CH(OH)- chain with (CH₂)₃-COOMe, CH₂-CH₂-CH₂-OPh side chain | silyl-protected analog | 1.2–2.3(m, 12H), 2.3–2.7(m, 5H), 2.8–3.0(m, 1H), 3.68(s, 3H), 3.77(s, 3H), 3.8–4.2(m, 2H), 4.6–5.0(m, 1H), 6.8–7.5(m, 6H) |

TABLE 19-continued

| | | | |
|---|---|---|---|
| 404 | (structure) | (structure) | 98 | 1.06(s, 3H), 1.16(s, 3H), 1.3–2.4(m, 13H), 2.62(d, 1H, J=3.6 Hz), 3.65(s, 3H), 3.8–4.1(m, 2H), 4.9–5.1(m, 1H), 6.66(s, 1H), 6.7–7.5(m, 7H) |
| 405 | (structure) | (structure) | 29 | 1.1–2.0(m, 9H), 2.0–3.3(m, 4H), 3.5–4.2(m, 3H), 3.71(s, 3H), 5.2–5.7(m, 1H), 6.7–8.1(m, 12H) |
| 406 | (structure) | (structure) | 81 | 0.7–1.1(m, 6H), 1.1–3.0(m, 15H), 3.5–4.3(m, 7H), 5.92(d, 1H, J=15.8Hz), 6.7–7.9(m, 10H) |
| 407 | (structure) | (structure) | 43 | 0.7–1.0(m, 3H), 1.0–3.0(m, 21H), 2.37(s, 3H), 3.4–4.3(m, 5H), 4.5–4.9(m, 1H), 5.5–6.1(m, 2H), 6.7–7.5(m, 2H) |

TABLE 19-continued

| | | | | |
|---|---|---|---|---|
| 408 | [structure with PhS, OH, OSi, cyclohexyl, OPh] | [structure with PhS, OH, cyclohexyl, OPh] | 81 | 0.7-1.1(m, 3H), 1.1-2.9(m, 28H), 3.6-4.4(m, 3H), 6.7-7.5 (m, 10H) |
| 409 | [structure with COOMe, OH, OSi, OPh, cyclohexyl-S] | [structure with COOMe, OH, OPh, cyclohexyl-S] | 55 | 0.7-1.0(m, 3H), 1.1-2.9(m, 36H), 3.68(s, 3H), 3.6-4.2(m, 3H), 6.7-7.0(m, 3H), 7.1-7.4 (m, 2H) |
| 410 | [structure with OSi, OH, OPh, N-Me thiocarbamate] | [structure with OH, OH, OPh, N-Me thiocarbamate] | 37 | 0.8-1.1(m, 3H), 1.1-2.8(m, 21H), 3.5-4.5(m, 6H), 3.69(s, 3H), 5.6-5.9(m, 2H), 6.7-7.5 (m, 7H) |
| 411 | [structure with COOEt, OMe, OMe, OH, OSi, Me, benzoxazole-S] | [structure with COOEt, OMe, OMe, OH, OH, Me, benzoxazole-S] | 62 | 1.2-3.1(m, 20H), 3.6-4.1(m, 3H), 3.82(s, 6H), 5.88(d, 1H, J=15.6Hz), 6.4-7.9(m, 8H) |
| 412 | [structure with OSi, OH, OSi, MeS] | [structure with OH, OH, OH, MeS] | 59 | 1.3-2.4(m, 7H), 2.35(s, 3H), 2.7-3.0(m, 1H), 3.5-3.8(m, 2H), 4.0-4.3(m, 1H), 4.5-5.1 (m, 2H), 5.6-5.9(m, 2H), 6.70 (d, 1H, J=2.8Hz) |

TABLE 19-continued

| No. | Structure (silyl) | No. | Structure (free) | NMR |
|---|---|---|---|---|
| 413 | | 61 | | 1.1-2.7(m, 9H), 3.5-4.0(m, 2H), 4.0-4.7(m, 2H), 4.8-5.1(m, 1H), 5.6-6.0(m, 2H), 6.83(d, 1H, J=2.1Hz) |
| 414 | | 72 | | 1.1-2.44(m, 12H), 2.4-2.9(m, 1H), 3.69(s, 3H), 3.7-4.1(m, 1H), 5.0-5.2(m, 1H), 7.2-8.0(m, 5H) |
| 415 | | 44 | | 1.1-2.2(m, 13H), 2.04(s, 3H), 2.35(s, 3H), 2.6-2.8(m, 1H), 3.5-3.8(m, 2H), 3.8-4.1(m, 2H), 4.1-4.5(m, 1H), 5.5-6.0(m, 1H), 6.0-6.5(m, 2H), 6.66(s, 1H), 6.7-7.1(m, 3H), 7.1-7.4(m, 2H) |
| 416 | | 37 | | 1.1-2.3(m, 13H), 2.03(s, 3H), 2.6-2.9(m, 1H), 3.5-3.8(m, 2H), 3.8-4.2(m, 3H), 5.6-5.9(m, 2H), 5.9-6.3(m, 1H), 6.6-7.1(m, 4H), 7.1-7.4(m, 7H) |
| 417 | | 45 | | 1.1-2.5(m, 24H), 2.05(s, 3H), 2.6-2.9(m, 1H), 3.5-3.8(m, 2H), 3.7-4.2(m, 3H), 5.6-5.9(m, 2H), 5.9-6.3(m, 1H), 6.6-7.1(m, 4H), 7.1-7.4(m, 2H) |

TABLE 19-continued

| | | | |
|---|---|---|---|
| 418 | [structure with OAc, OSi, OPh, thiazoline-Me] | [structure with OAc, OH, OPh, thiazoline-Me] | 39 | 1.1–2.3(m, 13H), 2.03(s, 3H), 2.6–2.9(m, 1H), 3.5–3.8(m, 2H), 3.69(s, 3H), 3.7–4.3(m, 3H), 5.6–5.9(m, 2H), 5.9–6.3(m, 1H), 6.6–7.5(m, 8H) |
| 419 | [structure with OAc, OSi, OPh, thiazoline-Me] | [structure with OAc, OH, OPh, thiazoline-Me] | 42 | 0.7–1.0(m, 3H), 1.1–2.4(m, 19H), 2.01(s, 3H), 2.6–2.9(m, 1H), 3.5–3.8(m, 2H), 3.70(s, 3H), 3.8–4.3(m, 3H), 5.6–5.9(m, 2H), 5.9–6.3(m, 1H), 6.6–7.5(m, 7H) |
| 420 | [structure with OCOOMe, OSi, OPh, MeS] | [structure with OCOOMe, OH, OPh, MeS] | 55 | 1.0–2.1(m, 13H), 2.34(s, 3H), 2.5–3.0(m, 1H), 3.5–3.7(m, 2H), 3.77(s, 3H), 3.8–4.2(m, 3H), 5.3–6.1(m, 3H), 6.6–7.1(m, 4H), 7.1–7.4(m, 2H) |
| 421 | [structure with OCOOMe, OSi, OPh, thiazoline-Me] | [structure with OCOOMe, OH, OPh, thiazoline-Me] | 43 | 1.0–2.2(m, 13H), 2.5–3.0(m, 2H), 3.5–3.7(m, 2H), 3.69(s, 3H), 3.76(s, 3H), 3.8–4.3(m, 3H), 5.3–6.2(m, 3H), 6.7–8.5(m, 8H) |
| 422 | [structure with OCOO$^i$Pr, OSi, OPh, MeS] | [structure with OCOO$^i$Pr, OH, OPh, MeS] | 20 | 1.26(d, 6H, J=6.2Hz), 1.2–2.2(m, 13H), 2.32(s, 3H), 2.7–2.9(m, 1H), 3.5–3.8(m, 2H), 3.8–4.1(m, 2H), 4.1–4.5(m, 1H), 4.6–5.0(m, 1H), 5.4–6.3(m, 3H), 6.5–7.1(m, 4H), 7.1–7.4(m, 2H) |

| | | |
|---|---|---|
| 423 | 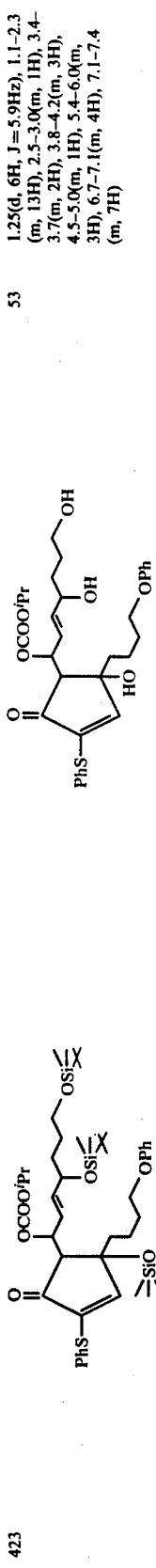 | 53 | 1.25(d, 6H, J=5.9Hz), 1.1-2.3 (m, 13H), 2.5-3.0(m, 1H), 3.4-3.7(m, 2H), 3.8-4.2(m, 3H), 4.5-5.0(m, 1H), 5.4-6.0(m, 3H), 6.7-7.1(m, 4H), 7.1-7.4 (m, 7H) |
| 424 | 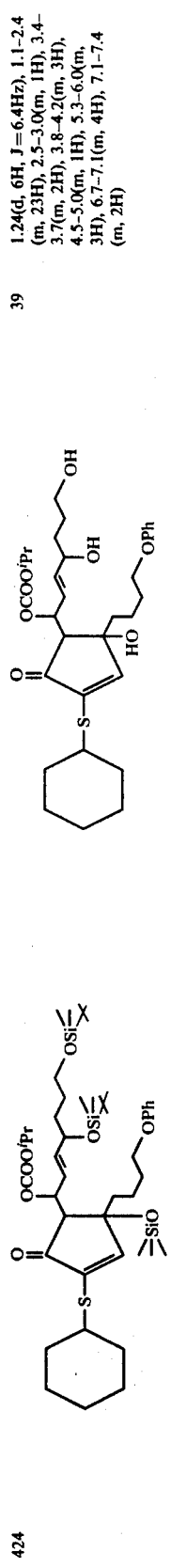 | 39 | 1.24(d, 6H, J=6.4Hz), 1.1-2.4 (m, 23H), 2.5-3.0(m, 1H), 3.4-3.7(m, 2H), 3.8-4.2(m, 3H), 4.5-5.0(m, 1H), 5.3-6.0(m, 3H), 6.7-7.1(m, 4H), 7.1-7.4 (m, 2H) |
| 425 | 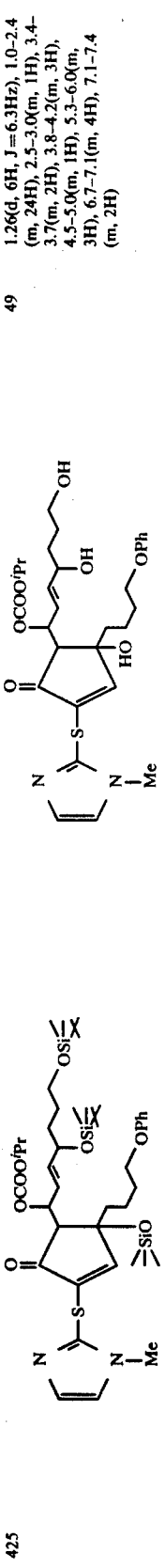 | 49 | 1.26(d, 6H, J=6.3Hz), 1.0-2.4 (m, 24H), 2.5-3.0(m, 1H), 3.4-3.7(m, 2H), 3.8-4.2(m, 3H), 4.5-5.0(m, 1H), 5.3-6.0(m, 3H), 6.7-7.1(m, 4H), 7.1-7.4 (m, 2H) |
| 426 | 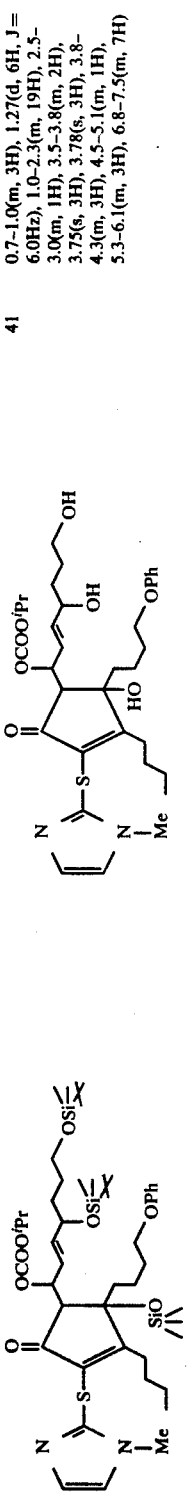 | 41 | 0.7-1.0(m, 3H), 1.27(d, 6H, J=6.0Hz), 1.0-2.3(m, 19H), 2.5-3.0(m, 1H), 3.5-3.8(m, 2H), 3.75(s, 3H), 3.78(s, 3H), 3.8-4.3(m, 3H), 4.5-5.1(m, 1H), 5.3-6.1(m, 3H), 6.8-7.5(m, 7H) |
| 427 | 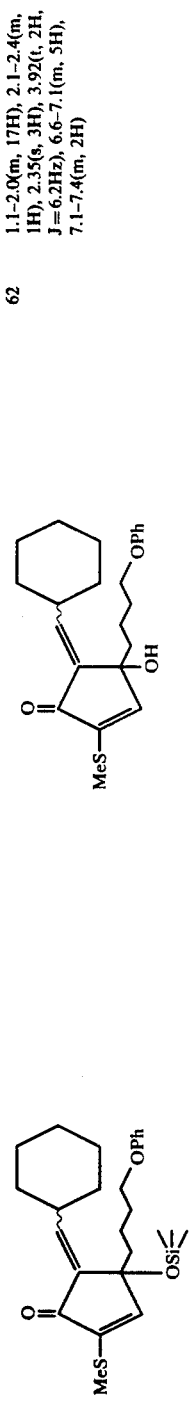 | 62 | 1.1-2.0(m, 17H), 2.1-2.4(m, 1H), 2.35(s, 3H), 3.92(t, 2H, J=6.2Hz), 6.6-7.1(m, 5H), 7.1-7.4(m, 2H) |

| | |
|---|---|
| 41 | 0.7-1.0(m, 6H), 1.1-2.1(m, 15H), 2.2-2.6(m, 2H), 2.35(s, 3H), 6.15(d, 1H, J=3.5Hz), 6.64(d, 1H, J=3.5Hz), 6.88(s, 1H), 7.32(s, 1H) |
| 38 | 0.7-1.3(m, 15H), 1.2-2.1(m, 13H), 2.28(s, 6H), 2.2-2.5(m, 1H), 6.6-7.0(m, 2H) |
| 59 | 1.0-2.1(m, 29H), 2.1-2.5(m, 5H), 3.68(s, 3H), 4.7-5.0(m, 1H), 5.4-5.8(m, 2H), 6.6-7.1(m, 2H) |
| 68 | 1.1-2.0(m, 17H), 2.1-2.5(m, 1H), 3.92(t, 2H, J=6.2Hz), 6.5-7.1(m, 5H), 7.1-7.5(m, 7H) |
| 75 | 1.2-2.0(m, 9H), 2.69(d, 2H, J=6.9Hz), 3.4-3.8(m, 4H), 3.94(t, 2H, J=6.4Hz), 6.5-7.5(m, 14H), 7.8-8.1(m, 2H) |

428
429
430
431
432

| | | |
|---|---|---|
| 433 | 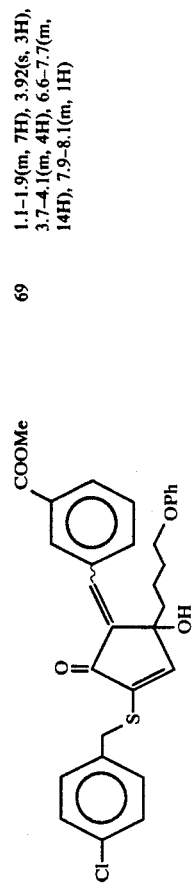 | 69 | 1.1–1.9(m, 7H), 3.92(s, 3H), 3.7–4.1(m, 4H), 6.6–7.7(m, 14H), 7.9–8.1(m, 1H) |
| 434 | 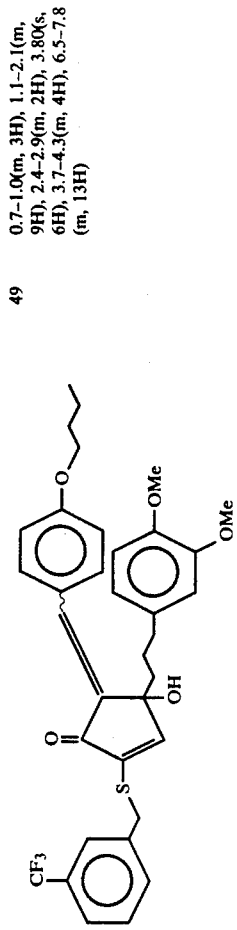 | 49 | 0.7–1.0(m, 3H), 1.1–2.1(m, 9H), 2.4–2.9(m, 2H), 3.80(s, 6H), 3.7–4.3(m, 4H), 6.5–7.8(m, 13H) |
| 435 | 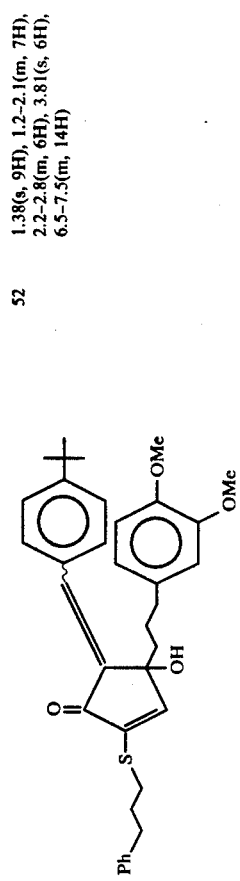 | 52 | 1.38(s, 9H), 1.2–2.1(m, 7H), 2.2–2.8(m, 6H), 3.81(s, 6H), 6.5–7.5(m, 14H) |
| 436 |  | 62 | 1.1–2.2(m, 26H), 2.4–2.8(m, 2H), 3.68(s, 3H), 3.9(2H, t, J=5.8Hz), 6.4–6.7(m, 2H), 6.7–7.0(m, 3H), 7.1–7.4(m, 2H) |
| | |
|---|---|
| 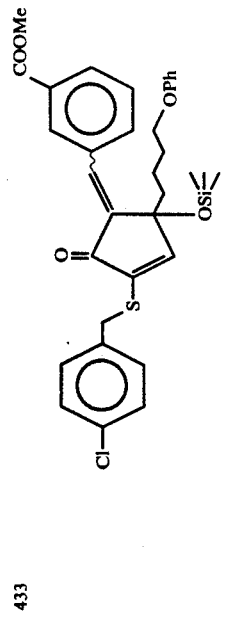 | 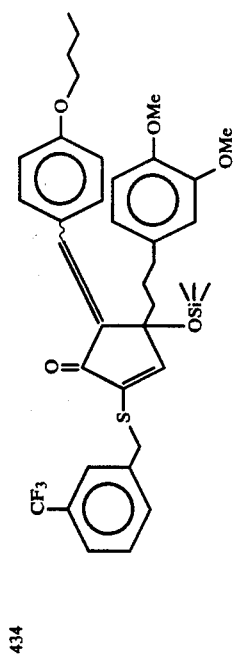 |
| 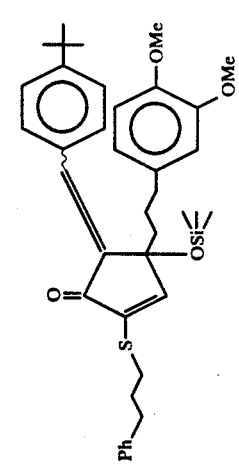 | 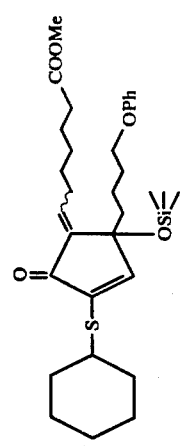 |

| | | |
|---|---|---|
| 42 |  | 1.1-2.0(m, 19H), 2.1-2.8(m, 5H), 3.1-3.3(m, 1H), 3.68(s, 3H), 3.96(t, 2H, J=5.9Hz), 6.4-6.7(m, 1H), 6.7-7.0(m, 4H), 7.1-7.4(m, 2H) |
| 69 | | 1.1-2.0(m, 19H), 2.2-2.6(m, 3H), 3.4-4.0(m, 4H), 3.76(s, 3H), 4.10(s, 2H), 6.4-6.7(m, 1H), 6.7-7.1(m, 4H), 7.1-7.4(m, 2H) |
| 70 | 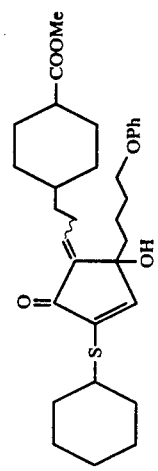 | 1.1-2.1(m, 28H), 2.2-2.7(m, 4H), 3.69(s, 3H), 3.94(t, J=6.0Hz), 6.4-6.7(m, 1H), 6.7-7.1(m, 4H), 7.1-7.4(m, 2H) |
| 69 | | 1.1-2.0(m, 17H), 2.2-2.5(m, 1H), 3.6-4.2(m, 2H), 3.79(s, 3H), 4.70(s, 2H), 6.6-7.6(m, 10H), 7.7-8.1(m, 1H) |
| 78 | 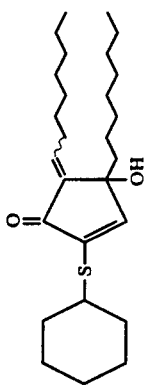 | 0.7-1.0(m, 6H), 1.1-2.1(m, 39H), 2.1-2.6(m, 3H), 6.4-6.8(m, 2H) |
| 437 | 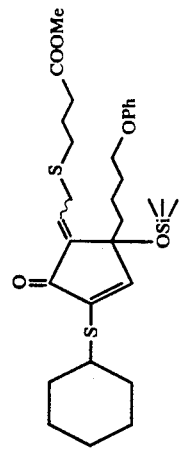 |
|---|---|
| 438 | 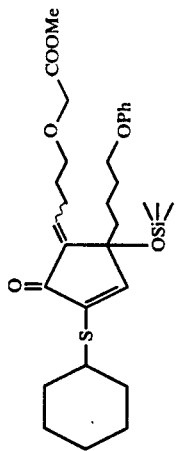 |
| 439 | 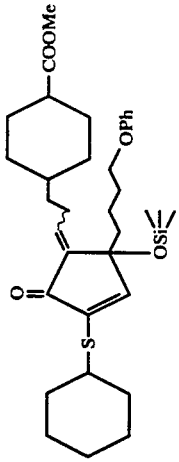 |
| 440 | 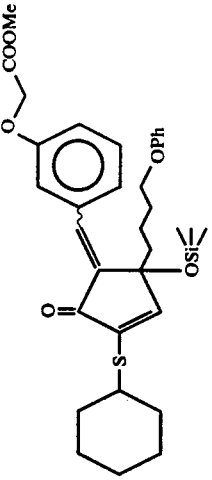 |
| 441 | 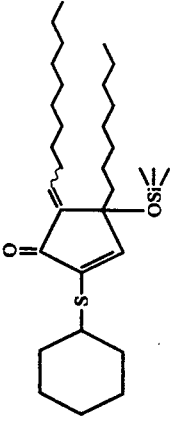 |

| | | |
|---|---|---|
| 83 | 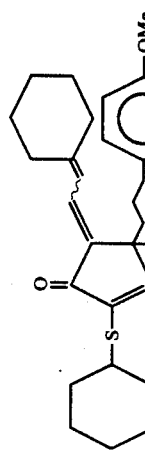 | 1.2-2.0(m, 21H), 2.1-2.5(m, 5H), 3.81(s, 6H), 6.3-7.4(m, 6H) |
| 70 | | 0.7-1.0(m, 3H), 1.1-2.0(m, 17H), 2.1-2.5(m, 3H), 3.93(t, 2H, J=6.2Hz), 6.4-7.1(m, 5H), 7.1-7.4(m, 2H) |
| 69 | | 1.1-2.0(m, 17H), 2.1-2.6(m, 5H), 3.76(s, 3H), 3.92(t, 2H, J=6.1Hz), 6.3-7.5(m, 11H) |
| 71 | | 0.83(d, 9H, J=5.0Hz), 0.9-2.1(m, 21H), 2.1-2.5(m, 1H), 6.6-7.5(m, 5H), 8.0-8.1(m, 1H) |
| 63 | | 1.2-2.5(m, 30H), 3.68(s, 3H), 3.8-4.1(m, 2H), 6.12(t, 1H, J=1.8Hz), 6.71(2, 1H), 6.8-7.1(m, 3H), 7.1-7.4(m, 2H) |
| 442 | 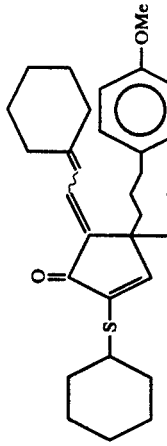 | |
| 443 | 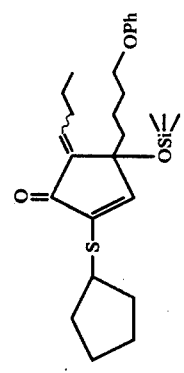 | |
| 444 | 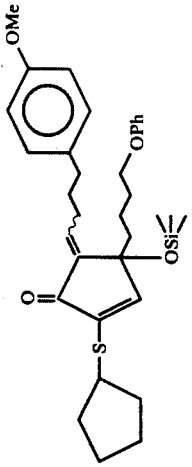 | |
| 445 | 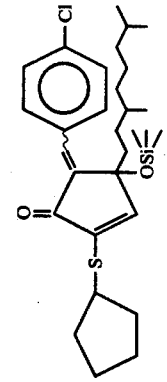 | |
| 446 | 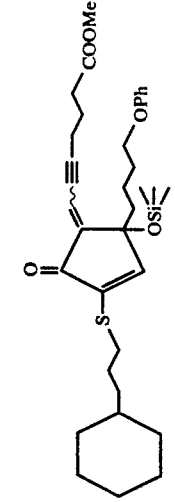 | |

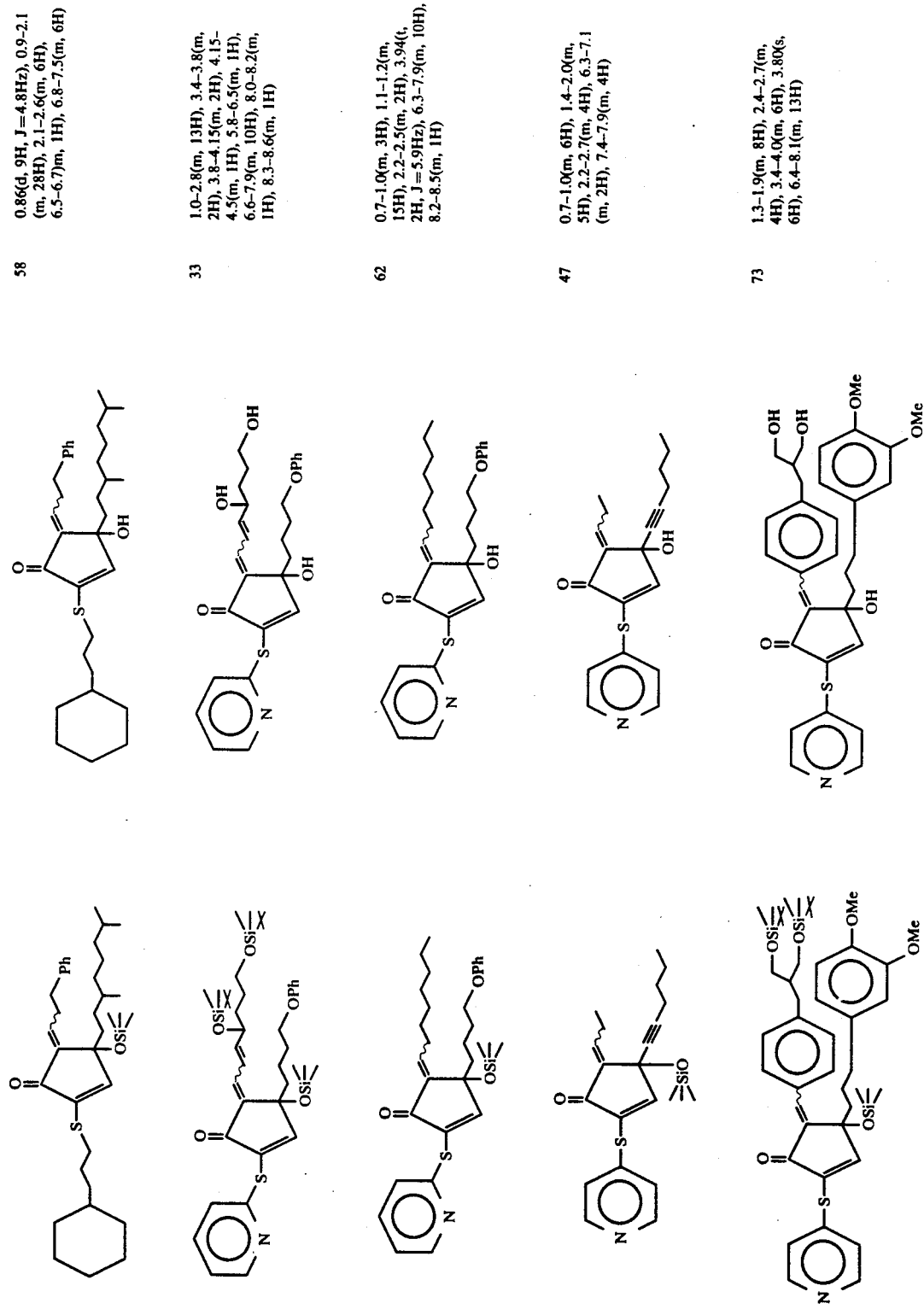

| | |
|---|---|
| 83 | 0.7–1.1(m, 3H), 1.1–2.5(m, 13H), 3.69(s, 3H), 3.89(t, 2H, J=6.2Hz), 6.0–7.4(m, 11H) |
| 27 | 1.2–2.3(m, 8H), 3.68(s, 3H), 3.88(t, 2H, J=6Hz), 4.1–4.4(m, 2H), 6.0–6.5(m, 1H), 6.5–7.4(m, 10H) |
| 71 | 1.0–2.2(m, 10H), 3.4–3.75(m, 2H), 3.69(s, 3H), 3.75–4.0(m, 2H), 4.0–4.9(m, 4H), 5.8–6.3(m, 1H), 6.4–7.8(m, 8H) |
| 84 | 1.1–2.1(m, 11H), 2.3–3.0(m, 5H), 3.4–3.7(m, 4H), 3.69(s, 3H), 3.89(t, 2H, J=6Hz), 6.4–6.7(m, 1H), 6.7–7.4(m, 7H) |
| 80 | 1.2–2.7(m, 16H), 3.4–3.8(m, 4H), 3.69(s, 3H), 3.89(t, 2H, J=6Hz), 5.9–6.4(m, 1H), 6.5–7.4(m, 10H) |

| 452 | 453 | 454 | 455 | 456 |

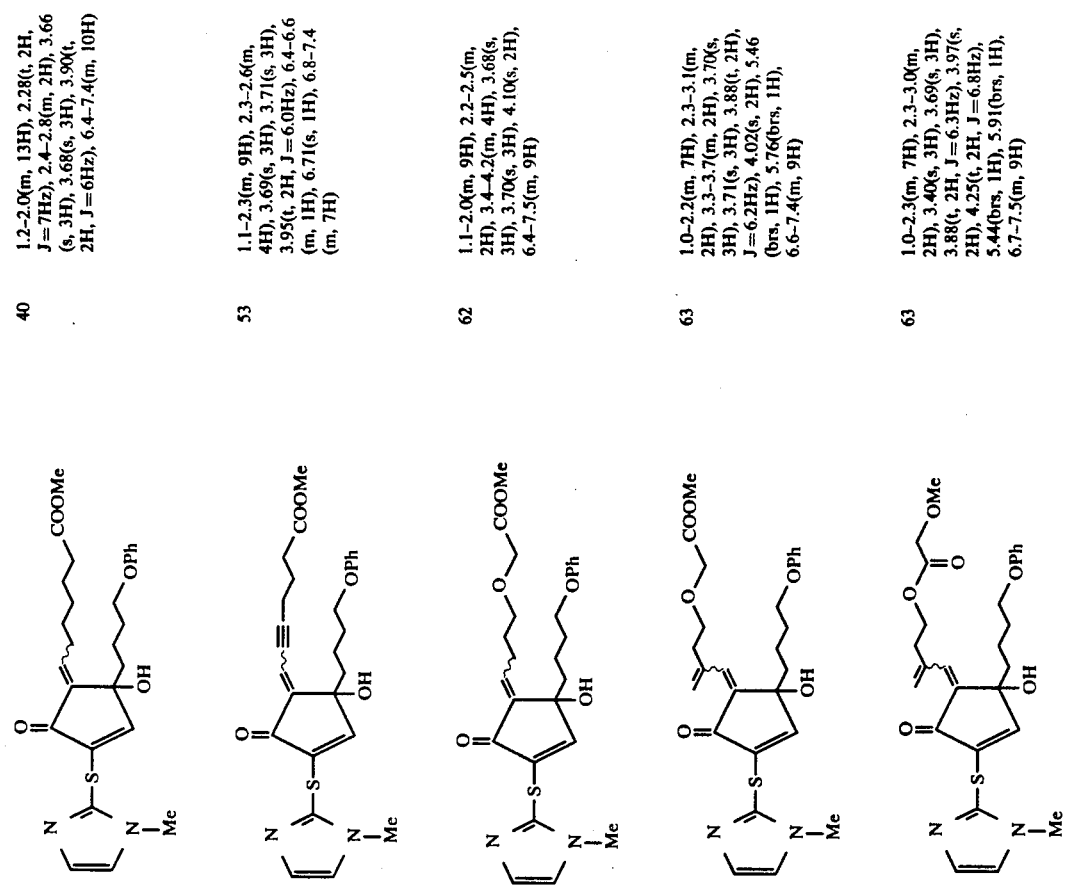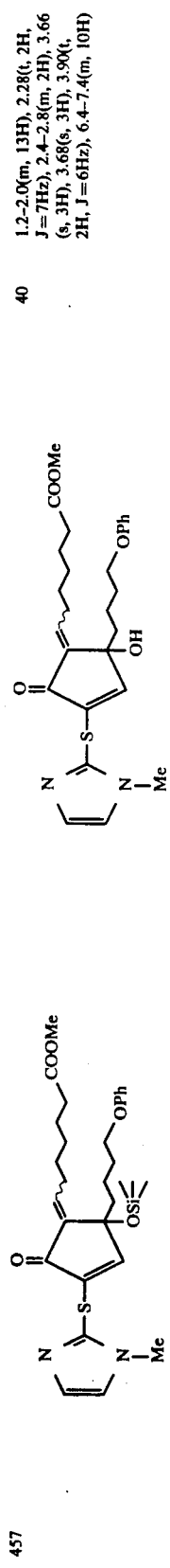

| | | | | |
|---|---|---|---|---|
| 95 | 72 | 54 | 77 | 90 |
| 1.1–2.1(m, 7H), 2.4–2.9(m, 5H), 3.68(s, 3H), 3.83(s, 6H), 3.8–4.0(m, 2H), 6.5–7.5(m, 7H) | 1.1–2.1(m, 18H), 3.66(s, 3H), 3.8–4.0(m, 2H), 6.1–7.8(m, 10H) | 1.2–2.2(m, 13H), 2.2–2.5(m, 4H), 3.68(s, 3H), 3.88(t, 2H, J=6Hz), 6.4–7.4(m, 9H), 7.5–7.8(m, 1H) | 1.2–2.0(m, 7H), 2.2–2.6(m, 8H), 3.58(s, 2H), 3.68(s, 3H), 3.97(t, 2H, J=5.8Hz), 6.4–7.4 (m, 14H), 7.5–7.8(m, 1H) | 1.0–2.2(m, 7H), 3.70(s, 3H), 3.6–3.8(m, 2H), 3.92(s, 3H), 6.6–7.4(m, 8H), 7.45(s, 1H), 8.02(s, 4H) |
-continued
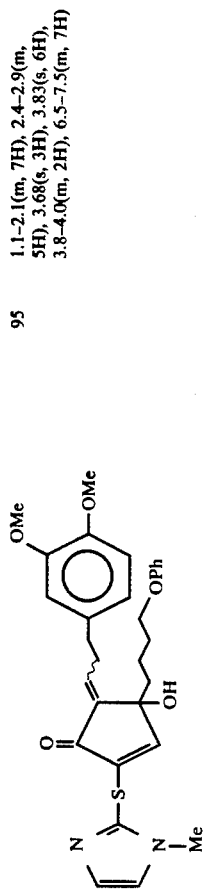 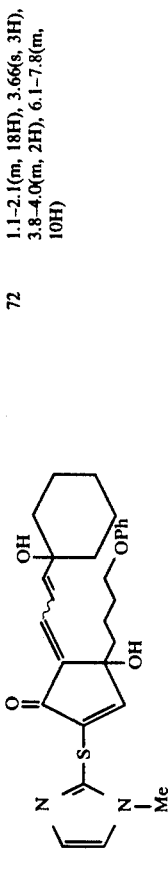 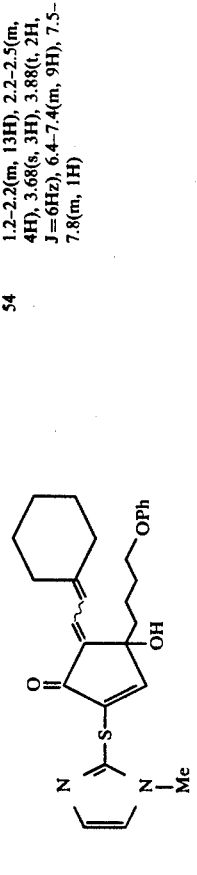 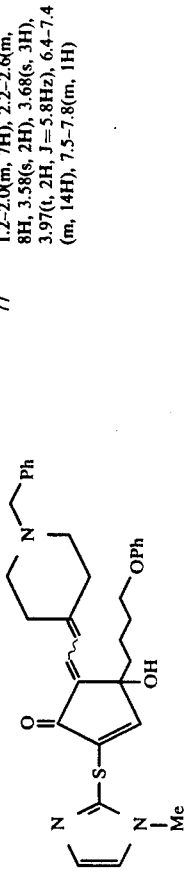 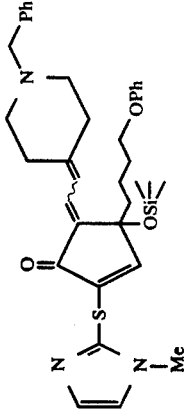
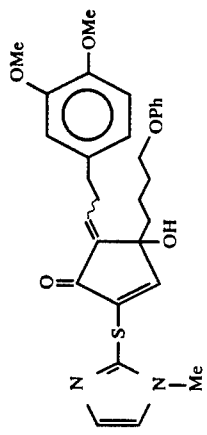 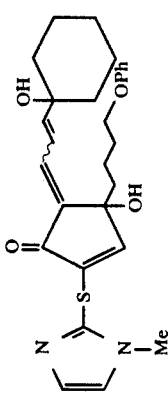 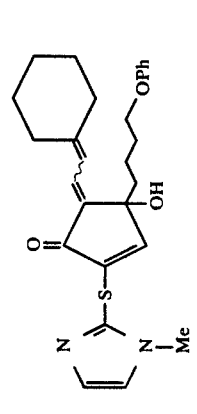 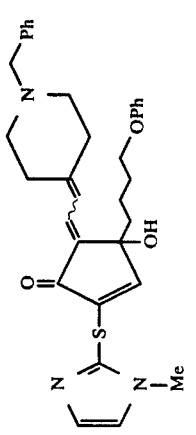 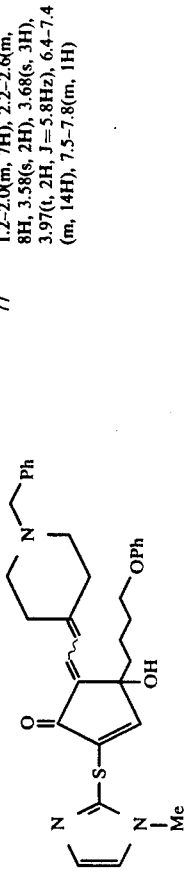
| 462 | 463 | 464 | 465 | 466 |

| | | |
|---|---|---|
| 467 | 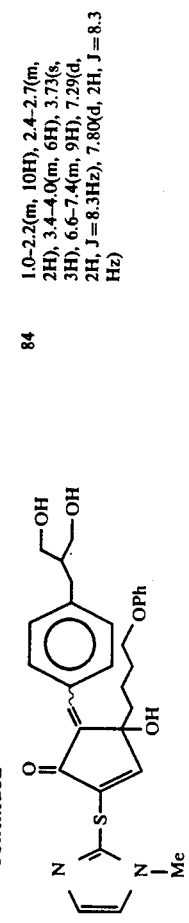 | 84 | 1.0–2.2(m, 10H), 2.4–2.7(m, 2H), 3.4–4.0(m, 6H), 3.73(s, 3H), 6.6–7.4(m, 9H), 7.29(d, 2H, J=8.3Hz), 7.80(d, 2H, J=8.3 Hz) | 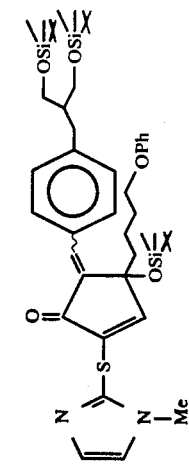 |
| 468 | 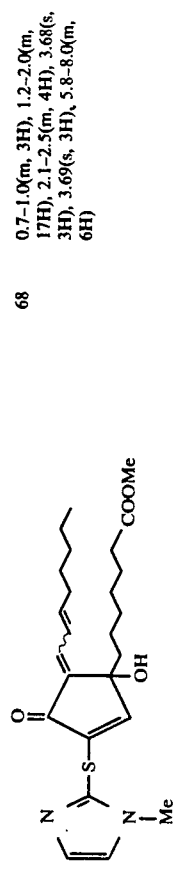 | 68 | 0.7–1.0(m, 3H), 1.2–2.0(m, 17H), 2.1–2.5(m, 4H), 3.68(s, 3H), 3.69(s, 3H), 5.8–8.0(m, 6H) | 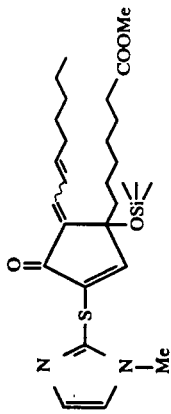 |
| 469 | 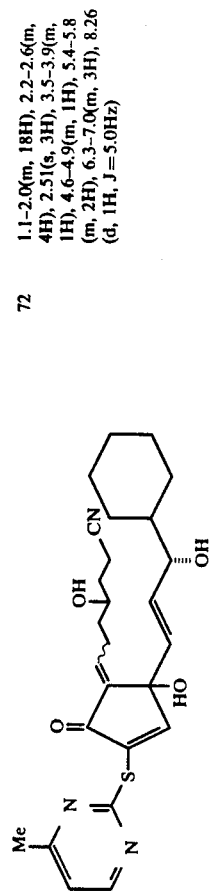 | 72 | 1.1–2.0(m, 18H), 2.2–2.6(m, 4H), 2.51(s, 3H), 3.5–3.9(m, 1H), 4.6–4.9(m, 1H), 5.4–5.8(m, 2H), 6.3–7.0(m, 3H), 8.26(d, 1H, J=5.0Hz) | 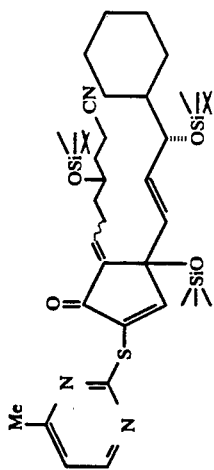 |
| 470 | 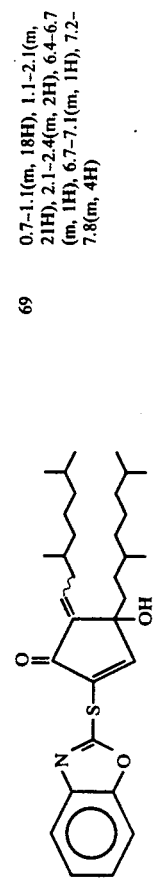 | 69 | 0.7–1.1(m, 18H), 1.1–2.1(m, 21H), 2.1–2.4(m, 2H), 6.4–6.7(m, 1H), 6.7–7.1(m, 1H), 7.2–7.8(m, 4H) | 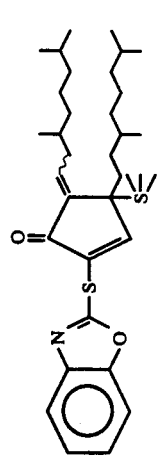 |
| 471 | 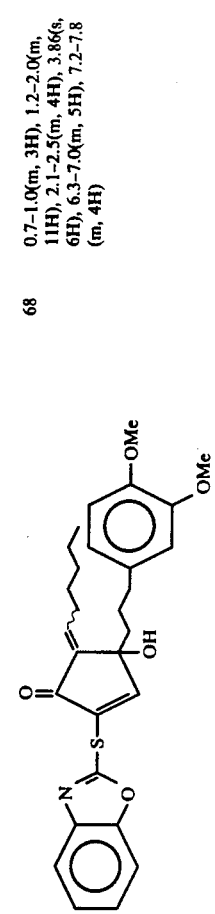 | 68 | 0.7–1.0(m, 3H), 1.2–2.0(m, 11H), 2.1–2.5(m, 4H), 3.86(s, 6H), 6.3–7.0(m, 5H), 7.2–7.8(m, 4H) | 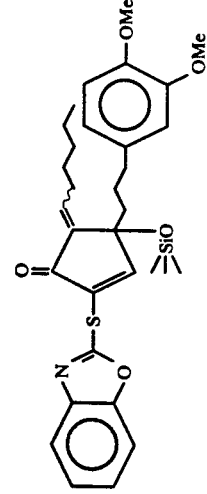 |

| | | |
|---|---|---|
| 71 | (structure 71) | 0.98(d, 6H, J=6.3Hz), 1.20(s, 3H), 1.5–1.9(m, 2H), 2.0–2.4 (m, 2H), 6.4–6.7(m, 1H), 6.9–7.9(m, 5H) |
| 75 | (structure 75) | 0.7–1.0(m, 3H), 1.1–2.0(m, 13H), 2.1–2.44(m, 2H), 4.6–4.9 (m, 1H), 5.4–5.8(m, 2H), 6.3–6.6(m, 1H), 6.9–7.8(m, 4H) |
| 78 | (structure 78) | 1.0–2.3(m, 13H), 3.0–3.75(m, 5H), 3.75–4.5(m, 5H), 5.9–6.4 (m, 1H), 6.5–7.9(m, 9H), 8.0–8.2(m, 1H), 8.3–8.5(m, 1H) |
| 48 | (structure 48) | 0.7–1.1(m, 6H), 1.1–2.1(m, 9H), 2.2–2.77(m, 4H), 3.5–4.3 (m, 6H), 5.92(d, 1H, J=15.6Hz), 6.4–7.9(m, 11H) |
| 63 | (structure 63) | 0.7–1.0(m, 3H), 1.39(t, 3H, J= 6.9Hz), 1.1–2.1(m, 7H), 2.2–2.6(m, 6H), 3.73(s, 3H), 4.02 (q, 2H, J=7.0Hz), 6.3–7.5(m, 9H) |
| 472 | (structure 472) | |
| 473 | (structure 473) | |
| 474 | (structure 474) | |
| 475 | (structure 475) | |
| 476 | (structure 476) | |

| | |
|---|---|
| 58 | 1.3–2.0(m, 7H), 2.2–2.6(m, 6H), 3.70(s, 3H), 3.79(s, 6H), 4.00(s, 2H), 6.0–6.6(m, 3H), 6.72(s, 1H), 7.3–7.6(m, 1H) |
| 65 | 1.10(s, 3H), 1.7–2.5(m, 5H), 3.88(s, 6H), 4.10(s, 2H), 6.0–7.1(m, 7H), 7.2–7.4(m, 1H) |
| 62 | 0.7–1.0(m, 3H), 1.1–2.36(m, 14H), 2.3–2.9(m, 5H), 2.36(s, 3H), 3.5–3.8(m, 2H), 3.8–4.1(m, 2H), 4.1–4.5(m, 1H), 5.9–6.4(m, 1H), 6.4–7.1(m, 4H), 7.1–7.9(m, 3H) |
| 66 | 0.7–1.0(m, 3H), 1.1–2.0(m, 12H), 2.35(s, 3H), 2.2–2.9(m, 7H), 3.67(s, 3H), 3.90(t, 2H, J=6.2Hz), 6.5–7.0(m, 4H), 17.1–7.4(m, 2H) |
| 42 | 0.7–1.1(m, 6H), 1.1–2.9(m, 21H), 2.35(s, 3H), 3.67(s, 3H), 6.4–6.8(m, 1H) |

477
478
479
480
481

| | | |
|---|---|---|
| 52 | 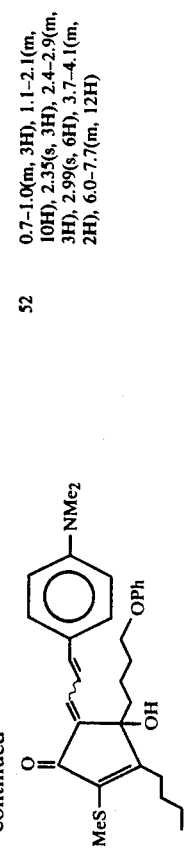 | 0.7–1.0(m, 3H), 1.1–2.1(m, 10H), 2.35(s, 3H), 2.4–2.9(m, 3H), 2.99(s, 6H), 3.7–4.1(m, 2H), 6.0–7.7(m, 12H) |
| 47 | 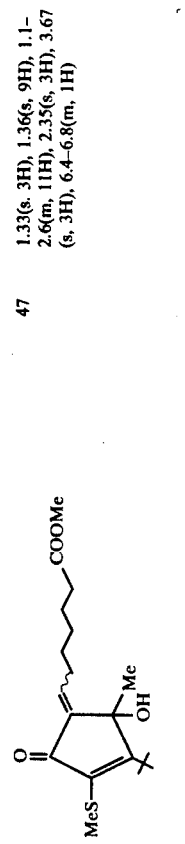 | 1.33(s, 3H), 1.36(s, 9H), 1.1–2.6(m, 11H), 2.35(s, 3H), 3.67(s, 3H), 6.4–6.8(m, 1H) |
| 40 | 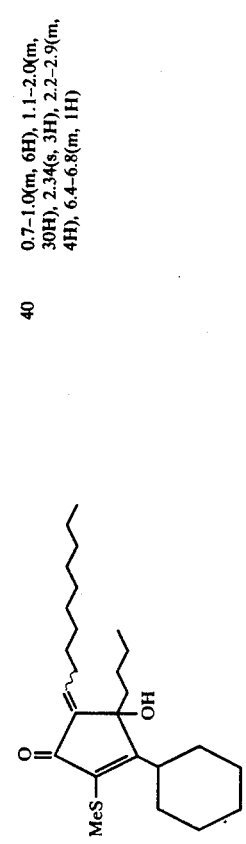 | 0.7–1.0(m, 6H), 1.1–2.0(m, 30H), 2.34(s, 3H), 2.2–2.9(m, 4H), 6.4–6.8(m, 1H) |
| 33 | 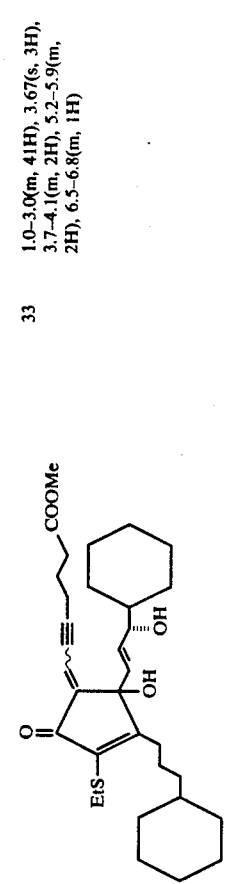 | 1.0–3.0(m, 41H), 3.67(s, 3H), 3.7–4.1(m, 2H), 5.2–5.9(m, 2H), 6.5–6.8(m, 1H) |
| 50 |  | 0.7–1.0(m, 3H), 1.1–2.0(m, 10H), 1.34(s, 9H), 2.4–2.8(m, 3H), 3.90(t, 2H, J=6.0Hz), 6.5–7.8(m, 11H) |
| 482 | 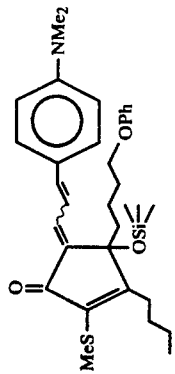 | |
| 483 | 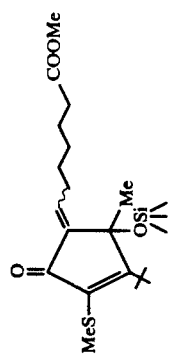 | |
| 484 | 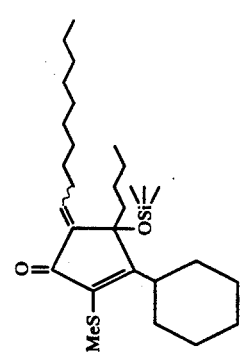 | |
| 485 | 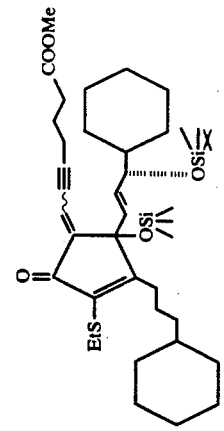 | |
| 486 | 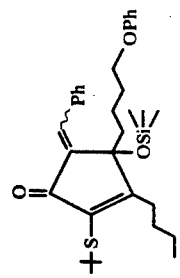 | |

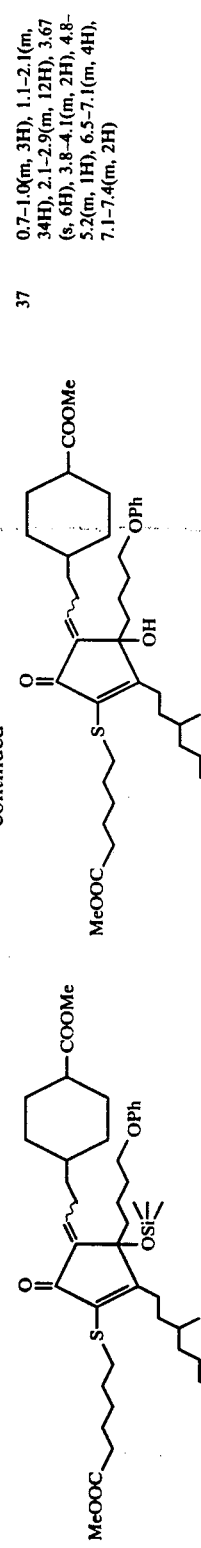
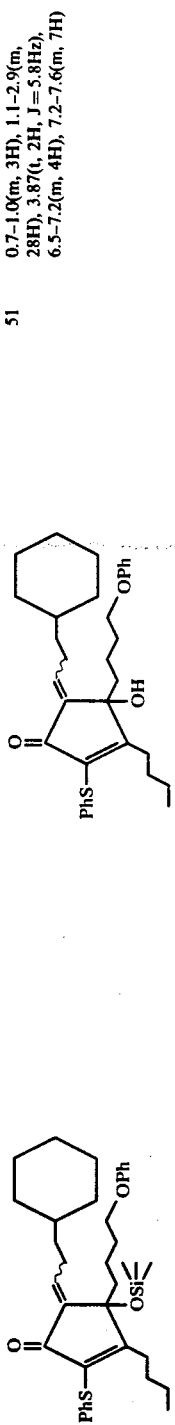
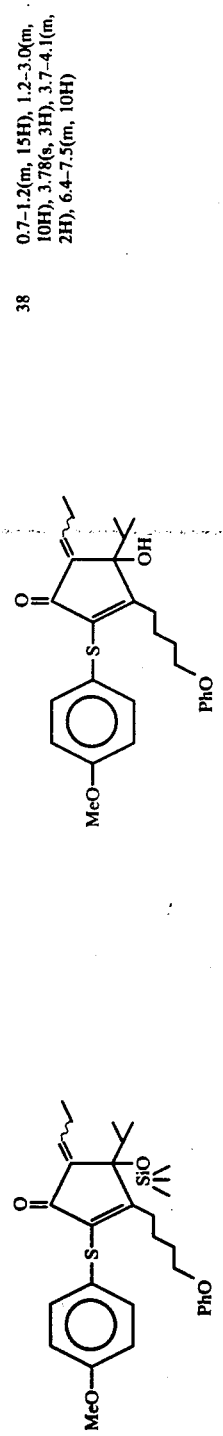
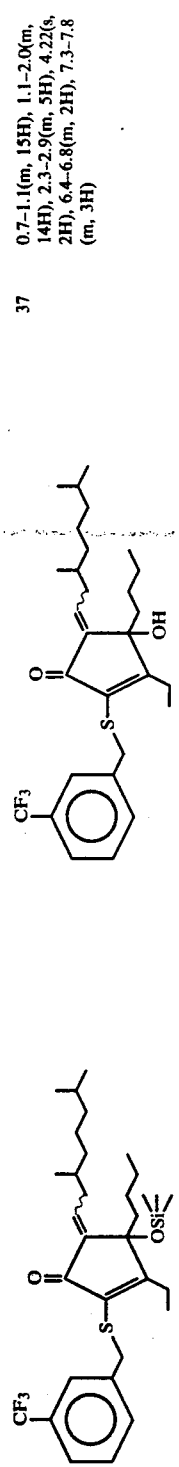
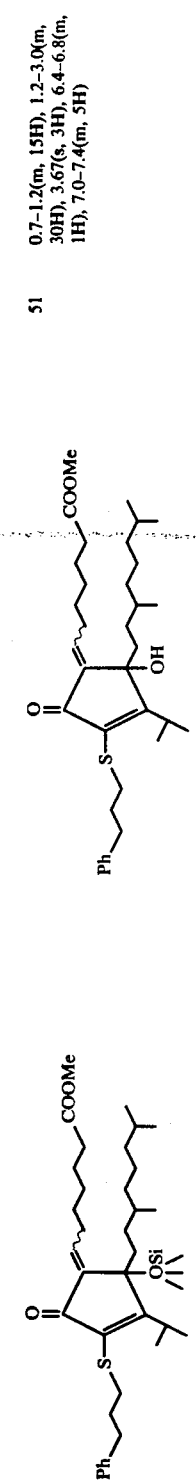

| | | |
|---|---|---|
| 492 | 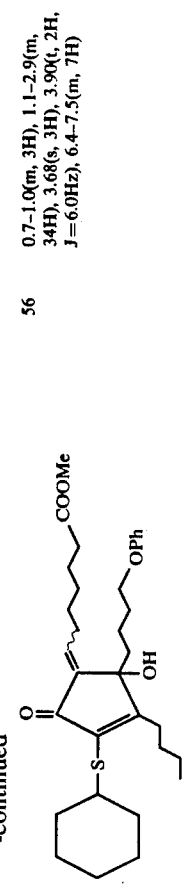<br>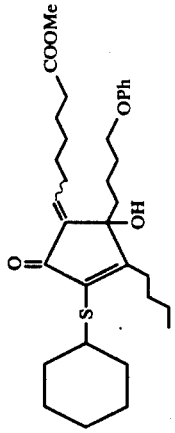 | 56 | 0.7-1.0(m, 3H), 1.1-2.9(m, 34H), 3.68(s, 3H), 3.90(t, 2H, J=6.0Hz), 6.4-7.5(m, 7H) |
| 493 | 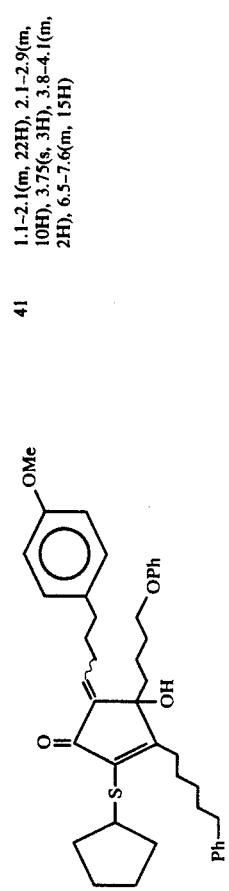<br>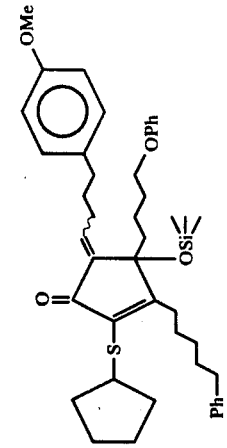 | 41 | 1.1-2.1(m, 22H), 2.1-2.9(m, 10H), 3.75(s, 3H), 3.8-4.1(m, 2H), 6.5-7.6(m, 15H) |
| 494 | 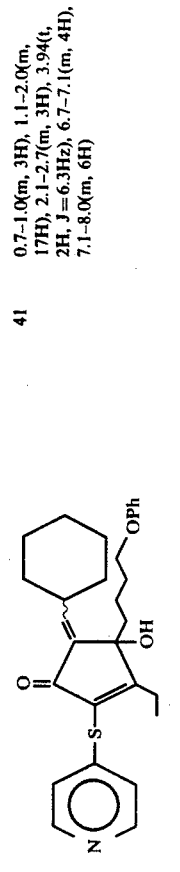<br>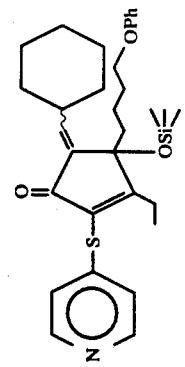 | 41 | 0.7-1.0(m, 3H), 1.1-2.0(m, 17H), 2.1-2.7(m, 3H), 3.94(t, 2H, J=6.3Hz), 6.7-7.1(m, 4H), 7.1-8.0(m, 6H) |
| 495 | 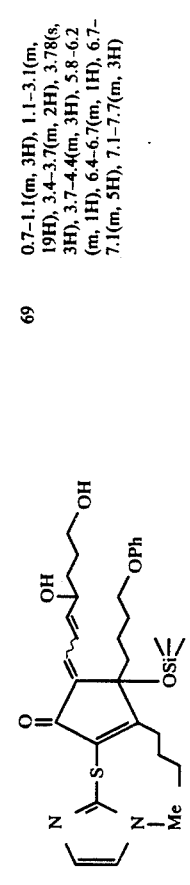<br>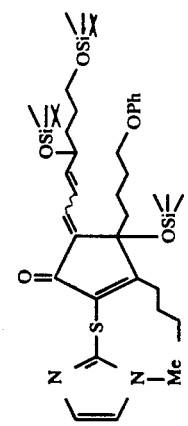 | 69 | 0.7-1.1(m, 3H), 1.1-3.1(m, 19H), 3.4-3.7(m, 2H), 3.78(s, 3H), 3.7-4.4(m, 3H), 5.8-6.2(m, 1H), 6.4-6.7(m, 1H), 6.7-7.1(m, 5H), 7.1-7.7(m, 3H) |
| 496 | 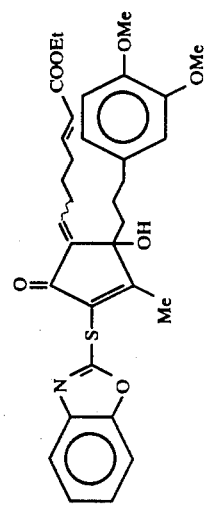<br>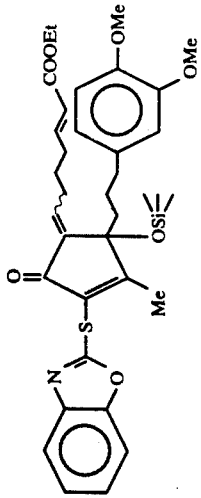 | 52 | 1.2-3.0(m, 16H), 2.43(s, 3H), 3.84(s, 6H), 3.7-4.0(m, 2H), 5.7-6.2(m, 2H), 6.4-7.1(m, 4H), 7.2-7.8(m, 4H) |

| | |
|---|---|
| 39 | 1.2-2.5(m, 11H), 2.35(s, 3H), 3.68(s, 3H), 4.8-5.3(m, 1H), 6.5-7.1(m, 2H) |
| 35 | 1.5-1.8(m, 7H), 2.39(s, 3H), 3.3-3.7(m, 2H), 4.0-4.5(m, 1H), 5.1-5.4(m, 1H), 6.0-7.9(m, 4H) |
| 62 | 1.9-2.1(m, 1H), 2.35(s, 3H), 3.01(s, 6H), 5.0-5.4(m, 1H), 6.6-6.7(m, 8H) |
| 49 | 1.1-2.0(m, 7H), 3.4-3.8(m, 2H), 4.1-4.5(m, 1H), 5.2-5.5(m, 1H), 6.0-7.6(m, 10H) |
| 52 | 1.1-2.0(m, 17H), 2.2-2.6(m, 1H), 3.5-3.8(m, 2H), 4.1-4.5(m, 1H), 5.1-5.5(m, 1H), 6.0-7.6(m, 4H) |
| 43 | 1.0-2.4(m, 11H), 3.71(s, 3H), 4.14(s, 3H), 4.9-5.3(m, 1H), 6.7-7.1(m, 1H), 7.74(d, 1H, J=2.2Hz) |

| | | |
|---|---|---|
| 57 | 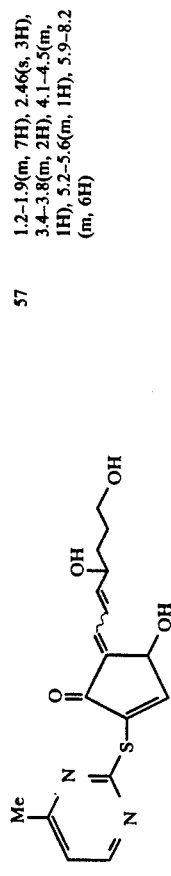 | 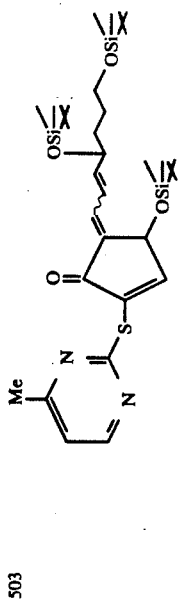 |
| | 503 | |
| 66 | 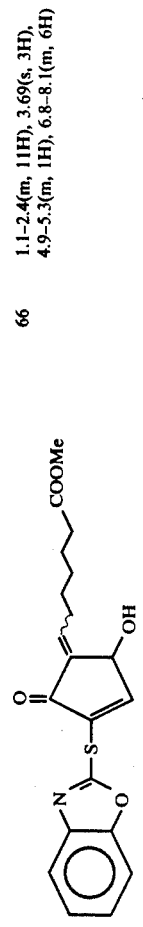 | 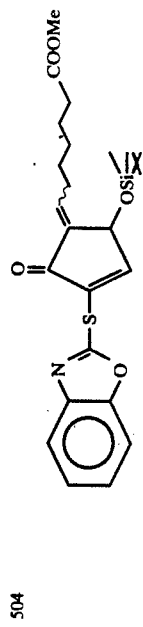 |
| | 504 | |
| 75 | 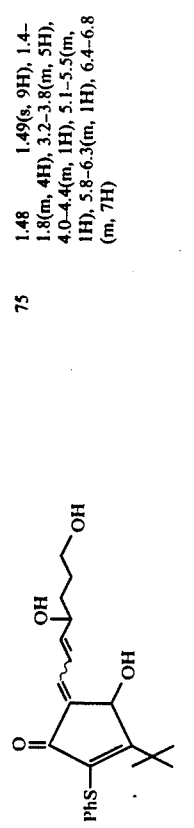 | 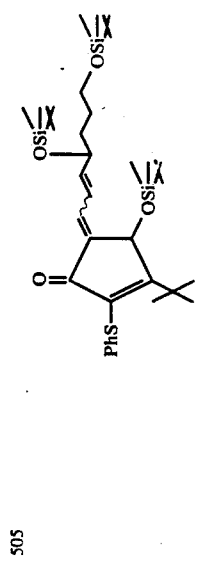 |
| | 505 | |
| 12 |  | 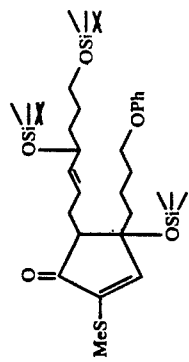 |
| | 506 | |
| 82 | 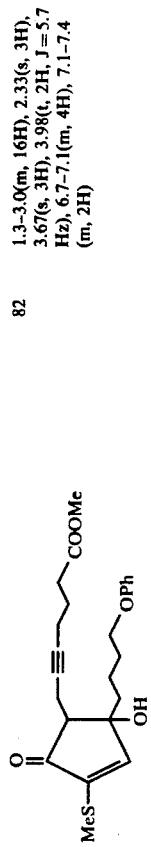 | 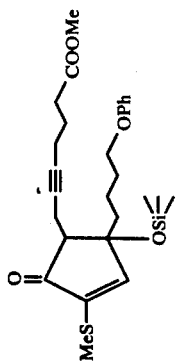 |
| | 507 | |
57: 1.2–1.9(m, 7H), 2.46(s, 3H), 3.4–3.8(m, 2H), 4.1–4.5(m, 1H), 5.2–5.6(m, 1H), 5.9–8.2(m, 6H)
66: 1.1–2.4(m, 11H), 3.69(s, 3H), 4.9–5.3(m, 1H), 6.8–8.1(m, 6H)
75: 1.48 1.49(s, 9H), 1.4–1.8(m, 4H), 3.2–3.8(m, 5H), 4.0–4.4(m, 1H), 5.1–5.5(m, 1H), 5.8–6.3(m, 1H), 6.4–6.8(m, 7H)
12: 1.2–2.1(m, 10H), 2.31(s, 3H), 2.3–3.2(m, 6H), 3.5–3.75(m, 2H), 3.8–4.2(m, 3H), 5.4–6.0(m, 2H), 6.5–7.1(m, 4H), 7.1–7.4(m, 2H)
82: 1.3–3.0(m, 16H), 2.33(s, 3H), 3.67(s, 3H), 3.98(t, 2H, J=5.7 Hz), 6.7–7.1(m, 4H), 7.1–7.4(m, 2H)

-continued
| | | | |
|---|---|---|---|
| 508 | 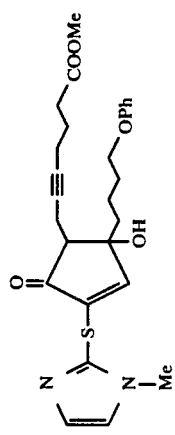 | 69 | 1.3-3.0(m, 16H), 3.68(s, 3H), 3.97(t, 2H, J=5.9Hz), 6.7-7.1 (m, 4H), 7.1-7.6(m, 7H) |
| 509 | 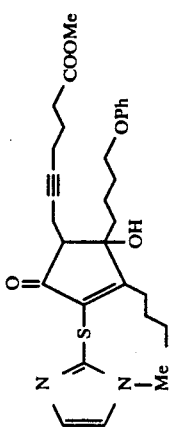 | 77 | 1.3-2.9(m, 27H), 3.69(s, 3H), 3.96(t, 2H, J=6.2Hz), 6.7-7.1 (m, 4H), 7.1-7.4(m, 2H) |
| 510 | 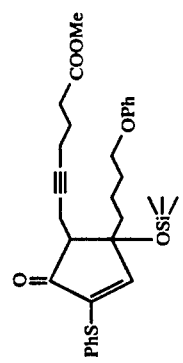 | 59 | 1.3-2.9(m, 16H), 3.67(s, 3H), 3.70(s, 3H), 3.97(t, 2H, J=6.2 Hz), 6.7-7.4(m, 8H) |
| 511 | 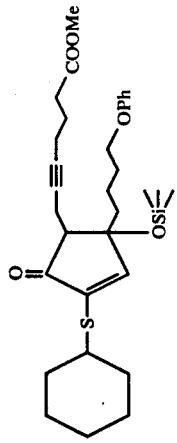 | 47 | 0.7-1.0(m, 3H), 1.2-2.9(m, 22H), 3.68(s, 3H), 3.69(s, 3H), 3.96(t, 2H, J=6.2Hz), 6.7-7.4(m, 7H) |

TABLE 20

| Ex. No. | Starting compd. (2-Substituted-2-cyclopentenones) | 2-Substituted-2-cyclopentenones | Yield (%) | NMR(δ, CDCl₃) |
|---|---|---|---|---|
| 512 | (structure with OSi groups, OPh, cyclohexyl-S) | (structure with OH groups, OPh, cyclohexyl-S) | 84 | 1.1–2.3(19H, m), 2.3–2.8(4H, m), 3.0–3.4(1H, m), 3.5–3.8(2H, m), 3.8–4.1(2H, m), 4.1–4.5(1H, m), 5.9–6.4(1H, m), 6.4–7.05(4H, m), 7.05–7.9 (4H, m) |
| | | (structure with OH groups, OPh, cyclohexyl-S) | 12 | 1.1–2.2(21H, m), 2.2–2.8(3H, m), 3.0–3.4(1H, m), 3.5–3.8(2H, m), 3.8–4.1(2H, m), 4.2–4.5(1H, m), 5.80(1H, t, J=7.9 Hz), 6.0–6.5(1H, m), 6.6–7.1 (4H, m), 7.1–7.7(3H, m), 7.88 (1H, dd, J=9.0, 4.5Hz) |
| 513 | (structure with COOMe, OPh, OSi, MeS) | (structure with COOMe, OPh, OH, MeS) | 75 | 1.1–3.0(7H, m), 2.36(3H, s), 3.6–4.2(2H, m), 3.82(3H, s), 4.72(2H, s), 6.6–7.6(10H, m), 7.6–8.1(1H, m) |
| | | (structure with COOMe, OPh, MeS) | 6 | 1.5–2.9(4H, m), 2.29(3H, s), 3.79(3H, s), 3.8–4.2(2H, m), 4.62(2H, s), 5.75–6.10(1H, m), 6.6–7.7(11H, m) |
| 514 | (structure with OH, OPh, MeS, butyl) | (structure with OH, OPh, MeS, butyl) | 53 | 0.7–1.0(m, 3H), 1.1–2.2(m, 10H), 2.3–2.9(m, 6H), 2.35(s, 3H), 3.5–3.8(m, 2H), 3.8–4.1(m, 2H), 4.2–4.5(m, 1H), 5.80 (t, 1H, J=8.0Hz,), 6.0–6.5(m, 1H), 6.6–7.1(m, 3H), 7.1–7.9 (m, 4H) |

TABLE 20-continued

| Ex. No. | Starting compd. (2-Substituted-2-cyclopentenones) | 2-Substituted-2-cyclopentenones | Yield (%) | NMR(δ, CDCl₃) |
|---|---|---|---|---|
| 515 | [structure with PhS, butyl, OH, OH chain] | [structure with PhS, butyl, OH, OH, OPh] | 49 | 0.7–1.0(m, 3H), 1.1–2.8(m, 16H), 3.5–3.8(m, 2H), 3.8–4.1(m, 2H), 4.2–4.5(m, 1H), 5.82(t, 1H, J=8.0Hz), 6.0–6.5(m, 1H), 6.6–8.1(m, 12H) |
| 516 | [structure with cyclohexyl-S, OH, OH, OPh] | [structure with cyclohexyl-S, OMe, OH, OPh] | 38 | 1.1–2.1(22H, m), 2.1–2.5(1H, m), 3.05(3H, s), 3.55–3.8(2H, m), 3.93(2H, t, J=6.0Hz), 4.1–4.5(1H, m), 6.17(1H, dd, J=15.0, 6.2Hz), 6.46(1H, d, J=11.0Hz), 6.53(1H, s), 6.7–7.0(3H, m), 7.1–7.4(2H, m), 7.72(1H, dd, J=15.3, 11.2Hz) |
| 517 | Same as above | [structure with cyclohexyl-S, OEt, OH, OPh] | 29 | 1.10(3H, t, J=7.0Hz), 1.1–2.1(22H, m), 2.1–2.5(1H, m), 3.21(2H, q, J=7.0Hz), 3.5–3.8(2H, m), 3.95(2H, t, J=6.1Hz), 4.1–4.5(1H, m), 6.20(1H, dd, J=15.2, 6.0Hz), 6.55(1H, s), 6.7–7.1(3H, m), 7.1–7.5(2H, m), 7.73(1H, dd, J=15.2, 11.0Hz) |
| 518 | [structure with cyclohexyl-S, OH, OH, OPh] | [structure with cyclohexyl-S, OAc, OAc, OPh] | 44 | 1.1–2.1(21H, m), 2.01(3H, s), 2.13(5H, m), 6.0–6.5(1H, m), 6.69(1H, s), 6.7–7.2(4H, m), 7.2–7.5(3H, m) |
|  |  | [structure with cyclohexyl-S, OAc, OAc, OPh] | 14 | 1.1–2.1(20H, m), 2.01(3H, s), 2.04(3H, s), 2.13(3H, s), 2.1–2.5(1H, m), 3.6–4.5(5H, m), 6.0–6.5(1H, m), 6.64(1H, s), 6.7–7.2(4H, m), 7.2–7.5(3H, m) |

TABLE 20-continued

| Ex. No. | Starting compd. (2-Substituted-2-cyclopentenones) | 2-Substituted-2-cyclopentenones | Yield (%) | NMR(δ, CDCl₃) |
|---|---|---|---|---|
| 519 | [structure: cyclopentenone with S-cyclohexyl, COOMe chain, OSi protected side chain] | [structure: cyclopentenone with S-cyclohexyl, COOH chain, OSi protected side chain] | 62 | 0.05(6H, s), 0.89(9H, s), 0.86(3H, brt, J=5.6Hz), 1.1–2.5(30H, m), 3.9–4.2(2H, m), 5.2–5.9(2H, m), 6.6–6.8(2H, m) |
| 520 | [structure: cyclopentenone with S-cyclohexyl, OH, COOMe chain, OPh side chain] | [structure: cyclopentenone with S-cyclohexyl, OH, COOH chain, OPh side chain] | 79 | 1.1–2.5(27H, m), 2.5–3.0(2H, m), 3.94(2H, t, J=6Hz), 6.4–7.1(5H, m), 7.1–7.4(2H, m) |
| 521 | [structure: cyclopentenone with S-cyclohexyl, COOH chain, OSi side chain] | [structure: cyclopentenone with S-cyclohexyl, CONH₂ chain, OH side chain] | 39 | 0.86(3H, brt, J=5.6Hz), 1.1–2.5(30H, m), 3.9–4.2(2H, m), 5.2–6.2(4H, m), 6.6–6.9(2H, m) |
| 522 | [structure: cyclopentenone with S-cyclohexyl, COOH chain, OSi side chain] | [structure: cyclopentenone with S-cyclohexyl, COON(Me)(cyclohexyl) chain, OH side chain] | 53 | 0.86(3H, brt, J=5.6Hz), 1.0–3.1(44H, m), 3.9–4.2(2H, m), 5.2–6.2(4H, m), 6.6–6.9(2H, m) |
| 523 | [structure: cyclopentenone with S-cyclohexyl, COOMe chain, OH side chain] | [structure: cyclopentenone with S(O)-cyclohexyl (sulfoxide), COOMe chain, OH side chain] | 62 | 0.89(3H, brt), 1.1–2.6(30H, m), 3.67(3H, s), 4.0–4.3(2H, m), 5.3–6.0(2H, m), 6.72(1H, t, J=7Hz), 7.7–7.8(1H, m) |

TABLE 20-continued
2-Substituted-2-cyclopentenones

| Ex. No. | Starting compd. (2-Substituted-2-cyclopentenones) | 2-Substituted-2-cyclopentenones | Yield (%) | NMR(δ, CDCl₃) |
|---|---|---|---|---|
| 524 | | | 28 | 1.1–3.0(24H, m), 3.5–3.8(2H, m), 3.92(2H, t, J=6.0Hz), 4.1–4.4(1H, m), 6.0–6.5(1H, m), 6.6–7.1(5H, m), 7.1–7.5(2H, m), 7.7(1H, s) |
| 525 | | | 61 | 0.7–1.0(m, 3H), 1.1–2.4(m, 28H), 3.0–3.3(m, 1H), 3.66(s, 3H), 4.0–4.5(m, 2H), 5.3–6.0(m, 2H), 6.82(t, J=7Hz, 1H), 8.06(d, J=3Hz, 1H) |
| 526 | | | 13 | 1.2–2.5(23H, m), 3.0–3.3(1H, m), 3.5–3.8(2H, m), 3.93(2H, t, J=5.9Hz), 4.1–4.4(1H, m), 6.1–6.4(1H, m), 6.65–7.05(4H, m), 7.05–7.4(2H, m), 7.99(1H, s) |
| 527 | | | 68 | 1.1–3.0(28H, m), 3.25(2H, m), 3.9(2H, t, J=6Hz), 4.5(2H, m), 6.4–7.1(4H, m), 7.1–7.4(3H, m) |
| 528 | | | 51 | 1.1–2.9(27H, m), 3.0–5.3(14H, m), 6.4–7.1(4H, m), 7.1–7.4(3H, m) |
| 529 | | | 39 | 1.1–2.9(27H, m), 3.0–5.3(12H, m), 6.4–7.1(4H, m), 7.1–7.4(3H, m) |

EXAMPLE 530

Synthesis of 2-methylthio-5-(1-hydroxy-6-methoxycarbonylhexyl)-4-(3-t-butyldimethylsilyloxy-1-octenyl)-2-cyclopentenone

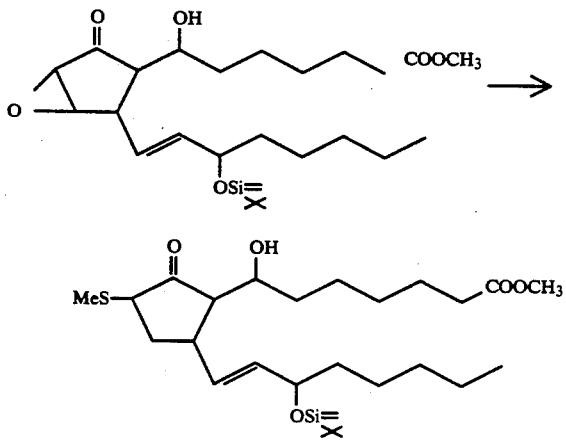

A solution of sodium thiomethoxide (2.30 g) in methanol (100 ml) was cooled to 0° C., acetic acid (2.82 ml) was added, the mixture was stirred for 5 minutes, Triethylamine (915 ml) was added, and a solution of 2,3-epoxy-5-(1-hydroxy-6-methoxycarbonylhexyl)-4-(3-t-butyldimethylsilyloxy-1-octenyl)cyclopentanone (3.26 g) in methanol (40 ml) was added. After stirring at room temperature for 12 hours, water was added to the mixture, and the mixture extracted with ethyl acetate. The extract was washed with a saturated aqueous sodium chloride solution, dried over anhydrous magnesium sulfate and filtered, followed by concentration. The concentrate was subjected to silica gel chromatography to give 3.47 g (yield 96%) of 2-methylthio-5-(1-hydroxy-6-methoxycarbonylhexyl)-4-(3-t-butyldimethylsilyloxy-1-octenyl)-2-cyclopentenone.

Spectrum data $^1$H-NMR CDCl$_3$ δ: 0.00 (3H, s), 0.03 (3H, s), 0.87 (9H, s), 0.7–1.1 (3H, brt), 1.1–2.3 (20H, m), 2.33 (3H, s), 3.1–3.3 (1H, m), 3.63 (3H, s), 3.6–3.8 (1H, brs), 3.9–4.2 (1H, m), 5.4–5.6 (2H, m), 6.78 (1H, d, J=3 Hz).

EXAMPLES 531–533

The 2-substituted-2-cyclopentenes listed in Table 21 were obtained in the same manner as in Example 530.

TABLE 21

| Example No. | Starting compound | 2-Substituted-2-cyclopentenones | Yield (%) | NMR (δCDCl₃) |
|---|---|---|---|---|
| 531 | 2,3-epoxy-5-(1-hydroxy-6-methoxycarbonyl-2-hexynyl)-4-(3-t-butyldimethylsilyloxy-3-cyclopentyl-1-propenyl)cyclopentanone | 2-methylthio-5-(1-hydroxy-6-methoxycarbonyl-2-hexynyl)-4-(3-t-butyldimethylsilyloxy-3-cyclopentyl-1-propenyl)-2-cyclopentenone | 54 | 0.04(6H, s), 0.89(9H, s), 1.1–2.1(11H, m), 2.1–3.1(6H, m), 2.32(3H, s), 3.1–3.5(1H, m), 3.68(3H, s), 3.8–4.0(1H, m), 4.6–4.85(1H, m), 5.3–5.9(2H, m), 6.90(1H, d, J=3.0Hz) |
| 532 | 2,3-epoxy-5-(1-hydroxy-6-methoxycarbonyl-5-hexenyl)-4-(3-t-butyldimethylsilyloxy-5-methyl-1-nonenyl)cyclopentanone | 2-methylthio-5-(1-hydroxy-6-methoxycarbonyl-5-hexenyl)-4-(3-t-butyldimethylsilyloxy-5-methyl-1-nonenyl)-2-cyclopentenone | 60 | 0.01(3H, s), 0.04(3H, s), 0.89(9H, s), 0.7–1.1(6H, m), 1.1–2.7(17H, m), 2.33(3H, s), 3.1–3.3(1H, m), 3.68(3H, s), 3.6–3.9(3H, m), 3.8–4.3(1H, m), 5.4–5.8(2H, m), 5.89(1H, d, J=16.0Hz), 6.82(1H, d, J=2.5Hz), 7.02(1H, dt, J=16.0, 7.4Hz) |
| 533 | 2,3-epoxy-5-(1-hydroxy-3-phenyl-2-propenyl)-4-butylcyclopentanone | 2-methylthio-5-(1-hydroxy-3-phenyl-2-propenyl)-4-butyl-2-cyclopentenone | 72 | 0.7–1.1(3H, m), 1.1–3.3(9H, m), 2.34(3H, s), 3.3–3.6(1H, m), 4.3–4.7(1H, m), 6.4–6.9(2H, m), 7.0–8.0(5H, m) |

EXAMPLE 534

Synthesis of 2-(2,3-dihydroxypropylthio)-5-(1-hydroxy-6-methoxycarbonyl-2-hexynyl)-4-(3-t-butyldimethylsilyloxy-3-cyclopentyl-1-propenyl)-2-cyclopentenone

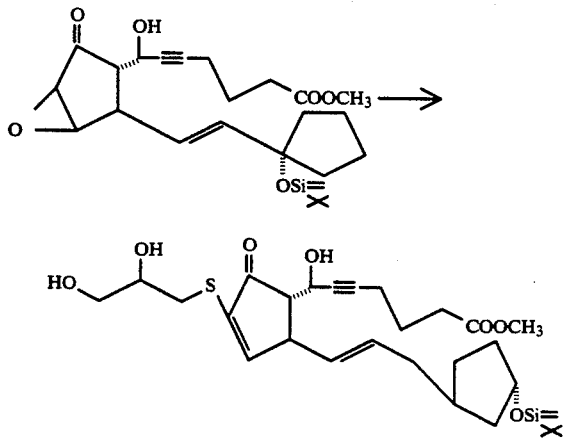

A 49 mg amount of 2,3-epoxy-5-(1-hydroxy-6-methoxycarbonyl-2-hexynyl}-4-(3-t-butyldimethylsilyloxy-3-cyclopentyl-1-propenyl)cyclopentanone was dissolved in 1 ml of methanol and 21 μl of triethylamine was added. Then, 12 mg of 2,3-dihydroxypropanethiol was added thereto, followed by stirring for 2 hours. The reaction mixture was poured on an aqueous saturated solution of potassium hydrogen sulfate, followed by extracting with ethyl acetate. The extracted solution was washed with a saturated sodium chloride solution and dried over anhydrous magnesium sulfate. After filtering and concentrating, the concentrate was subjected to silica gel chromatography to give 36 mg (yield 62%) of 2-(2,3-dihydroxypropylthio)-5-(1-hydroxy-6-methoxycarbonyl-2-hexynyl)-4-(3-t-butyldimethylsilyloxy-3-cyclopentyl-1-propenyl)-2-cyclopentenone.

Spectrum data $^1$H-NMR CDCl$_3$ δ: 0.05 (3H, s), 0.09 (3H, s), 0.89 (9H, s), 1.1–2.0 (11H, m), 2.0–2.7 (5H, m), 2.7–3.4 (6H, m), 3.67 (3H, s), 3.4–4.0 (4H, m), 4.5–4.9 (1H, m), 5.4–5.8 (2H, m), 7.1–7.3 (1H, m)

EXAMPLES 535–542

The 2-substituted-2-cyclopentenes listed in Table 22 were obtained in the same manner as in Example 534.

TABLE 22

| Example No. | Starting compound 2,3-epoxycyclopentanones | Starting compound Thiols | 2-Substituted-2-cyclopentenones | Yield (%) | NMR (δCDCl₃) |
|---|---|---|---|---|---|
| 535 | 2,3-epoxy-5-(1-hydroxy-6-methoxycarbonyl-2-hexynyl)-4-(3-t-butyldimethylsilyloxy-1-propenyl)cyclopentanone | 5-methoxycarbonylpentane-1-thiol | 2-(5-methoxycarbonylpentylthio)-5-(1-hydroxy-6-methoxycarbonyl-2-hexynyl)-4-(3-t-butyldimethylsilyloxy-1-propenyl)-2-cyclopentenone | 71 | 0.04(6H, s), 0.89(9H, s), 1.1–2.1(17H, m), 2.1–3.1(10H, m), 3.4–3.8(1H, m), 3.67(6H, s), 3.8–4.0(1H, m), 4.6–4.85(1H, m), 5.4–5.8(2H, m), 6.92(1H, d, J=3.2Hz) |
| 536 | | 3-phenylpropane-1-thiol | 2-(3-phenylpropylthio)-5-(1-hydroxy-6-methoxycarbonyl-2-hexynyl)-4-(3-t-butyldimethylsilyloxy-1-propenyl)-2-cyclopentenone | 74 | 0.04(6H, s), 0.90(9H, s), 1.0–3.0(23H, m), 3.35–3.7(1H, m), 3.68(3H, s), 3.8–4.0(1H, m), 4.6–4.8(1H, m), 5.4–5.7(2H, m), 6.89(1H, d, J=2.8Hz), 7.0–7.4(5H, m) |
| 537 | | Thiophenol | 2-phenylthio-5-(1-hydroxy-6-methoxycarbonyl-2-hexynyl)-4-(3-t-butyldimethylsilyloxy-1-propenyl)-2-cyclopentenone | 91 | 0.07(6H, s), 0.89(9H, s), 1.1–2.0(11H, m), 2.0–2.7(5H, m), 3.0–3.3(1H, m), 3.4–3.6(1H, m), 3.70(3H, s), 3.8–4.0(1H, m), 4.7–4.9(1H, m), 5.4–5.8(2H, m), 6.85(1H, d, J=2.7Hz), 7.2–7.7(5H, m) |

TABLE 22-continued

| Example No. | Starting compound | | 2-Substituted-2-cyclo-pentenones | Yield (%) | NMR (δCDCl₃) |
|---|---|---|---|---|---|
| | 2,3-epoxycyclopentanones | Thiols | | | |
| 538 | 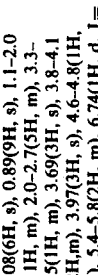 | 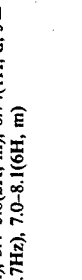  6-methoxynaphtha-lene-2-thiol | 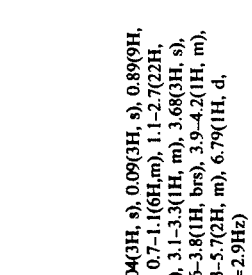  1-(6-methoxynaphthyl-2-thio)-5-(1-hydroxy-6-methoxy-carbonyl-2-hexynyl)-4-(3-t-butyldimethylsilyloxy-3-cyclo-pentyl-1-propenyl)-2-cyclo-pentenone | 85 | 0.08(6H, s), 0.89(9H, s), 1.1–2.0 (11H, m), 2.0–2.7(5H, m), 3.3–3.5(1H, m), 3.69(3H, s), 3.8–4.1 (2H, m), 3.97(3H, s), 4.6–4.8(1H, m), 5.4–5.8(2H, m), 6.74(1H, d, J=2.7Hz), 7.0–8.1(6H, m) |
| 539 |   2,3-epoxy-5-(1-hydroxy-6-methoxycarbonylhexyl)-4-(3-t-butyldimethylsilyloxy-1-octenyl)cyclopentanone | CH₃CH₂SH  ethanethiol | 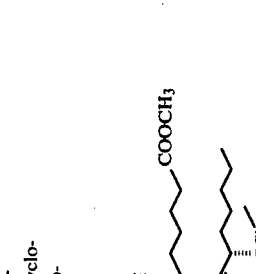  2-ethylthio-5-(1-hydroxy-6-methoxycarbonylhexyl)-4-(3-t-butyldimethylsilyloxy-1-octenyl)-2-cyclopentenone | 75 | 0.04(3H, s), 0.09(3H, s), 0.89(9H, s), 0.7–1.1(6H,m), 1.1–2.7(22H, m), 3.1–3.3(1H, m), 3.68(3H, s), 3.6–3.8(1H, brs), 3.9–4.2(1H, m), 5.3–5.7(2H, m), 6.79(1H, d, J=2.9Hz) |
| 540 |   2,3-epoxy-5-(1-hydroxy-6-methoxycarbonyl-5-hexenyl)-4-(3-t-butyldimethylsilyloxy-5-methyl-1-nonenyl)cyclo-pentanone | 4-chlorophenyl-methanethiol | 2-(4-chlorophenylmethylthio)-5-(1-hydroxy-6-methoxy-carbonyl-5-hexenyl)-4-(3-t-butyldimethylsilyloxy-5-methyl-1-nonenyl)-2-cyclo-pentenone | 62 | 0.01(3H, s), 0.05(3H, s), 0.89(9H, s), 0.7–1.1(6H, m), 1.1–2.7(17H, m), 3.1–3.5(1H, m), 3.69(3H, s), 3.6–3.9 (3H, m), 3.9–4.3(1H, m), 5.3–5.9 (2H, m), 5.88(1H, d, J=16.0Hz), 6.85(1H, d, J=2.7Hz), 7.04(1H, dt, J=16.0, 7.2Hz), 7.26(4H, s) |

TABLE 22-continued

| Example No. | Starting compound | | 2-Substituted-2-cyclo-pentenones | Yield (%) | NMR (δCDCl₃) |
|---|---|---|---|---|---|
| | 2,3-epoxycyclopentanones | Thiols | | | |
| 541 | 2,3-epoxy-5-(1-hydroxy-6-methoxycarbonylhexyl)-4-[3-(tetrahydropyran-2-yloxy)-3-cyclohexyl-1-propenyl]cyclopentanone | CH₃CH₂SH ethanethiol | 2-ethylthio-5-(1-hydroxy-6-methoxycarbonylhexyl)-4-[3-(tetrahydropyran-2-yloxy)-3-cyclohexyl-1-propenyl]-2-cyclopentenone | 57 | 0.7–1.1(3H, m), 1.1–2.7(31H, m), 3.0–3.3(1H, m), 3.69(3H, s), 3.3–4.3 (3H, m), 4.5–5.0(2H, m), 5.3–5.7 (2H, m), 6.80(1H, d, J=2.8Hz) |
| 542 | 2,3-epoxy-5-(1-hydroxy-3-phenyl-2-propenyl)-4-butylcyclopentanone | 4-methylbenzenethiol | 2-(4-methylphenylthio)-5-(1-hydroxy-3-phenyl-2-propenyl)-4-butyl-2-cyclopentenone | 82 | 0.7–1.1(3H, m), 1.1–3.3(9H, m), 2.30(3H, s), 3.3–3.6(1H, m), 4.3–4.7(1H, m), 6.4–6.9(2H, m), 6.9–8.0(9H, m) |

EXAMPLE 543

Synthesis of
2-methylthio-5-(6-methoxycarbonylhexylidene)-4-(3-t-butyldimethylsilyloxy-1-octenyl)-2-cyclopentenone

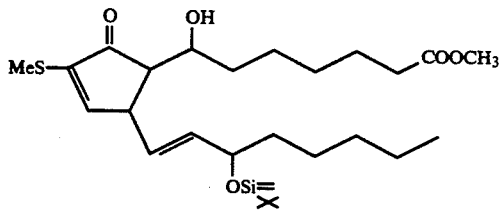

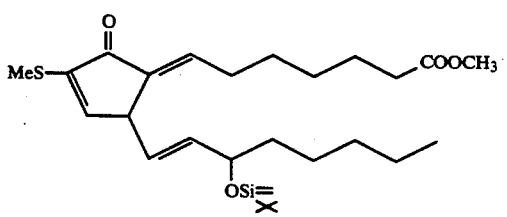

To a solution of 3.47 g of 2-methylthio-5-(1-hydroxy-6-methoxycarbonylhexyl)-4-(3-t-butyldimethylsilyloxy-1-octenyl)-2-cyclopentenone obtained in Example 6 in dichloromethane (30 ml) was added dimethylaminopyridine (1.54 g) and the mixture was cooled to 0° C. To the solution was dropwise added 0.59 ml of methanesulfonyl chloride, and the mixture was stirred at room temperature for 15 hours. To the reaction mixture were added ethyl acetate and an aqueous potassium hydrogensulfate, and the product was extracted into an organic layer. The extract was washed with saturated aqueous sodium hydrogencarbonate and saturated sodium chloride, dried over anhydrous magnesium sulfate, and filtered, followed by concentration. The concentrate was subjected to silica gel chromatography to give 2.15 g (yield 64%) of 2-methylthio-5-(6-methoxycarbonylhexylidene)-4-(3-t-butyldimethylsilyloxy-1-octenyl)-2-cyclopentenone.

Spectrum data $^1$H-NMR CDCl$_3$ δ: 0.00 (3H, s), 0.02 (3H, s), 0.87 (9H, s), 0.7–1.1 (3H, brt), 1.1–2.3 (18H, m), 2.33 (3H, s), 3.65 (3H, s), 3.9–4.1 (2H, m), 5.38 (1H, dd, J=7.5 Hz), 5.65 (1H, dd, J=15, 6 Hz), 6.5–6.8 (2H, m).

EXAMPLE 544

Synthesis of
2-methylthio-5-(6-methoxycarbonylhexylidene)-4-(3-hydroxy-1-octenyl)-2-cyclopentenone

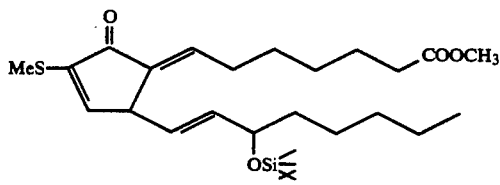

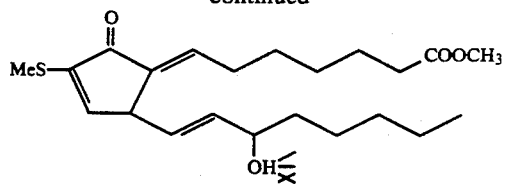

An amount of 1.42 g of 2-methylthio-5-(6-methoxycarbonylhexylidene-4-(3-t-butyldimethylsilyloxy-1-octenyl)-2-cyclopentenone obtained in Example 22 was added to a mixture of acetic acid (2.1 ml), tetrahydrofuran (1.4 ml) and water (0.7 ml), and the mixture was stirred at room temperature for 2 days. To the reaction mixture saturated aqueous sodium hydrogencarbonate and ethyl acetate were added, and the product was extracted into the organic layer. The extract was washed with saturated aqueous sodium chloride, then dried over anhydrous magnesium sulfate and filtered, followed by concentration. The concentrate was subjected to silica gel chromatography to give 0.93 g (yield 85%) of 2-methylthio-5-(6-methoxycarbonylhexylidene)-4-(3-hydroxy-1-octenyl)-2-cyclopentenone.

Spectrum data $^1$H-NMR CDCl$_3$ δ: 0.89 (3H, brt), 1.1–2.4 (19H, m), 2.35 (3H, s), 3.66 (3H, s), 3.9–4.2 (2H, m), 5.2–5.9 (2H, m), 6.6–6.8 (2H, m).

EXAMPLE 545

Synthesis of
2-methylsulfinyl-5-(6-methoxycarbonylhexylidene)-4-(3-hydroxy-1-octenyl)-2-cyclopentenone

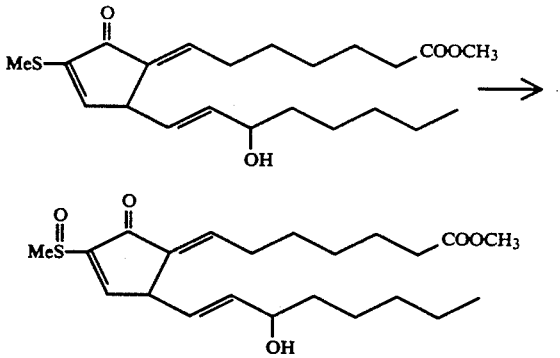

A solution of 252.2 mg of 2-methylthio-5-(6-methoxycarbonylhexylidene)-4-(3-hydroxy-1-octenyl)-2-cyclopentenone obtained in Example 544 in dichloromethane (20 ml) was cooled to 0° C., and a solution of 3-chloroperbenzoic acid (129.8 mg) in dichloromethane (10 ml) was added dropwise thereto. After the mixture was stirred at 0° C. for 1 hour, ethyl acetate and saturated aqueous sodium hydrogencarbonate was added, and the product was extracted into the organic layer. The extract was successively washed with saturated aqueous sodium chloride, saturated aqueous ammonium chloride and saturated aqueous sodium chloride, then dried over anhydrous magnesium sulfate, and filtered, followed by concentration. The concentrate was subjected to silica gel chromatography to give 186.8 mg (yield 71%) of a mixture of isomers of 2-methylsulfinyl-5-(6-methoxycarbonylhexylidene)-4-(3-hydroxy-1-octenyl)-2-cyclopentenone.

Spectrum data $^1$H-NMR CDCl$_3$ δ: 0.89 (3H, brt), 1.1–2.4 (19H, m), 2.86 and 2.88 (3H, s), 3.67 (3H, s), 4.0–4.3 (2H, m), 5.3–6.0 (2H, m), 6.72 (1H, t, J=7 Hz), 7.7–7.8 (1H, m).

EXAMPLE 546

Synthesis of
2-methylsulfinyl-5-(6-methoxycarbonylhexylidene)-4-(3-hydroxy-1-octenyl)-2-cyclopentenone

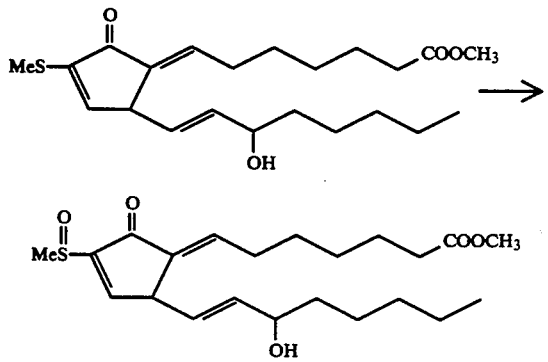

To a solution of 21.9 mg of 2-methylthio-5-(6-methoxycarbonylhexylidene)-4-(3-hydroxy-1-octenyl)-2-cyclopentenone obtained in Example 544 in methanol (3 ml) was added a solution of sodium metaperiodide (118.7 mg) in water (0.5 ml), and the mixture was stirred for 18 hours. To the reaction mixture were added ethyl acetate and saturated aqueous sodium chloride, and the product was extracted into the organic layer. The extract was washed with saturated aqueous sodium chloride, dried over anhydrous magnesium sulfate and filtered, followed by concentration. The concentrate was subjected to silica gel chromatography to give 9.6 mg (yield 42%) of 2-methylsulfinyl-5-(6-methoxycarbonylhexylidene)-4-(3-hydroxy-1-octenyl)-2-cyclopentenone.

EXAMPLE 547

Synthesis of
2-methylsulfonyl-5-(6-methoxycarbonylhexylidene)-4-(3-hydroxy-1-octenyl)-2-cyclopentenone

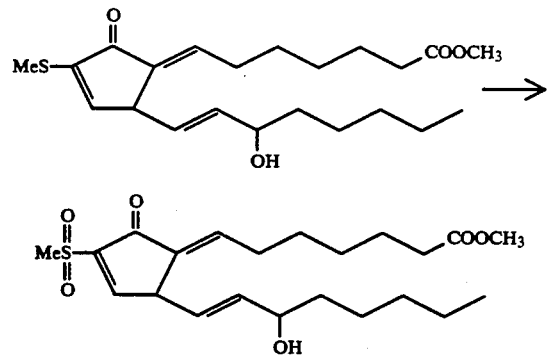

A solution of 18 mg of 2-methylthio-5-(6-methoxycarbonylhexylidene)-4-(3-hydroxy-1-octenyl)-2-cyclopentenone obtained in Example 544 in dichloromethane (1.5 ml) was cooled to 0° C., and a solution of 3-chloroperbenzoic acid (15.7 mg) in dichloromethane (1 ml) was added dropwise thereto. After the mixture was stirred at 0° C. for 2 hours, ethyl acetate and saturated aqueous sodium hydrogencarbonate were added and the product was extracted into the organic layer. The extract was successively washed with saturated aqueous sodium chloride, saturated aqueous ammonium chloride and saturated aqueous sodium chloride, then dried over anhydrous magnesium sulfate and filtered, followed by concentration. The concentrate was subjected to silica gel chromatography to give 16.6 mg (yield 85%) of 2-methylsulfonyl-5-(6-methoxycarbonylhexylidene)-4-(3-hydroxy-1-octenyl)-2-cyclopentenone.

Spectrum data $^1$H-NMR CDCl$_3$ δ: 0.7–1.0 (m 3H), 1.1–2.4 (m, 18H), 3.16 (s, 3H), 3.66 (s, 3H), 4.0–4.5 (m, 2H), 5.3–6.0 (m, 2H), 6.82 (t, J=7 Hz, 1H), 8.06 (d, J=3 Hz, 1H).

EXAMPLE 548

Synthesis of
5-(6-methoxycarbonylhexylidene)-2-methylsulfinyl-4-(1-octenyl)-2-cyclopentenone

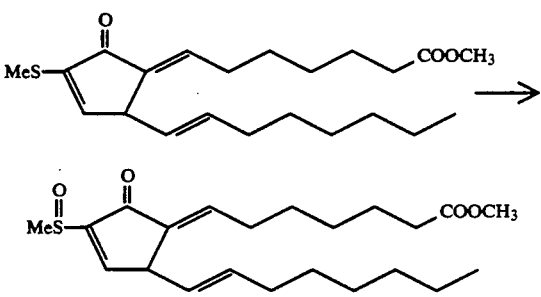

A solution of 9 mg of 5-(6-methoxycarbonylhexylidene)-2-methylthio-4-(1-octenyl)-2-cyclopentenone dissolved in 2 ml of methanol, and 500 µl of an aqueous solution of 150 mg of sodium periodate was added, and the mixture was stirred for 5 hours. Saturated aqueous sodium chloride was added, and the mixture was extracted with ethyl acetate. The organic layer was washed with saturated aqueous sodium chloride and dried over anhydrous magnesium sulfate. After filtration and concentration, the concentrate was subjected to silica gel column chromatography to give 4.3 mg (yield 48%) of a mixture of isomers of 5-(6-methoxycarbonylhexylidene)-2-methylsulfinyl-4-(1-octenyl)-2-cyclopentenone.

Spectrum data $^1$H-NMR (CDCl$_3$) δ: 0.88 (3H, brt, J=6.0 Hz), 1.0–2.5 (20H, m), 2.86 and 2.88 (3H, s), 3.67 (3H, s), 3.9–4.3 (1H, m), 5.0–6.0 (2H, m), 6.6–6.9 (1H, m), 7.80 (1H, d, J=3 Hz)

EXAMPLE 549

Syntheses of
2,3-epoxy-4-trimethylsilyloxy-4-(4-phenoxybutyl)cyclopentanone and
2,3-epoxy-4-hydroxy-4-(4-phenoxybutyl)cyclopentanone

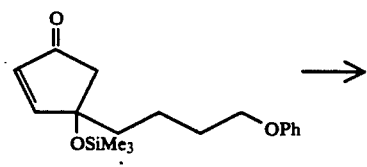

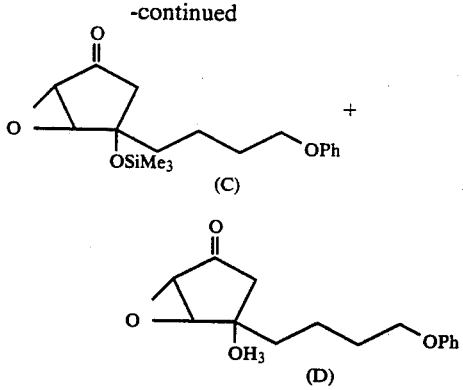

To a solution of 2.49 g of 4-trimethylsilyloxy-4-(4-phenoxybutyl)-2-cyclopentenone dissolved in 50 ml of methanol was added 3.9 ml of an aqueous 30% hydrogen peroxide under ice-cooling and stirring. An amount of 1 of 1N aqueous sodium hydroxide was added, and the mixture was stirred for 2 hours. Then saturated aqueous ammonium chloride was added, and the mixture was extracted with ethyl acetate. The organic layer was washed with saturated aqueous sodium chloride and dried over anhydrous magnesium sulfate. After filtration and concentration, the concentrate was subjected to silica gel column chromatography to give 892 mg (yield 34%) of 2,3-epoxy-4-trimethylsilyloxy-4-(4-phenoxybutyl)cyclopentanone and 1.38 g (yield 53%) of 2,3-epoxy-4-hydroxy-4-(4-phenoxybutyl)cyclopentanone.

Spectrum data (C) $^1$H-NMR (CDCl$_3$) δ: 0.20 (9H, s), 1.4–2.1 (6H, m), 2.16 (1H, d, J=17.5 Hz), 2.57 (1H, d, J=17.5 Hz), 3.45 (1H, d, J=2.5 Hz), 3.77 (1H, d, J=2.5 Hz), 3.8–4.1 (2H, m), 6.8–7.1 (3H, m), 7.15–7.45 (2H, m).

(D) $^1$H-NMR (CDCl$_3$) δ: 1.4–2.1 (6H, m), 2.31 (1H, d, J=16.3 Hz), 2.4 (1H, d, 16.3 Hz), 2.4–2.8 (1H, m), 3.35–3.6 (1H, m), 3.65–4.2 (3H, m), 6.7–7.05 (3H, m), 7.1–7.45 (2H, m).

EXAMPLE 550

Synthesis of 2-methylthio-4-hydroxy-4-(4-phenoxybutyl)-2-cyclopentenone

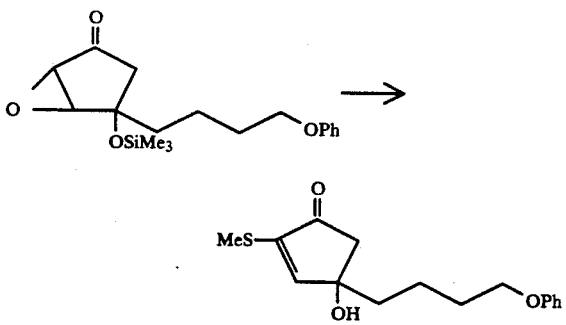

To a solution of 25 mg of sodium thiomethoxide dissolved in methanol, 51 μl of acetic acid was added, and the mixture was stirred for 10 minutes. Triethylamine (170 μl) was then added, and after the mixture was stirred for 10 minutes, a solution of 16 mg of 2,3-epoxy-4-trimethylsilyloxy-4-(4-phenoxybutyl)cyclopentanone obtained in Example 549 in 3 ml of methanol was added and the mixture was stirred for 5 hours. Then saturated aqueous ammonium chloride was added, and the mixture was extracted with ethyl acetate. The organic layer was washed with saturated aqueous sodium chloride and dried over anhydrous sodium sulfate. After filtration and concentration, the concentrate was subjected to silica gel column chromatography to obtain 7.1 mg (yield 51%) of 2-methylthio-4-hydroxy-4-(4-phenoxybutyl)-2-cyclopentenone.

Spectrum data $^1$H-NMR (CDCl$_3$) δ: 1.4–2.0 (6H, m), 2.18 (1H, s), 2.34 (3H, s), 2.63 (1H, d, J=17.5 Hz), 2.72 (1H, d, J=17.5 Hz), 4.0 (2H, brt, J=6.0 Hz), 6.76 (1H, s), 6.8–7.1 (3H, m), 7.15–7.45 (2H, m).

EXAMPLE 551

Synthesis of 2-methylthio-4-hydroxy-4-(4-phenoxybutyl)-2-cyclopentenone

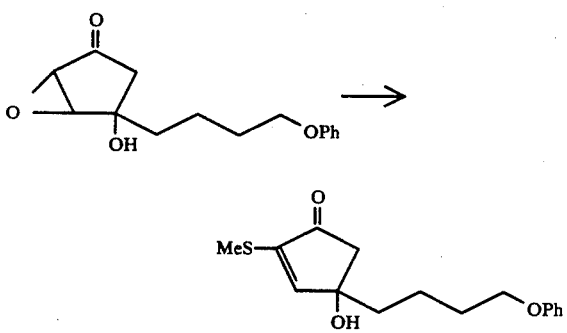

To a solution of 1.5 g of sodium thiomethoxide dissolved in 80 ml of methanol was added 1.8 ml of acetic acid under ice-cooling and stirring. After the mixture was stirred for 5 minutes, 4.8 ml of triethylamine was added, and the solution of 1.38 g of 2,3-epoxy-4-hydroxy-4-(4-phenoxybutyl)cyclopentanone obtained in Example 549 dissolved in 20 ml of methanol was added. After the mixture was stirred for 4 hours, water was added and the mixture was extracted with ethyl acetate. The organic layers were combined, washed with saturated aqueous sodium chloride and dried over anhydrous magnesium sulfate. After filtration and concentration, the concentrate was subjected to silica gel column chromatography to give 1.39 g (yield 83%) of 2-methylthio-4-hydroxy-4-(4-phenoxybutyl)-2-cyclopentenone.

EXAMPLE 552

Synthesis of 2-methylthio-4-(4-phenoxybutyl)-4-trimethylsilyloxy-2-cyclopentenone

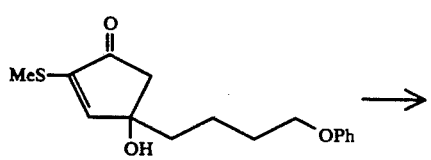

-continued

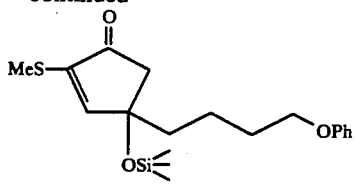

To a solution of 400 mg of 2-methylthio-4-hydroxy-4-(4-phenoxybutyl)-2-cyclopentenone obtained in Example 52 or Example 551 dissolved in 4 ml of dimethylformamide were added 279 mg of imidazole and 260 μl of chlorotrimethylsilane, under ice-cooling and stirring, and the mixture was stirred at 0° C. for 3 hours. The reaction mixture was extracted with an addition of water and hexane. The organic layer was washed with saturated aqueous sodium chloride, and the product dried over anhydrous sodium sulfate, filtered and concentrated, followed by silica gel column chromatography, to give 445 mg (yield 89%) of 2-methylthio-4-(4-phenoxybutyl)-4-trimethylsilyloxy-2-cyclopentenone.

Spectrum data $^1$H-NMR (CDCl$_3$) δ: 0.11 (9H, s), 1.3-1.9 (6H, m), 2.35 (3H, s), 2.66 (2H, s), 3.95 (2H, t, J=5.9 Hz), 6.80 (1H, s), 6.8-7.45 (5H, m).

EXAMPLE 553

Synthesis of 2-methylthio-4-octyl-4-trimethylsilyloxy-2-cyclopentenone

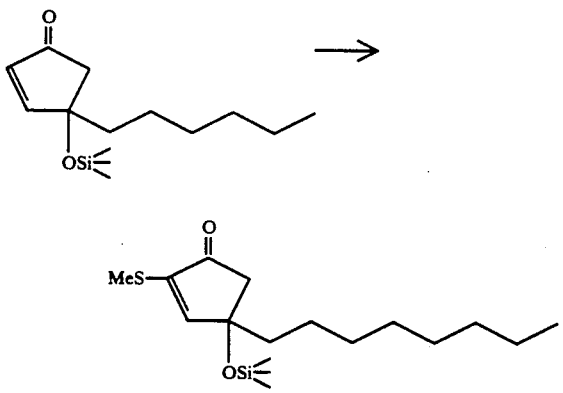

To a solution of 3.3 g of 4-octyl-4-trimethylsilyloxy-2-cyclopentenone dissolved in 50 ml of methanol was added, under ice-cooling and stirring, 5.0 ml of an aqueous 30% hydrogen peroxide, and 500 μl of an aqueous 1N sodium hydroxide was added. After the mixture was stirred for 3.5 hours, saturated aqueous ammonium chloride was added, and the mixture was extracted with ethyl acetate. The organic layer was washed with saturated aqueous sodium chloride and dried over anhydrous magnesium sulfate. The product was filtered and concentrated to give a crude oil of 2,3-epoxy-4-octyl-4-trimethylsilyloxycyclopentanone.

A solution of 910 mg of sodium thiomethoxide dissolved in 100 ml of methanol was stirred under ice-cooling and stirring for 15 minutes. Triethylamine (6 ml) was added, and after the mixture was stirred for 10 minutes, a solution of the above crude oil of 2,3-epoxy-4-octyl-4-trimethylsilyloxycyclopentanone in 15 ml of methanol was added dropwise. After the mixture was stirred for 6 hours, the reaction mixture was poured onto saturated aqueous ammonium chloride, and the mixture was extracted with ethyl acetate. The organic layer was washed with saturated aqueous sodium chloride, dried over anhydrous sodium sulfate, filtered and concentrated to give a crude oil of 2-methylthio-4-hydroxy-4-octyl-2-cyclopentenone.

To a solution of the crude oil dissolved in 80 ml of dimethylformamide was added 2.2 g of imidazole, under ice-cooling and stirring, and then 2.0 g of chlorotrimethylsilane was added, followed by stirring at 0° C. for 4.5 hours. The mixture was extracted with addition of water and hexane, and the organic layer was washed with saturated aqueous sodium chloride. After drying over anhydrous sodium sulfate, filtration and concentration, the concentrate was subjected to silica gel column chromatography to give 1.41 g (yield 37%) of 2-methylthio-4-octyl-4-trimethylsilyloxy-2-cyclopentenone.

Spectrum data $^1$H-NMR CDCl$_3$ δ: 0.06 (9H, s), 0.89 (3H, brt), 1.1-1.9 (14H, m), 2.34 (3H, s), 2.64 (2H, s), 6.85 (1H, s).

EXAMPLES 554-558

2-Substituted-2-cyclopentenones listed in Table 23 were obtained in the same manner as in Example 553.

TABLE 23

| Example No. | Starting compound | 2-Substituted-2-cyclopentanones | Yield (%) | NMR (δCDCl$_3$) |
|---|---|---|---|---|
| 554 | ![structure] OH 4-[3-(3,4-dimethoxyphenyl)propyl]-4-hydroxy-2-cyclopentenone | ![structure] 2-methylthio-4-[3-(3,4-dimethoxyphenyl)propyl]-4-trimethylsilyloxy-2-cyclopentenone | 41 | 0.09(9H, s), 1.4-1.9(4H, m), 2.3-2.9(4H, m), 2.35(3H, s), 3.82(6H, s), 6.6-7.1(4H, m) |

TABLE 23-continued

| Example No. | Starting compound | 2-Substituted-2-cyclopentanones | Yield (%) | NMR (δCDCl₃) |
|---|---|---|---|---|
| 555 | 4-(3,7-dimethyloctyl)-4-hydroxy-2-cyclopentenone | 2-methylthio-4-(3,7-dimethyloctyl)-4-trimethylsilyloxy-2-cyclopentenone | 37 | 0.08(9H, s), 0.83(9H, d, J=4.4Hz), 0.9–2.1(12H, m), 2.34(3H, s), 2.65(2H, s), 6.87(1H, s) |
| 556 | 4-(1-hexynyl)-4-hydroxy-2-cyclopentenone | 2-methylthio-4-(1-hexynyl)-4-trimethylsilyloxy-2-cyclopentenone | 33 | 0.05(9H, s),0.7–1.1(3H, m), 1.1–2.0(6H, m), 2.34(3H, s), 2.66(2H, s), 6.83(1H, s) |
| 557 | 4-(3-t-butyldimethylsilyloxy-3-cyclohexyl-1-propenyl)-4-hydroxy-2-cylcopentenone | 2-methylthio-4-(3-t-butyldimethylsilyloxy-3-cyclohexyl-1-propenyl)-4-trimethylsilyloxy-2-cyclopentenone | 26 | 0.01–0.08(15H, m), 0.89(9H, s), 1.0–2.0(11H, m), 2.36(3H, s), 2.68(2H, s), 4.6–4.85(1H, m), 5.4–5.8(2H, m), 6.85(1H, s) |
| 558 | 4-methyl-4-hydroxy-2-cyclopentenone | 2-methylthio-4-methyl-4-trimethylsilyloxy-2-cyclopentenone | 56 | 0.07(9H, s), 0.85(3H, s), 2.35(3H, s), 2.68(2H, s), 6.84(1H, s) |

EXAMPLE 559

Synthesis of 5-[4,7-bis(t-butyldimethylsilyloxy)-1-hydroxy-2-heptenyl]-2-methylthio-4-(4-phenoxybutyl)-4-trimethylsilyloxy-2-cyclopentenone

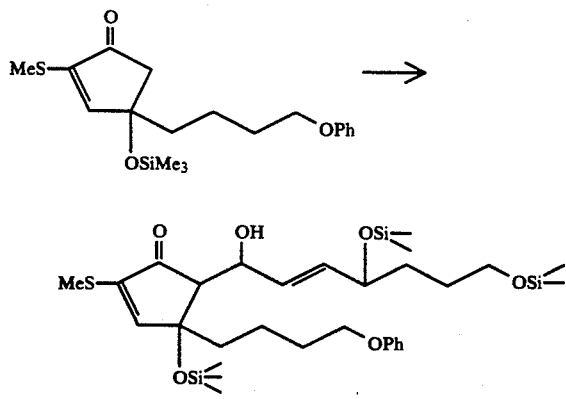

An amount of 1.195 g of 2-methylthio-4-(4-phenoxybutyl)-4-trimethylsilyloxy-2-cyclopentenone obtained in Example 552 was taken up, and after nitrogen replacement, 7.0 ml of dry ether and 7.0 ml of dry hexane were added. After 857 μl of diisopropylethylamine was added, the mixture was cooled to −70° C. A 1.0M dibutylborontrifrate dichloromethane solution (4.57 ml) was added, and the mixture was stirred at −70° C. for 1 hour. A solution of 1.47 g of 4,7-bis(t-butyldimethylsilyloxy)-2-heptenal in 10 ml of dry ether was cooled and added, followed by stirring at −70° C. for 3 hours. Saturated aqueous ammonium chloride was added, and the mixture was extracted with ether. The organic layers were combined, washed with saturated aqueous sodium chloride and dried over anhydrous magnesium sulfate. After filtration and concentration, the concentrate was subjected to silica gel column chromatography to give 1.81 g (yield 75%) of a mixture of isomers of 5-[4,7-bis(t-butyldimethylsilyloxy)-1-hydroxy-2-heptenyl]-2-methylthio-4-(4-phenoxybutyl)-4-trimethylsilyloxy-2-cyclopentenone.

Spectrum data

Less polar isomer

¹H-NMR (CDCl₃ δ: 0–0.2 (m, 21H), 0.90 (s, 18H), 1.0–2.1 (m, 10H), 2.34 (s, 3H), 2.74 (d, 1H, J=7.0 Hz), 3.5–3.7 (m, 2H), 3.98 (t, 2H, J=5.4 Hz), 4.05–4.35 (m, 1H), 4.35–4.7 (m, 1H), 5.5–6.2 (m, 2H), 6.7–7.1 (m, 4H), 7.1–7.5 (m, 2H).

More polar isomer

¹H-NMR CDCl₃ δ: 0–0.2 (m, 21H), 0.90 (s, 18H), 1.1–2.1 (m, 10H), 2.34 (s, 3H), 2.77 (d, 1H, J=6.3 Hz), 3.45–3.7 (m, 2H), 3.97 (t, 2H, J=5.3 Hz), 4.05–4.3 (m, 1H), 4.4–4.8 (m, 1H), 5.5–6.2 (m, 2H), 6.7–7.1 (m, 4H), 7.1–7.5 (m, 2H).

EXAMPLES 560–568

2-Substituted-2-cyclopentenones listed in Table 24 were obtained in the same manner as in Example 559.

TABLE 24

| Example No. | Starting compound 2-Substituted-2-cyclopentenones | Aldehydes | 2-Substituted-2-cyclopentenones | Yield (%) | NMR (δCDCl₃) |
|---|---|---|---|---|---|
| 560 | 2-methylthio-4-(4-phenoxybutyl)-4-trimethylsilyloxy-2-cyclopentenone | 3-(4-methoxycarbonylcyclohexyl)propanal | 2-methylthio-5-[1-hydroxy-3-(4-methoxycarbonylcyclohexyl)propyl]-4-(4-phenoxybutyl)-4-trimethylsilyl-2-cyclopentenone | 65 | 0.07(9H, s), 1.1–2.8(22H, m), 2.35(3H, s), 3.67(3H, s), 3.8–4.3 (3H, m), 6.7–7.5(6H, m) |
| 561 | | 4-(4-methoxyphenyl)butanal | 2-methylthio-5-[1-hydroxy-4-(4-methoxyphenyl)butyl]-4-(4-phenoxybutyl)-4-trimethylsilyloxy-2-cyclopentenone | 47 | 0.06(9H, s), 1.1–2.9(14H, m), 2.35(3H, s), 3.75(3H, s), 3.7–4.3 (3H, m), 6.6–7.5(10H, m) |
| 562 | 2-phenylthio-4-(4-phenoxybutyl)-4-trimethylsilyloxy 2-cyclopentenone | Octanal | 2-phenylthio-5-(1-hydroxyoctyl)-4-(4-phenoxybutyl)-4-trimethylsilyloxy-2-cyclopentenone | 55 | 0.07(9H, s), 0.7–1.0(3H, brt), 1.0–2.0(18H, m), 2.5–2.9(2H, m), 3.7–4.0(1H, m), 4.0(2H, brt, J = 6.0Hz), 6.7–7.5(11H, m) |

TABLE 24-continued

| Example No. | Starting compound | | 2-Substituted-2-cyclopentenones | Yield (%) | NMR (δCDCl₃) |
|---|---|---|---|---|---|
| | 2-Substituted-2-cyclopentenones | Aldehydes | | | |
| 563 | 2-methylthio-4-[3-(3,4-di-methoxyphenyl)propyl]-4-trimethylsilyloxy-2-cyclopentenone | methyl 7-oxoheptanoate | 2-methylthio-5-(1-hydroxy-6-methoxycarbonylhexyl)-4-[3-(3,4-dimethoxyphenyl)propyl]-4-trimethylsilyloxy-2-cyclopentenone | 37 | 0.17(9H, s), 1.0–2.1(12H, m), 2.1–2.8(6H, m), 2.35(3H, s), 3.65 (3H, s), 3.7–4.3(1H, m), 3.86 (6H, s), 6.6–7.1(4H, m) |
| 564 | 2-methylthio-4-(3,7-dimethyl-octyl)-4-trimethylsilyloxy-2-cyclopentenone | methyl 7-oxoheptanoate | 2-methylthio-5-(1-hydroxy-6-methoxycarbonylhexyl)-4-(3,7-dimethyloctyl)-4-trimethyl-silyloxy-2-cyclopentenone | 48 | 0.08(9H, s), 0.83(9H, d, J= 4.5Hz), 0.9–2.9(24H, m), 2.35 (3H, s), 3.68(3H, s), 3.7–4.1 (1H, m), 6.86(1H, s) |
| 565 | 2-methylthio-4-(1-hexynyl)-4-trimethylsilyloxy-2-cyclopentenone | methyl 7-oxoheptanoate | 2-methylthio-5-(1-hydroxy-6-methoxycarbonylhexyl)-4-(1-hexynyl)-4-trimethylsilyloxy-2-cyclopentenone | 42 | 0.05(9H, s), 0.7–10(3H, brt), 1.0–2.9(18H, m), 2.36(3H, s), 3.69 (3H, s), 3.7–4.0(1H, m), 6.87 (1H, s) |

TABLE 24-continued

| Example No. | Starting compound | | 2-Substituted-2-cyclopentenones | Yield (%) | NMR (δCDCl₃) |
|---|---|---|---|---|---|
| | 2-Substituted-2-cyclopentenones | Aldehydes | | | |
| 566 | 2-methylthio-4-(3-t-butyl-dimethylsilyloxy-3-cyclohexyl-1-propenyl)-4-trimethylsilyloxy-2-cyclopentenone | methyl 7-oxo-5-heptynoate | 2-methylthio-5-(1-hydroxy-6-methoxycarbonyl-2-hexynyl)-4-(3-t-butyldimethylsilyloxy-3-cyclohexyl-1-propenyl)-4-trimethylsilyloxy-2-cyclopentenone | 38 | 0.01–0.09(15H, m), 0.89(9H, s), 1.0–2.9(19H, m), 2.36(3H, s), 3.68(3H, s), 3.8–4.0(1H, m), 4.6–4.8(1H, m), 5.3–5.9(2H, m), 6.89(1H, s) |
| 567 | 2-methylthio-4-methyl-4-trimethylsilyloxy-2-cyclopentenone | methyl 7-oxoheptanoate | 2-methylthio-5-(1-hydroxy-6-methoxycarbonylhexyl)-4-methyl-4-trimethylsilyloxy-2-cyclopentenone | 51 | 0.06(9H, s), 1.25(3H, s), 1.1–2.8(12H, m), 2.36(3H, s), 3.68(3H, s), 3.7–4.0(1H, m), 6.87(1H, s) |
| 568 | 2-methylthio-4-octyl-4-trimethylsilyloxy-2-cyclopentenone | methyl 7-oxoheptanoate | 2-methylthio-5-(1-hydroxy-6-methoxycarbonylhexyl)-4-octyl-4-trimethylsilyloxy-2-cyclopentenone | 76 | 0.19(9H, s), 0.7–1.0(3H, brt), 1.0–2.2(23H, m), 2.31(2H, t, J=7.2Hz), 2.35(3H, s), 2.45(1H, d), 3.67(3H, s), 3.8–4.1(1H, m), 6.75(1H, s) |

EXAMPLE 569

Synthesis of 5-(1,4,7-trihydroxy-2-heptenyl)-4-hydroxy-2-methylthio-4-(4-phenoxybutyl)-2-cyclopentenone

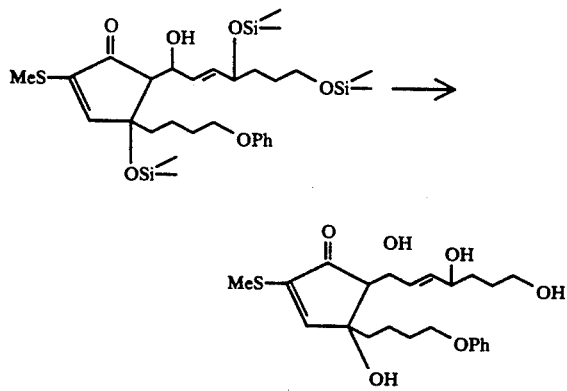

To a solution of 270 mg of 5-[4,7-bis(t-butyldimethylsilyloxy)-1-hydroxy-2-heptenyl]-2-methylthio-4-(4-phenoxybutyl)-4-trimethylsilyloxy-2-cyclopentenone obtained in Example 559 dissolved in 15 ml of acetonitrile, 2 ml of pyridine was added. While stirring the mixture under ice-cooling, 1 ml of a hydrogen fluoride-pyridine solution was added and the mixture was stirred at 0° C.—room temperature for 16 hours. The mixture was poured onto saturated aqueous sodium hydrogencarbonate, and the mixture was extracted with ethyl acetate. The organic layers were combined, washed with saturated aqueous sodium chloride and dried over anhydrous magnesium sulfate. After filtration and concentration, the concentrate was subjected to silica gel chromatography to give 114 mg (yield 71%) of 5-(1,4,7-trihydroxy-2-heptenyl)-4-hydroxy-2-methylthio-4-(4-phenoxybutyl)-2-cyclopentenone.

Spectrum data $^1$H-NMR CDCl$_3$ δ: 1.1–2.2 (15H, m), 2.35 (3H, s) 2.6–2.9 (1H, m), 3.5–3.7 (2H, m), 3.97 (2H, t, J=5.3 Hz), 4.0–4.3 (1H, m), 4.4–4.8 (1H, m), 5.5–6.2 (2H, m), 6.7–7.1 (4H, m), 7.1–7.5 (2H, m).

EXAMPLE 570

Synthesis of 5-[4,7-bis(t-butyldimethylsilyloxy)-2-heptenylidene]-2-methylthio-4-(4-phenoxybutyl)-4-trimethylsilyloxy-2-cyclopentenone

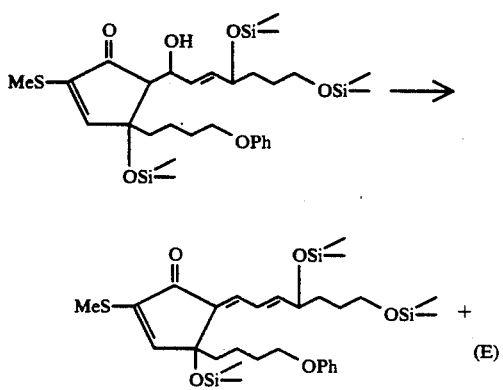

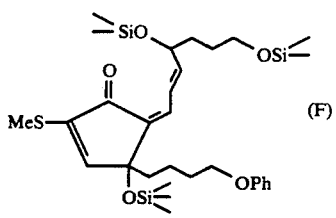

To a solution of 1.00 g of 5-[4,7-bis(t-butyldimethylsilyloxy)-1-hydroxy-2-heptenyl]-2-methylthio-4-(4-phenoxybutyl)-4-trimethylsilyloxy-2-cyclopentenone obtained in Example 559 dissolved in 10 ml of dichloromethane was added under ice-cooling and stirring 497 mg of dimethylaminopyridene, and then 147 μl of methanesulfonyl chloride was added dropwise. The temperature of the mixture was gradually elevated to room temperature, and then stirred for 6 hours. Saturated aqueous potassium hydrogensulfate was added, and the mixture was extracted with ethyl acetate. The organic layers were combined, washed with saturated aqueous sodium hydrogencarbonate and with saturated aqueous sodium chloride in the order mentioned, and dried over anhydrous sodium sulfate. After filtration and concentration, the concentrate was subjected to silica gel chromatography to give 644 mg (yield 66%) of low polarity isomer and 255 mg (yield 26%) of high polarity isomer of 5-[4,7-bis(t-butyldimethylsilyloxy)-2-heptenylidene]-2-methylthio-4-(4-phenoxybutyl)-4-trimethylsilyloxy-2-cyclopentenone.

Spectrum data

Less polar isomer (F)

$^1$H-NMR CDCl$_3$ δ: 0–0.1 (m, 21H), 0.90 (s, 9H), 0.93 (s, 9H), 1.1–2.1 (m, 10H), 2.36 (s, 3H), 3.4–3.75 (m, 2H), 3.98 (t, 2H, J=6.3 Hz), 4.1–4.5 (m, 1H), 6.13 (dd, 1H, J=15.0, 6.0 Hz), 6.54 (d, 1H, J=12.5 Hz), 6.63 (s, 1H), 6.75–7.10 (m, 3H), 7.15–7.45 (m, 2H), 7.68 (dd, 1H, J=15.0, 12.5 Hz).

More polar isomer (E)

$^1$H-NMR CDCl$_3$ δ: 0–0.1 (m, 21H), 0.89 (s, 18H), 1.1–2.2 (m, 10H), 2.37 (s, 3H), 3.4–3.75 (m, 2H), 3.93 (t, 2H, J=6.3 Hz), 4.15–4.55 (m, 1H), 5.9–6.5 (m, 1H), 6.67 (s, 1H), 6.5–7.1 (m, 5H), 7.15–7.45 (m, 2H).

EXAMPLE 571

Syntheses of 5-[(Z)-4,7-dihydroxy-2-heptenylidene]-2-methylthio-4-4-trimethylsilyloxy-(4-phenoxybutylidene)-2-cyclopentenone and 5-[(Z)-4,7-dihydroxy-2-heptenylidene]-4-hydroxy-2-methylthio-4-(4-phenoxybutyl)-2-cyclopentenone

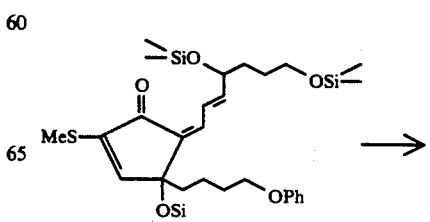

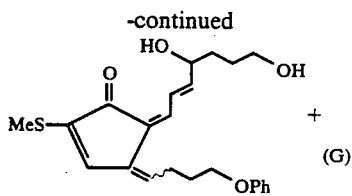

(G)

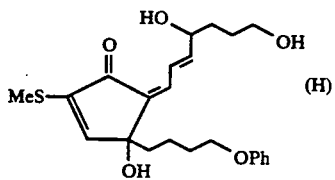

(H)

To a solution of 9 ml of pyridine dissolved in 50 ml of acetonitrile was added, 4.5 ml of hydrogen fluoride-pyridine solution, under ice-cooling and stirring. A solution of 1.41 g of 5-[(Z)-4,7-bis-(t-butyldimethylsilyloxy)-2-heptenylidene]-2-methylthio-4-(4-phenoxybutyl)-4-trimethylsilyloxy-2-cyclopentenone obtained in Example 570 in 15 ml of acetonitrile was added, and the mixture was stirred at 0° C. for 10 minutes, an at room temperature for 8 hours. The reaction mixture was poured onto saturated aqueous sodium hydrogencarbonate, and the mixture was extracted for 3 times with ethyl acetate. The organic layers were combined, washed once with saturated aqueous sodium hydrogencarbonate and twice with saturated aqueous sodium chloride. The product was dried over anhydrous magnesium sulfate, filtered and concentrated. The oily product obtained was subject to silica gel column chromatography to obtain 158 mg (yield 20%) of 5-[(Z)-4,7-dihydroxy-2-heptenylidene]-2-methylthio-4-(4-phenoxybutylidene)-2-cyclopentenone and 353 mg (yield 43%) of 5-[(Z)-4,7-dihydroxy-2-heptenylidene]-4-hydroxy-2-methylthio-4-(4-phenoxybutyl)-2-cyclopentenone.

Spectrum data (G) $^1$H-NMR-CDCl$_3$ δ: 1.4–2.9 (m, 10H), 2.26 (s, 3H), 3.4–3.9 (m, 2H), 4.01 (t, 2H, J=6.0 Hz), 5.83 (t, 1H, J=7.9 Hz), 6.23 (dd, 1H, J=16.0, 6.5 Hz), 6.74 (d, 1H, J =11.0 Hz), 6.7–7.5 (m, 8H), 7.87 (dd, J=16.0, 11.0 Hz).

(H) $^1$H-NMR-CDCl$_3$ δ: 1.2–2.7(13H, m), 2.33 (3H, s), 3.5–3.8 (2H, m), 3.94 (2H, t, J=6.0 Hz), 4.15–4.50 (1H, m), 6.15 (1H, dd, J=15.2, 6.4 Hz), 6.61 (1H, d, J=11.4 Hz), 6.62 (1H, s), 6.7–7.0 (3H, m), 7.1–7.4 (2H, m), 7.67 (1H, dd, J=15.4, 11.4 Hz).

EXAMPLE 572

Synthesis of 5-[(Z)-4,7-dihydroxy-2-heptenylidene)-2-methylthio-4-(4-phenoxybutylidene)-2-cyclopentenone

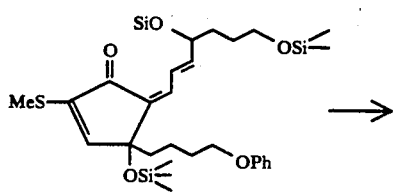

To 1.14 g of 5-[(Z)-4,7-bis(t-butydimethylsilyloxy)-2-heptenylidene]-2-methylthio-4-(4-phenoxybutyl)-4-trimethylsilyloxy-2-cyclopentenone obtained in Example 570 was added 40 ml of a mixture of acetic acid:tetrahydrofuran:water=3:1:1, and the mixture was stirred at room temperature for 18 hours. After the mixture was concentrated with an addition of toluene, saturated aqueous sodium hydrogen carbonate was added, and the mixture was extracted for 3 times with ethyl acetate. The organic layers were combined, washed successively with saturated aqueous sodium hydrogencarbonate and saturated aqueous sodium chloride, and dried over anhydrous magnesium sulfate. After filtration and concentration, the concentrate was subjected to silica gel column chromatography to give 407 mg (yield 61%) of 5-[(Z)-4,7-dihydroxy-2-heptenylidene]-4-hydroxy-2-methylthio-4-(4-phenoxybutylidene)-2-cyclopentenone.

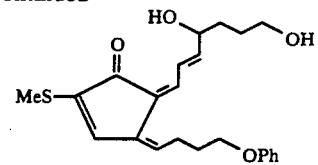

EXAMPLE 573

Synthesis of 5-[(Z)-4,7-dihydroxy-2-heptenylidene]-4-hydroxy-2-methylsulfinyl-4-(4-phenoxybutylidene)-2-cyclopentenone

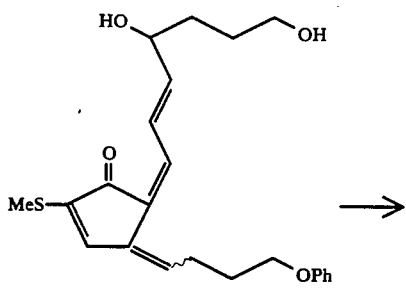

→

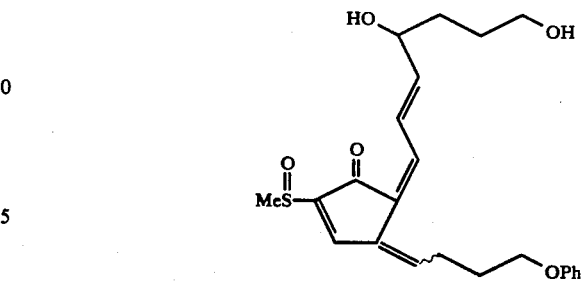

To a solution of 20 mg of 5-[(Z)-4,7-dihydroxy-2-heptenylidene]-4-hydroxy-2-methylthio-4-(4-phenoxybutylidene)-2-cyclopentenone obtained in Example 571 or Example 572 dissolved in 3 ml of methanol was added a solution of 102 mg of sodium periodate in 500 μl of water, and the mixture was stirred for 5 hours. Saturated aqueous sodium chloride was added, and the mixture was extracted for 3 times with ethyl acetate. The organic layers were combined, and washed with saturated aqueous sodium chloride, followed by drying over anhydrous magnesium sulfate. After filtration and concentration, the concentrate was subjected to silica gel column chromatography to give 13.3 mg (yield 64%) of 5-[(Z)-4,7-dihydroxy-2-heptenylidene]-4-hydroxy-2-methylsulfinyl-4-(4-phenoxybutylidene)-2-cyclopentenone.

Spectrum data $^1$H-NMR CDCl$_3$ δ: 1.2–2.2 (m, 7H), 2.2–3.2 (m, 3H), 2.85 (s, 3H), 3.5–3.8 (m, 2H), 4.03 (t, 2H, J=6.3 Hz), 4.1–4.6 (m, 1H), 6.0–6.75 (m, 2H), 6.75–7.15 (m, 5H), 7.15–7.45 (m, 3H) 7.81 (dd, 1H, J=15.0, 11.3 Hz), 8.29 and 8.36 (s, 1H).

EXAMPLE 574

Syntheses of 5-[(Z)-4,7-dihydroxy-2-heptenylidene]-2-methylsulfinyl-4-(4-phenoxybutylidene)-2-cyclopentenone and 5-[(Z)-4,7-dihydroxy-2-heptenylidene]-2-methylsulfonyl-4-(4-phenoxybutylidene)-2-cyclopentenone

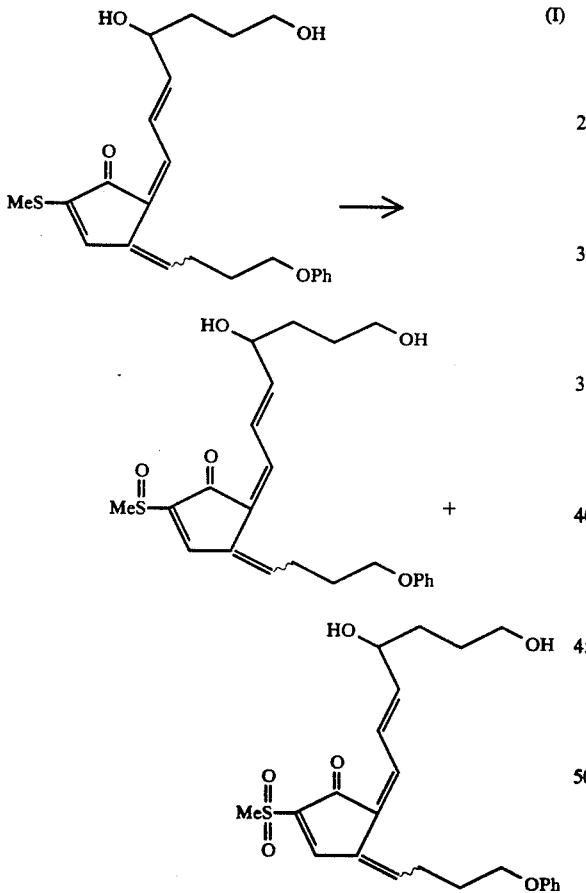

To a solution of 280 mg of 5-[(Z)-4,7-dihydroxy-2-heptenylidene]-2-methylthio-4-(4-phenoxybutylidene)-2-cyclopentenone obtained in Example 571 or Example 572 dissolved in 15 ml of dichloromethane was added a solution of 200 mg of 3-chloroperbenzoic acid in 5 ml of dichloromethane. Saturated aqueous sodium hydrogencarbonate was added, and the mixture was extracted with ethyl acetate. The organic layers were combined, washed with saturated aqueous sodium chloride and dried over anhydrous sodium sulfate. After filtration and concentration, the concentrate was subjected to silica gel column chromatography to give 36 mg (yield 13%) of 5-[(Z)-4,7-dihydroxy-2-heptenylidene]-2-methylsulfinyl-4-(4-phenoxybutylidene)-2-cyclopentenone and 66 mg (yield 24%) of 5-[(Z)-4,7-dihydroxy-2-heptenylidene]-2-methylsulfonyl-4-(4-phenoxybutylidene)-2-cyclopentenone.

Spectrum data $^1$H-NMR CDCl$_3$ δ: 1.3–2.3 (8H, m), 2.5–2.9 (2H, m), 3.10 and 3.11 (3H, s), 3.5–3.85 (2H, m), 4.00 (2H, t, J=5.9 Hz), 4.15–4.55 (1H, m), 6.0–6.75 (2H, m), 6.75–7.05 (4H, m), 7.05–7.40 (2H, m), 7.80 (1H, J=11.3, 15.0 Hz), 8.43 and 8.51 (1H, s).

EXAMPLE 575

Synthesis of 2-methylsulfonyl-5-[(Z)-4-,7-dihydroxy-2-heptenylidene]-4-(4-phenoxybutylidene)-2-cyclopentenone

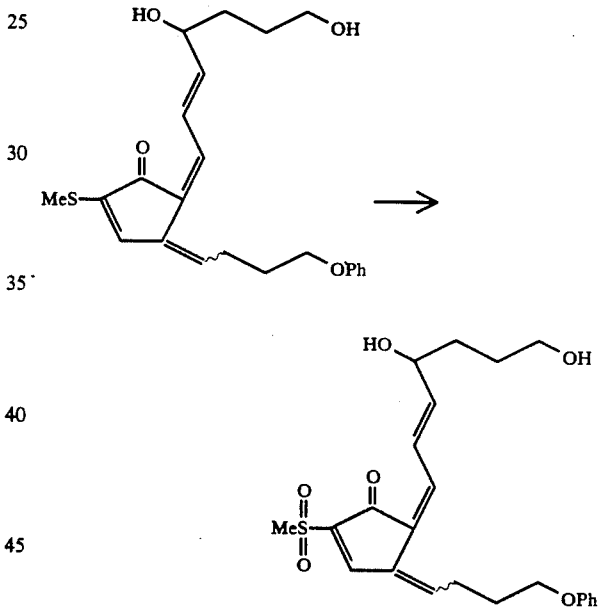

To a solution of 20 mg of 2-methylthio-5-[(Z)-4,7-dihydroxy-2-heptenylidene]-4-(4-phenoxybutylidne)-2-cyclopentenone obtained in Example 571 or Example 572 dissolved in 2 ml of methanol was added 2 ml of an aqueous solution of 60 mg of 2KHSO$_5$.KHSO$_4$.K$_2$SO$_4$, and the mixture was stirred for 20 hours. Saturated aqueous sodium hydrogencarbonate was added, and the mixture was extracted with ethyl acetate. The organic layers were combined, and washed with saturated aqueous sodium chloride, dried over anhydrous magnesium sulfate, filtered and concentrated, followed by silica gel chromatography to give 5.6 mg (yield 26%) of 2-methylsulfonyl-5-[(Z)-4,7-dihydroxy-2-heptenylidene]-4-(4-phenoxybutylidene)-2-cyclopentenone.

EXAMPLE 576

Synthesis of 2-methylsulfonyl-5-[(Z)-4,7-dihydroxy-2-heptenylidene]-4-(4-phenoxybutylidene)-2-cyclopentenone

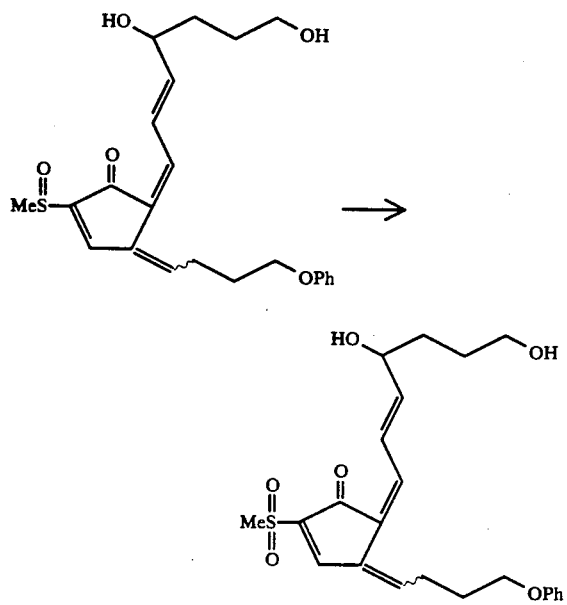

To a solution of 6.5 mg of 2-methylsulfinyl-5-[(Z)-4,7-dihydroxy-2-heptenylidene]-4-(4-phenoxybutylidene)-2-cyclopentenone obtained in Example 573 or Example 574 dissolved in 1.5 ml of dichloromethane was added 3 mg of 3-chloroperbenzoic acid, and the mixture was stirred for 4 hours. Saturated aqueous sodium hydrogencarbonate was added, and the mixture was extracted with ethyl acetate. The extract was washed with saturated aqueous sodium chloride, dried over anhydrous magnesium sulfate, filtered and concentrated, followed by silica gel chromatography to give 3.9 mg (yield 60%) of 2-methylsulfonyl-5-[(Z)-4,7-dihydroxy-2-heptenylidene]-4-(4-phenoxybutylidene)-2-cyclopentenone.

EXAMPLE 577

Synthesis of 5-[(E)-4,7-dihydroxy-2-heptenylidene]-4-hydroxy-2-methylthio-4-(4-phenoxybutyl)-2-cyclopentenone

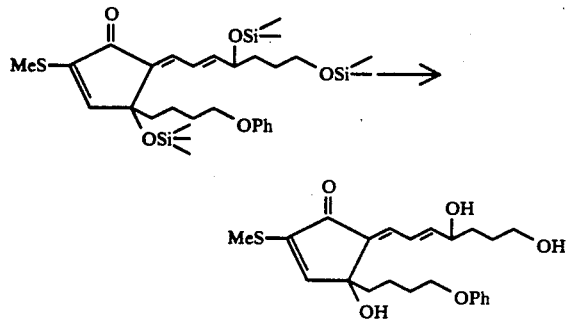

To 255 mg of 5-[(E)-4,7-bis(t-butyldimethylsilyloxy)-2-heptenylidene]-2-methylthio-4-(4-phenoxybutyl)-4-trimethylsilyloxy-2-cyclopentenone obtained in Example 570 was added 20 ml of a mixture of acetic acid:tetrahydrofuran:water=3:1:1, and the mixture was stirred at room temperature for 26 hours. After concentration with an addition of toluene, saturated aqueous sodium hydrogencarbonate was added, and the mixture was extracted 3 times with ethyl acetate. The organic layers were combined, washed successively with saturated aqueous sodium hydrogencarbonate and saturated aqueous sodium chloride, and dried over anhydrous magnesium sulfate. After filtration and concentration, the concentrate was subjected to silica gel column chromatography to give 94 mg (yield 63%) of 5-[(E)-4,7-dihydroxy-2-heptenylidene]-4-hydroxy-2-methylthio-4-(4-phenoxybutyl)-2-cyclopentenone.

EXAMPLE 578

Synthesis of 5-[(E)-4,7-dihydroxy-2-heptenylidene]-4-hydroxy-2-methylthio-4-(4-phenoxybutyl)-2-cyclopentenone

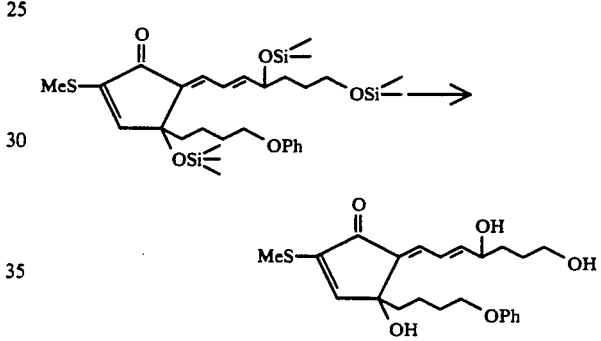

To a solution of 660 mg of 5-[(E)-4,7-bis(t-butyldimethylsilyloxy)-2-heptenylidene]-2-methylthio-4-(4-phenoxybutyl)-4-trimethylsilyloxy-2-cyclopentenone obtained in Example 570 dissolved in 50 ml of acetonitrile was added 4 ml of pyridine, under ice-cooling and stirring. A hydrogen-pyridine solution (2 ml) was added, and the mixture was stirred at 0° C. for 24 hours. The reaction mixture was poured onto saturated aqueous sodium hydrogencarbonate, and the mixture was extracted 3 times with ethyl acetate. The organic layers were combined, washed with saturated sodium chloride and dried over anhydrous magnesium sulfate. After filtration and concentration, the concentrate was subjected to silica gel column chromatography to give 320 mg (yield 83%) of 5-[(E)-4,7-dihydroxy-2-heptenylidene]-4-hydroxy-2-methylthio-4-(4-phenoxybutyl)-2-cyclopentenone.

Spectrum data $^1$H-NHR CDCl$_3$ δ: 1.2–2.9 (m, 13H), 2.37 (s, 3H), 3.5–3.8 (m, 2H), 3.95 (t, 2H, J=6.3 Hz), 4.15–4.5 (m, 1H), 6.0–6.5 (m, 1H), 6.67 (s, 1H), 6.7–7.15 (m, 4H), 7.15–7.5 (m, 3H).

EXAMPLE 579

2-Methylthio-4-hydroxy-5-(6-methoxycarbonylhexylidene)-4-octyl-2-cyclopentenone was obtained in the same manner as in Example 578. The results are as follows.

| Example No. | Starting compound | 2-Substituted-2-cyclopentenone | Yield (%) | NMR δCDCl₃ |
|---|---|---|---|---|
| 579 | 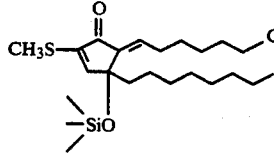 2-methylthio-5-(6-methoxy-carbonylhexylidene)-4-octyl-4-trimethylsilyloxy-2-cyclopentenone | 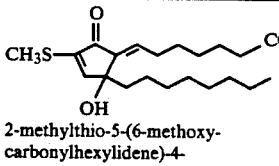 2-methylthio-5-(6-methoxy-carbonylhexylidene)-4-octyl-4-hydroxy-2-cyclopentenone | 62 | 0.86(3H, t, J=5.7Hz), 1.1–2.1(21H, m), 2.2–2.5(2H, m), 2.36(3H, s), 2.5–3.0(2H, m), 3.68(3H, s), 6.5–6.9(2H, m) |

EXAMPLE 580

Synthesis of 5-[(Z)-4,7-dihydroxy-2-heptenylidene]-4-hydroxy-2-methylsulfinyl-4-phenoxybutyl-2-cyclopentenone

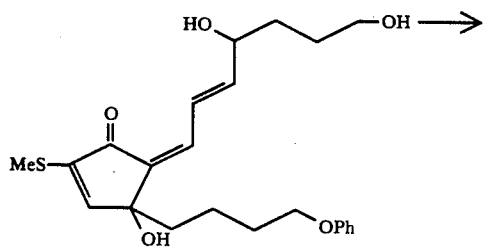

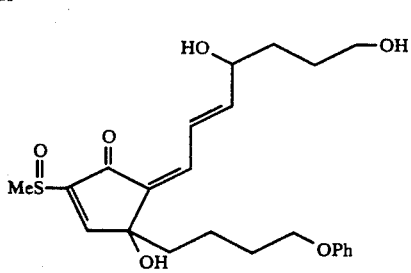

To a solution of 110 mg of 5-[(Z)-4,7-dihydroxy-2-heptenylidene]-4-hydroxy-2-methylthio-4-(4-phenoxybutyl)-2-cyclopentenone obtained in Example 571 dissolved in 15 ml of dichloromethane was added a solution of 75 mg of 3-chloroperbenzoic acid in 5 ml of dichloromethane, under ice-cooling and stirring, and the mixture was stirred at 0° C. to room temperature for 4 hours. Saturated aqueous sodium hydrogencarbonate was added, and the mixture was extracted for 3 times with ethyl acetate. The organic layer was washed with saturated aqueous sodium chloride and dried over anhydrous sodium sulfate. After filtration and concentration, the concentrate was subjected to silica gel column chromatography to give 33 mg (yield 30%) of low polarity isomer and 19 mg (yield 17%) of high polarity isomer of 5-[(Z)-4,7-dihydroxyheptenylidene]-4-hydroxy-2-methylsulfinyl-4-phenoxybutyl-2-cyclopentenone.

Spectrum data
Less polar isomer
¹H-NMR CDCl₃ δ: 1.2–2.4 (13H, m), 2.84 (3H, s), 3.5–3.8 (2H, m), 3.94 (2H, t, J=5.9 Hz), 4.1–4.5 (1H, m), 6.0–6.4 (1H, m), 6.55–7.0 (4H, m), 7.1–7.8 (3H, m), 7.70 (1H, s).

More polar isomer
¹H-NMR CDCl₃ δ: 1.2–2.5 (13H, m), 2.86 (3H, s), 3.5–3.8 (2H, m), 3.95 (2H, t, J=5.9 Hz), 4.1–4.5 (1H, m), 6.23 (1H, dd, J=15.8, 5.5 Hz), 6.70 (1H, d, J=11.4 Hz), 6.7–7.0 (3H, m), 7.1–7.4 (2H, m), 7.61 (1H, dd, J=14.5, 12.0 Hz), 7.71 (1H, s)

EXAMPLE 581

Synthesis of 5-[(Z)-4,7-dihydroxy-2-heptenylidene]-4-hydroxy-2-methylsulfonyl-4-(4-phenoxybutyl)-2-cyclopentenone

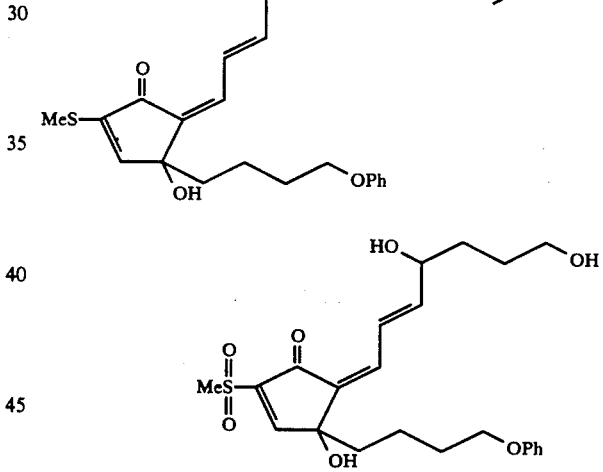

To a solution of 24 mg of 5-[(Z)-4,7-dihydroxy-2-heptenylidene]-4-hydroxy-2-methylthio-4-(4-phenoxybutyl)-2-cyclopentenone obtained in Example 571 dissolved in 2 ml of dichloromethane was added a solution of 24 mg of 3-chloroperbenzoic acid in 240 μl of dichloromethane, and the mixture was stirred for 18 hours. Saturated aqueous sodium hydrogencarbonate was added, and the mixture was extracted with ethyl acetate. The organic layers were combined, washed with saturated aqueous sodium chloride and dried over anhydrous magnesium sulfate. After filtration and concentration, the concentrate was subjected to silica gel column chromatography to give 7.3 mg (yield 30%) of 5-[(Z)-4,7-dihydroxy-2-heptenylidene]-4-hydroxy-2-methylsulfonyl-4-(4-phenoxybutyl)-2-cyclopentenone.

Spectrum data
¹H-NMR CDCl₃ δ: 1.0–2.5 (13H, m), 2.14 (1H, s), 3.6–3.8 (2H, m), 3.94 (2H, t, J=5.9 Hz), 4.1–4.5 (1H, m), 6.0–6.5 (1H, m), 6.5–7.0 (4H, m), 7.1–7.4 (2H, m), 7.4–7.8 (1H, m), 7.94 (1H,s).

EXAMPLE 582

Synthesis of 5-[(E)-4,7-dihydroxy-2-heptenylidene]-4-hydroxy-2-methylsulfinyl-4-(4-phenoxybutyl)-2-cyclopentenone

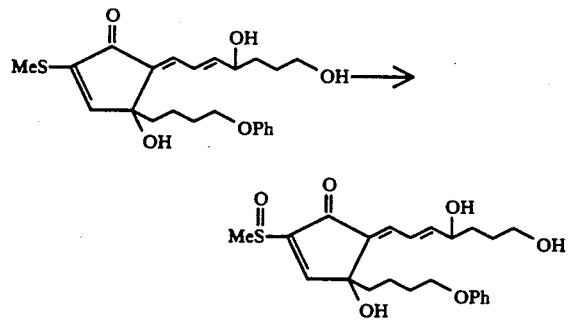

To a solution of 71 mg of 5-[(E)-4,7-dihydroxy-2-heptenylidene]-4-hydroxy-2-methylthio-4-(4-phenoxybutyl)-2-cyclopentenone obtained in Example 577 dissolved in 2 ml of dichloromethane was added a solution of 45 mg of 3-chloroperbenzoic acid in 2 ml of dichloromethane, and the mixture was stirred for 3 hours. Saturated aqueous sodium hydrogencarbonate was added. The mixture was extracted twice with ethyl acetate, and the organic layers were combined, washed with saturated aqueous sodium chloride and dried over anhydrous sodium sulfate. After filtration and concentration, the concentrate was subjected to silica gel column chromatography to give 27 mg (yield 38%) of low polarity isomer and 25 mg (yield 35%) of high polarity isomer of 5-[(E)-4,7-dihydroxyheptenylidene]-4-hydroxy-2-methylsulfinyl-4-(4-phenoxybutyl)-2-cyclopentenone.

Spectrum data
Less polar isomer
$^1$H-NMR CDCl$_3$ δ: 1.1–2.7 (13H, m), 2.85 (3H, s), 3.5–3.8 (2H, m), 3.92 (2H, t, J=6.0 Hz), 4.1–4.4 (1H, m), 6.0–6.45 (1H, m), 6.65–7.05 (5H, m), 7.1–7.4 (2H, m), 7.71 (1H, s).

More polar isomer
$^1$H-NMR CDCl$_3$ δ: 1.1–2.3 (10H, m), 2.3–3.3 (3H, m), 2.87 (3H, s), 3.5–3.8 (2H, m), 3.91 (2H, t, J=6.0 Hz), 4.1–4.4 (1H, m), 6.0–6.5 (1H, m), 6.6–7.05 (5H, m), 7.1–7.5 (2H, m), 7.69 (1H, s).

EXAMPLE 583

Synthesis of 5-[(E)-4,7-dihydroxy-2-heptenylidene]-4-hydroxy-2-methylsulfonyl-4-(4-phenoxybutyl)-2-cyclopentenone

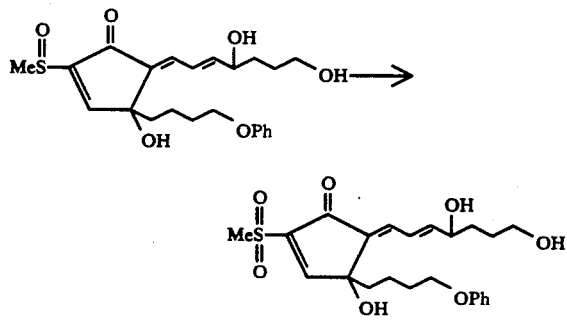

To a solution of 165 mg of 5-[(E)-4,7-dihydroxyheptenylidene]-4-hydroxy-2-methylsulfinyl-4-(4-phenoxybutyl)-2-cyclopentenone obtained in Example 582 dissolved in 30 ml of dichloromethane was added a solution 117 mg of 3-chloroperbenzoic acid in 5 ml of dichloromethane, and the mixture was stirred for 2 hours. The reaction mixture was poured onto saturated aqueous sodium thiosulfate, and the mixture was extracted 3 times with ethyl acetate. The organic layers were combined, washed twice with saturated aqueous sodium hydrogencarbonate and with saturated aqueous sodium chloride, and dried over anhydrous sodium sulfate. After filtration and concentration, the concentrate was subjected to chromatography to give 78 mg (yield 47%) of 5-[(E)-4,7-dihydroxy-2-heptenylidene]-4-hydroxy-2-methylsulfonyl-4-(4-phenoxybutyl)-2-cyclopentenone.

Spectrum data
$^1$H-NMR CDCl$_3$ δ: 1.2–2.5 (13H, m), 3.15 (3H, s), 3.5–3.8 (2H, m), 3.93 (2H, t, J=5.9 Hz), 4.1–4.4 (1H, m), 6.1–6.4 (1H, m), 6.65–7.05 (4H, m), 7.05–7.4 (2H, m), 7.99 (1H, s).

EXAMPLE 584

Synthesis of 5-[(E)-4,7-dihydroxy-2-heptenylidene]-4-hydroxy-2-methylsulfinyl-4-(4-phenoxybutyl)-2-cyclopentenone and
5[(E)-4,7-dihydroxy-2-heptenylidene]-4-hydroxy-2-methylsulfonyl-4-(4-phenoxybutyl)-2-cyclopentenone

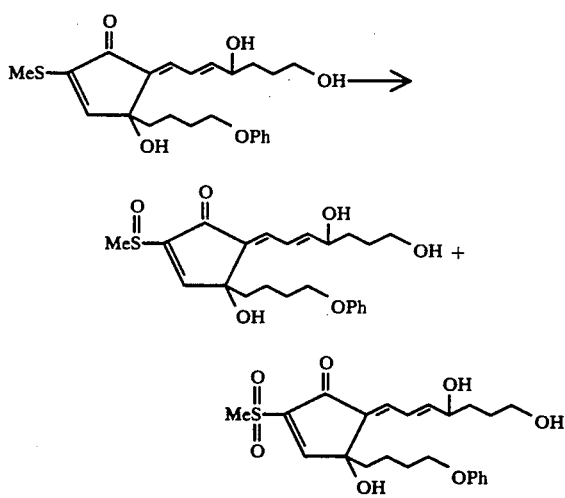

To a solution of 10 mg of 5-[(E)-4,7-dihydroxy-2-heptenylidene]-4-hydroxy-2-methylthio-4-(4-phenoxybutyl)-2-cyclopentenone obtained in Example 577 dissolved in 2 ml of dichloromethane was added 4.8 mg of 3-chloroperbenzoic acid, and the mixture was stirred for 16 hours. Saturated aqueous sodium hydrogencarbonate was added, the mixture was extracted with ethyl acetate, and the organic layer was washed with saturated aqueous sodium chloride. After drying over anhydrous sodium sulfate, filtration and concentration, the concentrate was subjected to silica gel chromatography to give 2.0 mg (yield 20%) of less polar isomer, 4.0 mg (yield 40%) of more polar isomer of 5-[(E)-4,7-dihydroxy-2-heptenylidene]-4-hydroxy-2-methylsulfinyl-4-(4-phenoxybutyl)-2-cyclopentenone and 1.6 mg (yield 16%) of 5-[(E)-4,7-dihydroxy-2-heptenylidene]-4-hydroxy-2-methylsulfonyl-4-(4-phenoxybutyl)-2-cyclopentenone.

EXAMPLE 585

Synthesis of
5-[(E)-4,7-dihydroxy-2-heptenylidene]-4-hydroxy-2-methylsulfonyl-4-(4-phenoxybutyl)-2-cyclopentenone

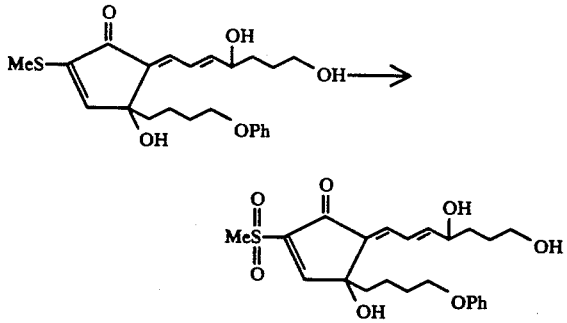

To a solution of 34 mg of 5-[(E)-4,7-dihydroxy-2-heptenylidene]-4-hydroxy-2-methylthio-4-(4-phenoxybutyl)-2-cyclopentenone obtained in Example 577 dissolved in 2 ml of dichloromethane was added a solution 33 mg of 3-chloroperbenzoic acid in 330 μl of dichloromethane, and the mixture was stirred for 18 hours. Saturated aqueous sodium hydrogencarbonate was added, and the mixture was extracted with ethyl acetate. The organic layers were combined, washed with saturated aqueous sodium chloride and dried over anhydrous magnesium sulfate. After filtration and concentration, the concentrate was subjected to silica gel column chromatography to give 13 mg (yield 38%) of 5-[(E)-4,7-dihydroxy-2-heptenylidene]-4-hydroxy-2-methylsulfonyl-4-(4-phenoxybutyl)-2-cyclopentenone.

EXAMPLE 586

Synthesis of
2-methylsulfinyl-4-hydroxy-5-(6-methoxycarbonylhexylidene)-4-octyl-2-cyclopentenone

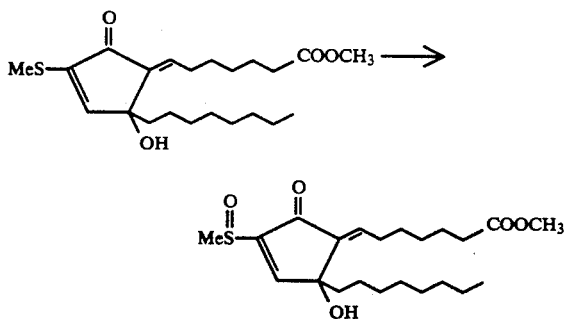

To a solution of 12 mg of 2-methylthio-4-hydroxy-5-(6-methoxycarbonylhexylidene)-4-octyl-2-cyclopentenone obtained in Example 579 dissolved in 2 ml of dichloromethane was added 6.5 mg of 3-chloroperbenzoic acid. After the mixture was stirred at 0° C. for 1 hour, saturated aqueous sodium hydrogencarbonate was added, and the mixture was extracted with ethyl acetate. After washing with saturated aqueous sodium chloride, the product was subjected to silica gel chromatography to obtain 7.3 mg (yield 61%).

Spectrum data $^1$H-NMR CDCl$_3$ δ: 0.86 (3H, t, J=5.7 Hz), 1.1–2.1 (21H, m), 2.2–2.5 (2H, m), 2.5–3.0 (2H, m), 2.87 (3H, s), 3.68 (3H, s), 6.72 (1H, t, J=7 Hz), 7.70 (1H, s).

EXAMPLE 587

Synthesis of
5-[(Z)-4,7-dihydroxy-2-heptenylidene]-2-methylthio-4-methoxy-4-(4-phenoxybutyl)-2-cyclopentenone

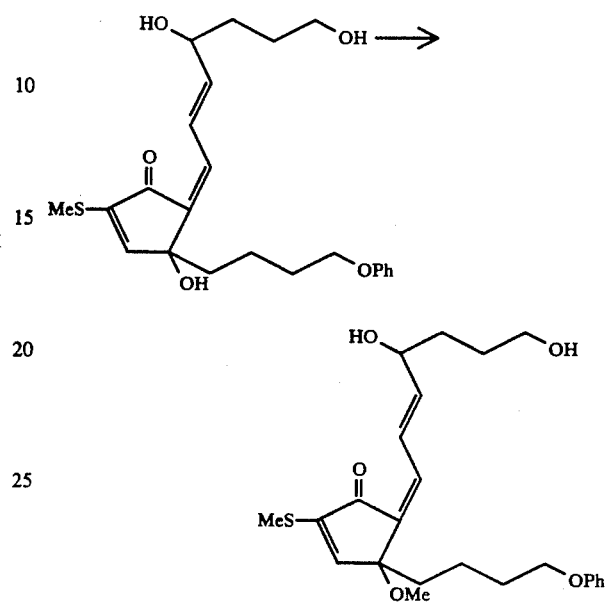

To a solution of 2 mg of 5-[(Z)-4,7-dihydroxy-2-heptenylidene]-2-methylthio-4-hydroxy-4-(4-phenoxybutyl)-2-cyclopentenone obtained in Example 571 dissolved in 1 ml of methanol was added 0.5 μl of acetic acid, and the mixture was stirred for 24 hours. Saturated aqueous sodium hydrogencarbonate was added, and the mixture was extracted with ethyl acetate. The extract was dried over anhydrous magnesium sulfate, filtered and concentrated, followed by silica gel chromatography to give 1.9 mg (yield 95%) of 5-[(Z)-4,7-dihydroxy-2-heptenylidene]-2-methylthio-4-methoxy-4-(4-phenoxybutyl)-2-cyclopentenone.

Spectrum data $^1$H-NMR CDCl$_3$ δ: 1.1–2.1 (12H, m), 2.36 (3H, s), 3.05 (3H, s), 3.55–3.8 (2H, m), 3.93 (2H, t, J=6.0 Hz), 4.1–4.5 (1H, m), 6.17 (1H, dd, J=6.2, 15.0 Hz), 6.46 (1H, d, J=11.0 Hz), 6.53 (1H, s), 6.7–7.0 (3H, m), 7.1–7.4 (2H, m), 7.72 (1H, dd, J=11.2, 15.3 Hz)

EXAMPLE 588

Measurement of anticancer activity

Tumor cells were grown in an RPMI 1640 medium containing of 10% fetal calf serum.

The compound was dissolved in 99.5% ethanol, adjusted before use so that the final concentration of ethanol was 0.1% or less, and added to the medium.

The control was 0.1% ethanol, and L1210 tumor cells were inoculated in the medium in a concentration of 2.5×10$^4$ cells/ml and grown for 2 days. The number of surviving cells were measured by trypan blue staining.

The results are given in the following Table 25.

EXAMPLE 589

Measurement of bone formation activity

Human osteoblasts (KK-3, 18PDL) were cultured in an α-MEM containing 10% fetal calf serum. After the growth became stationary, the compound was added in a given concentration in the presence of 2 mM α-glycerophosphate and treated for 14 days. The cell phase was washed with physiological saline, and the alkaline phosphatase activity (ALP) was measured through the absorption of $OD_{415}$. Then, calcium (Ca) and phosphorus (P) were extracted with a 2N hydrochloric acid and quantitatively determined. The results are given in Tables 26 to 36.

EXAMPLE 590

Evaluation of antitumor activity

Cancer cells were grown in an RPMI 1640 culture medium containing 10% of fetal calf serum.

The compound to be tested was dissolved in 99.5% ethanol and was added to the medium so that the final concentration of the ethanol was 0.1% or less. As a control, 0.1% ethanol was used. L1210 cancer cells were inoculated at a concentration of $1 \times 10^5$ cells/ml in the medium and were grown for 4 days. The number of live cells was determined by trypan blue staining.

The results are shown in Table 37.

TABLE 25

| Compound to be tested | $IC_{50}$ (μg/ml) |
|---|---|
| [structure] | 0.78 |
| [structure] | 0.83 |
| [structure] | 0.02 |
| [structure] | 0.15 |
| [structure] | 2.30 |
| [structure] | 0.10 |
| [structure] | 1.90 |

TABLE 25-continued

| Compound to be tested | IC$_{50}$ (μg/ml) |
|---|---|
| [structure: N-methyl imidazole-thio cyclopentenone with OH, OH, OH side chain and OH, OPh side chain] | 0.32 |

TABLE 26

| 2-Substituted-2-cyclopentenones | | C$_a$ μg/dish | P μg/dish | ALP OD$_{413}$/dish |
|---|---|---|---|---|
| Control (No compds.) | | 45.61 ± 6.19 | 30.68 ± 3.33 | 0.27 ± 0.04 |
| [pyridyl-thio cyclopentenone structure] | 10$^{-6}$ M | 70.42 ± 7.82 | 42.28 ± 6.99 | 0.36 ± 0.12 |
| | 10$^{-7}$ M | 56.85 ± 3.58 | 33.20 ± 2.26 | 0.29 ± 0.04 |
| [ethoxy-benzothiazolyl-thio cyclopentenone structure] | 10$^{-6}$ M | 81.88 ± 8.47 | 41.45 ± 7.21 | 0.10 ± 0.01 |
| | 10$^{-7}$ M | 61.19 ± 1.89 | 40.52 ± 4.45 | 0.34 ± 0.06 |
| [N-methyl imidazole-thio cyclopentenone structure] | 10$^{-6}$ M | 79.83 ± 0.58 | 46.43 ± 1.41 | 0.48 ± 0.04 |
| | 10$^{-7}$ M | 61.95 ± 3.42 | 38.43 ± 1.97 | 0.33 ± 0.06 |

TABLE 27

| 2-Substituted-2-cyclopentenones | | C$_a$ μg/dish | P μg/dish | ALP OD$_{413}$/dish |
|---|---|---|---|---|
| Control (No compd.) | | 11.83 ± 3.18 | 11.50 ± 1.73 | 0.58 ± 0.03 |
| [cyclohexyl-thio cyclopentenone structure] | 10$^{-6}$ M | 33.50 ± 3.91 | 24.83 ± 2.47 | 0.64 ± 0.05 |
| | 10$^{-7}$ M | 19.67 ± 1.61 | 16.67 ± 0.76 | 0.53 ± 0.05 |
| [cyclohexyl-thio cyclopentenone structure] | 10$^{-7}$ M | 13.83 ± 1.15 | 11.67 ± 3.18 | 0.55 ± 0.04 |
| | 10$^{-8}$ M | 20.17 ± 3.18 | 16.50 ± 1.73 | 0.36 ± 0.06 |

TABLE 28

| 2-Substituted-2-cyclopentenones | C$_a$ μg/dish | P μg/dish | ALP OD$_{413}$/dish |
|---|---|---|---|
| Control (No compds.) | 4.33 ± 0.58 | 4.33 ± 0.58 | 0.72 ± 0.01 |

TABLE 28-continued

| 2-Substituted-2-cyclopentenones | | $C_a$ μg/dish | P μg/dish | ALP $OD_{413}$/dish |
|---|---|---|---|---|
| [structure: cyclopentenone with N-methylimidazole-S, OH, OPh side chain, CH=CH-CH(OH)-CH2CH2CH2-OH] | $10^{-6}$ M $10^{-7}$ M | 26.17 ± 3.25 1.17 ± 0.29 | 19.33 ± 2.02 4.50 ± 0.50 | 0.76 ± 0.08 0.81 ± 0.01 |

TABLE 29

| 2-Substituted-2-cyclopentenones | | $C_a$ μg/dish | P μg/dish | ALP $OD_{413}$/dish |
|---|---|---|---|---|
| Control (No compds.) | | 31.26 ± 3.00 | 18.64 ± 3.16 | 0.77 ± 0.20 |
| [structure: MeS-cyclopentenone with OH, OPh side chain, =CH-C6H4-O-CH2-CO2Me] | $10^{-7}$ M $10^{-8}$ M | 36.18 ± 14.29 49.16 ± 26.04 | 21.72 ± 8.88 25.43 ± 9.23 | 0.52 ± 0.10 0.64 ± 0.04 |

TABLE 30

| 2-Substituted-2-cyclopentenones | | Ca μg/dish | P μg/dish | ALP $OD_{415}$/dish |
|---|---|---|---|---|
| Control (No compd.) | | 3.00 ± 1.73 | 5.33 ± 1.15 | 0.60 ± 0.02 |
| [structure: N-methylimidazole-S-cyclopentenone, OH, OPh, =CH-CH=CH-CH2CH2CH2-CH3] | $10^{-7}$ M $10^{-6}$ M | 13.33 ± 1.53 96.67 ± 0.58 | 12.67 ± 1.15 52.67 ± 0.58 | 0.57 ± 0.04 0.08 ± 0.00 |
| [structure: N-methylimidazole-S-cyclopentenone, OH, OPh, =CH-(CH2)4-COOMe] | $10^{-7}$ M $10^{-6}$ M | 3.67 ± 1.15 43.67 ± 0.58 | 6.33 ± 0.58 29.67 ± 0.58 | 0.63 ± 0.02 0.60 ± 0.03 |
| [structure: N-methylimidazole-S-cyclopentenone, OH, OPh, =CH-CH=CH-C(OH)(cyclohexyl)] | $10^{-7}$ M $10^{-6}$ M | 14.00 ± 1.00 85.67 ± 14.05 | 12.67 ± 1.15 49.00 ± 7.00 | 0.58 ± 0.03 0.11 ± 0.02 |
| [structure: N-methylimidazole-S-cyclopentenone, OH, OPh, =CH-C6H4-CH2-CH(CH2OH)2] | $10^{-7}$ M $10^{-6}$ M | 11.00 ± 1.73 116.00 ± 14.4 | 11.67 ± 1.15 61.33 ± 5.51 | 0.66 ± 0.03 0.08 ± 0.01 |

TABLE 30-continued

| 2-Substituted-2-cyclopentenones | | Ca μg/dish | P μg/dish | ALP OD$_{415}$/dish |
|---|---|---|---|---|
| Control (No compd.) | | 3.00 ± 1.73 | 5.33 ± 1.15 | 0.60 ± 0.02 |
| 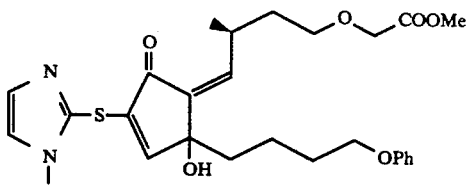 | $10^{-7}$ M $10^{-6}$ M | 1.33 ± 0.56 8.67 ± 1.15 | 5.00 ± 0.00 9.67 ± 0.58 | 0.62 ± 0.02 0.61 ± 0.02 |

TABLE 31

| 2-Substituted-2-cyclopentenones | | Ca μg/dish | P μg/dish | ALP OD$_{415}$/dish |
|---|---|---|---|---|
| Control (No compd.) | | 1.88 ± 0.31 | 4.73 ± 0.37 | 0.18 ± 0.06 |
| 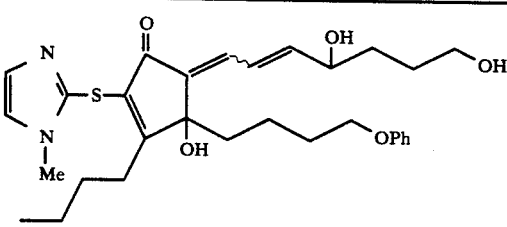 | $10^{-7}$ M $10^{-8}$ M | 4.85 ± 0.84 2.46 ± 0.22 | 6.68 ± 0.34 4.62 ± 0.04 | 0.12 ± 0.01 0.17 ± 0.01 |
| 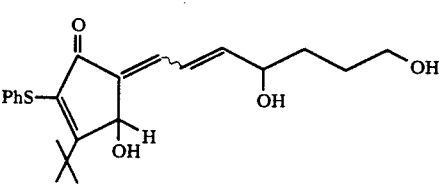 | $10^{-7}$ M $10^{-8}$ M | 2.43 ± 0.19 4.07 ± 1.20 | 4.68 ± 0.27 6.20 ± 0.61 | 0.16 ± 0.04 0.15 ± 0.02 |
| 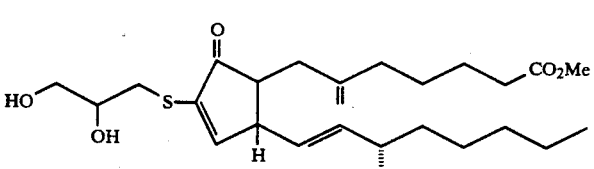 | $10^{-7}$ M $10^{-8}$ M | 3.73 ± 0.39 2.81 ± 0.17 | 5.65 ± 0.14 5.19 ± 0.77 | 0.12 ± 0.08 0.19 ± 0.02 |

TABLE 32

| 2-Substituted-2-cyclopentenones | | Ca μg/dish | P μg/dish | ALP OD$_{415}$/dish |
|---|---|---|---|---|
| Control (No compd.) | | 23.00 ± 1.00 | 15.67 ± 0.58 | 0.80 ± 0.01 |
| 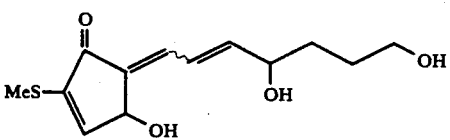 | $10^{-6}$ M $10^{-5}$ M | 23.00 ± 3.46 57.33 ± 2.08 | 16.33 ± 2.08 35.00 ± 1.0 | 0.81 ± 0.06 0.53 ± 0.04 |
| 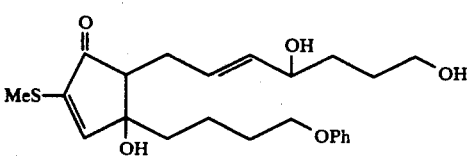 | $10^{-6}$ M $10^{-5}$ M | 10.67 ± 1.53 30.67 ± 2.31 | 9.33 ± 1.15 20.33 ± 1.15 | 0.84 ± 0.03 0.56 ± 0.04 |

TABLE 33

| 2-Substituted-2-cyclopentenones Control (No compd.) | | Ca μg/dish 22.67 ± 3.06 | P μg/dish 15.67 ± 1.53 | ALP OD₄₁₅/dish 0.80 ± 0.02 |
|---|---|---|---|---|
| 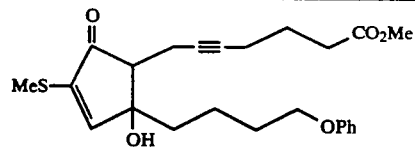 | $10^{-5}$ M<br>$10^{-6}$ M | 58.67 ± 1.53<br>24.33 ± 1.53 | 35.33 ± 0.58<br>17.67 ± 0.58 | 0.98 ± 0.08<br>0.90 ± 0.05 |
| 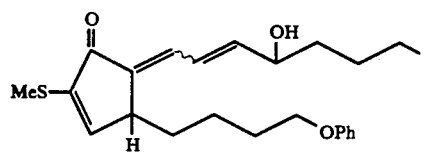 | $10^{-5}$ M<br>$10^{-6}$ M | 50.67 ± 1.15<br>19.67 ± 2.52 | 31.00 ± 1.00<br>15.00 ± 1.73 | 0.79 ± 0.02<br>0.76 ± 0.04 |

TABLE 34

| 2-Substituted-2-cyclopentenones Control (No compd.) | | Ca μg/dish 17.81 ± 0.50 | P μg/dish 12.41 ± 1.50 | ALP OD₄₁₅/dish 0.35 ± 0.02 |
|---|---|---|---|---|
| 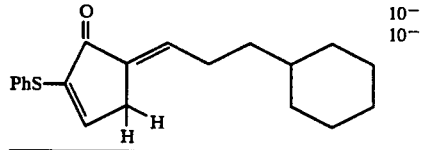 | $10^{-7}$ M<br>$10^{-8}$ M | 23.94 ± 5.80<br>18.13 ± 2.6 | 12.33 ± 2.80<br>8.98 ± 1.89 | 0.36 ± 0.04<br>0.30 ± 0.01 |

TABLE 35

| 2-Substituted-2-cyclopentenones Control (No compd.) | | Ca μg/dish 3.00 ± 1.00 | P μg/dish 5.67 ± 0.58 | ALP OD₄₁₅/dish 1.23 ± 0.02 |
|---|---|---|---|---|
| 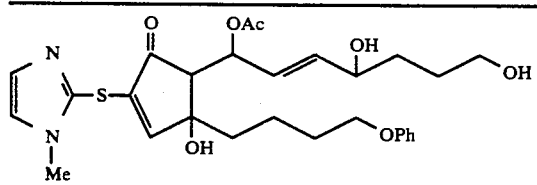 | $10^{-6}$ M<br>$10^{-5}$ M | 51.67 ± 8.08<br>137.00 ± 4.58 | 35.33 ± 5.03<br>70.67 ± 2.52 | 1.28 ± 0.03<br>0.15 ± 0.00 |
| 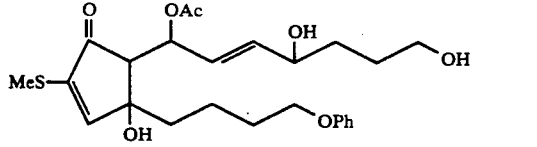 | $10^{-6}$ M<br>$10^{-5}$ M | 24.08 ± 2.00<br>104.00 ± 5.29 | 18.00 ± 1.00<br>55.67 ± 3.79 | 1.10 ± 0.06<br>0.17 ± 0.01 |
| 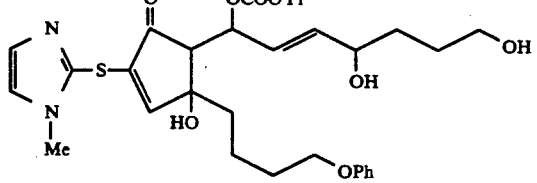 | $10^{-6}$ M<br>$10^{-5}$ M | 54.67 ± 2.08<br>136.67 ± 5.03 | 35.00 ± 2.00<br>70.00 ± 3.61 | 1.24 ± 0.03<br>0.165 ± 0.01 |
| 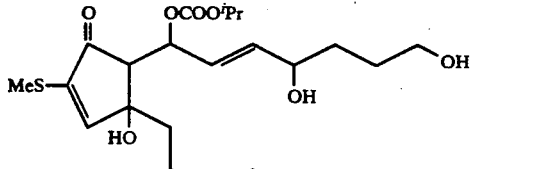 | $10^{-6}$ M<br>$10^{-5}$ M | 25.00 ± 1.73<br>109.67 ± 15.3 | 19.67 ± 1.15<br>57.33 ± 7.57 | 1.22 ± 0.06<br>0.18 ± 0.01 |

TABLE 36

| 2-Substituted-2-cyclopentenones | | Ca μg/dish | P μg/dish | ALP OD$_{415}$/dish |
|---|---|---|---|---|
| Control (No compd.) | | 2.33 ± 1.15 | 5.00 ± 0.00 | 1.17 ± 0.03 |
| [structure: cyclohexylidene vinyl] | $10^{-7}$ M<br>$10^{-6}$ M | 3.33 ± 0.58<br>15.33 ± 1.53 | 5.67 ± 0.58<br>13.33 ± 1.15 | 1.19 ± 0.06<br>1.09 ± 0.05 |
| [structure: CH=CH-CH=CH-CH$_2$OH] | $10^{-7}$ M<br>$10^{-6}$ M | 2.33 ± 0.58<br>37.33 ± 2.08 | 4.33 ± 0.58<br>25.00 ± 2.00 | 1.20 ± 0.03<br>1.18 ± 0.06 |
| [structure: cyclohexenyl with C(OH)(Me)$_2$ and CHOH] | $10^{-6}$ M<br>$10^{-5}$ M | 2.00 ± 0.00<br>50.67 ± 3.21 | 5.00 ± 1.00<br>32.00 ± 1.00 | 1.20 ± 0.05<br>0.87 ± 0.06 |
| [structure: =CH-CH$_2$-(3,4-dimethoxyphenyl)] | $10^{-7}$ M<br>$10^{-6}$ M | 2.00 ± 0.00<br>30.33 ± 0.58 | 4.33 ± 0.58<br>23.33 ± 0.58 | 1.08 ± 0.03<br>1.37 ± 0.04 |
| [structure: =CH-(CH$_2$)$_3$-CH(CH$_2$OH)$_2$] | $10^{-7}$ M<br>$10^{-6}$ M | 4.33 ± 0.58<br>48.00 ± 1.73 | 5.00 ± 1.00<br>31.00 ± 1.00 | 1.21 ± 0.08<br>1.32 ± 0.02 |
| [structure: =CH-CH=CH-(CH$_2$)$_3$-CH(CH$_2$OH)$_2$] | $10^{-7}$ M<br>$10^{-6}$ M | 4.67 ± 1.53<br>66.67 ± 0.58 | 4.33 ± 0.58<br>42.00 ± 0.00 | 1.08 ± 0.03<br>1.11 ± 0.06 |

TABLE 37

| Compound to be tested | | IC$_{50}$ (μg/ml) |
|---|---|---|
| 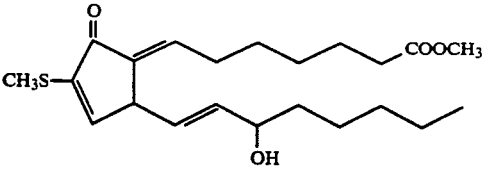 | 2-methylthio-5-(6-methoxycarbonyl-hexylidene)-4-(3-hydroxy-1-octenyl)-2-cyclopentenone | 5.0 |
| 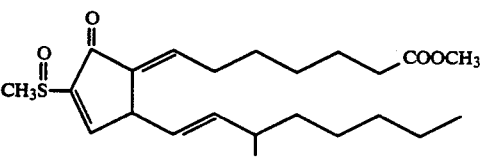 | 2-methylsulfinyl-5-(6-methoxycarbonyl-hexylidene)-4-(3-hydroxy-1-octenyl)-2-cyclopentenone | 4.0 |
| 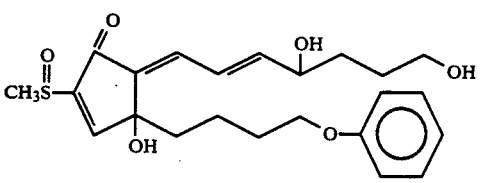 | 2-methylsulfinyl-5-[(E)-4,7-dihydroxy-2-heptenylidene]-4-(4-phenoxybutyl)-4-hydroxy-2-cyclopentenone | 1.0 |
| 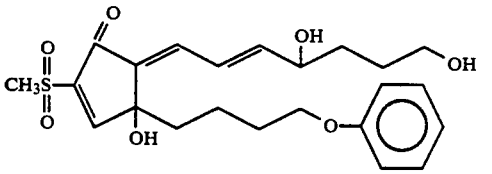 | 2-methylsulfonyl-5-[(E)-4,7-dihydroxy-2-heptenylidene]-4-(4-phenoxybutyl)-4-hydroxy-2-cyclopentenone | 2.0 |
| 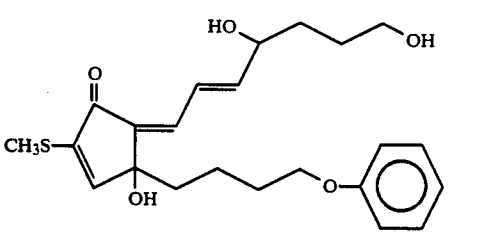 | 2-methylthio-5-[(Z)-4,7-dihydroxy-2-heptenylidene]-4-(4-phenoxybutyl)-4-hydroxy-2-cyclopentenone | 1.2 |
| 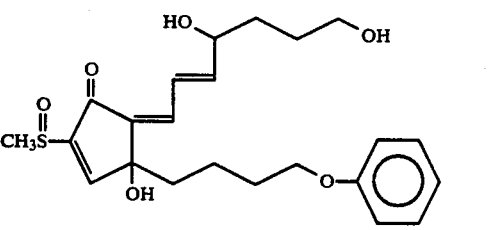 | 2-methylsulfinyl-5-[(Z)-4,7-dihydroxy-2-heptenylidene]-4-(4-phenoxybutyl)-4-hydroxy-2-cyclopentenone | 1.0 |
| 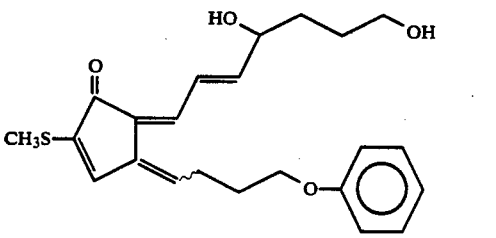 | 2-methylthio-5-[(Z)-4,7-dihydroxy-2-heptenylidene]-4-(4-phenoxybutylidene)-2-cyclopentenone | 3.5 |

TABLE 37-continued

| Compound to be tested | | $IC_{50}$ (μg/ml) |
|---|---|---|
| 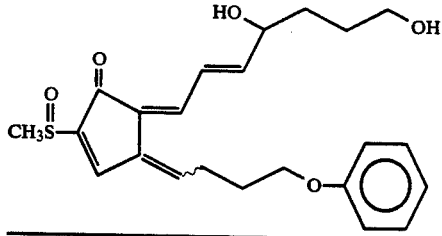 | 2-methylsulfinyl-5-[(Z)-4,7-dihydroxy-2-heptenylidene]-4-(4-phenoxybutylidene)-2-cyclopentenone | 0.1 |

EXAMPLE 591

TABLE 38

| | Measurement of alkali phosphatase (ALP), calcium (Ca), phosphorus (P) per DNA | | | |
|---|---|---|---|---|
| Compound | | ALP OD 410 nm/ μg DNA | Ca μg/μg DNA | P μg/μg DNA |
| Control | | 1.148 ± 0.050 | 0.386 ± 0.245 | 1.528 ± 0.316 |
| 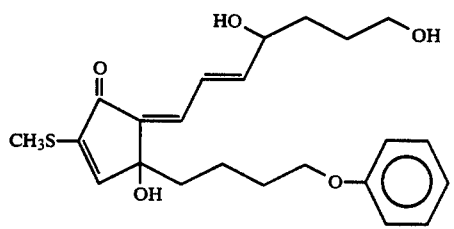 | $10^{-7}$ M | 0.333 ± 0.039 $p < 0.001$ | 8.847 ± 1.485 $p < 0.05$ | 5.270 ± 0.144 $p < 0.001$ |
| | $10^{-6}$ M | 1.447 ± 0.268 $p < 0.001$ | 29.410 ± 1.263 $p < 0.001$ | 15.743 ± 0.630 $p < 0.01$ |

2-methylthio-5-[(Z)-4,7-dihydroxy-2-heptenylidene]-4-(4-phenoxybutyl)-4-hydroxy-2-cyclopentenone

Determination (1) of bone formation activity

Human osteoblast (SAM-1, 12PDL) was cultured in α-MEM containing 10% fetal bovine serum, and when a stable growth was attained, a predetermined concentration of the compound was added in the presence of 2 mM α-glycerophosphoric acid salt, followed by treatment for 25 days. The cell layer was washed with Hank's solution and the alkali phosphatase activity then measured by absorption at $OD_{410}$. Next, calcium and phosphorus were extracted with a 5% perchloric acid solution and quantitated, and DNA was extracted with 5% perchloric acid at 90° C., and the weight thereof quantitated. These evaluations were conducted according to the methods of Koshihara et al (Biochemical and Biophysical Research Communication Vol 145, No. 2, 1987, p. 651). The results are shown in Table 38.

EXAMPLE 592

Determination (2) of bone formation activity

Human osteoblast (KK-3, 18PDL) was cultured in α-MEM containing 10% fetal bovine serum, and when a stable growth was attained, a predetermined concentration of the compound was added in the presence of 2 mM α-glycerophosphoric acid salt, followed by treatment for 14 days. The cell layer was washed with physiological salt solution and the alkali phosphatase activity then measured by absorption at $OD_{415}$. Then, calcium and phosphorus were extracted with a 2N hydrochloric acid solution and quantitated. The results are shown in Table 39.

TABLE 39

| Compound | | ALP OD 415 nm/dish | Ca μg/dish | P μg/dish |
|---|---|---|---|---|
| Control (No compound) | | 0.44 ± 0.12 | 106 ± 12 | 61 ± 10 |
| 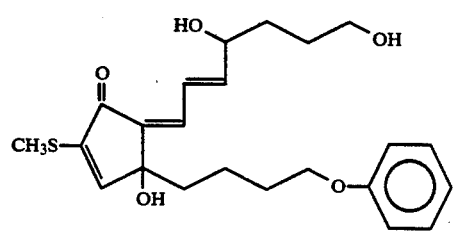 | $10^{-8}$ M | 0.28 ± 0.06 | 84 ± 10 | 47 ± 6 |
| | $10^{-7}$ M | 0.48 ± 0.08 | 111 ± 9 | 63 ± 6 |
| | $10^{-6}$ M | 1.12 ± 0.31 | 168 ± 1 | 92 ± 2 |

2-methylthio-5-[(Z)-4,7-dihydroxy-2-heptenylidene]-4-(4-phenoxybutyl)-4-hydroxy-2-cyclopentenone TABLE 39-continued

| Compound | | ALP OD 415 nm/dish | Ca μg/dish | P μg/dish |
|---|---|---|---|---|
| 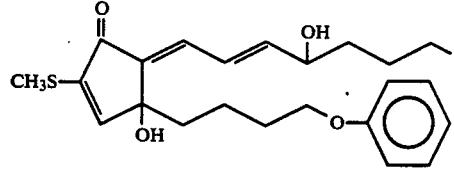<br>2-methylthio-5-[(E)-4,7-dihydroxy-2-heptenylidene]-4-(4-phenoxybutyl)-4-hydroxy-2-cyclopentenone | $10^{-8}$ M<br>$10^{-7}$ M<br>$10^{-6}$ M | 0.24 ± 0.02<br>0.56 ± 0.08<br>0.97 ± 0.07 | 87 ± 6<br>114 ± 4<br>168 ± 9 | 47 ± 2<br>64 ± 3<br>93 ± 4 |

EXAMPLE 593

Determination (3) of bone formation activity

Human osteoblast (KK-3, 18PDL) was cultured in α-MEM containing 10% fetal bovine serum, and when a stable growth was attained, a predetermined concentration of the compound was added in the presence of 2 mM α-glycerophosphoric acid salt, followed by treatment for 14 days. The cell layer was washed with a physioligical salt solution and the alkali phosphatase activity then measured by absorption at $OD_{415}$. Next, calcium and phosphorus were extracted with a 2N hydrochloric acid solution and quantitated.

The results are shown in Table 40.

TABLE 40

| Compound | | ALP OD 415 nm/dish | Ca μg/dish | P μg/dish |
|---|---|---|---|---|
| Control (No compound) | | 0.72 ± 0.17 | 90 ± 8 | 51 ± 5 |
| 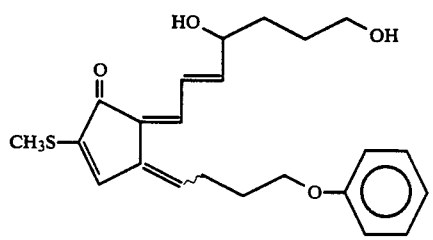<br>2-methylthio-5-[(Z)-4,7-dihydroxy-2-heptenylidene]-4-(4-phenoxybutylidene)-2-cyclopentenone | $10^{-7}$ M<br>$10^{-6}$ M | 0.69 ± 0.02<br>0.75 ± 0.17 | 110 ± 30<br>105 ± 5 | 60 ± 14<br>57 ± 1 |
| 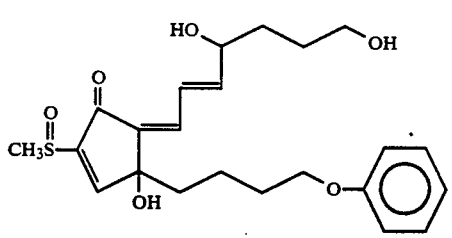<br>2-methylsulfinyl-5-[(Z)-4,7-dihydroxy-2-heptenylidene]-4-(4-phenoxybutylidene)-4-hydroxy-2-cyclopentenone | $10^{-7}$ M<br>$10^{-6}$ M | 0.81 ± 0.11<br>0.92 ± 0.9 | 89 ± 1<br>109 ± 7 | 52 ± 1<br>61 ± 4 |
| 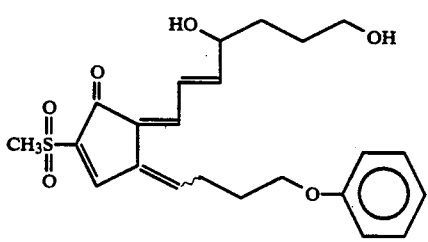<br>2-methylthio-5-[(Z)-4,7-dihydroxy-2-heptenylidene]-4-(4-phenoxybutylidene)-2-cyclopentenone | $10^{-7}$ M<br>$10^{-6}$ M | 0.94 ± 0.07<br>0.94 ± 0.11 | 85 ± 10<br>109 ± 3 | 48 ± 4<br>60 ± 0.5 |

TABLE 40-continued

| Compound | | ALP OD 415 nm/dish | Ca μg/dish | P μg/dish |
|---|---|---|---|---|
| 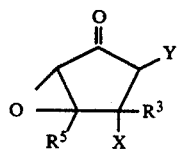 | $10^{-7}$ M | $0.73 \pm 0.02$ | $78 \pm 4$ | $46 \pm 2$ |
| | $10^{-6}$ M | $0.68 \pm 0.10$ | $79 \pm 8$ | $43 \pm 4$ |
| 2-methylthio-5-(6-methoxy-carbonylhexylidene)-4-(3-hydroxy-1-octenyl)-2-cyclopentenone | | | | |

We claim:

1. 2,3-epoxycyclopentanone represented by the formula (IV):

$$(IV)$$

wherein $R^3$ represents a substituted or unsubstituted (i) aliphatic hydrocarbon group having 1 to 10 carbon atoms, (ii) alicyclic hydrocarbon group having 4 to 10 carbon atoms, or (iii) aromatic hydrocarbon group having 6 to 10 carton atoms;

$R^5$ represents a hydrogen atom, or a substituted or unsubstituted (i) aliphatic hydrocarbon group having 1 to 10 carbon atom or (ii) alicyclic hydrocarbon group having 4 to 10 carbon atoms;

X represents a hydrogen atom or a group —OR$^4$ where R$^4$ is a hydrogen atom, an alkyl group having 1 to 4 carbon atoms, an acyl group having 2 to 7 carbon atoms, an alkoxycarbonyl group having 2 to 5 carbon atoms, a tri($C_1$-$C_7$) hydrocarbon silyl group, or a group capable of forming an acetal bond together with the oxygen atom attached to the R$^4$;

Y represents a hydrogen atom or a group —CH(OH)—R$^2$ where R$^2$ is a substituted or unsubstituted (i) aliphatic hydrocarbon group having 1 to 10 carbon atoms, (ii) alicyclic hydrocarbon group having 4 to 10 carbon atoms, (iii) aromatic hydrocarbon group having 6 to 10 carbon atoms or (iv) heterocyclic group having 1 to 9 carbon atoms; with the proviso that, when X is a hydrogen atom Y is a group —CH(OH)—R$^2$ and that, when X is a group —OR$^4$, Y is a hydrogen atom.

2. 2,3-epoxycyclopentanone in claim 1, wherein R$^3$ is a substituted or unsubstituted aliphatic hydrocarbon group having 1 to 10 carbon atoms, R$^5$ is a hydrogen atom, X is a hydrogen atom, and Y is a group —CH(OH)—R$^2$ where R$^2$ is as defined above.

3. 2,3-epoxycyclopentanone as claimed in claim 1, wherein R$^3$ is a substituted or unsubstituted aliphatic hydrocarbon group having 1 to 10 carbon atoms, R$^5$ is a hydrogen atom, X is a group —OR$^4$ where R$^4$ is as defined above, and Y is a hydrogen atom.

* * * * *